United States Patent
Wacker et al.

(10) Patent No.: US 10,307,473 B2
(45) Date of Patent: *Jun. 4, 2019

(54) CAPSULAR GRAM-POSITIVE BACTERIA BIOCONJUGATE VACCINES

(71) Applicant: GLAXOSMITHKLINE BIOLOGICALS S.A., Rixensart (BE)

(72) Inventors: Michael Wacker, Unterengstringen (CH); Michael Kowarik, Zurich (CH); Michael Wetter, Zurich (CH)

(73) Assignee: GlaxoSmithKline Biologicals SA, Rixensart (BE)

(*) Notice: Subject to any disclaimer, the term of this patent is extended or adjusted under 35 U.S.C. 154(b) by 0 days.

This patent is subject to a terminal disclaimer.

(21) Appl. No.: 15/414,900

(22) Filed: Jan. 25, 2017

(65) Prior Publication Data

US 2017/0128559 A1 May 11, 2017

Related U.S. Application Data

(62) Division of application No. 14/494,150, filed on Sep. 23, 2014, now Pat. No. 9,585,950, which is a division of application No. 13/100,603, filed on May 4, 2011, now Pat. No. 8,871,491.

(60) Provisional application No. 61/332,170, filed on May 6, 2010.

(51) Int. Cl.
| | | |
|---|---|---|
| A61K 39/085 | (2006.01) |
| C12N 15/70 | (2006.01) |
| C12N 15/74 | (2006.01) |
| C07K 14/21 | (2006.01) |
| C12N 9/10 | (2006.01) |
| C07K 16/12 | (2006.01) |
| A61K 39/00 | (2006.01) |

(52) U.S. Cl.
CPC ............ *A61K 39/085* (2013.01); *C07K 14/21* (2013.01); *C07K 16/1271* (2013.01); *C12N 9/1029* (2013.01); *C12N 9/1048* (2013.01); *C12N 15/70* (2013.01); *C12N 15/74* (2013.01); *A61K 2039/505* (2013.01); *A61K 2039/575* (2013.01); *A61K 2039/6037* (2013.01); *A61K 2039/6087* (2013.01); *A61K 2039/64* (2013.01); *A61K 2039/70* (2013.01); *C07K 2317/734* (2013.01); *C07K 2319/00* (2013.01); *C07K 2319/02* (2013.01); *C07K 2319/034* (2013.01); *C07K 2319/21* (2013.01); *Y02A 50/47* (2018.01)

(58) Field of Classification Search
None
See application file for complete search history.

(56) References Cited

U.S. PATENT DOCUMENTS

| | | |
|---|---|---|
| 5,643,758 A | 7/1997 | Guan et al. |
| 2002/0019342 A1 | 2/2002 | Bayer |
| 2004/0265954 A1 | 12/2004 | Aebi et al. |
| 2005/0287628 A1 | 12/2005 | Aebi et al. |
| 2011/0097357 A1 | 4/2011 | Fernandez et al. |

FOREIGN PATENT DOCUMENTS

| | | |
|---|---|---|
| CA | 1340184 | 12/1998 |
| CA | 2360205 | 8/2000 |
| CA | 2477794 | 3/2003 |
| EP | 1481057 | 2/2006 |
| WO | WO 1994/026906 | 11/1994 |
| WO | WO 2000/052135 | 9/2000 |
| WO | WO 2001/088117 | 11/2001 |
| WO | WO 2002/000856 | 1/2002 |
| WO | WO 2003/074687 | 9/2003 |
| WO | WO 2004/013151 A2 | 2/2004 |
| WO | WO 2005/116063 A1 | 12/2005 |
| WO | WO 2006/119987 A2 | 11/2006 |
| WO | WO 2007/113222 A2 | 10/2007 |
| WO | WO 2009/089396 A2 | 7/2009 |
| WO | WO 2009/104074 A2 | 8/2009 |

OTHER PUBLICATIONS

Fattom, A. et al., Synthesis and immunologic properties in mice of vaccines composed of *Staphylococcus aureus* type 5 and type 8 capsular polysaccharides conjugated to Pseudomonas aeruginosa exotoxin A., Infect. Immun., 1990, vol. 58 No. 7, pp. 2367-2374.

(Continued)

*Primary Examiner* — Jennifer E Graser
(74) *Attorney, Agent, or Firm* — Dana L. Broughton

(57) ABSTRACT

The present invention encompasses a novel *S. aureus* bioconjugate vaccine. More generally, the invention is directed to Gram-positive and other bioconjugate vaccines containing a protein carrier, at least one polysaccharide such as a capsular Gram-positive polysaccharide, and, optionally, an adjuvant or pharmaceutically acceptable carrier. The instant invention also includes methods of producing Gram-positive and other bioconjugate vaccines. An N-glycosylated protein is also provided that contains one or more polysaccharides such as Gram-positive polysaccharides. The invention is additionally directed to engineered prokaryotic organisms comprising nucleotide sequences encoding a glycosyltransferase of a first prokaryotic organism and a glycosyltransferase of a second prokaryotic organism. The invention further includes plasmids and prokaryotic cells transformed with plasmids encoding polysaccharides and enzymes which produce an N-glycosylated protein and/or bioconjugate vaccine. Further, the invention is directed to methods of inducing an immune response in a mammal comprising administering said bioconjugate vaccines.

8 Claims, 37 Drawing Sheets

Specification includes a Sequence Listing.

(56) References Cited

OTHER PUBLICATIONS

Mario F Feldman et al., "Engineering N-linked protein glycosylation with diverse O antigen lipopolysaccharide structures in *Escherichia coli*", Proceedings of the National Academy of Sciences, National Academy of Sciences, Washington, DC; US, vol. 102, No. 8, doi:DOI:10.1073/PNAS.0500044102, ISSN 0027-8424, (Feb. 22, 2005), pp. 3016-3021. Feb. 9, 2005.
Jones, C., Revised structures for the capsular polysaccharides from *Staphylococcus aureus* Types 5 and 8, components of novel glycoconjugate vaccines., Carbohydrate Res., 2005, vol. 340 No. 6, pp. 1097-1106.
Sau, S. et al., The *Staphylococcus aureus* allelic genetic loci for serotype 5 and 8 capsule expression contain the type-specific genes flanked by common genes., Microbiology, 1997, vol. 143 No. 7, pp. 2395-2405.
Chris Whitfield, Biosynthesis and assembly of capsular polysaccharides in *Escherichia coli*., Annu. Rev. Biothem., 75:39-68, Feb. 27, 2006.
Chris Whitfield, et al., Biosynthesis and assemably of Group 1, Carbohydrate Research, 338(2003):2491-2502.
Press Release, GlycoVaxyn and a Harvard University affiliated hospital receive USD 3.4 million NIH grant for *Staphylococcus aureus* vaccine development., GlycoVaxyn [online], May 4, 2010, pp. 1-2, <https://web.archive.org/web/20110626233433/http://www.glycovaxyn.com/content/news/releases/10%2005%2004.pdf> [retrieved on Jun. 16, 2015].
Abdian et al., 2000, "Identification of essential amino acids in the bacterial α-mannosyltransferase aceA", J Biol Chem; 275(51):40568-40575.
Aebi et al., 1996, "Cloning and characterization of the ALG3 gene of *Saccharomyces cerevisiae*", Glycobiology; 6:439-444.
Ahmed et al., 2006, "Safety and immunogenicity of *Escherichia coli* O157 O-specific polysaccharide conjugate vaccine in 2-5 year old children", J Infect Dis; 193(4):515-521.
Alaimo et al., 2006, "Two distinct but interchangeable mechanisms for flipping of lipid-linked oligosaccharides", EMBO J; 25:967-976.
Alexander et al., 1994, "Role of the rfe gene in the biosynthesis of the *Escherichia coli* O7-specific lipopolysaccharide and other O-specific polysaccharides containing N-acetylglucosamine", J Bacteriol; 176:7079-7084.
Allard et al., 2001, "Epimerases:structure, function and mechanism", Cell Mol Life Sci; 58:1650-1665.
Altmann et al., 1999, "Insect cells as hosts for the expression of recombinant glycoproteins", Glycoconjugate Journal; 16:109-123.
Amor et al., 1997, "Molecular and functional analysis of genes required for expression of group IB K antigens in *Escherichia coli*: characterization of the his-region containing gene clusters for multiple cell-surface polysaccharides", Mol Microbiol; 26:145-161.
Anderson, 1983, "Antibody responses to Haemophilus influenzae type b and diphtheria toxin induced by conjugates of oligosaccharides of the type b capsule with the nontoxic protein $CRM_{197}$", Infection and Immunity; 39(1):233-238.
Arbeit et al., 1984, "Predominance of two newly described capsular polysaccharide types among clinical isolates of *Staphylococcus aureus*", Diagn Microbiol Infect Dis; 2:85-91.
Avery et al., 1929, "Chemo-immunological studies on conjugated carbohydrate-proteins. II Immunological specificity of synthetic sugar-protein antigens", J Exp Med; 50(4):533-550.
Baggett et al., 2004, "Community-onset methicillin-resistant *Staphylococcus aureus* associated with antibiotic use and the cytotoxin Panton-Valentine leukocidin during a furunculosis outbreak in rural Alaska", J Infect Dis; 189:1565-1573.
Baneyx et al., 1999, "Recombinant protein expression in *Escherichia coli*", Curr Opin Biotechnol; 10:411-421.
Baqar et al., 1995, "Safety and immunogenicity of a prototype oral whole-cell killed Campylobacter vaccine administered with a mucosal adjuvant in non-human primates",Vaccine; 13(1):22-28.

Bematchez et al., 2005, "A single bifunctional UDP-ClcNAc/Glc 4-epimerase supports the synthesis of three cell surface glycoconjugates in Campylobacter jejuni", J Biol Chem; 280:4792-4802.
Berg et al., 1997, "2-oxo acid dehydrogenase multienzyme complexes: the central role of the lipoyl domain", Biological Chemistry; 378:617-634.
Berg et al., 2001, "Sequence properties of the 1,2-diacylglycerol 3-glucosyltransferase from acholeplasma laidlawii membranes", J Biol Chem; 276(25):22056-22063.
Bhasin et al., 1998, "Identification of a gene essential for O-acetylation of the *Staphylococcus aureus* type 5 capsular polysaccharide", Mol Microbiol; 27:9-21.
Bigge et al., 1995, "Nonselective and efficient fluorescent labeling of glycans using 2-amino benzamide and anthranilic acid", Anal Biochem; 230(2):229-238.
Bill et al., 1995, "Expression and mutagenesis of recombinant human and murine erythropoietins in *Escherichia coli*", Biochimica et Biophysica Acta; 1261:35-43.
Billman-Jacobe, 1996, "Expression in bacteria other than *Escherichia coli*", Curr Opin Biotechnol; 7:500-504.
Bligh et al., 1959, "A rapid method of total lipid extraction and purification", Can J Biochem Physiol; 37(8):911-917.
Bourne et al., 2001, "Glycoside hydrolases and glycosyltransferases: families and functional modules", Current Opinion in Structural Biology; 11:593-600.
Branden et al., 1991, "Introduction to protein structure", Garland Publishing Inc., New York; pp. 247-268.
Breton et al., 1999, "Structure/function studies of glycosyltransferases", Current Opinion in Structural Biology; 9:563-571.
Bubeck Wardenburg et al., 2008, "Panton-Valentine leukocidin is not a virulence determinant in murine models of community-associated methicillin-resistant *Staphylococcus aureus* disease", J Infect Dis; 198:1166-1170.
Bugg et al., 1994, "From peptidoglycan to glycoproteins: common features of lipid-linked oligosaccharide biosynthesis", FEMS Microbiol Lett; 119:255-262.
Burda et al., 1999, "The dolichol pathway of N-linked glycosylation", Biochimica et Biophysica Acta; 1426:239-257.
Burr et al., 2005, "Prevention of disease in ferrets fed an inactivated whole cell Campylobacter jejuni vaccine", Vaccine; 23:4315-4321.
Butzler, 2004, "Campylobacter, from obscurity to celebrity", Clinical Microbiology and Infection; pp. 868-876.
Campbell et al., 1997, "A classification of nucleotide-diphospho-sugar glycosyltransferases based on amino acid sequence similarities", Biochem J; 326:929-939.
Canals et al., 2006, "The UDP N-acetylgalactosamine 4-epimerase gene is essential for mesophilic Aeromaonas hydrophila serotype O34 virulence", Infect & Immun; 74(1):537-548.
Cardini et al., 1957, "Enzymatic formation of acetylgalactosamine", J Biol Chem; 225:317-327.
Casburn-Jones et al., 2004, "Traveler's diarrhea", Journal of Gastroenterology and Hepatology, 19:610-618.
CAZy (Carbohydrate-Active enZYmes) Database—GlycosylTransferase family classification (AFMB—CNRS—Universites Aix-Marseille I & II) last update: Oct. 25, 2010 at http://www.cazy.org/GlycosylTransferases.html.
CAZy (Carbohydrate-Active enZYmes) Database—Home (AFMB—CNRS—Universites Aix-Marseille I & II) last update: Oct. 25, 2010 at http://www.cazy.org.
Chang et al., 2003, "Infection with vancomycin-resistant *Staphylococcus aureus* containing the vanA resistance gene", New Engl J Med; 348:1342-1347.
Chart et al., 1991, "Serological identification of *Escherichia coli* O157:H7 infection in haemolytic uraemic syndrome", The Lancet; 337:138-140.
Choi et al., 2004, "Secretory and extracellular production of recombinant proteins using *Escherichia coli*", Appl Microbiol Biotechnol; 64:625-635.
Consortium for Functional Glycomics (CFG) Nature, Functional glycomics gateway—Nomenclature, last update: Apr. 28, 2010 at http://ww.functionalglycomics.org/static/consortium/Nomenclature.shtml.

(56) References Cited

OTHER PUBLICATIONS

Coutinho et al., 1999, "Life with no sugars?", J Mol Microbiol Biotech; 1(2):307-308.

Crooks et al., 2004, "WebLogo: A sequence logo generator", Genome Research; 14(6):1188-1190.

Cruezenet et al., 2000, "Expression, purification, and biochemical characterization of WbpP, a new UDP-GlcNAc C4 epimerase from Pseudomonas aeruginosa sertype O6", J Biol Chem; 275(25):19060-19067.

Crushell et al., 2004, "Enteric Campylobacter: purging its secrets?" Pediatric Research; 55(1):3-12.

Cunnion et al., 2001, "Capsule production and growth phase influence binding of complement to *Staphylococcus aureus*", Infect Immun; 69:6796-6803.

Datsenko et al., 2000, "One-step inactivation of chromosomal genes in *Escherichia coli* K-12 using PCR products", Proc Natl Acad Sci USA; 97:6640-6645.

Dean et al., 1999, "Characterization of the serogroup O11 O-antigen locus of Pseudomonas aeruginosa PA103", J Bacteriol; 181:4275-4284.

Dejonge et al., 2007, "Clinical trial of safety and efficacy of INH-A21 for the prevention of nosocomial staphylococcal bloodstream infection in premature infants", J Pediatr; 151:260-265.

Doig et al., 1996, "Characterization of a post-translational modification of Campylobacter flagellin: identification of a sero-specific glycosyl moiety", Molecular Microbiology; 19(2):379-387.

Dunphy et al., 1967, "The plurality of long chain isoprenoid alcohols (polyprenols) from natural sources", Biochim Biophys Acta; 136: 136-147.

Expression Library Screening (Procaryotic) Using AP-fusion proteins (last visited Nov. 1, 2010) at http://www.protocol-online.org/cgi-bin/prt/view_cache.cgi?ID=2752.

Fairweather et al, 1986, "Cloning, nucleotide sequencing, and expression of tetanus toxin fragment C in *Escherichia coli*", Journal of Bacteriology; 165(1):21-27.

Falt et al., 1996, "Construction of recombinant aroA salmonellae stably producing the Shigella Sysenteriae sertype 1 O-antigen and structural characterization of the *Salmonella*/Shigella hybrid LPS", Microb Pathog; 20(1):11-30.

Faridmoayer et al., 2007, "Functional characterization of bacterial oligosaccharyltransferases involved in O-linked protein glycosylation", J Bacteriol; 189(22):8088-8098.

Fass et al., 1991, "Use of high densitycultures of *Escherichia coli* for high level production of recombinant Pseudomonas aeruginosa exotoxin A", Applied Microbiology and Biotechnolgy, 36(1):65-69.

Fattom et al., 1990, "Synthesis and immunologic properties in mice of vaccines composed of *Staphylococcus aureus* type 5 and type 8 capsular polusaccharides conjugated to Pseudomonas aeruginosa exotoxin A", Infect Immun; 58:2367-2374.

Fattom et al., 1993, "Laboratory and clinical evaluation of conjugate vaccines composed of *Staphylococcus aureus* type 5 and type 8 capsular polysaccharides bound to Pseudomonas aeruginosa recombinant exoprotein A", Infection and Immunity; 61(3):1023-1032.

Fattom et al., 1996, "A *Staphylococcus aureus* capsular polysaccharide (CP) vaccine and CP-specific antibodies protect mice against bacterial challenge", Infect Immun; 64:1659-1665.

Fattom et al., 1998, "Antigenic determinants of *S. aureus* type 5 and type 8 capsular polysaccharide vaccines", Infect Immun; 66:4588-4592.

Feldman et al., 2005, "Engineering N-liked protein glycosylation with diverse O antigen lipopolysaccharide structures in *Escherichia coli*", Proc Natl Acad Sci USA; 102:3016-3021.

Feng et al., 2005, "Structural and genetic characterization of the Shigella boydii type 18 O antigen", Gene; 355:79-86.

Field et al., 2003, "Structural and mechanistic basis of bacterial sugar nucleotide-modifying enzymes", Biochemistry; 42:7637-7647.

Foster et al., 1998, "Surface protein adhesins of *Staphylococcus aureus*", Trends Microbiol; 6:484-488.

Foster, 2005, "Immune evasion by staphylococci", Nature Reviews Microbiology; 3:948-958.

Francisco et al., 1992, "Transport and anchoring of β-lactamase to the external surface of *Escherichia coli*", Proc Natl Acad Sci USA: 89:2713-2717.

Fridkin et al., 2005, "Methicillin-resistant *Staphylococcus aureus* disease in three communities", N Engl J Med; 352:1436-1411.

Fry et al., 1998, "The lipopolysaccharide biosynthesis locus of Campylobacter jejuni 81116", Microbiology; 144:2049-2061.

Fujita et al., 2000, "Synthesis of neoglycoenzymes with homogenous N-linked oligosaccharides using immobilized endo-S-N-acetylglucosaminidase A", Biochmeical and Biophysical Research Communications, 267:134-138.

Gavel et al., 1990, "Sequence differences between glycosylated and non-glycosylated Asn-X-Thr/Ser acceptor sites: implications for protein engineering", Protein Eng; 3:433-442.

Gilbert et al., 2006, "Outbreak in Alberta of community-acquired (USA300) methicillin-resistant *Staphylococcus aureus* in people with a history of drug use, homelessness or incarceration", Canad Med Assoc J; 175:149-154.

Global Alliance for Vaccines and Immunization—Press releases (Mar. 11, 2006) at http://www.gavialliance.org/media_centre/press_releases/2006_03_09_en_pr_queenrania_delhi.php.

Glover et al., 2005, "Chemoenzymatic synthesis of glycopeptides with PglB, a bacterial oligosaccharyl transferase from Campylobacter jejuni", Chemistry & Biology; 12:1311-1316.

Glover et al., 2005, "In vitro assembly of the undecaprenylpyrophosphate-linked heptasaccharide for prokaryotic N-linked glycosylation", Proc Natl Acad Sci USA; 102(40):14255-14259.

"GlycoVaxyn AG appoints renowned vaccinologist Dr. Stanley Plotkin to supervisory board", Press Release (Oct. 6, 2009) available at http://www.glycovaxyn.com/content/news/releases/09%2010%2006.pdf.

"GlycoVaxyn AG completes CHF 11.5 million series A financing to advance novel conjugated vaccine pipeline towards clinic", Press Release (Jul. 16, 2007) available at http://www.glycovaxyn.com/content/news/releases/06%2010%2019.pdf.

"GlycoVaxyn AG raises CHF 25 million in financing led by Edmond de Rothschild Investment Partners", Press Release (Mar. 5, 2009) available at http://www.glycovaxyn.com/downloads/GlycoVaxyn%20Financing%20Release%2005-03-09.pdf.

"GlycoVaxyn and a Harvard University affiliated hospital receive USD 3.4 million NIH grant for *Staphylococcus aureus* vaccine development", Press Release (May 4, 2010) available at http://www.glycovaxyn.com/content/news/releases/10%2005%2004.pdf.

"GlycoVaxyn appoints Philippe Dro as CEO", Press Release (May 20, 2008) available at http://www.sofinnova.fr/glycovaxyn-appoints-phillippe-dro-as-cco-actu-736.php.

"GlycoVaxyn opens to partnerships; series C financing round planned for 2011, CEO says mergermarket", pp. 1-2 (Nov. 25, 2009) at http://www.mergermarket.com/home/.

"GlycoVaxyn phase I clinical study shows positive data with Shigella dysenteriae vaccine candidate", (Oct. 8, 2010) available at http://www.glycovaxyn.com/content/news/releases/10%2010%2008.pdf.

"GlycoVaxyn winner of the life sciences prize 2006", Press Release (Oct. 19, 2006) available at http://www.glycovaxyn.com/content/news/releases/06%02010%2019.pdf.

"GlycoVaxyn's first clinical study with bioconjugate vaccine initiated", Press Release (Feb. 23, 2010) available at http://www.glycovaxyn.com/content/news/releases/10%2002%2023.pdf.

Goebel et al., 1929, "Chemo-immunological studies on conjugated carbohydrate-proteins" Journal of Experimental Medicine; 50(4):521-531.

Goldberg et al., 1992, "Cloning and surface expression of Pseudomonas aeruginosa O antigen in *Escherichia coli*", Proc Natl Acad Sci USA; 89(22):10716-10720.

Gordon et al., 1956, "Rapid paper chromatography of carbohydrates and related compounds", Anal Chem; 28:849-855.

Grabenhorst et al., 1999, "Genetic engineering of recombinant glycoproteins and the glycosylation pathway in mammalian host cells", Glycoconjugate Journal; 16:81-97.

(56) References Cited

OTHER PUBLICATIONS

Gray, 1979, "ELISA methodology for polysaccharide antigens: protein coupling of polysaccharides for adsorption to plastic tubes", J Immunol; 28:187-192.
Guan et al., 2005, "Extraction and identification by mass spectrometry of undecaprenyl diphosphate-MurNAc-pentapeptide-GlcNAc from *Escherichia coli*", Anal Biochem; 345:336-339.
Guerry et al., 1996, "Identification and characterization of genes required for post-translational modification of *Campylobacter coli* VC167 flagellin", Molecular Microbiology; 19(2):369-378.
Guo et al., 2007, "Three UDP-hexose 4-epimerases with overlapping substrate specificity coexist in *E. coli* O86:B7", Biochem Biophys Res Commun; 356:604-609.
Haberberger et al., 1994, "Prospects and problems for development of a vaccine against diarrhea caused by Campylobacter", Vaccine Research; 3:15-22.
Helenius et al., 2004, "Roles of N-linked glycans in the endopasmic reticulum", Annu Rev Biochem; 73:1019-1049.
Higgins et al., 2004, "Structure of the periplasmic component of a bacterial drug efflux pump", Proc Natl Acad Sci USA; 101:9994-9999.
Ilo et al., 2006, "Preclinical laboratory evaluation of a bivalent *Staphylococcus aureus* saccharide-exotoxin A protein conjugate vaccine", Hum Vaccin; 2:89-98.
Hoffmeister et al., 2001, "Two sequence elements of glycosyltransferases involved in urdamycin biosynthesis are responsible for substrate specificity and enzymatic activity", Chem & Bio; 8:557-567.
Hofmann et al., 1993, "A database of membrane spanning protein segments", Biol Chem; 374:166 (abstract).
Hoiseth et al., 1981, "Aromatic-dependent *Salmonella typhimurium* are non-virulent and effective as live vaccines", Nature; 291:238-239.
Ihssen et al., 2010, "Production of glycoprotein vaccines in *Escherichia coli*", Microbial Cell Factories; 9(1):61.
Imperiali et al., 1991, "Differences between Asn-Xaa-Thr-containing peptides; a comparison of solution conformation and substrate behavior with oligosaccharyl-transferase", Biochemistry; 30:4374-4380.
International Search Report of International application No. PCT/CH03/00153, dated May 19, 2003.
International Search Report of International application No. PCT/EP2006/004397, dated Dec. 13, 2006.
International Search Report of International application No. PCT/EP2011/057111, dated Jul. 28, 2011.
Jeong et al., 2001, "Secretory production of human granulocyte colony-stimulating factor in *Escherichia coli*", Protein Expression and Purification; 23:211-318.
Johnson et al., 1999, "Alignment and structure prediction of divergent protein families: periplasmic and outer membrane proteins of bacterial efflux pumps", J Mol Biol; 287:695-715.
Johnson et al., 1999, "Synthesis of oligosaccharides by bacterial enzymes", Glycoconjugate Journal; 16:141-146.
Jones et al., 2005, "Revised structures for the capsular polysaccharides from *Staphylococcus aureus* types 5 and 8, components of novel glycoconjugate vaccines", Carbohydr Res; 340:1097-1106.
Josefsson et al., 2001, "Protection against experimental *Staphylococcus aureus* arthritis by vaccination with clumping factor A, a novel virulence determinant", Journal of Infectious Diseases; 184:1572-1580.
Jursch et al., 1994, "Histidine residues near the N terminus of staphylococcal alpha-toxin as reporters of regions that are critical for oligomerization and pore formation", Infect Immun; 62(6):2249-2256.
Kaniuk et al., 2004, "Investigation of the structural requirements in the lipopolysaccharide core acceptor for ligation of O antigens in the genus *Salmonella*: WaaL 'ligase' is not the sole determinant of acceptor specificity", J Biol Chem; 279:36470-36480.
Kapitonov et al., 1999, "Conserved domains of glycosyltransferases", Glycobiol; 9(10):961-978.
Karlyshev et al., 2004, "The Campylobacter jejuni general glycosylation system is important for attachment to human epithelial cells and in the colonization of chicks", Microbiology; 150; 1957-1964.
Kazakova et al., 2005, "A clone of methicillin-resistant *Staphylococcus aureus* among professional football players", N Engl J Med; 352:468-475.
Kean 1966, "Separation of gluco- and galactocerebrosides by means of borate thin-layer chromatography", J Lipid Res; 7:449-452.
King et al., 2006, "Emergence of community-acquired methicillin-resistant *Staphylococcus aureus* USA 300 clone as the predominant cause of skin and soft-tissue infections", Ann Intern Med; 144:309-317.
Kiser et al., 1999, "*Staphylococcus aureus* cap5P encodes a UDP-N-acetylglucosamine 2-epimerase with functional redundancy", J Bacteriol; 181(16):4818-4824.
Klevens et al., 2007, "Invasive methicillin-resistant *Staphylococcus aureus* infections in the United States," Jama 298: 1763-71.
Knirel et al., 1988, "Somatic antigens of Shigella: structure of the O-specific polysaccharide chain of the Shigella dysenteriae type 7 lipoplysacharide."
Kollef eta l., 2005, "Epidemiology and outcomes of health-care associated pneumonia: results from a large US database of culture-positive pneumonia." Chest 128:3854-3862.
Konadu et al. 1998, "Investigational vaccine for *Escherichia coli* O157: phase 1 study of O157 O-specific polysaccharide-pseudomonas aeruginosa recombinant exoprotein A conjugates in adults", Journal of Infectious Diseases; 177(2):383-387.
Konadu et al., 1994, "Preparation, characterization, and immunological properties in mice of *Escherichia coli* O157 O-specific polysaccharide-protien conjugate vaccines", Infection and Immunity; 62(11):5048-5054.
Konadu et al., 1999, "Syntheses and immunologic properties of *Escherichia coli* O157 O-specific polysaccharide and shiga Toxin 1 B subunit conjugates in mice," Infection and Immunity; 67(11):6191-6193.
Kowarik et al., 2006, "N-Linked glycosylation of folded proteins by the bacterial oligosaccharvltransferase", Science; 314:1148-1150.
Kowarik et al., 2006, "Definition of the bacterial N-glycosylation site consensus sequence", EMBO J; 25(9):1957-1966.
Kuwajima et al., 1986, "Nucleotide sequence of the hag gene encoding flagellin of *Escherichia coli*", J Bacteriol; 168(3):1479-1483.
Laemmill, 1970, "Cleavage of Structural Proteins during the Assembly of the Head of bacteriophage T4." Nature 227:680-685.
Law, 2000, "Virulence factors of *Escherichia coli* O157 and other Shiga Toxin-producing *E. coli*." J. App. Microbiol. 88:729-745.
Lee et al., 1997, "Protective efficacy of antibodies to the *Staphylococcus aureus* type 5 capsular polysaccharide in a modified model of endocarditis in rats." Infect Immun. 65:4146-51.
Lee et al., 1999, "Evaluation of a truncated recombinant flagellin subunit vaccine against Campy/obaeter jejuni", Infection and Immunity; 67(11):5799-5805.
Lefebre, 2002, "Construction and Evaluation of Plasmind vectors Optimized for Consitutive and Regulated Gene Expression in Burkholdcria cepacia Complex Isolates," Appl. Environ Microbiol. 68:5956-5964.
Linton et al., 2002, "Identification of N-acetylgalactosamine-containing glycoproteins PEB3 and CgpA in Campylobacter jejuni", Molecular Microbiology; 43(2):497-508.
Linton et al., 2005, "Functional analysis of the Campylobacter jejuni N-linked protein glycoylation pathway", Molecular Microbiology; 55(6):1695-1703.
Liu et al., 2008, "Structure and genetics of Shigella O antigens." FEMS Microbiol. 32:627-653.
Lodish et al., 2000 "DNA Cloning with Plasmid vectors." Molec. Cell. Biology; 7.1 at http://www/ncbi.nlm.nih.gov/bookshelf/br.fcgi?book=mcb&part=A1582.
Lodish et al., 2000 "Protein Glycosylation in the ER and Golgi Complex"; 17.7 at http://www/ncbi.nlm.nih.gov/bookshelf/br.fcgi?book=mcb&part=A4816.
Lowy, 1998, "*Staphylococcus aureus* infections." New Eng. J Med. 339:520-32.

(56) References Cited

OTHER PUBLICATIONS

Lukac et al., 1988, "Toxoid of pseudomonas aeruginosa exotoxin A generated by deletion of an active-site residue", Infection and Immunity; 56(12):3095-3098.
Malissard et al., 1999, "The yeast expression system for recombinant glycosyltransferases", Glycoconjugate Journal; 16:125-139.
Maras et al., 1999, "Filamentous fungi as production organisms for glycoproteins of bio-medical interest", Glycoconjugate Journal; 16:99-107.
Marolda et al., 2006, "Interplay of the wzx translocase and the corresponding polymerase and chain length regulator proteins in the translocation and periplasmic assembly of lipopolysaccharide O antigen", Journal of Bacteriology; 188(14):5124-5135.
Marth et al., 1999, "Essentials of Glycobiology" Chapter 7 (Varki et al. eds.) available at http://www/ncbi.nlm.nih.gov/bookshelf/br.fcgi?book=glyco&part=A465.
McDevitt eta l., 1995, "Indentification of the ligand-binding domain of the surface-located fibrinogen receptor (clumping factor) of *Staphylococcus aureus*." Molecular Microbiology 16:895-907.
McDougal et al., 2003, "Pulsed-field gel electrophoresis typing of oxacillin-resistant *Staphylococcus aureus* isolates from the United States; establishing a national database." J. Clin. Microbiol. 41:5113-20.
Meier-Dieter, 1990, "Biosyntehsis of enterobacterial common antigen in *Escherichia coli*." J. Biol. Chem.; 265:13490-13497.
Menzies et al., 1996, "Passive immunization with antiserum to a nontoxic alpha-toxin mutant from *Staphylococcus aureus* is protective in a murine model." Infect Immun. 64:1839-41.
Merry et al., 2002, "Recovery of intact 2-aminobenzamide-labeled O-glycans released from glycoproteins by Hhydrazinolysis." Anal Biochem; 304(1):91-99.
Messner, 1997, "Bacterial glycoproteins," Glycoconjugate Journal 14:3-11.
Middlebrook et al., 1984, "Bacterial toxins: cellular mechanisms of action", Microbiological Reviews; 48(3): 199-221.
Mikusova et al., 2005, "Decaprenylphosphoryl Arabinofuranose, the Donor of the D-Arabinofuranosyl Residues of Mycobacterial Arabinan, is formed via a Two-Step Epimerization of Decaprenylphosphoryl Ribose." J. Bacteriol. 187:8020-8025.
Moreillon et al., 1995, "Role of *Staphylococcus aureus* coagulase and clumping factor in pathogenesis of experimental endocarditis." Infection & Immunity; 63:4738-43.
Muller et al., 2005, "An ATP-binding cassette-type cysteine transporter in Campylobacter jejuni inferred from the structure of an extracytoplasmic solute receptor protein", Mol Microbiol; 57:143-155.
Nairn et al., 1990, "Solutions, emulsions, suspensions and extracts", Remington's Pharmaceutical Sciences, 18th ed., Mack Publishing Co., Chapter 83, pp. 1519-1544.
Nanra et al, 2009, "Heterogenous in vivo expression of clumping factor A and capsular polysacchardie *Staphylococcus aureus*: Implications for vaccine design." Vaccine; 27:3276-80.
Nilsson et al.m, 1997, "The role of staphylococcal polysaccharide microcapsule expression in septicemia and septic arthritis." Infect Immun 65:4216-4221.
Nita-Lazar et al., 2005, "The N-X-S/T consensus sequence is required but not sufficient for bacterial N-linked protein glycosylation", Glycobiology; 15(4):361-367.
Notice of Abandonment of U.S. Appl. No. 10/506,917, dated Sep. 12, 2008.
Office Action of U.S. Appl. No. 10/506,917, dated Jan. 23, 2008.
Office Action of U.S. Appl. No. 10/506,917, dated May 9, 2007.
Office Action of U.S. Appl. No. 11/920,175, dated Nov. 9, 2011.
Office Action of U.S. Appl. No. 12/219,383, dated Jul. 23, 2009.
Office Action of U.S. Appl. No. 12/219,383, dated Mar. 20, 2009.
Office Action of U.S. Appl. No. 12/219,383, dated May 12, 2010.
Office Action of U.S. Appl. No. 12/219,383, dated Oct. 28, 2010 (Interview Summary).
Office Action of U.S. Appl. No. 12/219,383, dated Oct. 3, 2011.

O'Riordan et al., 2004, "*Staphylococcus aureus* capsular polysaccharides." Clin Microbiol Rev. 17(1):218-34.
Paetzel et al., 2002, "Signal peptidases", Chem Rev; 102:4549-4580.
Panina-Bordignon et al., 1989, "Universally immunogenic T cell epitopes: promiscuous binding to human MHC class II and promiscuous recognition by T cells" European Journal of Immunolgy; 19:2237-2242.
Parkhill et al., 2000, "The genome sequence of the food-borne pathogen Campylobacter jejuni reveals hypervariable sequences", Nature; 403:665-668.
Passwell et al., 2001, "Safety and immunogenicity of improved Shegella O-specific polysaccharide-protein conjugate vaccines in adults in Israel", Infection and Immunity, 69(3):1351-1357.
Paton & Paton, 1999, "Molecular Characterization of the Locus Encoding Biosynthesis of the Lipopolysaccharide O Antigen of *Escherichia coli* Serotype O113," Infect & Immun. 67(11): 5930-5937.
Pawlowski, 2000, "Preparation of pneumococcal capsular polysaccharide-protein conjugate vaccines utilizing new fragmentation and conjugation technologies." Vaccine 18:1873-1885.
Pearson et al., 2003, "Comparative genome analysis of Campylobacter jejuni using whole genome DNA microarrays", FEBS Letter; 554:224-230, FEBS 27782.
Perry, 1986, "Structure of the O-chain polysaccharide of the phenol-phase soluble lipopolysaccharide of *Escherichia coli* 0:157:h7." Biochem. Cell Biol.; 64:21-28.
Petrescu et al., 2004, "Statistical analysis of the protein environment of N-glycosylation sites: implications for occupancy, structure, and folding", Glycobiology; 14(2):103-114.
Pozscay et al., 1999, "Protein conjugates of synthetic saccharides elicit higher levels of serum IgG lipopolysaccharide antibodies in mice than do those of the O-specific polysaccharide from Shigella dysenteriae type 1", Proc Natl Acad Sci USA; 96:5194-5197.
Pozsgay, 1998, "Synthesis of glycoconjugatc vaccines again Shigella dysenteriae type 1", Journal of Organic Chemistry; 63:5983-5999.
Qian et al., 2007, "Conjugating recombinant proteins to Psudomonas aeruglnosa Exoprotein A: A strategy for enhancing immunogenicity to malaria vaccine candidates." Vaccine 25:3923-3933.
Raetz et al., 2002, "Lipopolysaccharide endotoxins", NIH-PA author manuscript, pp. 1-57, 19-25 (published in final edited form as: Annual Rev Biochem; 71:635-700, 2002.
Reeves et al., 1996, "Bacterial polysaccharide synthesis and gene nomenclature", Reviews, Elseview Science Ltd., pp. 495-503.
Robbins et al, 2009, "Synthesis, characterization, and immunogenicity in mice on Shigella sonnei O-specific oligosacchardie-core-protein conjugates." Proc. Natl. Acad Sci USA 106:7974-7978.
Royle et al., 2002, "An analytical and structural database provides a strategy for sequencing O-glycans from microgram quantities of glycoproteins." Anal Biochem; 304(1): 70-90.
Rubires, 1997, "A gene (wbbL) from Serratia marcesens N28b (O4) complements the rfb-50 mutation of *Escherichia coli* K-12 derivatives" J Bacteriol 179(23):7581-7586.
Rudd et al., 1997, "Glycosylation: heterogeneity and the 3D structure of proteins", Crit Rev Biochem Mol Biol; 32:1-100.
Rush, 1997, "Polyisoprenyl phosphate specificity of UDP-GlcNAc: undecaprenyl phosphate N-acetylgluosaminyl 1-P transferase from *E. coli*" Glycobiology; 7:315-322.
Sambrook & Russell, 2006, "Screening Bacterial Colonies by Hybridization: Small Numbers." Cold Spring Harb. Protoc; doi:10.1101/pdb.prot3925 at http://cshprotocols.cshlp.org/cgi/content/full/2006/2/pdb.prot3925.
Samuel, 2003, "Biosynthesis of O-antigens: genes and pathways involved in nucleotide sugar precursor synthesis and O-antigen assembly." Carbohydrate Res. 338: 2503-2519.
Sau et al., 1997, "The *Staphylococcus aureus* allelic genetic loci for serotype 5 and 8 capsule expression contain the type-specific genes flanked by common genes." Microbiology 143: 2395-405.
Schaad et al., 1991, "Safety and immunogenicity of Pseudomonas aeruginosa conjugate A vaccine in cystic fibrosis", The Lancet; 338:1236-1237.

(56) References Cited

OTHER PUBLICATIONS

Schaffer et al, 2008, "Vaccination and passive immunisation against *Staphylococcus aureus*" Ing J Antimicrob Agents 32 Suppl. 1:S71-78.
Schneerson et al., 1991, "Preparation, characterization, and immunogenicity of Haemophilus influenzae type B polysaccharide-proteins conjugates", Journal of Experimental Medicine; 152:361-376.
Schultz et al., 1998, "Prototype of a heme chaperone essential for cytochrome c maturation", Science; 281:1197-1200.
Schwimmer et al., 1956, "Reagent for Differentiation on 1,4- and 1,6-Linked Glucosaccharides." Science; 123:543-544.
Scott, 1997, "Vaccines against Campylobacter jejuni", Journal of Infectious Diseases; 176(Suppl. 2):S183-S188.
Seffernick et al., 2001, "Melamine deaminase and atrazine chlorohydrolase: 98 percent identical but functionally different", J Bacteriol; 183(8):2405-2410.
Shorr, 2007, "Epidemiology and economic impact of meticillin-resistant *Staphylococcus aureus*: review and analysis of the literature." Phamacoeconomis 25: 751-68.
Simons et al., 1984, "High-level expression of human interferon gamma in *Escherichia coli* under control of the $p_L$ promoter of bacteriophage lambda", Gene; 28:55-64.
Spears et al., 2006, "A comparison of enterphathogenic *Escherichia coli* pathogenesis," FEMS Microbiol. Lett 255:187-202.
Spirig et al., 1997, "The STT3 protein is a component of the yast oligosaccharyltransferase complex." Mol. Gen Genet 356:628-637.
Stenutz, 2006, "The structures of *Escherichia coli* O-polysaccharide antigens." FEMS Microbiol. Rev. 30:382-403.
Stephan et al., 2004, "First isolation and further characterization of enteropathogenic *Escherichia coli* (EPC) O 157:H45 strains from cattle" BMC Microbiol. 4:10.
Stevenson, 1994, "Structure of the O Antigen of *Escherichia coli* K-12 and the Sequence of rfb Gene Cluster." J Bacteriol.; 176:4144-4156.
Sullam, 1996, "Diminished platelet binding in vitro by *Staphylococcus areus* is associated reduced virulence in a rabbit model of infective endocarditis." Infection & Immun. 66:5183-5189.
Szu et al., 1994, "Laboratory and preliminary clinical characterization of Vi capsular polysaccharide-protein conjugate vaccines", Infection and Immunity; 62(10):4440-4444.
Szymanski et al., 1999, "Evidence for a system of general protein glycosylation in Campylobacter jejuni", Molecular Microbiology; 32(5):1022-1030.
Szymanski et al., 2002, "Campylobacter protein glycosyation affects host cell interactions", Infection and Immunity; 70(4):2242-2244.
Szymanski et al., 2005, "Protein glycosylation in bacterial mucosal pathogens", Nature Reviews, Microbiology; 3:225-237.
Taylor et al., 1993, "Synthesis, characterization and clinical evaluation of conjugate vaccines composed of the O-specific polysaccharides of Shigella dysenteriae type 1, Shigella flexneri type 2a, and Shigella sonnei (Plesiomonas shigelloides) bound to bacterial toxoids", Infection and Immunity; 61(9):3678-3687.
Thakker et al., 1998, "*Staphylococcus aureus* serotype 5 capsular polysaccharide is antiphagocytic and enhances bacterial virulence in a murine bactermia model." Infect Immun. 66:5183-5189.
Thibault et al., 2001, "Identification of the carbohydrate moieties and glycosylation motifs in Campylobactor jejuni flagellin", J Biol Chem; 276(37):34862-34870.
Tsai et al., 1982, "A sensitive silver stain for detecting lipopolysaccharides in polyacrylamide gels." Anal Biochem. 119:115-119.
Tuchscherr, 2008, "Antibodies to capsular polysaccharide and clumping factor A prevent mastitis and the emergence of uncapsulated and small-colony variants of *Staphylococcus aureus* in mice." Infect Immun 76:5738-44.
Unligil et al., 2000, "Glycosyltransferase structre and mechanism." Curr. Op. Struct. Bio. 10:510-517.
Valvano, 2003, "Export of O-specific lipopolysaccharide", Front Biosci; 8:s452-471.
Vanbleu et al., 2004, "Genetic and physical map of the pLAFR1 vector DNA seq." 15(3): 225-227.
Vandaux et al, 1995, "Use of adhesion-defective mutants of *Staphylococcus aureus* to define the role of specific plasma proteins in promoting bacterial adhesion to canine arteriovenous shuts." Infect & Immunity 63:585-90.
Varki et al., 1999, "Essentials of Glycobiology", Cold Spring Harbor Laboratory Press; Cold Spring Harbor, New York pp. 85-100.
Vernachio et al., 2003, "Anti-clumping factor A immunoglobulin reduces the duration of methicillin-resistant *Staphylococcus aureus* bacteremia in an experimental model of infective endocarditis," Antimicrobial Agents & Chemotherapy, 47:3400-3406.
Wacheter et al., 1976, "Lipid Intermediates Involved in the Assembly of Membrane-Associated Glycoproteins in Calf Brain White Matter." Arch Biochem Biophys.; 174:726-737.
Wacker et al., 2001, "PgIB, an oligosaccharyltransferase in the eubacterium Campylobacter jejuni?", Glycobiology; 11:871.
Wacker et al., 2002, "N-linked glycosylation in Campylobacter jejuni and its functional transfer into *E. coli*", Science; 298:1790-1793.
Wacker et al., 2006, "Substrate specificity of bacterial oligosaccharyltransferase suggests a common transfer mechanism for the bacterial and eukaryotic systems", Proc Natl Acad Sci; 103:7088-7093.
Waechter et al., 1977, "Evidence for the Enzymatic Transfer of N-Acetylglucosamine form UDP-N-Acetylglucosamine into Dolichol Derivatcs and glycoprotcins by Calf Brain Membrane." Arch. Biochem. Biophys. 181:185-198.
Wang et al., 2002, "The O-Antigen gene Cluster of *Escherichia coli* O55:H7 and Identification of a New UDP-GlcNAc C4 Epimerase Gene." J Bacteriol 184:2620-2625.
Wang et al.,1998, "Organization of *Escherichia coli* 0157 O Antigen Gene cluster and Identification of its specific genes." Infect. Immune 66:3545-3551.
Watts et al., 2005, "*Staphylococcus aureus* strains that express serotype 5 of srotype 8 capsular polysaccharides differ in virulence," Infect Immun. 73:3502-11.
Wernerus et al., 2004, "Biotechnological applications for surface-engineered bacteria", Biotechnol Appl Biochem; 40:209-228.
Whisstock et al., 2003, "Prediction of protein function from protein sequence and structure", Q Rev Biophys; 36(3):307-340.
Whitfield et al., 1999, "Structure, assembly and regulation of express of capsules in *Escherichia coli*", Molecular Microbiology; 31(5):1307-1319.
Whitfield et al., 2006, "Biosynthesis and Assembly of Capsular Polysaccharides in *Escherichia coli*." Annu Rev. Biochem. 75:39-68.
Witkowski et al., 1999, "Conversion of a beta-ketoacyl synthase to a malonyl decarboxylase by replacement of the active-site cysteine with glutamine", Biochemistry; 38(36):11643-11650.
Wolfe et al., 1993, "Reactions adding Sugar Units to Proteins in the ER and Golgi Complex, Molecular and Cellular Biology." Wadsworth Publishing Co., CA 873-75.
Wyszynska et al., 2004, "Oral immunization of chickens with avirlent salmonella vaccine strain carrying C. jejuni 72Dz/92 cjaA gene elicits specific humoral immune response associated with protection against challenge with wild-type Campylobacter", Vaccine; 22:1379-1389.
Yao et al., 1994, "Isolation of motile and non-motile insertional mutants of Campylobacter jejuni: the role of motility in adherance and invasion of eukaryotic cells", Molecular Microbiology; 14(5):883-893.
Young et al., 2002,"Structure of the N-linked glycan present on multiple glycoproteins in the gramnegative bacterium, Campylobacter jejuni", J Biol Chem; 277(45):42530-42539.
Zhang et al., 1997, "Molecular and chemical characterization of the lipopolysaccharide O-antigen and its role in the virulence of Yersinia enterocolitica serotype O:8." Mol. Microbiol. 23:63-76.
Zufferey eta l., 1995, "STT3, a highly conserved protein required for yeast oligosaccharyl transferase activity in vivo." The EMBO Journal 14(20):4949-4960.

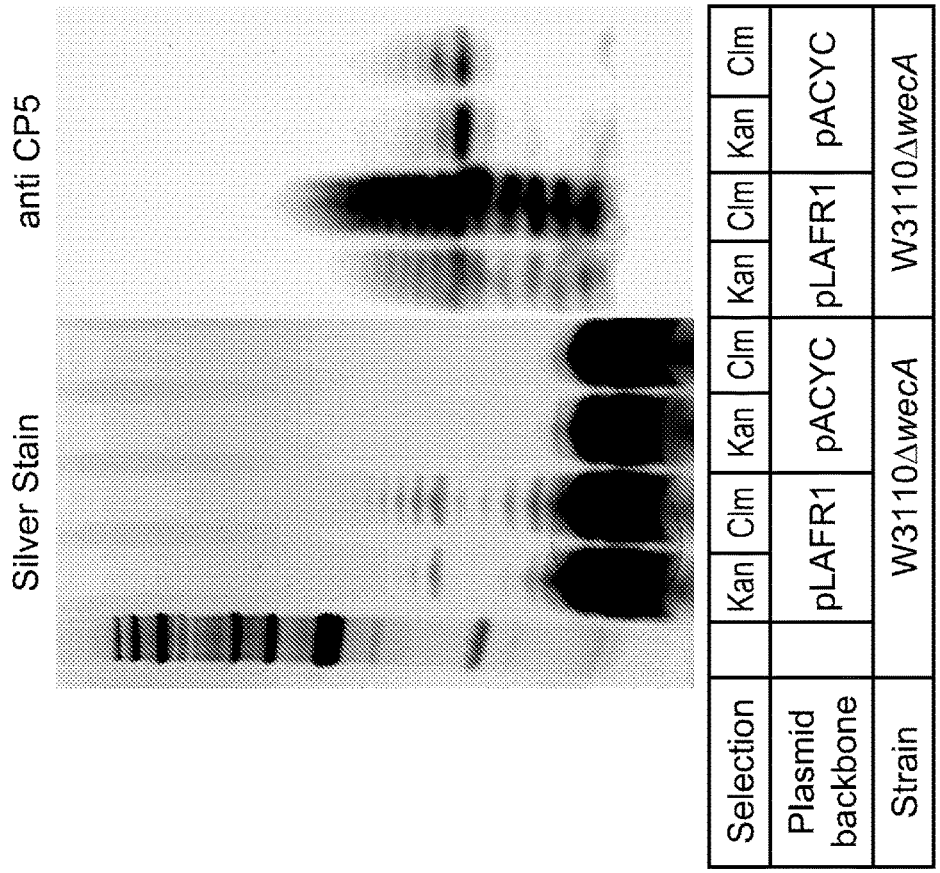
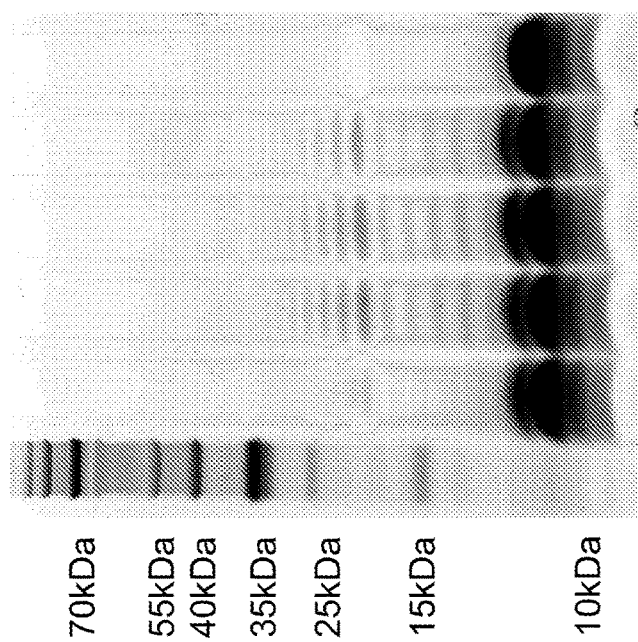
FIG. 8B
FIG. 8A

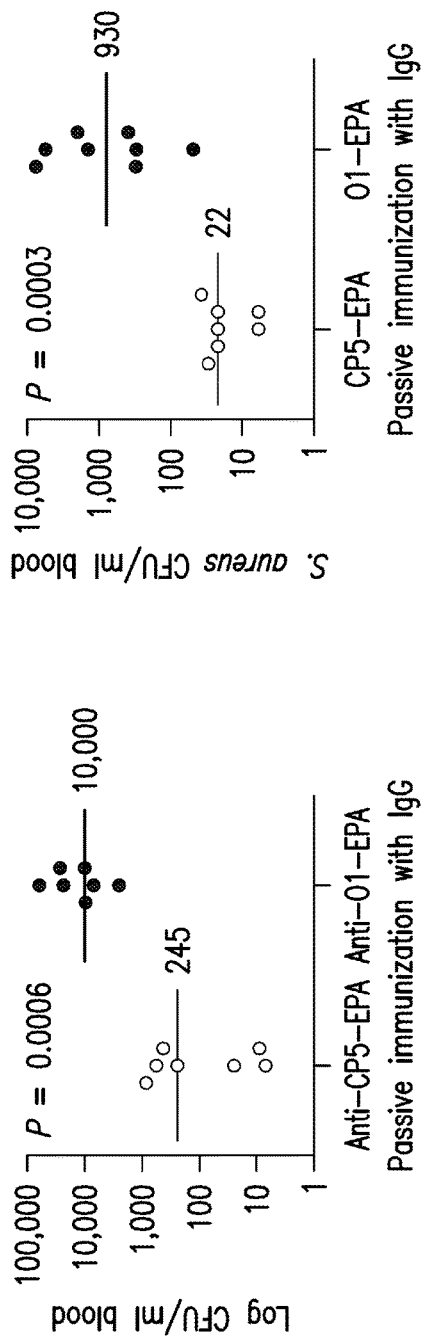
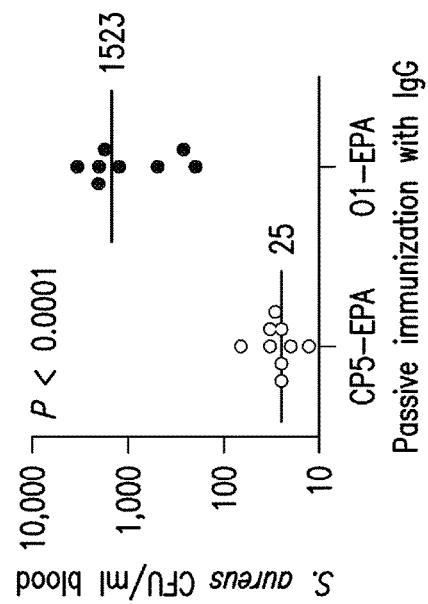
FIG. 17A
FIG. 17B
FIG. 17C

SEQUENCE LISTING

```
<160> NUMBER OF SEQ ID NOS: 27

<210> SEQ ID NO 1
<211> LENGTH: 13369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
```

```
aattcacatg ttgcccatcc acgaaaccac cttatcgccg tggaacgcac ctggatcgac    60
agccccagca aagcagtcgc ttcctggtcc ggcaccggaa acatcgtacg gagaaaacaa   120
aaaaggccgc taggcggcct tttccggaga acgatgactc agggttctcg ccgcctctgg   180
cgatagatcc agtcgacgat ttcaccgtca ggcgcatagc cgctgacggt ttcccgcagc   240
aactggcgaa cccgcgagta gtcgtccttc tccacggcgg ccagcaactg ctccagcacg   300
accttgaagg cctcccagct caggtgttcc tcgttggccc gcatgatcat cggatggtcg   360
gtgggattca cgttgtcacc gatcagcagc tcttcgtaga gcttctcgcc aggacgcagg   420
ccactgaact cgatggcgat gtcaccatgg ggcgaacgct cggaacgcac gctcaggccg   480
gacaggtgga tcatcttctc ggcgagctcc aggatcttca ccggcggccc catgtccagc   540
acgaatacat ctccgccctg ccccatcgaa ccggcctgga tgaccaactg cgccgcctcg   600
ggaatggtca tgaagtaacg ggtgatgctc gggtgggtga ccgtcaccgg ccgccgcgc   660 ttgatctgct cgcggaacag cggaatgacc gaaccgacg aaccgaggac gttgccgaag   720
cggaccatgg tgaaacgggt cttgttgacg tgatgcacgt ccttccggtc gccgaacagc   780 accgcgccg attcgttgct gagcgcctga aggaccattt ccgccaggcg cttggtgctg   840
cccatcacat tggtcggccg caccgccttg tcggtggaaa tcagcacgaa gttctgcacg   900
ccgacctgca ccgcggcctg caccgcatgc aaggtgccta tcacgttgtt gagaacgccc   960
tcggcgatgt tgtgctcgac gatcggcaca tgcttgtagg ccgccgcatg gtagacggta  1020
ttgaccttcc aggtacgcat cacgtccacc aggcgctcgg gattgcgcac cgaaccgagg  1080
atcggcaaca ggttcaccga aagcgactcg cgcttgatcc gacgctccag ttcctgatgg  1140
atgctataga ggttgtattc gctgtgttcg aacaggatca gcacgctagg cgaacaactc  1200
atgatctgcc gacagagttc cgaaccgata gagccgcccg ccccggtcac catcaccacc  1260
tgaccgcgga tgcaccgttc cagcagctcc ttgcgcggtg cgacgctgtc gcgcccccagc  1320 aggtcagcga tgtccacctc ctgcaggtca tccaccttga cccggccgct ggccaggtcc  1380
atgaagccgg gcatgctgcg cacgtgcagc gggaacggct ccagggactc gagaatctct  1440
cggcgccggg cccgagtggc ggaaggaatc gccaggagaa cctcctgcgc gcccgtctcg  1500
tcgatcatct ggcggatatg cttggcggta tagacccgca gaccggcaat gacccggttg  1560
gcgatctgct tgtcgtcatc gatgaacgcc accggacgca tcgcccgacc gagacgcaac  1620
gccgcaacca actggttgcc ggccgccccc gccccataga taaccaccct gggcaggcca  1680
tcctggcggt tgagaaatgg taccgactgc acagcagagt accagtcgcc catgaaatac  1740
tggcgcatgg ccagacgcaa gccgccgatc agcagcatgc tcaaccacca gtagttgaac  1800
accagggaac gcggcaccgg cgccggcgcg ccacgatacc agtacaccac cagcgacagc  1860
accagagccg agatggtcac cgccttggcg atggcgatca atgcgtcgtt accgagatag  1920
cgcatcaccg cgcgatacat gccgaagcga atgaatagtg gaatggcgat gaccggcgca  1980
gtgatgaaaa gccatgcatg ctcgccgaac acgtcgatca tatcgtctgt gcctagacgg  2040
accacaaaag cgagccacag agacagccat accagaagga tatccgtagc cacttgaagc  2100
aaacgtttcc agcgacgagg catggataac aactttactc ttaaacgatc tagcattccc  2160
ctactccttt aggcctgagc ggacgactct agcttacccg ccttgaacct cactgccaga  2220
aaaacgagag ggacgtaggc tatgacgatg cccatcaaag gctctagaga cccactcccg  2280
accaacaagg ctataggag gagccagatg acgttcaatg ccgtgacgcc aatcgtaaca  2340
```

```
ggagcatgct ttccatagta tcggcttgcg tattgatagg catggcttcg atgagcctca   2400
tacaccttgt cccctctcag caagcgacga atcagggtat aggtcgcatc gacgatgaaa   2460
acgcctaaca ggaccaacca tgcccagaaa aaattcgtat tcatccacat ggcatgaatg   2520
gaaagaattc ctaaaacaat ccccagaaga ccactacccg catctcccat gaaaattttt   2580
gggggtggaa aattccagaa caagaatcca aaaacggcaa aagctagcga taaggggagc   2640
aaagcctgcg tcagttggcc attcagccag tataataatg ccccaccaac acagacaaaa   2700
atggcctgaa ggctagcaag tccatcgatc ccatccatga agttatagag attcagcaac   2760
cacacgagat agaaagcaaa gagaagtcct ccgaaccacc ccaggtccca actgacacca   2820
acaatctgaa atggtggtat gccattcaaa aagtacaatg agaccaaggc tgcactaaaa   2880
tgtcccagca gacgccagcg tgcggcgata tgaccgtgat catccatgaa tccaataatg   2940
gcaaccccgc cgccagcgag aagtaaagcc caggacacgg cccatgagat atttcccagt   3000
acagcccaaa taggcagcat gagacaaaaa gtaactacaa tggcgacccc tcctccgcgt   3060
ggagtgggaa cgacatggga acttcgagag ttaggggtgt caagtaagct cctcgctaag   3120
gcataacgac gcaagaggcc tgtaagcagt cccgaaaccc cagctgcagc gagtaacaaa   3180
taccattctt ccatttataa atttatcccc aaaaatactc tcaccccttc aacagggttc   3240
tattcgattg ttctgcgtgg tacgccatgc tagtagcaaa gcgcctgcag ataatcattc   3300
agtacgtttg acatatattc taccaacatc ttccaacgcg gaaagggtgc tcttgcgggg   3360
ttcccaacca agcaaaagcc tgcctttcga cgagtcgacc tctagtgagc agcataactg   3420
agtgtataac ccacccttc ctactaattt aagaaacctc agaataaacc taggaacagg   3480
ccacatgatg gggcgacgcc ccattcccgc agcaagcgca gtcaccagtt gcttggtaga   3540
aatctcctga ccatcggata ccaaaaacag ttcgccggca gcagaagggt gcgtcataca   3600
gcaagctaga aagtcaacta aattatccag agaaacaaaa cttcgtcggt tatctatgca   3660
accaaatgga gaggaagtc ccgaagcaac cagcttcaac aatcgcgaga aatttccagg   3720
agctttccag tcgtaaacga gtggaggcct gacgataaca agttctgttg aggaatgctt   3780
gaaaagctcc cgaagcgcta cttcagcctc aaactttgaa atcgcatatt ctgcatgagg   3840
agccggcttg gagttctcat cgaagggctt ttctttggtt aaagcgccat ttacaccaat   3900
agaactaaca aaaatgaaac gctttacaga tgcttcgatc gcctgccgag caagcgccag   3960
agtagcatcg cgattcacct tccgaaaaat atctagtgaa tcacgctgcc ttccaaagat   4020
atgggctcgt ccagctagat gaactacaca ttcaacaccc cgcagcgcag catcaagctt   4080
agtgctctct ttcagctccg ctcgaacata ctcaaccccc gtaacgggat tgtacaggga   4140
tcgtacttgt ccgacaacct gaaggggggc ggcagcaagc gacctgcaaa gcgcactccc   4200
gacaaaaccg ctagccccgg ttaccagcac cttcatcata ttttcgactc agacagaagc   4260
ggtcgaacac aggcagcgaa ttttccaat gaaatatatt cagaataatt ttgctgaagg   4320
acactccgcg ggactccgcc taaactagac aagtcgagtt cacaaatctc atcgatcaat   4380
cttgccaaag caaccggatc attcggcgga cagttccaac cgattccggt ctcatctatt   4440
atacgggaga tttcagcccc ttttccatg acagctagaa tcggtttgtc tgctgccatg   4500
gagaaatatg ccttgctggg aaccccaagc ccgaacattc cttcttctaa ggtaactaag   4560
gcaacgtcac aggcagccaa accaaaattc ttttcggcta atggcagcct tccaaaatac   4620
ctcaaccgag cacactgatc ttccagcgcg tgttttttta cactgtcgac caaggcacca   4680
tctccaataa aagcaaaagc cgccttctcg ttttttaacca actgaatagc agaaagtatg   4740
```

```
tttctatac cttgtaatcg accgacatta ccaaaaaatt ggaaaccct tttacctttc    4800
cattcaggaa tattgataaa aggagcatcc tctctcggta ctgggaaaac ctctttctca    4860
caggcccaat tcgaaataaa gaccaaagat cgcgggtcat tcaccttctc tttcataaga    4920
gcttccatat cgcgccctat tacgactaga cgatcagcgg atgagtaaat gaagaaaag    4980
agacgacgta gaagccggta ggcaatacta tctttcttca gaacgcccgc cggcaccaag    5040
ttctcgggaa acacatcatg caccagcagc acccacttga aaccgagggc ataccttagc    5100
aagggaaacg tcatcagtag aagagcaggg ttggttccac tcaataccac atctcctcgt    5160
ctggcacgag aagtcaattt tactgagaac agaaacgcct gaaaaatctg cgccaatcct    5220
ctagaaagga gcctattctt attgctcctc ggaaacttaa agcattcttg ctcaacggaa    5280
ggtgaaacca caggcggggt ttcacctgcg gtcagcggga aaattacggt tagcccacca    5340
aactcccgct gcatctttcc tattatcttc tcccaatagt atcccgtgga gttctgattg    5400
gcaccgacat actcagaaac cacaaatatc cttgccatca actccacgcc tcaagttaat    5460
attttttcca gacagttcgc atgacatagt cccgatagct atgaactatg cgaacaatct    5520
tttcagaaac gttgggcatg ctatagtcag cgaccaagcg taacatgcgc tctgcgtcgc    5580
gcctctgtcc ctccaacacc tcgagtgctt gtagtactcg atccgaatcc agtccgacca    5640
tcatcaccac agcctcttcc atgccttctg ggcgttcatg agcctcacga atattcaaag    5700
cgggaaaatt cagtattgaa gactcctcac tgatggtccc actgtcagaa ataactgcct    5760
tggctgtaat ttgcagttta ttgtaatcct taaagccgag gggtttcagc agtttaatac    5820
cctcgtgaaa ctttgcctcc gtcgcctcaa ttctcttttt tgttctaggg tgagttgata    5880
cgatgacggg cagcgagtac ttttctgcca cagcgttgag catagaaacc aacttcaaga    5940
aattcttatc cgaatctatg ttttcctctc ggtgcgcact cacgacaaag aaccgctctg    6000
ttttcaaccc gagcctttca agaatatcgg aggactcgat cccgtcacga tagtgctcga    6060
gaacttcgaa catagggcta ccagtcttga taaccatgtc tggagaaagt ccttcacgca    6120
agagataatc acgcgcaatt gtactatagg tcaaatttac atcagctgta tgatcgacaa    6180
tgcgccgatt tatctcttca ggcacacgca tatcgaaaca gcgattgcct gcttccatat    6240
gaaaggtcgg tatcttacgc cgttttgcag gcagtaccgc catacaacta ttggtatcac    6300
ccagcacgag cagcgcatcg ggatctattt cgcccagaac acgatcgact gcgattatta    6360
cattccctat cgtttcagcc ccggaagacc cggcggcgtt tagaaaataa tccggctttc    6420
ttataccgag gtcctgaaaa aatatttcat taagttcgta atcataattc tgtccagtat    6480
ggacaagtac atgatcgcag tactgatcaa gcttcgccat gaccctagac aagcgaataa    6540
tctcaggacg agttccaaca accgtaacga cttttagctt ctgcattgtt atctcactat    6600
accttacgca ccttcgccta ctgaacaagc gtaggtatcc ggattttccc gatcaaatac    6660
ttcgttagcc cacaacatga ctaccatatc gtcagttccg acattagtaa tgtcatgagt    6720
ccatccaggt actgtttcga caatttctgc cttttcacca ttagtgcaaa tttcgtaaaa    6780
tgccccggtc aggatgtttc taaacttgaa acgtgccatc cctttgataa ccagaaactt    6840
ttcggttttc gagtgatggt aatgcccgcc cctggtaaca cctggatgag ccgtaaaaaa    6900
cgagaactgg ccagagtccg cggtcttcag catctcgacg aatgtgccac gcggatccga    6960
atgcattggc acgtcgtaac taaaactatc ttctggcaag aaacttagat aagtcgagta    7020
caaggcgcgc gtcaatcccg agccaaccct tgcggtagtc agtgactttc gactattacg    7080
```

```
aaactcatac aattgttctg cgagctcacc aacagaaatc tgatactggg gctcgacctg   7140
tagtgaaact gcattggata gcttccatc catgactttc atgaaggtgc gaaccacatc    7200
atctatgtat acaagagtga tctctgccga ggaattgtta atttgaatcg gaatatctcg   7260
aataatatta tgacaaaaag tcgcaaccgc tgaattataa ttcggacgcg accatttacc   7320
gaatacatta ggaaggcgaa atatgtagac aggacaacca atatcctcac ctagcacttg   7380
gagatgctct tctgcggctc gcttgcttaa accgtactca ttatccacct cagcctgaat   7440
ggatgaagta taagaagtg gtatggctcg tccattggac cttaccgcct cacacagagc    7500
atacgtgagt tcggaattcc cgatcttaaa ctcttctggt ttttccggac gattgacccc   7560
ggcaagatga aaataaaat cgacggaacg aattagctca ggcaaattac caacactact    7620
ctcgcgggtg aatggcacca cctcgatacc accccgctct gcaagatgag cgcacagatt   7680
ccttccaaca aatccattcg cgccagttac aagaactttc atcgtttatt cctctggact   7740
ggcactctcg ccacgctgaa tagcacgaat gaaatccaac ttcagcaaca gcttttttcat  7800 tccttcgata tccagacgtt tggtattatg agaattatag tcctctgtat gagtaatttt   7860
ttcctcgcct tgctccacaa acttactata gttcagatca cgcaaatctg gggggatacg   7920
ataatagtca cccatgtctt cagcacaggc catttcctct cgactaagaa cgcctcata    7980 aagcttctct ccatgacgcg tacctattac attgatagga taaccattct tgccaagcaa   8040
ttgagtaagc gcatgagcca gcacctcgat ggttgcagcc ggtgctttct gtacaaaaag   8100
atctccattg gtaccatgct cgaaagcata aagcacaagg tctacggcat ccgtaagcgt   8160
catcatgaaa cgtgtcatgt ttggatcagt gattgtgaga ggctggcctg atcgcatttg   8220
ctcgataaag agaggaatga ccgagcccct tgaagccatg acgttaccat aacgggtgcc   8280
acaaattacg gtaggagtgc gttccaggtt tcgagacttg gcgaccatga ccttttccat   8340
catggccttt gaaataccca tggcattgat tgggtaaact gccttatccg tactcagaca   8400
aacgactttt ttgacgccat tctggatagc agattcgagg acattttccg ttccgatgac   8460
attggtcttc acagcctcca tcgggtagaa ctcacaagag ggaacctgtt tcaatgcagc   8520
cgcatggaaa atgtagtcca caccgcgagt agcattcaga gtgctttgat agtcgcggac   8580
atctccaata taaaacctca acttggggtg agcatagcac ttacgcatat catcttgctt   8640
cttctcatcc cgactgaata cacgtatttc accaatatct gtatccagaa aacgcttcaa   8700
aacggcattt ccaaaggaac cagttccacc ggtaattaac agaacagagt tcttatccat   8760
acaccacctc tttactaatg tgttcaacgt ccctttttccg cctcaaaata taagaaaagc   8820
gaaaaacaac gagccagaac aatgcagccc ctaccggatg gaaaagccca ccgccgctaa   8880
agacataatt aacgaaccag attataaatg cagagcataa gaagcctaac tctgtacaag   8940 ctgttttttct tcgccggaag acaagcaaaa atacagagta gacaaaaagc aacaatagca   9000 aagaacagc caagccacca aaaatgaaac catgatgca aagcagctcg acaatacat     9060 tgtgcgccat tggatattgc gcatacccta gaaccccccc tccccaaaa acgcccgcgc    9120 ccaaaacaag tatctcgcta ccgtagaaag acaatgtttc caaggcagt gcagttaccc    9180 gatcgaatat ggattcgaag aatgaacat cttgcgagac tgaggaatcg gaggtgagga   9240
gcccgacaat cagtcgatgc acggtttcca gactgccagc cccgaagtct gcaaggaaaa   9300
atacagataa acccagccct gcaagaagga aggtgaaaaa caagtatgtc ttttttgatca  9360 gttttagcca ataggcaaag aataagacaa tgacgatatt ggccagagca gctttctgca   9420
gcgacagcat cgccccccaag caaagaagaa ggaaacatac cacgcgcgcc caacccttta   9480
```

```
gataaaagag tgaagcaagt gcgggaactc ccaccataac accatatgcg gtcaaacttc   9540
ctaccaatga tgcaaaacgg gcgcccccag cacgctcact ggcttcagcg aaccattcta   9600
taggtccaaa tacatactgc cagagaaaag aaagagccgc cagactgaag aaaaatgaaa   9660
taagttgcat gggcactttt agattatctc tggcaagaac catagcaaca aagagaagag   9720
gtaatgatgc ccacaacctg aaaatcccta tggaatagtc tccatataga tcgaaccata   9780
acaccgaaac gagcgaggca tacgtccaga agaaaataac aaatataccT aatgcgctat   9840
atttaatatc cctccagtta ttaataaata agagaaaaaa cagcccacaa acccagcaa    9900
gaactaaata atacgcaccg gatagattcc ggagaatatg aaagagaaac acaaaaagga   9960
gaaccagagc aacgcttctc tgcttcatga gtaccaccca tctttgtttg ctttctcttt  10020
ggaaagtttc gactttctat cgagaacccc cttccgatag gatgaggcca aaacgagcct  10080
ataagcagct ctagagtaga gccatcgaat agagtccgtt ttctctagag aatgaataag  10140
aatatttgaa aactttgact ccagcgcaag acacagcact gctctgaata gactctgaaa  10200
cttgcttgac aaagcaaagc ccggctccat ccatcgtata ggaccaagag tctcaaggtc  10260
atcagttgtt gcaactttca tgaattccgg cattccgtca cgggcggcat gatagtactt  10320
gcgacagaac ttcgaaatac tgccttccgg ttcgacatgc tcgatttcag cccgacaagg  10380
aagaacagaa taccaagct tgccaaccct taacccaaac tccgtatctt caaagccgta   10440
cccaacaaat cgctcatcaa aaagagcatt atcttggagc agaatatccc tctcagcgag  10500
catattcatg gtaacaatag ttttatcccc caaggagttg ggcagcggct tgtcagcaga  10560
gaagtgacaa ctatccctat agcgatagta attactcgtc gacaccaatg agcaagaaaa  10620
tctgacacca ccgcaccaga taacgcgttc cccccttcga gagttagcag cgttcagaaa  10680
attcgagaga tgagcaggat ctggcacaca atcatcatca agaagcacta cgtagcgccc  10740
cttcgctaaa cgaacgcctt tatttcgttt tgcactagcc gaattcagct cggcctgctc  10800
aagacggacg ttgaagccct gaaccgcttc gaactcgcgg accacatcgg gtgtttcatc  10860
accactatta ctgtcgacaa caataacttc aaaatcctta aaagccagag actgcgctac  10920
aaggccggcc aggaccaatt ttagttcctt gggacgacgc caagtactaa cgacgacact  10980
caacaacatc aaagtcccct tttctctctc aacttaaccg tggccaggaa aaacattccc  11040
atccccaaag agacctctgt aacgaccagc gtccacgctc caaaaagctc atcccccaa   11100
agcgccaaga ggataaatgt taatacccCg cccaattccg caaaaaaaat tgctcgcaaa  11160
tataccaccat catacccaga aggaacaaga gtcaaccctc catacagaac accaatacaa  11220
gcaaacactg gcactatcga aacattctt attacaacag ttagacctct ggactgttcc  11280
gggaatagga gatatgaaat gtattcagaa aataagaaaa gaaataaaca actaggaata  11340
gctattagta acatcagacc tagcgctttc cttcttaaac tgccgactgc cgggtcggca  11400
ctcgcataca tcctgctaaa agtcggaaat agagcgctag ctatgggtga agtagcagcc  11460
gcgatcccgc gaaggaattt atccgcagta gaaagcactc cggccgcgga ggctccacca  11520
acaacaccaa ccgccgcaac gagcacttgc atgtgcaagc taagaaaagc cagagaaaga  11580
aaagatcgag caccgtcacg caatatatcg agaattctgt ctttctcgag aaccgggcgc  11640
caccgtattc ccatagaaaa taaaatacaa cagagagcac ttccacctat gacataggaa  11700
aaaccaaacc ccaacgaagc cagcacaagg tcagaatcct tcgtgacaaa aaaaacgacc  11760
aataggaaat aaaatacctt agacaaaaaa ttggtaagcg ccaaccatcc aaacagcgct  11820
```

| | | |
|---|---|---|
| cttccctgaa agaaccatac tgcttgaaga taatttccaa ctactgccgg aagagcagcc | 11880 |
| gcaaccaata caagcaaggg gattggtaaa atagaagata cagccaaaat ggccagcact | 11940 |
| aaaagtgaaa gcagcaacaa taagaatcta gcactctgta caacagaaaa gaaactagac | 12000 |
| agttcaactt tgttatcgat aatggcagcc tttcttgatc ctgccagaat aaatccaaag | 12060 |
| tctaccagtt gacatagaat gacagccacg gcctgggcaa tcaccaattg gccaaacgct | 12120 |
| tcgcttgaca atgttctcgt gagaaaagga atcgcagcaa gaggcaaaag atagttgctg | 12180 |
| cccatggata taccggagta gaaaacgccc cgccttattg acattctact cgataccccc | 12240 |
| taatacaatt caacaactac aacaagtaag ccctgatgcc agtaagtggc atcagggttt | 12300 |
| agatcaaaac ttagcgaaga gagccatcgc tacgaagctt ccttataaaa ccagcgagca | 12360 |
| ctgcgagtag aattccaatt atcaatcctg ccaaagtacc tatagtaact ataagaatct | 12420 |
| tcttcggctt aatgggttga tttgaaaaag agagtccctc gtcttccttg tagacagcca | 12480 |
| ccgcatcaga atccacagac aaactggagt tccaagatag tttctcttgg agagttctca | 12540 |
| actcaggaat gaatggagca tctacactac gcgactcaag attgttgatt tcagcgcgca | 12600 |
| gcgccttagc tcctcgcatg tacatcaagt caccatccat gatcgaggag agttgttgct | 12660 |
| cggacgcccc ttctattaat ggcgggccat ctatcttgag cgactccgca atcagcaatg | 12720 |
| cctccttcaa acgtgcaatt ctatcatcac ggcggccctt cgccatattc tgcagcacgg | 12780 |
| ttatgcggct ctgcattgca gcatttctta cctggaaatc tctacctgca ctatcaataa | 12840 |
| cctcatgcac ggcccgatcc gcagccaaac gcacgaaagc ttgtgcccat gtagcaagaa | 12900 |
| cctctcgctt cgtgccctcc acaattaccg tataacggtc tgcatctggc ttgttagcag | 12960 |
| gatcaatctt tacctctttg gagaacttct tataaaactc ctcctgctca tcttcgcttt | 13020 |
| ccgctccctc acccacctgg ggaaggtata tcttatagaa gaactctttt ttattctcat | 13080 |
| ccgaaagcag attgcgcgaa aagatcgcat agatacttct aacagtatat gcatctaggc | 13140 |
| cattctccct tctaccaaca ttgaaaacctt cgatagaccc aagagcagga ggcactactg | 13200 |
| caaccctata ttcatataca ggcttactca gatacgcata ggtaaaagac ccgattaatg | 13260 |
| caagaagagt agtcagaaga atcagaacct tgttaaccca aagctccttg accagcttca | 13320 |
| ccaggtcaac ctcaccatca gccgtcatca aagaagaatt gcctcaggg | 13369 |

<210> SEQ ID NO 2
<211> LENGTH: 15244
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

| | | |
|---|---|---|
| aattcacatg ttgcccatcc acgaaaccac cttatcgccg tggaacgcac ctggatcgac | 60 |
| agccccagca aagcagtcgc ttcctggtcc ggcaccggaa acatcgtacg agaaaacaa | 120 |
| aaaaggccgc taggcggcct tttccggaga acgatgactc agggttctcg ccgcctctgg | 180 |
| cgatagatcc agtcgacgat ttcaccgtca ggcgcatagc cgctgacggt ttcccgcagc | 240 |
| aactggcgaa cccgcgagta gtcgtccttc tccacgcgcg gccagcaactg ctccagcacg | 300 |
| accttgaagg cctcccagct caggtgttcc tcgttggccc gcatgatcat cggatggtcg | 360 |
| gtgggattca cgttgtcacc gatcagcagc tcttcgtaga gcttctcgcc aggacgcagg | 420 |
| ccactgaact cgatggcgat gtcaccatgg ggcgaacgct cggaacgcac gctcaggccg | 480 |

```
gacaggtgga tcatcttctc ggcgagctcc aggatcttca ccggcggccc catgtccagc     540
acgaatacat ctccgccctg ccccatcgaa ccggcctgga tgaccaactg cgccgcctcg     600
ggaatggtca tgaagtaacg ggtgatgctc gggtgggtga ccgtcaccgg ccgccgcgc     660 ttgatctgct cgcggaacag cggaatgacc gaaccgacg aaccgaggac gttgccgaag     720
cggaccatgg tgaaacgggt cttgttgacg tgatgcacgt ccttccggtc gccgaacagc     780
accggcgccg attcgttgct gagcgcctga aggaccattt ccgccaggcg cttggtgctg     840
cccatcacat tggtcggccg caccgccttg tcggtggaaa tcagcacgaa gttctgcacg     900
ccgacctgca ccgcggcctg caccgcatgc aaggtgccta tcacgttgtt gagaacgccc     960
tcggcgatgt tgtgctcgac gatcggcaca tgcttgtagg ccgccgcatg gtagacggta    1020
ttgaccttcc aggtacgcat cacgtccacc aggcgctcgg gattgcgcac cgaaccgagg    1080
atcggcaaca ggttcaccga aagcgactcg cgcttgatcc gacgctccag ttcctgatgg    1140
atgctataga ggttgtattc gctgtgttcg aacaggatca gcacgctagg cgaacaactc    1200
atgatctgcc gacagagttc cgaaccgata gagccgcccg ccccggtcac catcaccacc    1260
tgaccgcgga tgcaccgttc cagcagctcc ttgcgcggtg cgacgctgtc gcgcccagc    1320 aggtcagcga tgtccacctc ctgcaggtca tccaccttga cccggccgct ggccaggtcc    1380
atgaagccgg gcatgctgcg cacgtgcagc gggaacggct ccagggactc gagaatctct    1440
cggcgccggg cccgagtggc ggaaggaatc gccaggagaa cctcctgcgc gcccgtctcg    1500
tcgatcatct ggcggatatg cttggcggta tagacccgca gaccggcaat gacccggttg    1560
gcgatctgct tgtcgtcatc gatgaacgcc accggacgaa tcgcccgacc gagacgcaac    1620
gccgcaacca actggttgcc ggccgccccc gccccataga taaccaccct gggcaggcca    1680
tcctggcggt tgagaaatgg taccgactgc acagcagagt accagtcgcc catgaaatac    1740
tggcgcatgg ccagacgcaa gccgccgatc agcagcatgc tcaaccacca gtagttgaac    1800
accagggaac gcggcaccgg cgccggcgcg ccacgatacc agtacaccac cagcgacagc    1860
accagagccg agatggtcac cgccttggcg atggcgatca atgcgtcgtt accgagatag    1920
cgcatcaccg cgcgatacat gccgaagcga atgaatagtg gaatggcgat gaccggcgca    1980
gtgatgaaaa gccatgcatg ctcgccgaac acgtcgatca tatcgtctgt gcctagacgg    2040
accacaaaag cgagccacag agacagccat accagaagga tatccgtagc cacttgaagc    2100
aaacgtttcc agcgacgagg catggataac aactttactc ttaaacgatc tagcattccc    2160
ctactccttt aggcctgagc ggacgactct agcttacccg ccttgaacct cactgccaga    2220
aaaacgagag ggacgtaggc tatgacgatg cccatcaaag gctctagaga cccactcccg    2280
accaacaagg ctatagggag gagccagatg acgttcaatg ccgtgacgcc aatcgtaaca    2340
ggagcatgct ttccatagta tcggcttgcg tattgatagg catggcttcg atgagcctca    2400
tacaccttgt cccctctcag caagcgacga atcagggtat aggtcgcatc gacgatgaaa    2460
acgcctaaca ggaccaacca tgcccagaaa aaattcgtat tcatccacat ggcatgaatg    2520
gaaagaattc ctaaaacaat ccccagaaga ccactacccg catctcccat gaaaattttt    2580
gggggtggaa aattccagaa caagaatcca aaaacggcaa aagctagcga taaggggagc    2640
aaagcctgcg tcagttggcc attcagccag tataataatg ccccaccaac acagacaaaa    2700
atggcctgaa ggctagcaag tccatcgatc ccatccatga agttatagag attcagcaac    2760
cacacgagat agaaagcaaa gagaagtcct ccgaaccacc ccaggtccca actgacacca    2820
acaatctgaa atggtggtat gccattcaaa aagtacaatg agaccaaggc tgcactaaaa    2880
```

```
tgtcccagca gacgccagcg tgcggcgata tgaccgtgat catccatgaa tccaataatg   2940
gcaaccccgc cgccagcgag aagtaaagcc caggacacgg cccatgagat atttcccagt   3000
acagcccaaa taggcagcat gagacaaaaa gtaactacaa tggcgacccc tcctccgcgt   3060
ggagtgggaa cgacatggga acttcgagag ttaggggtgt caagtaagct cctcgctaag   3120
gcataacgac gcaagaggcc tgtaagcagt cccgaaaccc cagctgcagc gagtaacaaa   3180
taccattctt ccatttataa atttatcccc aaaaatactc tcacccsttc aacagggttc   3240
tattcgattg ttctgcgtgg tacgccatgc tagtagcaaa gcgcctgcag ataatcattc   3300
agtacgtttg acatatattc taccaacatc ttccaacgcg gaaagggtgc tcttgcgggg   3360
ttcccaacca agcaaaagcc tgcctttcga cgagtcgacc tctagtgagc agcataactg   3420
agtgtataac ccacccttc ctactaattt aagaaacctc agaataaacc taggaacagg    3480
ccacatgatg gggcgacgcc ccattcccgc agcaagcgca gtcaccagtt gcttggtaga   3540
aatctcctga ccatcggata ccaaaaacag ttcgccggca gcagaagggt gcgtcataca   3600
gcaagctaga aagtcaacta aattatccag agaaacaaaa cttcgtcggt tatctatgca   3660
accaaatgga agaggaagtc ccgaagcaac cagcttcaac aatcgcgaga aatttccagg   3720
agctttccag tcgtaaacga gtggaggcct gacgataaca agttctgttg aggaatgctt   3780
gaaaagctcc cgaagcgcta cttcagcctc aaactttgaa atcgcatatt ctgcatgagg   3840
agccggcttg gagttctcat cgaagggctt ttctttggtt aaagcgccat ttacaccaat   3900
agaactaaca aaaatgaaac gctttacaga tgcttcgatc gcctgccgag caagcgccag   3960
agtagcatcg cgattcacct tccgaaaaat atctagtgaa tcacgctgcc ttccaaagat   4020
atgggctcgt ccagctagat gaactacaca ttcaacaccc cgcagcgcag catcaagctt   4080
agtgctctct ttcagctccg ctcgaacata ctcaaccccc gtaacgggat tgtacaggga   4140
tcgtacttgt ccgacaacct gaaaggggggc ggcagcaagc gacctgcaaa gcgcactccc   4200
gacaaaaccg ctagccccgg ttaccagcac cttcatcata ttttcgactc agacagaagc   4260
ggtcgaacac aggcagcgaa ttttttccaat gaaatatatt cagaataatt ttgctgaagg   4320
acactccgcg ggactccgcc taaactagac aagtcgagtt cacaaatctc atcgatcaat   4380
cttgccaaag caaccggatc attcggcgga cagttccaac cgattccggt ctcatctatt   4440
atacgggaga tttcagcccc ttttccatg acagctagaa tcggtttgtc tgctgccatg    4500
gagaaatatg ccttgctggg aaccccaagc ccgaacattc cttcttctaa ggtaactaag   4560
gcaacgtcac aggcagccaa accaaaattc ttttcggcta atggcagcct tccaaaatac   4620
ctcaaccgag cacactgatc ttccagcgcg tgttttttta cactgtcgac caaggcacca   4680
tctccaataa aagcaaaagc cgccttctcg tttttaacca actgaatagc agaaagtatg   4740
ttttctatac cttgtaatcg accgacatta ccaaaaaatt ggaaaaccct tttaccttc    4800 cattcaggaa tattgataaa aggagcatcc tctctcggta ctgggaaaac ctctttctca   4860
caggcccaat tcgaaataaa gaccaaagat cgcgggtcat tcaccttctc tttcataaga   4920
gcttccatat cgcgccctat tacgactaga cgatcagcgg atgagtaaat gaagaaaag    4980 agacgacgta gaagccggta ggcaatacta tctttcttca gaacgcccgc cggcaccaag   5040
ttctcgggaa acacatcatg caccagcagc acccacttga aaccgagggc ataccttagc   5100
aagggaaacg tcatcagtag aagagcaggg ttggttccac tcaataccac atctcctcgt   5160
ctggcacgag aagtcaattt tactgagaac agaaacgcct gaaaaatctg cgccaatcct   5220
```

```
ctagaaagga gcctattctt attgctcctc ggaaacttaa agcattcttg ctcaacggaa    5280
ggtgaaacca caggcggggt ttcacctgcg gtcagcggga aaattacggt tagcccacca    5340
aactcccgct gcatctttcc tattatcttc tcccaatagt atcccgtgga gttctgattg    5400
gcaccgacat actcagaaac cacaaatatc cttgccatca actccacgcc tcaagttaat    5460 atttttttcca gacagttcgc atgacatagt cccgatagct atgaactatg cgaacaatct    5520
tttcagaaac gttgggcatg ctatagtcag cgaccaagcg taacatgcgc tctgcgtcgc    5580
gcctctgtcc ctccaacacc tcgagtgctt gtagtactcg atccgaatcc agtccgacca    5640
tcatcaccac agcctcttcc atgccttctg ggcgttcatg agcctcacga atattcaaag    5700
cgggaaaatt cagtattgaa gactcctcac tgatggtccc actgtcagaa ataactgcct    5760
tggctgtaat ttgcagttta ttgtaatcct taaagccgag gggtttcagc agtttaatac    5820
cctcgtgaaa ctttgcctcc gtcgcctcaa ttctcttttt tgttctaggg tgagttgata    5880
cgatgacggg cagcgagtac ttttctgcca cagcgttgag catagaaacc aacttcaaga    5940
aattcttatc cgaatctatg ttttcctctc ggtgcgcact cacgacaaag aaccgctctg    6000
ttttcaaccc gagcctttca agaatatcgg aggactcgat cccgtcacga tagtgctcga    6060
gaacttcgaa catagggcta ccagtcttga taaccatgtc tggagaaagt ccttcacgca    6120
agagataatc acgcgcaatt gtactatagg tcaaatttac atcagctgta tgatcgacaa    6180
tgcgccgatt tatctcttca ggcacacgca tatcgaaaca gcgattgcct gcttccatat    6240
gaaaggtcgg tatcttacgc cgttttgcag gcagtaccgc catacaacta ttggtatcac    6300
ccagcacgag cagcgcatcg ggatctattt cgcccagaac acgatcgact gcgattatta    6360
cattccctat cgtttcagcc ccggaagacc cggcggcgtt tagaaaataa tccggctttc    6420
ttataccgag gtcctgaaaa aatatttcat taagttcgta atcataattc tgtccagtat    6480
ggacaagtac atgatcgcag tactgatcaa gcttcgccat gaccctagac aagcgaataa    6540
tctcaggacg agttccaaca accgtaacga cttttagctt ctgcattgtt atctcactat    6600
accttacgca ccttcgccta ctgaacaagc gtaggtatcc ggattttccc gatcaaatac    6660
ttcgttagcc cacaacatga ctaccatatc gtcagttccg acattagtaa tgtcatgagt    6720
ccatccaggt actgtttcga caatttctgc cttttcacca ttagtgcaaa tttcgtaaaa    6780
tgccccggtc aggatgtttc taaacttgaa acgtgccatc cctttgataa ccagaaactt    6840
ttcggttttc gagtgatggt aatgcccgcc cctggtaaca cctggatgag ccgtaaaaaa    6900
cgagaactgg ccagagtccg cggtcttcag catctcgacg aatgtgccac gcggatccga    6960
atgcattggc acgtcgtaac taaaactatc ttctggcaag aaacttagat aagtcgagta    7020
caaggcgcgc gtcaatcccg agccaaccct tgcggtagtc agtgactttc gactattacg    7080
aaactcatac aattgttctg cgagctcacc aacagaaatc tgatactggg gctcgacctg    7140
tagtgaaact gcattggata gcttcccatc catgactttc atgaaggtgc gaaccacatc    7200
atctatgtat acaagagtga tctctgccga ggaattgtta atttgaatcg gaatatctcg    7260
aataatatta tgacaaaaag tcgcaaccgc tgaattataa ttcggacgcg accatttacc    7320
gaatacatta ggaaggcgaa atatgtgacc aggacaacca atatcctcac ctagcacttg    7380
gagatgctct tctgcggctc gcttgcttaa accgtactca ttatccacct cagcctgaat    7440
ggatgaagta taagaagtg gtatggctcg tccattggac cttaccgcct cacacagagc    7500
atacgtgagt tcggaattcc cgatcttaaa ctcttctggt ttttccggac gattgacccc    7560
ggcaagatga aaaataaaat cgacggaacg aattagctca ggcaaattac caacactact    7620
```

```
ctcgcgggtg aatggcacca cctcgatacc accccgctct gcaagatgag cgcacagatt    7680
ccttccaaca aatccattcg cgccagttac aagaactttc atcgtttatt cctctggact    7740
ggcactctcg ccacgctgaa tagcacgaat gaaatccaac ttcagcaaca gcttttcat     7800 tccttcgata tccagacgtt tggtattatg agaattatag tcctctgtat gagtaatttt    7860
ttcctcgcct tgctccacaa acttactata gttcagatca cgcaaatctg ggggatacg     7920 ataatagtca cccatgtctt cagcacaggc catttcctct cgactaagaa cgcctcata     7980 aagcttctct ccatgacgcg tacctattac attgatagga taaccattct tgccaagcaa    8040
ttgagtaagc gcatgagcca gcacctcgat ggttgcagcc ggtgctttct gtacaaaaag    8100
atctccattg gtaccatgct cgaaagcata agcacaagg tctacggcat ccgtaagcgt     8160
catcatgaaa cgtgtcatgt ttggatcagt gattgtgaga ggctggcctg atcgcatttg    8220
ctcgataaag agaggaatga ccgagcccct tgaagccatg acgttaccat aacgggtgcc    8280
acaaattacg gtaggagtgc gttccaggtt tcgagacttg gcgaccatga ccttttccat    8340
catggccttt gaaatacccca tggcattgat tgggtaaact gccttatccg tactcagaca    8400
aacgactttt ttgacgccat tctggatagc agattcgagg acattttccg ttccgatgac    8460
attggtcttc acagcctcca tcgggtagaa ctcacaagag ggaacctgtt tcaatgcagc    8520
cgcatggaaa atgtagtcca caccgcgagt agcattcaga gtgctttgat agtcgcggac    8580
atctccaata taaaacctca acttggggtg agcatagcac ttacgcatat catcttgctt    8640
cttctcatcc cgactgaata cacgtatttc accaatatct gtatccagaa aacgcttcaa    8700
aacggcattt ccaaaggaac cagttccacc ggtaattaac agaacagagt tcttatccat    8760
acaccacctc tttacgtgta ggctggagct gcttcgaagt tcctatactt tctagagaat    8820
aggaacttcg gaataggaac ttcatttaaa tggcgcgcct tacgcccgc cctgccactc     8880 atcgcagtac tgttgtattc attaagcatc tgccgacatg gaagccatca caaacggcat    8940
gatgaacctg aatcgccagc ggcatcagca ccttgtcgcc ttgcgtataa tatttgccca    9000
tggtgaaaac gggggcgaag aagttgtcca tattggccac gtttaaatca aaactggtga    9060
aactcaccca gggattggct gagacgaaaa acatattctc aataaaccct ttagggaaat    9120
aggccaggtt ttcaccgtaa cacgccacat cttgcgaata tatgtgtaga aactgccgga    9180
aatcgtcgtg gtattcactc cagagcgatg aaaacgtttc agtttgctca tggaaaacgg    9240
tgtaacaagg gtgaacacta tcccatatca ccagctcacc gtctttcatt gccatacgta    9300
attccggatg agcattcatc aggcgggcaa gaatgtgaat aaaggccgga taaaacttgt    9360
gcttattttt ctttacggtc tttaaaaagg ccgtaatatc cagctgaacg gtctggttat    9420
aggtacattg agcaactgac tgaaatgcct caaaatgttc tttacgatgc cattgggata    9480
tatcaacggt ggtatatcca gtgatttttt tctccatttt agcttcctta gctcctgaaa    9540
atctcgacaa ctcaaaaaat acgcccggta gtgatcttat ttcattatgg tgaaagttgg    9600
aacctcttac gtgccgatca acgtctcatt ttcgccaaaa gttggcccag gcttcccgg    9660 tatcaacagg gacaccagga tttatttatt ctgcgaagtg atcttccgtc acaggtaggc    9720
gcgccgaagt tcctatactt tctagagaat aggaacttcg gaataggaac taaggaggat    9780
attcatatgg tgcacggaag tttaaactta tttatcatca tcatctttat aatcaccatg    9840
atgacgccgt cctttgtaa taaaatagaa caacacaaac caaaattcac ttacaactaa     9900
ataatttgaa ctaaacatta ataatgtgat tggatagatt gctataaaca taacgagtaa    9960
```

```
atctatagtg tttggatcat agttcctaat cattttataa actagtagca aaatgcaaat    10020
cattatgata aaaaaccta ataagccaaa tgatagaatc aactcaataa tgatgttatg    10080
tggtatattt ccgattagtt tataatagtt aaatggccca tagcctaata acggactttg    10140
ttgaataaag taaataccct tttcataaat cggtcctctt ccagaagtac cttctaaatt    10200
aagtgttcca ccttgtagat atgaaaatgt tctagtattc gaacctttg taaaaagaaa    10260
gtaaatcaat acactagata tgcttaatgc aaaaatatac ataatgcttt ttactgcaat    10320
aggtattcct cttttaaacg taataagtat aaatgcaaat aagccgtaaa gaattaataa    10380
aatagcacct ccacgccctc ctggtataaa cacaataggg atatcaatta ttgtaaatag    10440
aacatatatc cacttatgtt tcactgaacc tttcataatg aaataaatgc ctaatccggc    10500
agtaaatgct gaaaggtacg aagcgttttg atagttcata agtccaaaat tgatatagct    10560
aggtatctca cctgtaagtt ttggtattaa aattacaaaa ataaatgaaa tagaaaatat    10620
gaaaaatact aatttaaaaa atctttctac cgtagccttg tttatatatt taatataaat    10680
accactaatt gccgctggaa ctgcccatgt taaaaagaat agaatattat ttttagctag    10740
tttctcttcc ttatctggtg aaaaataata aaaagctaga taaagcaaac atatagcaat    10800
taataatatt aaccctcgcg gaatttcttg cgtgacaatt atcttataaa tagcaaacac    10860
cgtagtaatt aatgctatac caaccatggt tgagtaatac accggctcta tagggaaccc    10920
taatacttct ttagtaaatg tagagattac tataaatatg ttcatgctga taattgcaca    10980
aagtacaaaa aatttcatag ttcctcctgc tagaggatcc ccgggtcctt acagatcctc    11040
ttctgagatg agttttgtt caaatttata taattctact aatcgttcac tttctatttg    11100
ccaattcaaa attttagacg ccttaattgc attttgacgt aaatgattaa acaaatcgtg    11160
attatctctt aatttttctaa ccgccttttc aatttctaac ggcgtaactt cctttaaaac    11220
aatgccaaat ttatattttt cattgagata aatatgctct ttgacaggag ataaaattac    11280
tggtaaacca gcatgtatac attcaaaaat tttattagat actgtatatt caaaattaat    11340
agatacaggt ttcgtcaaga taacaccaac attactttct gctaacttat caaccaattc    11400
ttttacttca actggtttat ccaacctaat attttccgag ttataactaa tcagttcttt    11460
tatcacttct tcatgcggac caaaccctcg aattatgaat gaaggagcat tttgtttaaa    11520
agctgatgaa gcaataataa actcttcata tcctctgtcc attacaattt gaccttgata    11580
tacgatttct ttaaagtttt cgatttcttt aaattctctg ctatcattta aaataggtgc    11640
attcgtaata acattcgctt ccttcttata tcctttagat tgataatatt cttttgctgc    11700
atgacttact gttacgaagg cattaacacg atgttttact atgtgttttt ctatactttc    11760
tacaaacttt gaaataagtg gaactttatt aataaaggca ttttcgcat atatttcatg    11820
cgcatcataa acaatattag cttttttata attgcttaaa tagaccatta ataatacgtc    11880
gaaatcattt gcatgaatca cgtcaggttt aaaagcttta atttctcgga taacacctgt    11940
tgcaaatctt atacgcttaa ttaatttaga aagaatattt ttgggatcta ccttgctacc    12000
taacaaacga taattacaat ctaaattttc caatcgccta ttagtagctt gtgaattatt    12060
cattccaaca attttataat cattcgtaac gcctttaatt gtttctattt gtttaagtac    12120
ccttgggtct tgaacaatat tactcgatac aatatttaaa attctcattg tacacctcct    12180
gctcattgta cacctcctgt tacgcataat ccggcacatc atacggataa ctagtatcct    12240
ttttatttaa atattcaacc gaaaatcctt ttagtttgtc aggcgttttc tcccaccact    12300
tgctttccaa aagttttca attgtttat tgtcaaatcg cttcttaatc acttttgcag    12360
```

```
gaaccccacc aacaacctca tatgctccta cattttttagt aacaactgag ccggctgcta   12420
tgactgcacc agtatttatt gttaatccat ccataataat tacatttgca ccaatccaca   12480
catcattttt aattgttgta cggcttggtt ggtcattaaa gtctataaac ttttgcttta   12540
tgttaaatgg attattatta gaataaaaaa tcggtgatga gctaaaaaag tgtgtaggat   12600
gttttcctaa cccaattttt acatccgaag atatcgaaca atatcttcct acttctacat   12660
tattaaaatc actaccaaat ccaatataac tgtattcacc aatgtgagaa ttcctgattt   12720
tacaccatct atctatatag ttattgccat caaattttga gtttgtaata tacgccaagc   12780
gatgaatctt aacattcgat tctttagagg actggttttt cagcaaacca attatctttt   12840
caatcgctat cctcatctta agatcaaagt ccccttttct ctctcaactt aaccgtggcc   12900
aggaaaaaca ttcccatccc caaagagacc tctgtaacga ccagcgtcca cgctccaaaa   12960
agctcatccc cccaaagcgc caagaggata aatgttaata ccccgcccaa ttccgcaaaa   13020
aaaattgctc gcaaatatac accatcatac ccagaaggaa caagagtcaa ccctccatac   13080
agaacaccaa tacaagcaaa cactggcact atcgaaaaca ttcttattac aacagttaga   13140
cctctggact gttccgggaa taggagatat gaaatgtatt cagaaaataa gaaagaaat    13200 aaacaactag gaatagctat tagtaacatc agacctagcg ctttccttct taaactgccg   13260
actgccgggt cggcactcgc atacatcctg ctaaaagtcg gaaatagagc gctagctatg   13320
ggtgaagtag cagccgcgat cccgcgaagg aatttatccg cagtagaaag cactccggcc   13380
gcggaggctc caccaacaac accaaccgcc gcaacgagca cttgcatgtg caagctaaga   13440
aaagccagag aaagaaaaga tcgagcaccg tcacgcaata tatcgagaat tctgtctttc   13500
tcgagaaccg ggcgccaccg tattcccata gaaaataaaa tacaacagag agcacttcca   13560
cctatgacat aggaaaaacc aaaccccaac gaagccagca caaggtcaga atccttcgtg   13620
acaaaaaaaa cgaccaatag gaaataaaat accttagaca aaaaattggt aagcgccaac   13680
catccaaaca gcgctcttcc ctgaaagaac catactgctt gaagataatt tccaactact   13740
gccggaagag cagccgcaac caatacaagc aaggggattg gtaaaataga agatacagcc   13800
aaaatggcca gcactaaaag tgaaagcagc aacaataaga atctagcact ctgtacaaca   13860
gaaaagaaac tagacagttc aactttgtta tcgataatgg cagcctttct tgatcctgcc   13920 agaataaaatc caaagtctac cagttgacat agaatgacag ccacggcctg ggcaatcacc   13980
aattggccaa acgcttcgct tgacaatgtt ctcgtgagaa aaggaatcgc agcaagaggc   14040
aaaagatagt tgctgcccat ggatataccg gagtagaaaa cgccccgcct tattgacatt   14100
ctactcgata cccctaata caattcaaca actacaacaa gtaagccctg atgccagtaa   14160
gtggcatcag ggtttagatc aaaacttagc gaagagagcc atcgctacga agcttcctta   14220
taaaaccagc gagcactgcg agtagaattc caattatcaa tcctgccaaa gtacctatag   14280
taactataag aatcttcttc ggcttaatgg gttgatttga aaagagagt ccctcgtctt    14340 ccttgtagac agccaccgca tcagaatcca cagacaaact ggagttccaa gatagtttct   14400
cttggagagt tctcaactca ggaatgaatg gagcatctac actacgcgac tcaagattgt   14460
tgatttcagc gcgcagcgcc ttagctcctc gcatgtacat caagtcacca tccatgatcg   14520
aggagagttg ttgctcggac gccccttcta ttaatggcgg gccatctatc ttgagcgact   14580
ccgcaatcag caatgcctcc ttcaaacgtg caattctatc atcacggcgg cccttcgcca   14640
tattctgcag cacggttatg cggctctgca ttgcagcatt tcttacctgg aaatctctac   14700
```

```
ctgcactatc aataacctca tgcacggccc gatccgcagc caaacgcacg aaagcttgtg      14760
cccatgtagc aagaacctct cgcttcgtgc cctccacaat taccgtataa cggtctgcat      14820
ctggcttgtt agcaggatca atctttacct ctttggagaa cttcttataa aactcctcct      14880
gctcatcttc gctttccgct ccctcaccca cctggggaag gtatatctta tagaagaact      14940
cttttttatt ctcatccgaa agcagattgc gcgaaaagat cgcatagata cttctaacag      15000
tatatgcatc taggccattc tcccttctac caacattgaa accttcgata gacccaagag      15060
caggaggcac tactgcaacc ctatattcat atacaggctt actcagatac gcataggtaa      15120
aagacccgat taatgcaaga agagtagtca gaagaatcag aaccttgtta acccaaagct      15180
ccttgaccag cttcaccagg tcaacctcac catcagccgt catcaaagaa gaattgcctc      15240
aggg                                                                  15244
```

```
<210> SEQ ID NO 3
<211> LENGTH: 16483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
tcacatgttg cccatccacg aaaccacctt atcgccgtgg aacgcacctg gatcgacagc        60
cccagcaaag cagtcgcttc ctggtccggc accggaaaca tcgtacggag aaaacaaaaa       120
aggccgctag gcggcctttt ccggagaacg atgactcagg gttctcgccg cctctggcga       180
tagatccagt cgacgatttc accgtcaggc gcatagccgc tgacggtttc ccgcagcaac       240
tggcgaaccc gcgagtagtc gtccttctcc acggcggcca gcaactgctc cagcacgacc       300
ttgaaggcct cccagctcag gtgttcctcg ttggcccgca tgatcatcgg atggtcggtg       360
ggattcacgt tgtcaccgat cagcagctct tcgtagagct tctcgccagg acgcaggcca       420
ctgaactcga tggcgatgtc accatggggc gaacgctcgg aacgcacgct caggccggac       480
aggtggatca tcttctcggc gagctccagg atcttcaccg gcggcccat gtccagcacg       540 aatacatctc cgccctgccc catcgaaccg gcctggatga ccaactgcgc cgcctcggga       600
atggtcatga agtaacgggt gatgctcggg tgggtgaccg tcaccgggcc gccgcgcttg       660
atctgctcgc ggaacagcgg aatgaccgaa ccggacgaac cgaggacgtt gccgaagcgg       720
accatggtga acgggtgtct gttgacgtga tgcacgtcct tccggtcgcc gaacagcacc       780
ggcgccgatt cgttgctgag cgcctgaagg accatttccg ccaggcgctt ggtgctgccc       840
atcacattgg tcggccgcac cgccttgtcg gtggaaatca gcacgaagtt ctgcacgccg       900
acctgcaccg cggcctgcac cgcatgcaag gtgcctatca cgttgttgag aacgccctcg       960
gcgatgttgt gctcgacgat cggcacatgc ttgtaggccg ccgcatggta gacggtattg      1020
accttccagg tacgcatcac gtccaccagg cgctcgggat tgcgcaccga accgaggatc      1080
ggcaacaggt tcaccgaaag cgactcgcgc ttgatccgac gctccagttc ctgatggatg      1140
ctatagaggt tgtattcgct gtgttcgaac aggatcagca cgctaggcga caactcatg       1200 atctgccgac agagttccga accgatagag ccgcccgccc cggtcaccat cacccacctga     1260 ccgcggatgc accgttccag cagctccttg cgcggtgcga cgctgtcgcg ccccagcagg      1320
tcagcgatgt ccacctcctg caggtcatcc accttgaccc ggccgctggc caggtccatg      1380
aagccgggca tgctgcgcac gtgcagcggg aacggctcca gggactcgag aatctctcgg      1440
```

```
cgccgggccc gagtggcgga aggaatcgcc aggagaacct cctgcgcgcc cgtctcgtcg    1500
atcatctggc ggatatgctt ggcggtatag acccgcagac cggcaatgac ccggttggcg    1560
atctgcttgt cgtcatcgat gaacgccacc ggacgcatcg cccgaccgag acgcaacgcc    1620
gcaaccaact ggttgccggc cgcccccgcc ccatagataa ccaccctggg caggccatcc    1680
tggcggttga gaaatggtac cgactgcaca gcagagtacc agtcgcccat gaaatactgg    1740
cgcatggcca gacgcaagcc gccgatcagc agcatgctca accaccagta gttgaacacc    1800
agggaacgcg gcaccggcgc cggcgcgcca cgataccagt acaccaccag cgacagcacc    1860
agagccgaga tggtcaccgc cttggcgatg gcgatcaatg cgtcgttacc gagatagcgc    1920
atcaccgcgc gatacatgcc gaagcgaatg aatagtggaa tggcgatgac cggcgcagtg    1980
atgaaaagcc atgcatgctc gccgaacacg tcgatcatat cgtctgtgcc tagacggacc    2040
acaaaagcga gccacagaga cagccatacc agaaggatat ccgtagccac ttgaagcaaa    2100
cgtttccagc gacgaggcat ggataacaac tttactctta aacgatctag cattccccta    2160
ctcctttagg cctgagcgga cgactctagc ttacccgcct tgaacctcac tgccagaaaa    2220
acgagaggga cgtaggctat gacgatgccc atcaaaggct ctagagaccc actcccgacc    2280
aacaaggcta tagggaggag ccagatgacg ttcaatgccg tgacgccaat cgtaacagga    2340
gcatgctttc catagtatcg gcttgcgtat tgataggcat ggcttcgatg agcctcatac    2400
accttgtccc ctctcagcaa gcgacgaatc agggtatagg tcgcatcgac gatgaaaacg    2460
cctaacagga ccaaccatgc ccagaaaaaa ttcgtattca tccacatggc atgaatggaa    2520
agaattccta aaacaatccc cagaagacca ctacccgcat ctcccatgaa aatttttggg    2580
ggtggaaaat tccagaacaa gaatccaaaa acggcaaaag ctagcgataa ggggagcaaa    2640
gcctgcgtca gttggccatt cagccagtat aataatgccc caccaacaca gacaaaaatg    2700
gcctgaaggc tagcaagtcc atcgatccca tccatgaagt tatagagatt cagcaaccac    2760
acgagataga aagcaaagag aagtcctccg aaccacccca ggtcccaact gacaccaaca    2820
atctgaaatg gtggtatgcc attcaaaaag tacaatgaga ccaaggctgc actaaaatgt    2880
cccagcagac gccagcgtgc ggcgatatga ccgtgatcat ccatgaatcc aataatggca    2940
accccgccgc cagcgagaag taaagcccag acacggcccc atgagatatt tcccagtaca    3000
gcccaaatag gcagcatgag acaaaaagta actacaatgg cgaccccctcc tccgcgtgga    3060 gtgggaacga catgggaact tcgagagtta ggggtgtcaa gtaagctcct cgctaaggca    3120
taacgacgca agaggcctgt aagcagtccc gaaacccccag ctgcagcgag taacaaatac    3180
cattcttcca tttataaatt tatccccaaa aatactctca cccccttcaac agggttctat    3240 tcgattgttc tgcgtggtac gccatgctag tagcaaagcg cctgcagata atcattcagt    3300
acgtttgaca tatattctac caacatcttc caacgcggaa agggtgctct tgcggggttc    3360
ccaaccaagc aaaagcctgc ctttcgacga gtcgacctct agtgagcagc ataactgagt    3420
gtataaccca ccctttccta ctaatttaag aaacctcaga ataaacctag gaacaggcca    3480
catgatgggg cgacgcccca ttcccgcagc aagcgcagtc accagttgct tggtagaaat    3540
ctcctgacca tcggataccca aaaacagttc gccggcagca gaagggtgcg tcatacagca    3600
agctagaaag tcaactaaat tatccagaga aacaaaactt cgtcggttat ctatgcaacc    3660
aaatggaaga ggaagtcccg aagcaaccag cttcaacaat cgcgagaaat ttccaggagc    3720
tttccagtcg taaacgagtg gaggcctgac gataacaagt tctgttgagg aatgcttgaa    3780
aagctcccga agcgctactt cagcctcaaa ctttgaaatc gcatattctg catgaggagc    3840
```

```
cggcttggag ttctcatcga agggcttttc tttggttaaa gcgccattta caccaataga   3900
actaacaaaa atgaaacgct ttacagatgc ttcgatcgcc tgccgagcaa gcgccagagt   3960
agcatcgcga ttcaccttcc gaaaaatatc tagtgaatca cgctgccttc caaagatatg   4020
ggctcgtcca gctagatgaa ctacacattc aacaccccgc agcgcagcat caagcttagt   4080
gctctctttc agctccgctc gaacatactc aaccccgta acgggattgt acagggatcg   4140
tacttgtccg acaacctgaa aggggcggc agcaagcgac ctgcaaagcg cactcccgac   4200
aaaaccgcta gccccggtta ccagcacctt catcatattt tcgactcaga cagaagcggt   4260
cgaacacagg cagcgaattt ttccaatgaa atatattcag ataaattttg ctgaaggaca   4320
ctccgcggga ctccgcctaa actagacaag tcgagttcac aaatctcatc gatcaatctt   4380
gccaaagcaa ccggatcatt cggcggacag ttccaaccga ttccggtctc atctattata   4440
cgggagattt cagccccttt ttccatgaca gctagaatcg gtttgtctgc tgccatggag   4500
aaatatgcct tgctgggaac cccaagcccg aacattcctt cttctaaggt aactaaggca   4560
acgtcacagg cagccaaacc aaaattcttt tcggctaatg gcagccttcc aaaataccte   4620 aaccgagcac actgatcttc cagcgcgtgt ttttttacac tgtcgaccaa ggcaccatct   4680
ccaataaaag caaaagccgc cttctcgttt ttaaccaact gaatagcaga aagtatgttt   4740
tctatacctt gtaatcgacc gacattacca aaaaattgga aaacccttttt acctttccat   4800 tcaggaatat tgataaaagg agcatcctct ctcggtactg ggaaaacctc tttctcacag   4860
gcccaattcg aaataaagac caaagatcgc gggtcattca ccttctcttt cataagagct   4920
tccatatcgc gccctattac gactagacga tcagcggatg agtaaatgaa agaaaagaga   4980
cgacgtagaa gccggtaggc aatactatct ttcttcagaa cgcccgccgg caccaagttc   5040
tcgggaaaca catcatgcac cagcagcacc cacttgaaac cgagggcata ccttagcaag   5100
ggaaacgtca tcagtagaag agcagggttg gttccactca ataccacatc tcctcgtctg   5160
gcacgagaag tcaattttac tgagaacaga aacgcctgaa aaatctgcgc caatcctcta   5220
gaaaggagcc tattcttatt gctcctcgga aacttaaagc attcttgctc aacggaaggt   5280
gaaaccacag gcggggtttc acctgcggtc agcggaaaaa ttacggttag cccaccaaac   5340
tcccgctgca tctttcctat tatcttctcc caatagtatc ccgtggagtt ctgattggca   5400
ccgacatact cagaaaccac aaatatcctt gccatcaact ccacgcctca agttaatatt   5460
ttttccagac agttcgcatg acatagtccc gatagctatg aactatgcga acaatctttt   5520
cagaaacgtt gggcatgcta tagtcagcga ccaagcgtaa catgcgctct gcgtcgcgcc   5580
tctgtccctc caacacctcg agtgcttgta gtactcgatc cgaatccagt ccgaccatca   5640
tcaccacagc ctcttccatg ccttctgggc gttcatgagc ctcacgaata ttcaaagcgg   5700
gaaaattcag tattgaagac tcctcactga tggtcccact gtcagaaata actgccttgg   5760
ctgtaatttg cagtttattg taatccttaa agccgagggg tttcagcagt ttaatacccct   5820 cgtgaaactt tgcctccgtc gcctcaattc tctttttgt tctagggtga gttgatacga   5880
tgacgggcag cgagtacttt tctgccacag cgttgagcat agaaaccaac ttcaagaaat   5940
tcttatccga atctatgttt tcctctcggt gcgcactcac gacaaagaac cgctctgttt   6000
tcaacccgag cctttcaaga atatcggagg actcgatccc gtcacgatag tgctcgagaa   6060
cttcgaacat agggctacca gtcttgataa ccatgtctgg agaaagtcct tcacgcaaga   6120
gataatcacg cgcaattgta ctataggtca aatttacatc agctgtatga tcgacaatgc   6180
```

```
gccgatttat ctcttcaggc acacgcatat cgaaacagcg attgcctgct tccatatgaa    6240
aggtcggtat cttacgccgt tttgcaggca gtaccgccat acaactattg gtatcaccca    6300
gcacgagcag cgcatcggga tctatttcgc ccagaacacg atcgactgcg attattacat    6360
tccctatcgt ttcagccccg gaagacccgg cggcgtttag aaaataatcc ggctttctta    6420
taccgaggtc ctgaaaaaat atttcattaa gttcgtaatc ataattctgt ccagtatgga    6480
caagtacatg atcgcagtac tgatcaagct tcgccatgac cctagacaag cgaataatct    6540
caggacgagt tccaacaacc gtaacgactt ttagcttctg cattgttatc tcactatacc    6600
ttacgcacct tcgcctactg aacaagcgta ggtatccgga ttttcccgat caaatacttc    6660
gttagcccac aacatgacta ccatatcgtc agttccgaca ttagtaatgt catgagtcca    6720
tccaggtact gtttcgacaa tttctgcctt tcaccatta gtgcaaattt cgtaaaatgc    6780
cccggtcagg atgtttctaa acttgaaacg tgccatccct ttgataacca gaaacttttc    6840
ggttttcgag tgatggtaat gcccgcccct ggtaacacct ggatgagccg taaaaaacga    6900
gaactggcca gagtccgcgg tcttcagcat ctcgacgaat gtgccacgcg gatccgaatg    6960
cattggcacg tcgtaactaa aactatcttc tggcaagaaa cttagataag tcgagtacaa    7020
ggcgcgcgtc aatcccgagc caacccttgc ggtagtcagt gactttcgac tattacgaaa    7080
ctcatacaat tgttctgcga gctcaccaac agaaatctga tactggggct cgacctgtag    7140
tgaaactgca ttggatagct tcccatccat gactttcatg aaggtgcgaa ccacatcatc    7200
tatgtataca agagtgatct ctgccgagga attgttaatt tgaatcggaa tatctcgaat    7260
aatattatga caaaaagtcg caaccgctga attataattc ggacgcgacc atttaccgaa    7320
tacattagga aggcgaaata tgtagacagg acaaccaata tcctcaccta gcacttggag    7380
atgctcttct gcggctcgct tgcttaaacc gtactcatta tccacctcag cctgaatgga    7440
tgaagtataa agaagtggta tggctcgtcc attggacctt accgcctcac acagagcata    7500
cgtgagttcg gaattcccga tcttaaactc ttctggtttt tccggacgat tgaccccggc    7560
aagatgaaaa ataaaatcga cggaacgaat tagctcaggc aaattaccaa cactactctc    7620
gcgggtgaat ggcaccacct cgataccacc ccgctctgca agatgagcgc acagattcct    7680
tccaacaaat ccattcgcgc cagttacaag aactttcatc gtttattcct ctggactggc    7740
actctcgcca cgctgaatag cacgaatgaa atccaacttc agcaacagct ttttcattcc    7800
ttcgatatcc agacgtttgg tattatgaga attatagtcc tctgtatgag taattttttc    7860
ctcgccttgc tccacaaact tactatagtt cagatcacgc aaatctgggg ggatacgata    7920
atagtcaccc atgtcttcag cacaggccat ttcctctcga ctaagaagcg cctcataaag    7980
cttctctcca tgacgcgtac ctattacatt gataggataa ccattcttgc caagcaattg    8040
agtaagcgca tgagccagca cctcgatggt tgcagccggt gctttctgta caaaaagatc    8100
tccattggta ccatgctcga aagcataaag cacaaggtct acggcatccg taagcgtcat    8160
catgaaacgt gtcatgtttg gatcagtgat tgtgagaggc tggcctgatc gcatttgctc    8220
gataaagaga ggaatgaccg agcccttga agccatgacg ttaccataac gggtgccaca    8280
aattacggta ggagtgcgtt ccaggtttcg agacttggcg accatgacct tttccatcat    8340
ggcctttgaa atacccatgg cattgattgg gtaaactgcc ttatccgtac tcagacaaac    8400
gacttttttg acgccattct ggatagcaga ttcgaggaca ttttccgttc cgatgacatt    8460
ggtcttcaca gcctccatcg ggtagaactc acaagaggga acctgtttca atgcagccgc    8520
atggaaaatg tagtccacac cgcgagtagc attcagagtg ctttgatagt cgcggacatc    8580
```

```
tccaatataa aacctcaact tggggtgagc atagcactta cgcatatcat cttgcttctt   8640
ctcatcccga ctgaatacac gtatttcacc aatatctgta tccagaaaac gcttcaaaac   8700
ggcatttcca aaggaaccag ttccaccggt aattaacaga acagagttct tatccataca   8760
ccacctcttt acgtgtaggc tggagctgct tcgaagttcc tatactttct agagaatagg   8820
aacttcggaa taggaacttc atttaaatgg cgcgccttac gccccgccct gccactcatc   8880
gcagtactgt tgtattcatt aagcatctgc cgacatggaa gccatcacaa acggcatgat   8940
gaacctgaat cgccagcggc atcagcacct tgtcgccttg cgtataatat ttgcccatgg   9000
tgaaaacggg ggcgaagaag ttgtccatat tggccacgtt taaatcaaaa ctggtgaaac   9060
tcacccaggg attggctgag acgaaaaaca tattctcaat aaacccttta gggaaatagg   9120
ccaggttttc accgtaacac gccacatctt gcgaatatat gtgtagaaac tgccggaaat   9180
cgtcgtggta ttcactccag agcgatgaaa acgtttcagt ttgctcatgg aaaacggtgt   9240
aacaagggtg aacactatcc catatcacca gctcaccgtc tttcattgcc atacgtaatt   9300
ccggatgagc attcatcagg cgggcaagaa tgtgaataaa ggccggataa aacttgtgct   9360
tatttttctt tacggtcttt aaaaaggccg taatatccag ctgaacggtc tggttatagg   9420
tacattgagc aactgactga aatgcctcaa aatgttcttt acgatgccat gggatatat    9480 caacggtggt atatccagtg attttttttct ccattttagc ttccttagct cctgaaaatc   9540
tcgacaactc aaaaaatacg cccggtagtg atcttatttc attatggtga agttggaac    9600 ctcttacgtg ccgatcaacg tctcattttc gccaaaagtt ggcccagggc ttcccggtat   9660
caacagggac accaggattt atttattctg cgaagtgatc ttccgtcaca ggtaggcgcg   9720
ccgaagttcc tatactttct agagaatagg aacttcggaa taggaactaa ggaggatatt   9780
catatggtgc acttacgcat aatccggcac atcatacgga taactatcga cgtcctttt    9840 attaatgaat ttagacttta aacctataat atttaaaatc acatacttaa taatgttgct   9900
gaacagcgtt gtccaaaaga atccatttag accaaacgca attgtcatta aaatagttat   9960
gaatataaat gtaatcgtgt gaagcgtcat ataattcgct tgtaatgtta ttgatgcgtg  10020
ttttgtattt aaagtttgga tcataatact cactgcattg aataaaacac ctatattacc  10080
taaaataata aacttcgaat ataaacttga atcaatgtta tacagtaaag agacaataat  10140
taatgtaatt ggataacata taatcatgac taaacatagt gcagctatag caaatagatt  10200
agttttcaaa tattgcttct ttatattgtc gctttcattt acagaaatat atgaaagtac  10260
tacattatta atcggataca gaaatgtagc taacattttc ccaataaatg ttgaaagaaa  10320
tgatatagtt acagctgttc cacctataat tggtaataag attaatctat ctaagtagag  10380
attcaaatta ttaaggctat ttgtactcag tagcatcaca taatctttga ccacattatt  10440
atcttcactt tgatactcgc ctatagttaa tccccgtaat ttaaccaatg tatatatcgt  10500
tgcaaacaat tcactggtaa taaaacaaac aatccagttt tggattaaat aatatagaaa  10560
tagtcctatc agcaaaccta aaaattgaat aagagcaata tacaaaatct gattatattt  10620
taaagtcatc ctaaaaaata cattcagata aatccttaaa cacattaaaa tattaagtag  10680
aattaaaaag ataatatcga tggtgttcaa attaaaaaag taaagaaata caataattaa  10740
agctatactc tcaatcagaa ttgaaattaa aagtatcgac acaaatttcc agtagtaatg  10800
attggatttg tatagattca tattaattaa tcgtatattg ttaagcgtat tgcctaatac  10860
aacactcgtg attgttatta ttgtataaat cgttaaaata gaaccaaacg cttcattacc  10920
```

```
tactcgttga ttaataattg gataagctaa aaattgtaat cctaaagcta taagcaacgt    10980
accaattatt gtctttacgc tatccataat aaaaactttc ttaaccatga tgcctcctgt    11040
ttaaacttat ttatcatcat catctttata atcaccatga tgacgccgtc cttttgtaat    11100
aaaatagaac aacacaaacc aaaattcact tacaactaaa taatttgaac taaacattaa    11160
taatgtgatt ggatagattg ctataaacat aacgagtaaa tctatagtgt ttggatcata    11220
gttcctaatc attttataaa ctagtagcaa aatgcaaatc attatgataa aaaacccctaa   11280 taagccaaat gatagaatca actcaataat gatgttatgt ggtatatttc cgattagttt    11340
ataatagtta aatggcccat agcctaataa cggactttgt tgaataaagt aaataccttt    11400
ttcataaatc ggtcctcttc cagaagtacc ttctaaatta agtgttccac cttgtagata    11460
tgaaaatgtt ctagtattcg aaccttttgt aaaagaaag taaatcaata cactagatat     11520
gcttaatgca aaaatataca taatgctttt tactgcaata ggtattcctc ttttaaacgt    11580
aataagtata aatgcaaata agccgtaaag aattaataaa atagcacctc cacgccctcc    11640
tggtataaac acaataggga tatcaattat tgtaaataga acatatatcc acttatgttt    11700
cactgaacct ttcataatga aataaatgcc taatccggca gtaaatgctg aaaggtacga    11760
agcgttttga tagttcataa gtccaaaatt gatatagcta ggtatctcac ctgtaagttt    11820
tggtattaaa attacaaaaa taaatgaaat agaaaatatg aaaaatacta atttaaaaaa    11880
tctttctacc gtagccttgt ttatatattt aatataaata ccactaattg ccgctggaac    11940
tgcccatgtt aaaagaata gaatattatt tttagctagt ttctcttcct tatctggtga     12000
aaaataataa aaagctagat aaagcaaaca tatagcaatt aataatatta accctcgcgg    12060
aatttcttgc gtgacaatta tcttataaat agcaaacacc gtagtaatta atgctatacc    12120
aaccatggtt gagtaataca ccggctctat agggaaccct aatacttctt tagtaaatgt    12180
agagattact ataaatatgt tcatgctgat aattgcacaa agtacaaaaa atttcatagt    12240
tcctcctgct agaggatccc cgggtcctta cagatcctct tctgagatga gttttgttc     12300 aaatttatat aattctacta atcgttcact ttctatttgc caattcaaaa ttttagacgc    12360
cttaattgca ttttgacgta aatgattaaa caaatcgtga ttatctctta attttctaac    12420
cgccttttca atttctaacg gcgtaacttc ctttaaaaca atgccaaatt tatattttc     12480 attgagataa atatgctctt tgacaggaga taaaattact ggtaaaccag catgtataca    12540
ttcaaaaatt ttattagata ctgtatattc aaaattaata gatacaggtt tcgtcaagat    12600
aacaccaaca ttactttctg ctaacttatc aaccaattct tttacttcaa ctggtttatc    12660
caacctaata ttttccgagt tataactaat cagttctttt atcacttctt catgcggacc    12720
aaaccctcga attatgaatg aaggagcatt ttgtttaaaa gctgatgaag caataataaa    12780
ctcttcatat cctctgtcca ttacaatttg accttgatat acgatttctt taaagttttc    12840
gatttcttta aattctctgc tatcatttaa aataggtgca ttcgtaataa cattcgcttc    12900
cttcttatat cctttagatt gataatattc ttttgctgca tgacttactg ttacgaaggc    12960
attaacacga tgttttacta tgtgtttttc tatactttct acaaactttg aaataagtgg    13020
aactttatta ataaaggcat ttttcgcata tatttcatgc gcatcataaa caatattagc    13080
ttttttataa ttgcttaaat agaccattaa taatacgtcg aaatcatttg catgaatcac    13140
gtcaggttta aaagctttaa tttctcggat aacacctgtt gcaaatctta tacgcttaat    13200
taatttagaa agaatatttt tgggatctac cttgctacct aacaaacgat aattacaatc    13260
taaattttcc aatcgcctat tagtagcttg tgaattattc attccaacaa ttttataatc    13320
```

```
attcgtaacg cctttaattg tttctatttg tttaagtacc cttgggtctt gaacaatatt    13380
actcgataca atatttaaaa ttctcattgt acacctcctg ctcattgtac acctcctgtt    13440
acgcataatc cggcacatca tacggataac tagtatcctt tttatttaaa tattcaaccg    13500
aaaatccttt tagtttgtca ggcgttttct cccaccactt gctttccaaa agttttcaa    13560 ttgttttatt gtcaaatcgc ttcttaatca cttttgcagg aaccccacca caacctcat    13620 atgctcctac atttttagta acaactgagc cggctgctat gactgcacca gtatttattg    13680
ttaatccatc cataataatt acatttgcac caatccacac atcattttta attgttgtac    13740
ggcttggttg gtcattaaag tctataaact tttgctttat gttaaatgga ttattattag    13800
aataaaaaat cggtgatgag ctaaaaaagt gtgtaggatg ttttcctaac ccaatttta    13860 catccgaaga tatcgaacaa tatcttccta cttctacatt attaaaatca ctaccaaatc    13920
caatataact gtattcacca atgtgagaat tcctgatttt acaccatcta tctatatagt    13980
tattgccatc aaattttgag tttgtaatat acgccaagcg atgaatctta acattcgatt    14040
ctttagagga ctggttttc agcaaaccaa ttatctttc aatcgctatc ctcatcttaa     14100
gatcaaagtc ccctttctc tctcaactta accgtggcca ggaaaaacat tcccatcccc      14160
aaagagacct ctgtaacgac cagcgtccac gctccaaaaa gctcatcccc ccaaagcgcc    14220
aagaggataa atgttaatac cccgcccaat tccgcaaaaa aaattgctcg caaatataca    14280
ccatcatacc cagaaggaac aagagtcaac cctccataca gaacaccaat acaagcaaac    14340
actggcacta tcgaaaacat tcttattaca acagttagac ctctggactg ttccgggaat    14400
aggagatatg aaatgtattc agaaaataag aaaagaaata aacaactagg aatagctatt    14460
agtaacatca gacctagcgc tttccttctt aaactgccga ctgccgggtc ggcactcgca    14520
tacatcctgc taaaagtcgg aaatagagcg ctagctatgg gtgaagtagc agccgcgatc    14580
ccgcgaagga atttatccgc agtagaaagc actccggccg cggaggctcc accaacaaca    14640
ccaaccgccg caacgagcac ttgcatgtgc aagctaagaa aagccagaga agaaaaagat    14700
cgagcaccgt cacgcaatat atcgagaatt ctgtctttct cgagaaccgg gcgccaccgt    14760
attcccatag aaaataaaat acaacagaga gcacttccac ctatgacata ggaaaaacca    14820
aaccccaacg aagccagcac aaggtcagaa tccttcgtga caaaaaaaac gaccaatagg    14880
aaataaaata ccttagacaa aaaattggta agcgccaacc atccaaacag cgctcttccc    14940
tgaaagaacc atactgcttg aagataattt ccaactactg ccggaagagc agccgcaacc    15000
aatacaagca aggggattgg taaaatagaa gatacagcca aaatggccag cactaaaagt    15060
gaaagcagca acaataagaa tctagcactc tgtacaacag aaaagaaact agacagttca    15120
actttgttat cgataatggc agcctttctt gatcctgcca gaataaatcc aaagtctacc    15180
agttgacata gaatgacagc cacggcctgg gcaatcacca attggccaaa cgcttcgctt    15240
gacaatgttc tcgtgagaaa aggaatcgca gcaagaggca aagatagtt gctgccatg     15300 gatataccgg agtagaaaac gccccgcctt attgacattc tactcgatac ccctaatac     15360 aattcaacaa ctacaacaag taagccctga tgccagtaag tggcatcagg gtttagatca    15420
aaacttagcg aagagagcca tcgctacgaa gcttccttat aaaaccagcg agcactgcga    15480
gtagaattcc aattatcaat cctgccaaag tacctatagt aactataaga atcttcttcg    15540
gcttaatggg ttgatttgaa aaagagagtc cctcgtcttc cttgtagaca gccaccgcat    15600
cagaatccac agacaaactg gagttccaag atagtttctc ttggagagtt ctcaactcag    15660
```

| gaatgaatgg agcatctaca ctacgcgact caagattgtt gatttcagcg cgcagcgcct | 15720 |
| tagctcctcg catgtacatc aagtcaccat ccatgatcga ggagagttgt tgctcggacg | 15780 |
| cccccttctat taatggcggg ccatctatct tgagcgactc cgcaatcagc aatgcctcct | 15840 |
| tcaaacgtgc aattctatca tcacggcggc ccttcgccat attctgcagc acggttatgc | 15900 |
| ggctctgcat tgcagcattt cttacctgga aatctctacc tgcactatca ataacctcat | 15960 |
| gcacggcccg atccgcagcc aaacgcacga aagcttgtgc ccatgtagca agaacctctc | 16020 |
| gcttcgtgcc ctccacaatt accgtataac ggtctgcatc tggcttgtta gcaggatcaa | 16080 |
| tctttacctc tttggagaac ttcttataaa actcctcctg ctcatcttcg ctttccgctc | 16140 |
| cctcacccac ctggggaagg tatatcttat agaagaactc ttttttattc tcatccgaaa | 16200 |
| gcagattgcg cgaaaagatc gcatagatac ttctaacagt atatgcatct aggccattct | 16260 |
| cccttctacc aacattgaaa ccttcgatag acccaagagc aggaggcact actgcaaccc | 16320 |
| tatattcata tacaggctta ctcagatacg cataggtaaa agacccgatt aatgcaagaa | 16380 |
| gagtagtcag aagaatcaga accttgttaa cccaaagctc cttgaccagc ttcaccaggt | 16440 |
| caacctcacc atcagccgtc atcaaagaag aattgcctca ggg | 16483 |

<210> SEQ ID NO 4
<211> LENGTH: 16660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

| aattccctga ggcaattctt ctttgatgac ggctgatggt gaggttgacc tggtgaagct | 60 |
| ggtcaaggag ctttgggtta acaaggttct gattcttctg actactcttc ttgcattaat | 120 |
| cgggtctttt acctatgcgt atctgagtaa gcctgtatat gaatataggg ttgcagtagt | 180 |
| gcctcctgct cttgggtcta tcgaaggttt caatgttggt agaagggaga atggcctaga | 240 |
| tgcatatact gttagaagta tctatgcgat cttttcgcgc aatctgcttt cggatgagaa | 300 |
| taaaaagag ttcttctata agatatacct tccccaggtg ggtgagggag cggaaagcga | 360 |
| agatgagcag gaggagtttt ataagaagtt ctccaaagag gtaaagattg atcctgctaa | 420 |
| caagccagat gcagaccgtt atacggtaat tgtggagggc acgaagcgag aggttcttgc | 480 |
| tacatgggca caagctttcg tgcgtttggc tgcggatcgg gccgtgcatg aggttattga | 540 |
| tagtgcaggt agagatttcc aggtaagaaa tgctgcaatg cagagccgca taaccgtgct | 600 |
| gcagaatatg gcgaagggcc gccgtgatga tagaattgca cgtttgaagg aggcattgct | 660 |
| gattgcggag tcgctcaaga tagatggccc gccattaata gaagggggcgt ccagcaaca | 720 |
| actctcctcg atcatggatg gtgacttgat gtacatgcga ggagctaagg cgctgcgcgc | 780 |
| tgaaatcaac aatcttgagt cgcgtagtgt agatgctcca ttcattcctg agttgagaac | 840 |
| tctccaagag aaactatctt ggaactccag tttgtctgtg gattctgatg cggtggctgt | 900 |
| ctacaaggaa gacgagggac tctctttttc aaatcaaccc attaagccga agaagattct | 960 |
| tatagttact ataggtactt tggcaggatt gataattgga attctactcg cagtgctcgc | 1020 |
| tggttttata aggaagcttc gtagcgatgg ctctcttcgc taagttttga tctaaaccct | 1080 |
| gatgccactt actggcatca gggcttactt gttgtagttg ttgaattgta ttaggggta | 1140 |
| tcgagtagaa tgtcaataag gcggggcgtt ttctactccg gtatatccat gggcagcaac | 1200 |

```
tatcttttgc tcttgctgc gattcctttt ctcacgagaa cattgtcaag cgaagcgttt    1260
ggccaattgg tgattgccca ggccgtggct gtcattctat gtcaactggt agactttgga    1320
tttattctgg caggatcaag aaaggctgcc attatcgata caaagttga actgtctagt     1380 ttcttttctg ttgtacagag tgctagattc ttattgttgc tgctttcact tttagtgctg    1440
gccattttgg ctgtatcttc tattttacca atccccttgc ttgtattggt tgcggctgct    1500
cttccggcag tagttggaaa ttatcttcaa gcagtatggt tctttcaggg aagagcgctg    1560
tttggatggt tggcgcttac caattttttg tctaaggtat tttatttcct attggtcgtt    1620
ttttttgtca cgaaggattc tgaccttgtg ctggcttcgt tggggtttgg ttttccctat    1680
gtcataggtg gaagtgctct ctgttgtatt ttattttcta tgggaatacg gtggcgcccg    1740
gttctcgaga aagacagaat tctcgatata ttgcgtgacg gtgctcgatc ttttctttct    1800
ctggcttttc ttagcttgca catgcaagtg ctcgttgcgg cggttggtgt tgttggtgga    1860
gcctccgcgg ccggagtgct ttctactgcg gataaattcc ttcgcgggat cgcggctgct    1920
acttcaccca tagctagcgc tctatttccg acttttagca ggatgtatgc gagtgccgac    1980
ccggcagtcg gcagtttaag aaggaaagcg ctaggtctga tgttactaat agctattcct    2040
agttgtttat ttcttttctt attttctgaa tacatttcat atctcctatt cccggaacag    2100
tccagaggtc taactgttgt aataagaatg ttttcgatag tgccagtgtt tgcttgtatt    2160
ggtgttctgt atggagggtt gactcttgtt ccttctgggt atgatggtgt atatttgcga    2220 gcaattttt ttgcggaatt gggcggggta ttaacattta tcctcttggc gctttggggg    2280
gatgagcttt ttggagcgtg gacgctggtc gttacagagg tctctttggg gatgggaatg    2340
tttttcctgg ccacggttaa gttgagagag aaaagggac tttgatctta aggcgatcgc    2400
taggaggaca gctatgcgta ttgcgattct gggcgcgacc aacattaaac atatgagcct    2460
gctgagccat tatctgaacc atattgatct gaacattaac gaagtggata ttatttatac    2520
cgataaatat gatattgaag aacatattca gggcatcaac aactactaca aatcaaagt     2580 ggatatcaaa gaagattgga ccttcatcaa gaaagcgatt gcgtattatc gttttcgtcc    2640
gtatgcgatg aaaattctga agaaaaaccg ttatgatttt tgtgattgtgt ggggcagcta    2700 caccggccat ctgttcaaaa gctttctgga aaaacattac aaaaacaaat tcatcctgaa    2760
catccgtgat tactttttcg aaaacaacaa actgattaaa tatcgtatga agaaaatcgt    2820
ggatgcgagc cgtgtgacca ccctgagcag cgaaggcttt ctgaaattcc tgccgaaaag    2880
cgaaaaatac cgtatcatct acagctacaa catgagcatc atccgtgaaa gcaacgtgac    2940
cgatggcttt aaaaaacgtt ggccgattaa cattggcttt attggcaacg tgcgttttaa    3000
cgaaattaac cagaaactga ttaaagaact ggcgaacgat agccgttttc atatgcagta    3060
ttttggcacc ggcagcgaaa actggaagt gtttgcgcgt gaaaactta ttaacaacat     3120 tacctttagc ggcggctttg atctgaaaga accccgaaa tatctgaacg aaattgatat     3180
tctgaacaac ctgtttggca accagaacat tgcgctggaa ccgcgctga gcattcgtat    3240 gtattatgcg ctgttctga caaaccgat tattaccacc gatgataccat ttaccgcgac    3300 cgaagcgaac aaatttggcc tgggctttag cattaacccg gaaaacctga aaggcattgg    3360
cgatgaactg atggattggt ataacaacct ggatgtgatg gatattaacc ataaacgtga    3420
agcgtatcgt aacgatgtga ttgaaaacaa caaacagttt tatcaggaaa ttggccgtat    3480
ttttaacgaa gaacagaaac tgattagcga agaagatctg taacgtttaa acaggaggac    3540
agctatgaac aaaatttata acgtgaccag ctatgtgatt gcgattctga tgtttccgtg    3600
```

```
cctgatgctg ggcgataaac cgctgctgtt tctggcgccg attagctatg gcgtgggcaa    3660
actgttcatc agcttcagca acaacccgaa cttcaaattc agcaaaatcg tgtacgatgt    3720 gctgggctt  ctgcgtctgg tgtttattcc ggcgatgatt gtgttttccc aggatagcac    3780
cattgataac ctgccgctgg gccaggcgta ttttaaccag gcggtgattt atatgagcgt    3840
ggaatttatt attggcagcc tgtttattct gattctgagc aaactgttca agcatgaagt    3900
tgtgagccgt aacagcttta ccctgagcgg cagcagcatt tattatattg tgtttggcct    3960
ggtgatttgc ggcattttg  tggcgttccc ggaagtgcgt aaaaacatta gctttctgat    4020
tattaaaacc gatgcgatgg gccgtggcac cgaagcgacc agcggcctga acgtgctgtt    4080
tgtgatgctg tttcagctgg cgctggcgct gctgtttctg atcatcgcgt acgcgagcta    4140
caaaaaatac aaagaaaacc cgaaaatcat ctacgtggtg ctgccgctgg cgattggcat    4200
tctgaacatt agcctgattg tgggcgaacg tcgtagctat cagctgtata ccatggtggc    4260
ggtgctgacc gttgtgagca tcctgtttag caaacataaa cgtcgtatca acatcatcat    4320
catcagcgtg ggcatcttcg tgctggcgct gatgacccctg tataaagaac tgtatgtgtt    4380
taactatagc agctatagcg aagcgctgaa cagcaccagc gtgagcaacc tgaaaattgt    4440 ggatacccctg cagagctatt tttatggccc gagcaacatt gcggcgagca ttgattatct    4500
gaactattat aacggcagct ttaaacagta tctgtttgat aacacccgtg cggtgtttgg    4560
ctttaacttt ttcctggata aaaacagct  gattaccagc cagctgttta ccagctgat    4620 ttatggcagc aaaacagctga ccggccatct gattagcagc gcgggctatg gcattattta    4680
ttttggcccg ctgttttct  acctgaacct gattgcgaac atctttttcg cgtttctgag    4740
cgaatacatc atccgtaaaa gccatagcct ggaagtgatc ttcatcggca cctacatcta    4800
catgcgtctg attaccagca tttttagcca tccgaccccg ctgattaccc tgattagcat    4860
gattctggtg gtgtatgtga ttgcgatcat cccgggcatc atcatcaaga aattcaccaa    4920
aaaagtgggc atcgaagatt acaaagatga tgatgataaa taacgtttaa acaggaggac    4980
agctatgatt gtgaaaaacct ttatgaaaag caaaattttt cgtctgatga caccccgct    5040 gctgctgttt tataaaaaag aatatctgac cggctattat tttgaaaaca aagtggcggg    5100
ctggctgtgg gcgtggaaag cggtgccatt caagctgctg ggcattaaca ccagcctgcc    5160
gtttccggcg gatattaccg tgcgtatgca taacccgaac aacattgtgt ttgataaaaa    5220
cgatattcat attttcaga  gcccgggcac ctatttaac aactttagcg cggtgattta    5280
tattggccgt ggcgtgtata ttgcgccgaa cgtgggcatt attaccgcga accataacat    5340
taaaaacctg aaaagccatg cgccgggcga agatgtgaaa attggcaact atagctggat    5400
tggcatgaac agcgtgattc tgccgggcgt ggaactgggc gaacatacca ttgtgggcgc    5460
gggcagcgtg gtgaccaaaa gcttccggga aggcaacgtg gtgattggcg gcaacccggc    5520
gaaaattatt aagaaaatca gctatccgta tgatgtgccg gattatgcgt aattaattaa    5580
ccaggtgcac gaagaaaatt atgagattaa ataaatttat tggcgattcg tttttaatga    5640
ttttaagcag tggcatcgct caagtcatat taatcatcac tacccccaatt attacaagac    5700 tatattcacc tacagaattt ggtgagttta caatttttc aaatatcgca atgatttta     5760 taccaataat aaatgcaaga tacgatttgt tgattgtgaa taccaaaat gaccgtagtg     5820 ctaatatact ttcacaaatc agtttttga tatcattgct tatttattta atactgatac     5880
caatatttgc gattagtgca tgtttatacc caaactttat attagatttt attttcatta    5940
```

```
ttattatgtt gttttttggta agtttaacaa acattttttac aaattatcta aataaggaaa    6000
gaaagtataa agtgttaagt ttgattaatg tgtttagagc tggatcaatg gctttacttc    6060
aaatcatttt cggacttttta gcattaggaa gtttaggatt aattattggt ttttcattat    6120
cctatatcgc aggcattaca ctaggatata aaacgtttaa aaagcacttt aatattgtga    6180
gagataaaga agaaactaaa gcattatttt tagaaaataa aaatcagtta gtttattcaa    6240
caccatcaat attattaaat agtttgtctt tctcggttgt tgtgttcttt ataggtattt    6300
tgtataccaa tacagaagtg ggtatttatg gtatggccat aagagtacta ggcataccag    6360
tgacaattat ttcattaggg ttatcaaaaa tatttatgca acaagccaat gactattata    6420
ttgaacatgg taacttccga aatttattac ttaaatttag ttccatactg gttatagttt    6480
ctataattct ttatgtgcca ctttatttgt tcagtgaaga attagtcaat atattattag    6540
gacatagctg ggttgacgca attacagtta taaaaattgt tatcccatta tttgttataa    6600
ggctgattgt atcaacggta tcactttctg tgattgtatt acaaaaacaa cagttagaat    6660
taatactaca agcgttatttt ttaataggta ctactgcaac atttgttata tcaaaaatgc    6720
ttaatttaac ttttttaaac tttgtatcta ttaatacaat tgttttaatc gtatcgtaca    6780
tgatattttt catagcactc tattattttg ctaaaaataa acagttcaaa aattctagtt    6840
atccgtatga tgtgccggat tatgcgtaag tgcaccatat gaatatcctc cttagttcct    6900
attccgaagt tccatttctc tagaaagtat aggaacttcg gcgcgcctac ctgtgacgga    6960
agatcacttc gcagaataaa taaatcctgg tgtccctgtt gataccggga agccctgggc    7020
caacttttgg cgaaaatgag acgttgatcg gcacgtaaga ggttccaact ttcaccataa    7080
tgaaataaga tcactaccgg gcgtattttt tgagttgtcg attttcag gagctaagga    7140
agctaaaatg gagaaaaaaa tcactggata taccaccgtt gatatatccc aatggcatcg    7200
taaagaacat tttgaggcat ttcagtcagt tgctcaatgt acctataacc agaccgttca    7260
gctggatatt acggcctttt taagaccgt aagaaaaat aagcacaagt tttatccggc    7320
ctttattcac attcttgccc gcctgatgaa tgctcatccg gaattacgta tggcaatgaa    7380
agacggtgag ctggtgatat gggatagtgt tcacccttgt tacaccgttt tccatgagca    7440
aactgaaacg ttttcatcgc tctggagtga ataccacgac gatttccggc agtttctaca    7500
catatattcg caagatgtgg cgtgttacgg tgaaaacctg gcctatttcc ctaaagggtt    7560
tattgagaat atgtttttcg tctcagccaa tccctgggtg agtttcacca gttttgattt    7620
aaacgtggcc aatatggaca acttcttcgc ccccgttttc accatgggca atatattac    7680
gcaaggcgac aaggtgctga tgccgctggc gattcaggtt catcatgccg tttgtgatgg    7740
cttccatgtc ggcagatgct taatgaatac aacagtactg cgatgagtgg cagggcgggg    7800
cgtaaggcgc gccatttaaa tgaagttcct attccgaagt tcctattctc tagaaagtat    7860
aggaacttcg aagcagctcc agcctacacg taaagaggtg gtgtatggat aagaactctg    7920
ttctgttaat taccggtgga actggttcct ttggaaatgc cgttttgaag cgttttctgg    7980
atacagatat tggtgaaata cgtgtattca gtcgggatga aagaagcaa gatgatatgc    8040
gtaagtgcta tgctcacccc aagttgaggt tttatattgg agatgtccgc gactatcaaa    8100
gcactctgaa tgctactcgc ggtgtggact acatttttca tgcggctgca ttgaaacagg    8160
ttccctcttg tgagttctac ccgatggagg ctgtgaagac caatgtcatc ggaacggaaa    8220
atgtcctcga atctgctatc cagaatgcg tcaaaaaagt cgtttgtctg agtacgata    8280
aggcagttta cccaatcaat gccatgggta tttcaaaggc catgatggaa aaggtcatgg    8340
```

```
tcgccaagtc tcgaaacctg gaacgcactc ctaccgtaat ttgtggcacc cgttatggta      8400
acgtcatggc ttcaaggggc tcggtcattc ctctctttat cgagcaaatg cgatcaggcc      8460
agcctctcac aatcactgat ccaaacatga cacgtttcat gatgacgctt acggatgccg      8520
tagaccttgt gctttatgct ttcgagcatg gtaccaatgg agatcttttt gtacagaaag      8580
caccggctgc aaccatcgag gtgctggctc atgcgcttac tcaattgctt ggcaagaatg      8640
gttatcctat caatgtaata ggtacgcgtc atggagagaa gctttatgag gcgcttctta      8700
gtcgagagga aatggcctgt gctgaagaca tgggtgacta ttatcgtatc cccccagatt      8760
tgcgtgatct gaactatagt aagtttgtgg agcaaggcga ggaaaaaatt actcatacag      8820
aggactataa ttctcataat accaaacgtc tggatatcga aggaatgaaa aagctgttgc      8880
tgaagttgga tttcattcgt gctattcagc gtggcgagag tgccagtcca gaggaataaa      8940
cgatgaaagt tcttgtaact ggcgcgaatg gatttgttgg aaggaatctg tgcgctcatc      9000
ttgcagagcg gggtggtatc gaggtggtgc cattcacccg cgagagtagt gttggtaatt      9060
tgcctgagct aattcgttcc gtcgatttta tttttcatct tgccggggtc aatcgtccgg      9120
aaaaaccaga gagtttaagg atcgggaatt ccgaactcac gtatgctctg tgtgaggcgg      9180
taaggtccaa tggacgagcc ataccacttc tttatacttc atccattcag gctgaggtgg      9240
ataatgagta cggtttaagc aagcgagccg cagaagagca tctccaagtg ctaggtgagg      9300
atattggttg tcctgtctac atatttcgcc ttcctaatgt attcggtaaa tggtcgcgtc      9360
cgaattataa ttcagcggtt gcgactttt gtcataatat tattcgagat attccgattc      9420
aaattaacaa ttcctcggca gagatcactc ttgtatacat agatgatgtg gttcgcacct      9480
tcatgaaagt catggatggg aagctatcca atgcagtttc actacaggtc gagccccagt      9540
atcagatttc tgttggtgag ctcgcagaac aattgtatga gtttcgtaat agtcgaaagt      9600
cactgactac cgcaagggtt ggctcgggat tgacgcgcgc cttgtactcg acttatctaa      9660
gtttcttgcc agaagatagt tttagttacg acgtgccaat gcattcggat ccgcgtggca      9720
cattcgtcga gatgctgaag accgcggact ctggccagtt ctcgttttt acggctcatc      9780 caggtgttac caggggcggg cattaccatc actcgaaaac cgaaaagttt ctggttatca      9840
aagggatggc acgtttcaag tttagaaaca tcctgaccgg ggcattttac gaaatttgca      9900
ctaatggtga aaaggcagaa attgtcgaaa cagtacctgg atggactcat gacattacta      9960
atgtcggaac tgacgatatg gtagtcatgt tgtgggctaa cgaagtattt gatcgggaaa     10020
atccggatac ctacgcttgt tcagtaggcg aaggtgcgta aggtatagtg agataacaat     10080
gcagaagcta aaagtcgtta cggttgttgg aactcgtcct gagattattc gcttgtctag     10140
ggtcatggcg aagcttgatc agtactgcga tcatgtactt gtccatactg gacagaatta     10200
tgattacgaa cttaatgaaa tatttttca ggacctcggt ataagaaagc cggattattt     10260
tctaaacgcc gccgggtctt ccggggctga acgataggg aatgtaataa tcgcagtcga     10320
tcgtgttctg ggcgaaatag atcccgatgc gctgctcgtg ctgggtgata ccaatagttg     10380
tatggcggta ctgcctgcaa aacggcgtaa gataccgacc tttcatatgg aagcaggcaa     10440
tcgctgtttc gatatgcgtg tgcctgaaga gataaatcgg cgcattgtcg atcatacagc     10500
tgatgtaaat ttgacctata gtacaattgc gcgtgattat ctcttgcgtg aaggactttc     10560
tccagacatg gttatcaaga ctggtagccc tatgttcgaa gttctcgagc actatcgtga     10620
cgggatcgag tcctccgata ttcttgaaag gctcggggttg aaaacagagc ggttctttgt     10680
```

```
cgtgagtgcg caccgagagg aaaacataga ttcggataag aatttcttga agttggtttc   10740
tatgctcaac gctgtggcag aaaagtactc gctgcccgtc atcgtatcaa ctcaccctag   10800
aacaaaaaag agaattgagg cgacggaggc aaagtttcac gagggtatta aactgctgaa   10860 accccctcggc tttaaggatt acaataaact gcaaattaca gccaaggcag ttatttctga   10920
cagtgggacc atcagtgagg agtcttcaat actgaatttt cccgctttga atattcgtga   10980
ggctcatgaa cgcccagaag gcatggaaga ggctgtggtg atgatggtcg gactggattc   11040
ggatcgagta ctacaagcac tcgaggtgtt ggagggacag aggcgcgacg cagagcgcat   11100
gttacgcttg gtcgctgact atagcatgcc caacgtttct gaaaagattg ttcgcatagt   11160
tcatagctat cgggactatg tcatgcgaac tgtctggaaa aaatattaac ttgaggcgtg   11220
gagttgatgg caaggatatt tgtggtttct gagtatgtcg gtgccaatca gaactccacg   11280
ggatactatt gggagaagat aataggaaag atgcagcggg agtttggtgg gctaaccgta   11340
attttcccgc tgaccgcagg tgaaaccccg cctgtggttt caccttccgt tgagcaagaa   11400
tgctttaagt ttccgaggag caataagaat aggctccttt ctagaggatt ggcgcagatt   11460
tttcaggcgt ttctgttctc agtaaaattg acttctcgtg ccagacgagg agatgtggta   11520
ttgagtggaa ccaaccctgc tcttctactg atgacgtttc ccttgctaag gtatgccctc   11580
ggtttcaagt gggtgctgct ggtgcatgat gtgtttcccg agaacttggt gccggcgggc   11640
gttctgaaga aagatagtat tgcctaccgg cttctacgtc gtctcttttc tttcatttac   11700
tcatccgctg atcgtctagt cgtaataggg cgcgatatgg aagctcttat gaaagagaag   11760
gtgaatgacc cgcgatcttt ggtctttatt tcgaattggg cctgtgagaa agaggttttc   11820
ccagtaccga gagaggatgc tcctttatc aatattcctg aatggaaagg taaagggtt   11880 ttccaatttt ttggtaatgt cggtcgatta caaggtatag aaaacatact ttctgctatt   11940
cagttggtta aaaacgagaa ggcggctttt gcttttattg gagatggtgc cttggtcgac   12000
agtgtaaaaa aacacgcgct ggaagatcag tgtgctcggt tgaggtattt tggaaggctg   12060
ccattagccg aaaagaattt tggtttggct gcctgtgacg ttgccttagt taccttagaa   12120
gaaggaatgt tcgggcttgg ggttcccagc aaggcatatt tctccatggc agcagacaaa   12180
ccgattctag ctgtcatgga aaaagggggct gaaatctccc gtataatag tgagaccgga   12240 atcggttgga actgtccgcc gaatgatccg gttgctttgg caagattgat cgatgagatt   12300
tgtgaactcg acttgtctag tttaggcgga gtcccgcgga gtgtccttca gcaaaattat   12360
tctgaatata tttcattgga aaaattcgct gcctgtgttc gaccgcttct gtctgagtcg   12420
aaaatatgat gaaggtgctg gtaaccgggg ctagcggttt tgtcgggagt gcgctttgca   12480
ggtcgcttgc tgccgccccc tttcaggttg tcggacaagt acgatccctg tacaatcccg   12540
ttacgggggt tgagtatgtt cgagcggagc tgaaagagag cactaagctt gatgctgcgc   12600
tgcggggtgt tgaatgtgta gttcatctag ctggacgagc ccatatcttt ggaaggcagc   12660
gtgattcact agatatttttt cggaaggtga atcgcgatgc tactctggcg cttgctcggc   12720
aggcgatcga agcatctgta aagcgtttca ttttttgttag ttctattggt gtaaatggcg   12780
ctttaaccaa agaaaagccc ttcgatgaga actccaagcc ggctcctcat gcagaatatg   12840
cgatttcaaa gtttgaggct gaagtagcgc ttcgggagct tttcaagcat tcctcaacag   12900
aacttgttat cgtcaggcct ccactcgttt acgactggaa agctcctgga aatttctcgc   12960
gattgttgaa gctggttgct tcgggacttc ctcttccatt tggttgcata gataaccgac   13020
gaagttttgt ttctctggat aatttagttg actttctagc ttgctgtatg acgcacccttt   13080
```

```
ctgctgccgg cgaactgttt ttggtatccg atggtcagga gatttctacc aagcaactgg    13140
tgactgcgct tgctgcggga atggggcgtc gccccatcat gtggcctgtt cctaggttta    13200
ttctgaggtt tcttaaatta gtaggaaagg gtgggttata cactcagtta tgctgctcac    13260
tagaggtcga ctcgtcgaaa ggcaggcttt tgcttggttg gaacccccgc aagagcaccc    13320
tttccgcgtt ggaagatgtt ggtagaatat atgtcaaacg tactgaatga ttatctgcag    13380
gcgctttgct actagcatgg cgtaccacgc agaacaatcg aatagaaccc tgttgaaggg    13440
gtgagagtat ttttggggat aaatttataa atggaagaat ggtatttgtt actcgctgca    13500
gctggggttt cgggactgct tacaggcctc ttgcgtcgtt atgccttagc gaggagctta    13560
cttgacaccc ctaactctcg aagttcccat gtcgttccca ctccacgcgg aggaggggtc    13620
gccattgtag ttacttttg tctcatgctg cctatttggg ctgtactggg aaatatctca    13680
tgggccgtgt cctgggcttt acttctcgct ggcggcgggg ttgccattat tggattcatg    13740
gatgatcacg gtcatatcgc cgcacgctgg cgtctgctgg acattttag tgcagccttg    13800 gtctcattgt acttttgaa tggcatacca ccatttcaga ttgttggtgt cagttgggac    13860
ctggggtggt tcgaggact tctctttgct ttctatctcg tgtggttgct gaatctctat    13920
aacttcatgg atgggatcga tggacttgct agccttcagg ccattttgt ctgtgttggt    13980 ggggcattat tatactggct gaatggccaa ctgacgcagg ctttgctccc cttatcgcta    14040
gcttttgccg ttttggatt cttgttctgg aattttccac ccccaaaaat tttcatggga    14100
gatgcgggta gtggtcttct ggggattgtt ttaggaattc tttccattca tgccatgtgg    14160
atgaatacga atttttctg gcatggttg gtcctgttag gcgttttcat cgtcgatgcg    14220
acctataccc tgattcgtcg cttgctgaga ggggacaagg tgtatgaggc tcatcgaagc    14280
catgcctatc aatacgcaag ccgatactat ggaaagcatg ctcctgttac gattggcgtc    14340
acggcattga acgtcatctg gctcctccct atagccttgt tggtcgggag tgggtctcta    14400
gagcctttga tgggcatcgt catagcctac gtccctctcg ttttttctggc agtgaggttc    14460 aaggcgggta agctagagtc gtccgctcag gcctaaagga gtaggggaat gctagatcgt    14520
ttaagagtaa agttgttatc catgcctcgt cgctggaaac gtttgcttca agtggctacg    14580
gatatccttc tggtatggct gtctctgtgg ctcgcttttg tggtccgtct aggcacagac    14640
gatatgatcg acgtgttcgg cgagcatgca tggcttttca tcactgcgcc ggtcatcgcc    14700
attccactat tcattcgctt cggcatgtat cgcgcggtga tgcgctatct cggtaacgac    14760
gcattgatcg ccatcgccaa ggcggtgacc atctcggctc tggtgctgtc gctggtggta    14820
tactggtatc gtggcgcgcc ggcgccggtg ccgcgttccc tggtgttcaa ctactggtgg    14880
ttgagcatgc tgctgatcgg cggcttgcgt ctggccatgc gccagtattt catgggcgac    14940
tggtactctg ctgtgcagtc ggtaccattt ctcaaccgcc aggatggcct gcccagggtg    15000
gttatctatg gggcggggc ggccggcaac cagttggttg cggcgttgcg tctcggtcgg    15060
gcgatgcgtc cggtggcgtt catcgatgac gacaagcaga tcgccaaccg ggtcattgcc    15120
ggtctgcggg tctataccgc caagcatatc cgccagatga tcgacgagac gggcgcgcag    15180
gaggttctcc tggcgattcc ttccgccact cgggcccggc gccgagagat tctcgagtcc    15240
ctggagccgt tcccgctgca cgtgcgcagc atgcccggct tcatggacct ggccagcggc    15300
cgggtcaagg tggatgacct gcaggaggtg gacatcgctg acctgctggg gcgcgacagc    15360
gtcgcaccgc gcaaggagct gctggaacgg tgcatccgcg gtcaggtggt gatggtgacc    15420
```

```
ggggcgggcg gctctatcgg ttcggaactc tgtcggcaga tcatgagttg ttcgcctagc   15480
gtgctgatcc tgttcgaaca cagcgaatac aacctctata gcatccatca ggaactggag   15540
cgtcggatca agcgcgagtc gctttcggtg aacctgttgc cgatcctcgg ttcggtgcgc   15600
aatcccgagc gcctggtgga cgtgatgcgt acctggaagg tcaataccgt ctaccatgcg   15660
gcggcctaca agcatgtgcc gatcgtcgag cacaacatcg ccgagggcgt tctcaacaac   15720
gtgataggca ccttgcatgc ggtgcaggcc gcggtgcagg tcggcgtgca gaacttcgtg   15780
ctgatttcca ccgacaaggc ggtgcggccg accaatgtga tgggcagcac caagcgcctg   15840
gcggaaatgg tccttcaggc gctcagcaac gaatcggcgc cggtgctgtt cggcgaccgg   15900
aaggacgtgc atcacgtcaa caagacccgt ttcaccatgg tccgcttcgg caacgtcctc   15960
ggttcgtccg gttcggtcat tccgctgttc cgcgagcaga tcaagcgcgg cggcccggtg   16020
acggtcaccc acccgagcat cacccgttac ttcatgacca ttcccgaggc ggcgcagttg   16080
gtcatccagg ccggttcgat ggggcagggc ggagatgtat tcgtgctgga catgggccg    16140 ccggtgaaga tcctggagct cgccgagaag atgatccacc tgtccggcct gagcgtgcgt   16200
tccgagcgtt cgccccatgg tgacatcgcc atcgagttca gtggcctgcg tcctggcgag   16260
aagctctacg aagagctgct gatcggtgac aacgtgaatc ccaccgacca tccgatgatc   16320
atgcgggcca acgaggaaca cctgagctgg gaggccttca aggtcgtgct ggagcagttg   16380
ctggccgccg tggagaagga cgactactcg cgggttcgcc agttgctgcg ggaaaccgtc   16440
agcggctatg cgcctgacgg tgaaatcgtc gactggatct atcgccagag cggcgagaa    16500 ccctgagtca tcgttctccg gaaaaggccg cctagcggcc ttttttgttt tctccgtacg   16560
atgtttccgg tgccggacca ggaagcgact gctttgctgg ggctgtcgat ccaggtgcgt   16620
tccacggcga taaggtggtt tcgtggatgg gcaacatgtg                         16660

<210> SEQ ID NO 5
<211> LENGTH: 972
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
catatgaaga aaatctggct ggcgctggcg ggcctggtgc tggcgtttag cgctagcgcg     60
gcggatagcg atattaacat taaaaccggc accaccgata ttggcagcaa caccaccgtg    120
aaaaccggca atctggtgac ctatgataaa gaaaacggca tgctgaaaaa agtgttttat    180
agcttcatcg atgataaaaa ccataacaaa aaactgctgg tgatccgtac caaaggcacc    240
attgcgggcc agtatcgtgt gtatagcgaa gaaggcgcgc acaaaagcgg cctggcgtgg    300
ccgagcgcgt ttaaagtgca gctgcagctg ccggataacg aagtggcgca gattagcgat    360
tattatccgc gtaacagcat tgataccaaa gaatatatga gcaccctgac ctatggcttt    420
aacggcaacg tgaccggcga tgataccggc aaaattggtg gactgattgg cgcgaacgtg    480
agcattggcc ataccctgaa atatgtgcag ccggattttn aaaccattct ggaaagcccg    540
accgataaaa agtgggctg aaagtgatt tttaacaaca tggtgaacca gaactggggc    600
ccgtatgatc gtgatagctg gaacccggtg tatggcaacc agctgtttat gaaaacccgt    660
aacggcagca tgaaagcggc ggataacttt ctggatccga acaaagcgag cagcctgctg    720
agcagcggct ttagcccgga ttttgcgacc gtgattacca tggatcgtaa agcgagcaaa    780
```

| | |
|---|---|
| cagcagacca acattgatgt gatttatgaa cgtgtgcgtg atgattatca gctgcattgg | 840 |
| accagcacca actggaaagg caccaacacc aaagataaat ggattgatcg tagcagcgaa | 900 |
| cgttataaaa ttgattggga aaaagaagaa atgaccaacg gcagccatca tcatcatcat | 960 |
| cattaggtcg ac | 972 |

<210> SEQ ID NO 6
<211> LENGTH: 990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

| | |
|---|---|
| catatgaaga aaatctggct ggcgctggcg ggcctggtgc tggcgtttag cgctagcgcg | 60 |
| gcggatagcg atattaacat taaaaccggc accaccgata ttggcagcaa caccaccgtg | 120 |
| aaaaccggcg atctggtgac ctatgataaa gaaaacggca tgctgaaaaa agtgttttat | 180 |
| agcttcatcg atgataaaaa ccataacaaa aaactgctgg tgatccgtac caaaggcacc | 240 |
| attgcgggcc agtatcgtgt gtatagcgaa gaaggcgcga acaaaagcgg cctggcgtgg | 300 |
| ccgagcgcgt ttaaagtgca gctgcagctg ccggataacg aagtggcgca gattagcgat | 360 |
| tattatccgc gtaacagcat tgataccaaa gaatatatga gcaccctgac ctatggcttt | 420 |
| aacggcaacg tgaccggcga tgataccggc aaaattggtg gactgattgg cgcgaacgtg | 480 |
| agcattggcc atacctgaa atatgtgcag ccggatttta aaccattct ggaaagcccg | 540 |
| accgataaaa aagtgggctg aaagtgatt tttaacaaca tggtgaacca gaactggggc | 600 |
| ccgtatgatc gtgatagctg gaacccggtg tatggcaacc agctgtttat gaaaacccgt | 660 |
| aacggcaaag atcaaaatag aactaaaatg aaagcggcgg ataactttct ggatccgaac | 720 |
| aaagcgagca gcctgctgag cagcggcttt agcccggatt ttgcgaccgt gattaccatg | 780 |
| gatcgtaaag cgagcaaaca gcagaccaac attgatgtga tttatgaacg tgtgcgtgat | 840 |
| gattatcagc tgcattggac cagcaccaac tggaaaggca ccaacaccaa agataaatgg | 900 |
| attgatcgta gcagcgaacg ttataaaatt gattgggaaa agaagaaat gaccaacggc | 960 |
| agccatcatc atcatcatca ttaagtcgac | 990 |

<210> SEQ ID NO 7
<211> LENGTH: 990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

| | |
|---|---|
| catatgaaga aaatctggct ggcgctggcg ggcctggtgc tggcgtttag cgctagcgcg | 60 |
| gcggatagcg atattaacat taaaaccggc accaccgata ttggcagcaa caccaccgtg | 120 |
| aaaaccggcg atctggtgac ctatgataaa gaaaacggca tgctgaaaaa agtgttttat | 180 |
| agcttcatcg atgataaaaa ccataacaaa aaactgctgg tgatccgtac caaaggcacc | 240 |
| attgcgggcc agtatcgtgt gtatagcgaa gaaggcgcga acaaaagcgg cctggcgtgg | 300 |
| ccgagcgcgt ttaaagtgca gctgcagctg ccggataacg aagtggcgca gattagcgat | 360 |
| tattatccgc gtaacagcat tgataccaaa gaatatatga gcaccctgac ctatggcttt | 420 |
| aacggcaacg tgaccggcga tgataccggc aaaattggtg gactgattgg cgcgaacgtg | 480 |

```
agcattggcc ataccctgaa atatgtgcag ccggatttta aaaccattct ggaaagcccg    540
accgataaaa aagtgggctg gaaagtgatt tttaacaaca tggtgaacca gaactggggc    600
ccgtatgatc gtgatagctg aacccggtg tatggcaacc agctgtttat gaaaacccgt    660
aacggcagca tgaaagcggc ggataacttt ctggatccga caaagcgag cagcctgctg    720 agcagcggct ttagcccgga ttttgcgacc gtgattacca tggatcgtaa agcgaaagat    780
caaaatagaa ctaaaaaaca gcagaccaac attgatgtga tttatgaacg tgtgcgtgat    840
gattatcagc tgcattggac cagcaccaac tggaaaggca ccaacaccaa agataaatgg    900
attgatcgta gcagcgaacg ttataaaatt gattgggaaa agaagaaat gaccaacggc    960 agccatcatc atcatcatca ttaagtcgac                                    990
```

<210> SEQ ID NO 8
<211> LENGTH: 990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
catatgaaga aaatctggct ggcgctggcg ggcctggtgc tggcgtttag cgctagcgcg    60
gcggatagcg atattaacat taaaaccggc accaccgata ttggcagcaa caccaccgtg   120
aaaaccggcg atctggtgac ctatgataaa gaaaacggca tgctgaaaaa agtgttttat   180
agcttcatcg atgataaaaa ccataacaaa aaactgctgg tgatccgtac caaaggcacc   240
attgcgggcc agtatcgtgt gtatagcgaa gaaggcgcga caaaagcgg cctggcgtgg   300 ccgagcgcgt ttaaagtgca gctgcagctg ccggataacg aagtggcgca gattagcgat   360
tattatccgc gtaacagcat tgataccaaa gaatatatga gcaccctgac ctatggcttt   420
aacggcaacg tgaccggcga tgataccggc aaaattggtg gactgattgg cgcgaacgtg   480
agcattggcc ataccctgaa atatgtgcag ccggatttta aaaccattct ggaaagcccg   540
accgataaaa aagtgggctg gaaagtgatt tttaacaaca tggtgaacca gaactggggc   600
ccgtatgatc gtgatagctg aacccggtg tatggcaacc agctgtttat gaaaacccgt   660
aacggcagca tgaaagcggc ggataacttt ctggatccga caaagcgag cagcctgctg   720 agcagcggct ttagcccgga ttttgcgacc gtgattacca tggatcgtaa agcgagcaaa   780
cagcagacca acattgatgt gatttatgaa cgtgtgcgtg atgattatca gctgcattgg   840
accagcacca actggaaagg caccaacacc aaagataaag atcaaaatag aactaaatgg   900
attgatcgta gcagcgaacg ttataaaatt gattgggaaa agaagaaat gaccaacggc   960 agccatcatc atcatcatca ttaagtcgac                                    990
```

<210> SEQ ID NO 9
<211> LENGTH: 1659
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
catatgaaga aaatctggct ggcgctggcg ggcctggtgc tggcgtttag cgctagcgcc    60
gcgagcgaaa acagcgtgac ccagagcgat agcgcgagca cgaaaagcaa aagcaacgat   120
```

| | |
|---|---:|
| agcagcagcg tgagcgcggc gccgaaaacc gatgatacca acgtgagcga taccaaaacc | 180 |
| agcagcaaca ccaacaacgg cgaaaccagc gtggcgcaga acccggcgca gcaggaaacc | 240 |
| acccagagca gcagcaccaa cgcgaccacc gaagaaaccc cggtgaccgg tgaagccacc | 300 |
| accaccacca ccaaccaggc caacaccccg gcgaccaccc agagcagcaa caccaacgcg | 360 |
| gaagaactgg tgaaccagac cagcaacgaa accacccttta acgataccaa caccgtgagc | 420 |
| agcgtgaaca gcccgcagaa cagcaccaac gcggaaaacg tgagcaccac ccaggatacc | 480 |
| agcaccgaag cgaccccgag caacaacgaa agcgcgccgc agagcaccga tgcgagcaac | 540 |
| aaagatgtgg tgaatcaggc cgttaatacc agcgcgccgc gtatgcgtgc ctttagcctg | 600 |
| gcggccgtgg ccgccgatgc tccagcagca ggtaccgata ttaccaacca gctgaccaac | 660 |
| gtgaccgtgg gcattgatag cggcaccacc gtgtatccgc atcaggcagg ttatgtgaaa | 720 |
| ctgaactatg gctttagcgt gccgaacagc gcggtgaaag gcgataccct taaaattacc | 780 |
| gtgccgaaag aactgaacct gaacggcgtg accagcaccg cgaaagtgcc gccgattatg | 840 |
| gcaggtgatc aggtgctggc gaacggcgtg attgatagcg atggcaacgt gatttatacc | 900 |
| tttaccgatt atgtgaacac caaagatgat gtgaaagcga ccctgaccat gccagcatat | 960 |
| attgatccgg aaaacgtgaa gaaaccggc aacgtgaccc tggcgaccgg cattggcagc | 1020 |
| accaccgcga acaaaaccgt tctggtggat tatgaaaaat acggcaaatt ctacaacctg | 1080 |
| agcatcaaag gcaccatcga tcagatcgat aaaaccaaca cacctatcg tcagaccatt | 1140 |
| tatgtgaacc cgagcggcga taacgtgatt gcgccggtgc tgaccggcaa cctgaaaccg | 1200 |
| aacaccgata gcaacgcgct gattgatcag cagaacacca gcattaaagt gtataaagtg | 1260 |
| gataacgcgg cggatctgag cgaaagctat tttgtgaacc cggaaaactt tgaagatgtg | 1320 |
| accaacagcg tgaacattac ctttccgaac ccgaaccagt ataaagtgga atttaacacc | 1380 |
| ccggatgatc agattaccac cccgtatatt gtggtggtga acggccatat tgatccgaac | 1440 |
| agcaaaggcg atctggcgct gcgtagcacc ctgtatggct ataacagcaa cattatttgg | 1500 |
| cgtagcatga gctgggataa cgaagtggcg tttaacaacg gcagcggcag cggcgatggc | 1560 |
| attgataaac cggtggtgcc ggaacagccg gatgaaccgg gcgaaattga accgattccg | 1620 |
| gaagatggca gccatcatca tcatcatcat taggtcgac | 1659 |

<210> SEQ ID NO 10
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

| | |
|---|---:|
| catatgaaga aaatctggct ggcgctggcg ggcctggtgc tggcgtttag cgctagcgcc | 60 |
| gcgagcgaaa acagcgtgac ccagagcgat agcgcgagca cgaaagcaa aagcaacgat | 120 |
| agcagcagcg tgagcgcggc gccgaaaacc gatgatacca acgtgagcga taccaaaacc | 180 |
| agcagcaaca ccaacaacgg cgaaaccagc gtggcgcaga acccggcgca gcaggaaacc | 240 |
| acccagagca gcagcaccaa cgcgaccacc gaagaaaccc cggtgaccgg tgaagccacc | 300 |
| accaccacca ccaaccaggc caacaccccg gcgaccaccc agagcagcaa caccaacgcg | 360 |
| gaagaactgg tgaaccagac cagcaacgaa accacccttta acgataccaa caccgtgagc | 420 |
| agcgtgaaca gcccgcagaa cagcaccaac gcggaaaacg tgagcaccac ccaggatacc | 480 |

```
agcaccgaag cgaccccgag caacaacgaa agcgcgccgc agagcaccga tgcgagcaac    540
aaagatgtgg tgaatcaggc cgttaatacc agcgcgccgc gtatgcgtgc ctttagcctg    600
gcggccgtgg ccgccgatgc tccagcagca ggtaccgata ttaccaacca gctgaccaac    660
gtgaccgtgg gcattgatag cggcaccacc gtgtatccgc atcaggcagg ttatgtgaaa    720
ctgaactatg gctttagcgt gccgaacagc gcggtgaaag gcgatacctt taaaattacc    780
gtgccgaaag aactgaacct gaacggcgtg accagcaaag atcaaaatag aactaaagcg    840
aaagtgccgc cgattatggc aggtgatcag gtgctggcga acggcgtgat tgatagcgat    900
ggcaacgtga tttataccct taccgattat gtgaacacca agatgatgt gaaagcgacc    960 ctgaccatgc cagcatatat tgatccggaa aacgtgaaga aaaccggcaa cgtgaccctg    1020
gcgaccggca ttggcagcac caccgcgaac aaaaccgttc tggtggatta tgaaaaatac    1080
ggcaaattct acaacctgag catcaaaggc accatcgatc agatcgataa aaccaacaac    1140
acctatcgtc agaccatttta tgtgaacccg agcggcgata cgtgattgc gccggtgctg    1200 accggcaacc tgaaaccgaa caccgatagc aacgcgctga ttgatcagca gaacaccagc    1260
attaaagtgt ataaagtgga taacgcggcg gatctgagcg aaagctattt tgtgaacccg    1320
gaaaactttg aagatgtgac caacagcgtg aacattacct ttccgaaccc gaaccagtat    1380
aaagtggaat taacacccc ggatgatcag attaccaccc cgtatattgt ggtggtgaac    1440
ggccatattg atccgaacag caaaggcgat ctggcgctgc gtagcaccct gtatggctat    1500
aacagcaaca ttatttggcg tagcatgagc tgggataacg aagtggcgtt taacaacggc    1560
agcggcagcg gcgatggcat tgataaaccg gtggtgccgg aacagccgga tgaaccgggc    1620
gaaattgaac cgattccgga agatggcagc catcatcatc atcatcatta agtcgac       1677

<210> SEQ ID NO 11
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
catatgaaga aaatctggct ggcgctggcg ggcctggtgc tggcgtttag cgctagcgcc     60
gcgagcgaaa acagcgtgac ccagagcgat agcgcgagca cgaaagcaa agcaacgat    120 agcagcagcg tgagcgcggc gccgaaaacc gatgatacca acgtgagcga taccaaaacc    180
agcagcaaca ccaacaacgg cgaaaccagc gtggcgcaga acccggcgca gcaggaaacc    240
acccagagca gcagcaccaa cgcgaccacc gaagaaaccc cggtgaccgg tgaagccacc    300
accaccacca ccaaccaggc caacaccccg gcgaccaccc agagcagcaa caccaacgcg    360
gaagaactgg tgaaccagac cagcaacgaa accacccttta acgataccaa caccgtgagc    420
agcgtgaaca gcccgcagaa cagcaccaac gcggaaaacg tgagcaccac ccaggatacc    480
agcaccgaag cgaccccgag caacaacgaa agcgcgccgc agagcaccga tgcgagcaac    540
aaagatgtgg tgaatcaggc cgttaatacc agcgcgccgc gtatgcgtgc ctttagcctg    600
gcggccgtgg ccgccgatgc tccagcagca ggtaccgata ttaccaacca gctgaccaac    660
gtgaccgtgg gcattgatag cggcaccacc gtgtatccgc atcaggcagg ttatgtgaaa    720
ctgaactatg gctttagcgt gccgaacagc gcggtgaaag gcgatacctt taaaattacc    780
gtgccgaaag aactgaacct gaacggcgtg accagcaccg cgaaagtgcc gccgattatg    840
```

```
gcaggtgatc aggtgctggc gaacggcgtg attgatagcg atggcaacgt gatttatacc    900
tttaccgatt atgtgaacac caaagataaa gatcaaaata gaactaaagt gaaagcgacc    960
ctgaccatgc cagcatatat tgatccggaa aacgtgaaga aaaccggcaa cgtgacccctg   1020 gcgaccggca ttggcagcac caccgcgaac aaaaccgttc tggtggatta tgaaaaatac   1080
ggcaaattct acaacctgag catcaaaggc accatcgatc agatcgataa aaccaacaac   1140
acctatcgtc agaccatttta tgtgaacccg agcggcgata acgtgattgc gccggtgctg   1200
accggcaacc tgaaaccgaa caccgatagc aacgcgctga ttgatcagca gaacaccagc   1260
attaaagtgt ataaagtgga taacgcgcg gatctgagcg aaagctatttt tgtgaacccg   1320 gaaaactttg aagatgtgac caacagcgtg aacattacct ttccgaaccc gaaccagtat   1380
aaagtggaat ttaacaccccc ggatgatcag attaccacccc cgtatattgt ggtggtgaac   1440
ggccatattg atccgaacag caaaggcgat ctggcgctgc gtagcaccct gtatggctat   1500
aacagcaaca ttatttggcg tagcatgagc tgggataacg aagtggcgtt taacaacggc   1560
agcggcagcg gcgatggcat tgataaaccg gtggtgccgg aacagccgga tgaaccgggc   1620
gaaattgaac cgattccgga agatggcagc catcatcatc atcatcatta agtcgac      1677

<210> SEQ ID NO 12
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
catatgaaga aaatctggct ggcgctggcg ggcctggtgc tggcgtttag cgctagcgcc     60
gcgagcgaaa acagcgtgac ccagagcgat agcgcgagca acgaaagcaa agcaacgat    120 agcagcagcg tgagcgcggc gccgaaaacc gatgatacca acgtgagcga taccaaaaccc   180 agcagcaaca ccaacaacgg cgaaaccagc gtggcgcaga accggcgca gcaggaaacc    240 acccagagca gcagcaccaa cgcgaccacc gaagaaaccc cggtgaccgg tgaagccacc    300
accaccacca ccaaccaggc caacacccccg gcgaccaccc agagcagcaa caccaacgcg   360
gaagaactgg tgaaccagac cagcaacgaa accacccttta acgataccaa caccgtgagc   420
agcgtgaaca gcccgcagaa cagcaccaac gcggaaaacg tgagcaccac ccaggatacc    480
agcaccgaag cgaccccgag caacaacgaa agcgcgccgc agagcaccga tgcgagcaac   540
aaagatgtgt tgaatcaggc cgttaatacc agcgcgccgc gtatgcgtgc ctttagcctg   600
gcggccgtgg ccgccgatgc tccagcagca ggtaccgata ttaccaacca gctgaccaac   660
gtgaccgtgg gcattgatag cggcaccacc gtgtatccgc atcaggcagg ttatgtgaaa   720
ctgaactatg gctttagcgt gccgaacagc gcggtgaaag gcgatacctt taaaattacc   780
gtgccgaaag aactgaacct gaacggcgtg accagccacg cgaaagtgcc gccgattatg   840
gcaggtgatc aggtgctggc gaacggcgtg attgatagcg atggcaacgt gatttatacc   900
tttaccgatt atgtgaacac caaagatgat gtgaaagcga ccctgaccat gccagcatat   960
attgatccgg aaaacgtgaa gaaaccggc aacgtgaccc tggcgaccgg cattggcagc   1020
accaccgcga acaaaaccgt tctggtggat tatgaaaaat acggcaaatt ctacaacctg   1080
agcatcaaag gcaccatcga tcagatcgat aaaaccaaca cacctatcg tcagaccatt   1140 tatgtgaacc cgagcggcga taacgtgatt gcgccggtgc tgaccggcaa cctgaaaccg   1200
```

-continued

```
aacaccgata gcaacgcgct gattgatcag cagaacacca gcattaaagt gtataaagtg    1260
gataacgcgg cggatctgag cgaaagctat tttgtgaacc cggaaaactt tgaagatgtg    1320
accaacagcg tgaacattac ctttccgaac ccgaaccagt ataaagtgga atttaacacc    1380
ccggatgatc agattaccac cccgtatatt gtggtggtga acggccatat tgatccgaac    1440
agcaaaggcg atctggcgct gcgtagcacc ctgtatggct ataacagcaa cattatttgg    1500
cgtagcatga gctgggataa cgaagtggcg tttaacaacg gcaaagatca aaatagaact    1560
aaaggcagcg gcgatggcat tgataaaccg gtggtgccgg aacagccgga tgaaccgggc    1620
gaaattgaac cgattccgga agatggcagc catcatcatc atcatcatta agtcgac      1677
```

<210> SEQ ID NO 13
<211> LENGTH: 643
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Lys Lys Ile Trp Leu Ala Leu Ala Gly Leu Val Leu Ala Phe Ser
1               5                   10                  15

Ala Ser Ala Ala Glu Glu Ala Phe Asp Leu Trp Asn Glu Cys Ala Lys
            20                  25                  30

Ala Cys Val Leu Asp Leu Lys Asp Gly Val Arg Ser Ser Arg Met Ser
        35                  40                  45

Val Asp Pro Ala Ile Ala Asp Thr Asn Gly Gln Gly Val Leu His Tyr
    50                  55                  60

Ser Met Val Leu Glu Gly Gly Asn Asp Ala Leu Lys Leu Ala Ile Asp
65                  70                  75                  80

Asn Ala Leu Ser Ile Thr Ser Asp Gly Leu Thr Ile Arg Leu Glu Gly
                85                  90                  95

Gly Val Glu Pro Asn Lys Pro Val Arg Tyr Ser Tyr Thr Arg Gln Ala
            100                 105                 110

Arg Gly Ser Trp Ser Leu Asn Trp Leu Val Pro Ile Gly His Glu Lys
        115                 120                 125

Pro Ser Asn Ile Lys Val Phe Ile His Glu Leu Asn Ala Gly Asn Gln
    130                 135                 140

Leu Ser His Met Ser Pro Ile Tyr Thr Ile Glu Met Gly Asp Glu Leu
145                 150                 155                 160

Leu Ala Lys Leu Ala Arg Asp Ala Thr Phe Phe Val Arg Ala His Glu
                165                 170                 175

Ser Asn Glu Met Gln Pro Thr Leu Ala Ile Ser His Ala Gly Val Ser
            180                 185                 190

Val Val Met Ala Gln Ala Gln Pro Arg Arg Glu Lys Arg Trp Ser Glu
        195                 200                 205

Trp Ala Ser Gly Lys Val Leu Cys Leu Leu Asp Pro Leu Asp Gly Val
    210                 215                 220

Tyr Asn Tyr Leu Ala Gln Gln Arg Cys Asn Leu Asp Asp Thr Trp Glu
225                 230                 235                 240

Gly Lys Ile Tyr Arg Val Leu Ala Gly Asn Pro Ala Lys His Asp Leu
                245                 250                 255

Asp Ile Lys Asp Asn Asn Asn Ser Thr Pro Thr Val Ile Ser His Arg
            260                 265                 270

Leu His Phe Pro Glu Gly Gly Ser Leu Ala Ala Leu Thr Ala His Gln
```

```
            275                 280                 285
Ala Cys His Leu Pro Leu Glu Ala Phe Thr Arg His Arg Gln Pro Arg
290                 295                 300
Gly Trp Glu Gln Leu Glu Gln Cys Gly Tyr Pro Val Gln Arg Leu Val
305                 310                 315                 320
Ala Leu Tyr Leu Ala Ala Arg Leu Ser Trp Asn Gln Val Asp Gln Val
                325                 330                 335
Ile Arg Asn Ala Leu Ala Ser Pro Gly Ser Gly Asp Leu Gly Glu
            340                 345                 350
Ala Ile Arg Glu Gln Pro Glu Gln Ala Arg Leu Ala Leu Thr Leu Ala
            355                 360                 365
Ala Ala Glu Ser Glu Arg Phe Val Arg Gln Gly Thr Gly Asn Asp Glu
370                 375                 380
Ala Gly Ala Ala Ser Ala Asp Val Val Ser Leu Thr Cys Pro Val Ala
385                 390                 395                 400
Lys Asp Gln Asn Arg Thr Lys Gly Glu Cys Ala Gly Pro Ala Asp Ser
                405                 410                 415
Gly Asp Ala Leu Leu Glu Arg Asn Tyr Pro Thr Gly Ala Glu Phe Leu
            420                 425                 430
Gly Asp Gly Asp Val Ser Phe Ser Thr Arg Gly Thr Gln Asn Trp
            435                 440                 445
Thr Val Glu Arg Leu Leu Gln Ala His Arg Gln Leu Glu Glu Arg Gly
450                 455                 460
Tyr Val Phe Val Gly Tyr His Gly Thr Phe Leu Glu Ala Ala Gln Ser
465                 470                 475                 480
Ile Val Phe Gly Gly Val Arg Ala Arg Ser Gln Asp Leu Asp Ala Ile
                485                 490                 495
Trp Arg Gly Phe Tyr Ile Ala Gly Asp Pro Ala Leu Ala Tyr Gly Tyr
            500                 505                 510
Ala Gln Asp Gln Glu Pro Asp Ala Arg Gly Arg Ile Arg Asn Gly Ala
            515                 520                 525
Leu Leu Arg Val Tyr Val Pro Arg Trp Ser Leu Pro Gly Phe Tyr Arg
530                 535                 540
Thr Gly Leu Thr Leu Ala Ala Pro Glu Ala Ala Gly Glu Val Glu Arg
545                 550                 555                 560
Leu Ile Gly His Pro Leu Pro Leu Arg Leu Asp Ala Ile Thr Gly Pro
                565                 570                 575
Glu Glu Glu Gly Gly Arg Val Thr Ile Leu Gly Trp Pro Leu Ala Glu
            580                 585                 590
Arg Thr Val Val Ile Pro Ser Ala Ile Pro Thr Asp Pro Arg Asn Val
            595                 600                 605
Gly Gly Asp Leu Asp Pro Ser Ser Ile Pro Asp Lys Glu Gln Ala Ile
        610                 615                 620
Ser Ala Leu Pro Asp Tyr Ala Ser Gln Pro Gly Lys Pro Pro Arg Glu
625                 630                 635                 640
Asp Leu Lys

<210> SEQ ID NO 14
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 14

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Asp Asn Asn Asn Ser Thr Pro Thr Val Ile Ser His Arg Leu His Phe
                245                 250                 255

Pro Glu Gly Gly Ser Leu Ala Ala Leu Thr Ala His Gln Ala Cys His
            260                 265                 270

Leu Pro Leu Glu Ala Phe Thr Arg His Arg Gln Pro Arg Gly Trp Glu
        275                 280                 285

Gln Leu Glu Gln Cys Gly Tyr Pro Val Gln Arg Leu Val Ala Leu Tyr
    290                 295                 300

Leu Ala Ala Arg Leu Ser Trp Asn Gln Val Asp Gln Val Ile Arg Asn
305                 310                 315                 320

Ala Leu Ala Ser Pro Gly Ser Gly Gly Asp Leu Gly Glu Ala Ile Arg
                325                 330                 335

Glu Gln Pro Glu Gln Ala Arg Leu Ala Leu Thr Leu Ala Ala Ala Glu
            340                 345                 350

Ser Glu Arg Phe Val Arg Gln Gly Thr Gly Asn Asp Glu Ala Gly Ala
        355                 360                 365

Ala Ser Ala Asp Val Val Ser Leu Thr Cys Pro Val Ala Lys Asp Gln
    370                 375                 380

Asn Arg Thr Lys Gly Glu Cys Ala Gly Pro Ala Asp Ser Gly Asp Ala
385                 390                 395                 400

Leu Leu Glu Arg Asn Tyr Pro Thr Gly Ala Glu Phe Leu Gly Asp Gly
                405                 410                 415
```

Gly Asp Val Ser Phe Ser Thr Arg Gly Thr Gln Asn Trp Thr Val Glu
             420                 425                 430

Arg Leu Leu Gln Ala His Arg Gln Leu Glu Glu Arg Gly Tyr Val Phe
         435                 440                 445

Val Gly Tyr His Gly Thr Phe Leu Glu Ala Ala Gln Ser Ile Val Phe
    450                 455                 460

Gly Gly Val Arg Ala Arg Ser Gln Asp Leu Asp Ala Ile Trp Arg Gly
465                 470                 475                 480

Phe Tyr Ile Ala Gly Asp Pro Ala Leu Ala Tyr Gly Tyr Ala Gln Asp
                485                 490                 495

Gln Glu Pro Asp Ala Arg Gly Arg Ile Arg Asn Gly Ala Leu Leu Arg
            500                 505                 510

Val Tyr Val Pro Arg Trp Ser Leu Pro Gly Phe Tyr Arg Thr Gly Leu
        515                 520                 525

Thr Leu Ala Ala Pro Glu Ala Ala Gly Glu Val Glu Arg Leu Ile Gly
    530                 535                 540

His Pro Leu Pro Leu Arg Leu Asp Ala Ile Thr Gly Pro Glu Glu Glu
545                 550                 555                 560

Gly Gly Arg Val Thr Ile Leu Gly Trp Pro Leu Ala Glu Arg Thr Val
                565                 570                 575

Val Ile Pro Ser Ala Ile Pro Thr Asp Pro Arg Asn Val Gly Gly Asp
            580                 585                 590

Leu Asp Pro Ser Ser Ile Pro Asp Lys Glu Gln Ala Ile Ser Ala Leu
        595                 600                 605

Pro Asp Tyr Ala Ser Gln Pro Gly Lys Pro Pro Arg Glu Asp Leu Lys
    610                 615                 620

<210> SEQ ID NO 15
<211> LENGTH: 1148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
taatgaaata cctgctgccg accgctgctg ctggtctgct gctcctcgct gcccagccgg      60
cgatggccat gcatatgagc aaagaagaag caccaaaaat acaaatgccg cctcaacctg     120
taacaaccat gagtgctaaa tctgaagatt taccacttag ttttacttac cctgctaaac     180
ttgtcagtga ttatgatgtc attataaaac ctcaagttag cggcgtaata gtaaataaac     240
tttttaaagc tggagataag gtaaaaaaag gacaaacatt atttattata gaacaagata     300
aatttaaagc tagtgttgat tcagcttacg gacaagcttt aatggctaag caacttccg      360 aaaatgcaag caaggatttt aatcgttcta aagctctttt tagcaaaagt gcaatctctc     420
aaaaagaata cgactcttct cttgctacat ttaacaattc aaaagctagt ctagcaagtg     480
ctagagcaca gcttgcaaat gcaagaattg atctagatca taccgagata aaagctcctt     540
ttgatggtac tataggagat gctttagtta atataggaga ttatgtaagt gcttcaacaa     600
ctgaactagt tagagttaca aatttaaatc ctatttacgc agatttcttt atttcagata     660
cagataaact aaatttagtc cgcaatactc aaagtggaaa atgggattta gacagcattc     720
atgcaaattt aaatcttaat ggagaaaccg ttcaaggcaa actttatttt attgattcgg     780
ttatagatgc taatagtgga acagtaaaag ccaaagccgt atttgataac aataactcaa     840

```
cacttttacc gggtgctttt gcaacaatta cttcagaagg ttttatacaa aaaaatggct        900
ttaaagtgcc tcaaataggt gttaaacaag atcaaaatga tgtttatgtt cttcttgtta        960
aaaatggaaa agtagaaaaa tcttctgtac atataagcta ccaaaacaat gaatacgcca       1020
ttattgacaa aggattgcaa aatggcgata aaatcatttt agataacttt aaaaaaattc       1080
aagttggtag cgaagttaaa gaaattggag cacaactcga gcaccaccac caccaccact       1140
gagtcgac                                                               1148
```

<210> SEQ ID NO 16
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
catatgaaga aaatctggct ggcgctggcg ggcctggtgc tggcgtttag cgctagcgcg         60
gcggatagcg atattaacat taaaaccggc accaccgata ttggcagcaa caccaccgtg        120
aaaaccggcg atctggtgac ctatgataaa gaaaacggca tgctgaaaaa agtgttttat        180
agcttcatcg atgataaaaa ccataacaaa aaactgctgg tgatccgtac caaaggcacc        240
attgcgggcc agtatcgtgt gtatagcgaa gaaggcgcga caaaagcgg cctggcgtgg         300 ccgagcgcgt ttaaagtgca gctgcagctg ccggataacg aagtggcgca gattagcgat        360
tattatccgc gtaacagcat tgataccaaa gaatatatga gcaccctgac ctatggcttt        420
aacggcaacg tgaccggcga tgataccggc aaagatcaaa atagaactaa aattggtgga        480
ctgattggcg cgaacgtgag cattggccat accctgaaat atgtgcagcc ggattttaaa        540
accattctgg aaagcccgac cgataaaaaa gtgggctgga agtgatttt taacaacatg        600 gtgaaccaga ctggggccc gtatgatcgt gatagctgga accggtgta tgcaaccag         660 ctgtttatga aacccgtaa cggcagcatg aaagcggcgg ataactttct ggatccgaac        720
aaagcgagca gcctgctgag cagcggcttt agcccggatt ttgcgaccgt gattaccatg        780
gatcgtaaag cgagcaaaca gcagaccaac attgatgtga tttatgaacg tgtgcgtgat        840
gattatcagc tgcattggac cagcaccaac tggaaaggca ccaacaccaa agataaatgg        900
attgatcgta gcagcgaacg ttataaaatt gattgggaaa agaagaaat gaccaacggc        960 agccatcatc atcatcatca ttaagtcgac                                        990
```

<210> SEQ ID NO 17
<211> LENGTH: 19442
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gaattccctg aggcaattct tctttgatga cggctgatgg tgaggttgac ctggtgaagc         60
tggtcaagga gctttgggtt aacaaggttc tgattcttct gactactctt cttgcattaa        120
tcgggtcttt tacctatgcg tatctgagta agcctgtata tgaatatagg gttgcagtag        180
tgcctcctgc tcttgggtct atcgaaggtt tcaatgttgg tagaagggag aatggcctag        240
atgcatatac tgttagaagt atctatgcga tcttttcgcg caatctgctt tcggatgaga        300
ataaaaaaga gttcttctat aagatatacc ttccccaggt gggtgaggga gcggaaagcg        360
```

```
aagatgagca ggaggagttt tataagaagt tctccaaaga ggtaaagatt gatcctgcta    420
acaagccaga tgcagaccgt tatacggtaa ttgtggaggg cacgaagcga gaggttcttg    480
ctacatgggc acaagctttc gtgcgtttgg ctgcggatcg ggccgtgcat gaggttattg    540
atagtgcagg tagagatttc caggtaagaa atgctgcaat gcagagccgc ataaccgtgc    600
tgcagaatat ggcgaagggc cgccgtgatg atagaattgc acgtttgaag gaggcattgc    660
tgattgcgga gtcgctcaag atagatggcc cgccattaat agaaggggcg tccgagcaac    720
aactctcctc gatcatggat ggtgacttga tgtacatgcg aggagctaag gcgctgcgcg    780
ctgaaatcaa caatcttgag tcgcgtagtg tagatgctcc attcattcct gagttgagaa    840
ctctccaaga gaaactatct tggaactcca gtttgtctgt ggattctgat gcggtggctg    900
tctacaagga gacgaggga ctctcttttt caaatcaacc cattaagccg aagaagattc    960
ttatagttac tataggtact ttggcaggat tgataattgg aattctactc gcagtgctcg   1020
ctggttttat aaggaagctt cgtagcgatg gctctcttcg ctaagttttg atctaaaccc   1080
tgatgccact tactggcatc agggcttact tgttgtagtt gttgaattgt attaggggt    1140 atcgagtaga atgtcaataa ggcggggcgt tttctactcc ggtatatcca tgggcagcaa   1200
ctatcttttg cctcttgctg cgattccttt tctcacgaga acattgtcaa gcgaagcgtt   1260
tggccaattg gtgattgccc aggccgtggc tgtcattcta tgtcaactgg tagactttgg   1320
atttattctg gcaggatcaa gaaaggctgc cattatcgat aacaaagttg aactgtctag   1380
tttcttttct gttgtacaga gtgctagatt cttattgttg ctgctttcac ttttagtgct   1440
ggccattttg gctgtatctt ctattttacc aatccccttg cttgtattgg ttgcggctgc   1500
tcttccggca gtagttggaa attatcttca agcagtatgg ttctttcagg aagagcgct    1560 gtttggatgg ttggcgctta ccaattttt gtctaaggta ttttatttcc tattggtcgt   1620 ttttttttgtc acgaaggatt ctgacccttgt gctggcttcg ttggggtttg gtttttccta   1680
tgtcataggt ggaagtgctc tctgttgtat tttattttct atgggaatac ggtggcgccc   1740
ggttctcgag aaagacagaa ttctcgatat attgcgtgac ggtgctcgat ctttctttc    1800 tctggctttt cttagcttgc acatgcaagt gctcgttgcg gcggttggtg ttgttggtgg   1860
agcctccgcg gccggagtgc tttctactgc ggataaattc cttcgcggga tcgcggctgc   1920
tacttcaccc atagctagcg ctctatttcc gactttttagc aggatgtatg cgagtgccga   1980
cccggcagtc ggcagtttaa gaaggaaagc gctaggtctg atgttactaa tagctattcc   2040
tagttgttta tttctttcct tattttctga atacatttca tatctcctat tcccggaaca   2100
gtccagaggt ctaactgttg taataagaat gttttcgata gtgccagtgt ttgcttgtat   2160
tggtgttctg tatggagggt tgactcttgt tccttctggg tatgatggtg tatatttgcg   2220
agcaattttt tttgcggaat tgggcggggt attaacattt atcctcttgg cgctttgggg   2280
ggatgagctt tttggagcgt ggacgctggt cgttacagag gtctctttgg ggatgggaat   2340 gttttttcctg gccacggtta agttgagaga gaaaagggga ctttgatctt aagatgagga   2400
tagcgattga aaagataatt ggtttgctga aaaccagtc ctctaaagaa tcgaatgtta    2460
agattcatcg cttggcgtat attacaaact caaaatttga tggcaataac tatatagata   2520
gatggtgtaa aatcaggaat tctcacattg gtgaatacag ttatattgga tttggtagtg   2580
attttaataa tgtagaagta ggaagatatt gttcgatatc ttcggatgta aaaattgggt   2640
taggaaaaca tcctacacac tttttttagct catcaccgat ttttttattct aataataatc   2700
```

```
catttaacat aaagcaaaag tttatagact ttaatgacca accaagccgt acaacaatta   2760
aaaatgatgt gtggattggt gcaaatgtaa ttattatgga tggattaaca ataaatactg   2820
gtgcagtcat agcagccggc tcagttgtta ctaaaaatgt aggagcatat gaggttgttg   2880
gtggggttcc tgcaaaagtg attaagaagc gatttgacaa taaaacaatt gaaaaacttt   2940
tggaaagcaa gtggtgggag aaaacgcctg acaaactaaa aggattttcg gttgaatatt   3000
taaataaaaa ggatactagt tatccgtatg atgtgccgga ttatgcgtaa caggaggtgt   3060
acaatgagca ggaggtgtac aatgagaatt ttaaatattg tatcgagtaa tattgttcaa   3120
gacccaaggg tacttaaaca aatagaaaca attaaaggcg ttacgaatga ttataaaatt   3180
gttggaatga ataattcaca agctactaat aggcgattgg aaaatttaga ttgtaattat   3240
cgtttgttag gtagcaaggt agatcccaaa aatattcttt ctaaattaat taagcgtata   3300
agatttgcaa caggtgttat ccgagaaatt aaagctttta aacctgacgt gattcatgca   3360
aatgatttcg acgtattatt aatggtctat ttaagcaatt ataaaaagc taatattgtt   3420
tatgatgcgc atgaaatata tgcgaaaaat gcctttatta ataaagttcc acttatttca   3480
aagtttgtag aaagtataga aaacacata gtaaaacatc gtgttaatgc cttcgtaaca   3540
gtaagtcatg cagcaaaaga atattatcaa tctaaaggat ataagaagga agcgaatgtt   3600
attacgaatg cacctatttt aaatgatagc agagaattta agaaatcga aaactttaaa   3660
gaaatcgtat atcaaggtca aattgtaatg gacagaggat atgaagagtt tattattgct   3720
tcatcagctt ttaaacaaaa tgctccttca ttcataattc gagggtttgg tccgcatgaa   3780
gaagtgataa aagaactgat tagttataac tcggaaaata ttaggttgga taaaccagtt   3840
gaagtaaaag aattggttga taagttagca gaaagtaatg ttggtgttat cttgacgaaa   3900
cctgtatcta ttaattttga atatacagta tctaataaaa ttttttgaatg tatacatgct   3960
ggtttaccag taattttatc tcctgtcaaa gagcatattt atctcaatga aaaatataaa   4020
tttggcattg ttttaaagga agttacgccg ttagaaattg aaaaggcggt tagaaaatta   4080
agagataatc acgatttgtt taatcattta cgtcaaaatg caattaaggc gtctaaaatt   4140
ttgaattggc aaatagaaag tgaacgatta gtagaattat ataaatttga acaaaaactc   4200
atctcagaag aggatctgta aggacccggg gatcctctag caggaggaac tatgaaattt   4260
tttgtacttt gtgcaattat cagcatgaac atatttatag taatctctac atttactaaa   4320
gaagtattag ggttccctat agagccggtg tattactcaa ccatggttgg tatagcatta   4380
attactacgg tgtttgctat ttataagata attgtcacgc aagaaattcc gcgagggtta   4440
atattattaa ttgctatatg tttgctttat ctagcttttt attattttc accagataag   4500
gaagagaaac tagctaaaaa taatattcta ttcttttttaa catgggcagt tccagcggca   4560
attagtggta tttatattaa atatataaac aaggctacgg tagaaagatt ttttaaatta   4620
gtattttttca tatttctat ttcatttatt tttgtaattt taataccaaa acttacaggt   4680
gagataccta gctatatcaa ttttggactt atgaactatc aaaacgcttc gtacctttca   4740
gcatttactg ccggattagg catttatttc attatgaaag gttcagtgaa acataagtgg   4800
atatatgttc tatttacaat aattgatatc cctattgtgt ttataccagg agggcgtgga   4860
ggtgctattt tattaattct ttacggctta tttgcattta tacttattac gtttaaaaga   4920
ggaatacctg ttgcagtaaa aagcattatg tatattttg cattaagcat atctagtgta   4980
ttgatttact ttcttttac aaaaggttcg aatactagaa cattttcata tctacaaggt   5040
ggaacactta atttagaagg tacttctgga agaggaccga tttatgaaaa aggtatttac   5100
```

```
tttattcaac aaagtccgtt attaggctat gggccattta actattataa actaatcgga    5160
aatataccac ataacatcat tattgagttg attctatcat ttggcttatt agggtttttt    5220
atcataatga tttgcatttt gctactagtt tataaaatga ttaggaacta tgatccaaac    5280
actatagatt tactcgttat gtttatagca atctatccaa tcacattatt aatgtttagt    5340
tcaaattatt tagttgtaag tgaattttgg tttgtgttgt tctattttat tacaaaagga    5400
cggcgtcatc atggtgatta taagatgat gatgataaat aagtttaaac aggaggcatc     5460
atggttaaga aagttttat tatggatagc gtaaagacaa taattggtac gttgcttata     5520
gctttaggat tacaatttt agcttatcca attattaatc aacgagtagg taatgaagcg     5580
tttggttcta ttttaacgat ttatacaata ataacaatca cgagtgttgt attaggcaat    5640
acgcttaaca atatacgatt aattaatatg aatctataca aatccaatca ttactactgg    5700
aaatttgtgt cgatactttt aatttcaatt ctgattgaga gtatagcttt aattattgta    5760
tttctttact tttttaattt gaacaccatc gatattatct ttttaattct acttaatatt    5820
ttaatgtgtt taaggattta tctgaatgta ttttttagga tgactttaaa atataatcag    5880
attttgtata ttgctcttat tcaattttta ggtttgctga taggactatt tctatattat    5940
ttaatccaaa actggattgt ttgttttatt accagtgaat tgtttgcaac gatatataca    6000
ttggttaaat tacggggatt aactataggc gagtatcaaa gtgaagataa taatgtggtc    6060
aaagattatg tgatgctact gagtacaaat agccttaata atttgaatct ctacttagat    6120
agattaatct tattaccaat tataggtgga acagctgtaa ctatatcatt tctttcaaca    6180
tttattggga aaatgttagc tacatttctg tatccgatta ataatgtagt actttcatat    6240
atttctgtaa atgaaagcga caatataaag aagcaatatt tgaaaactaa tctatttgct    6300
atagctgcac tatgtttagt catgattata tgttatccaa ttacattaat tattgtctct    6360
ttactgtata acattgattc aagtttatat tcgaagttta ttattttagg taatataggt    6420
gttttattca atgcagtgag tattatgatc caaactttaa atacaaaaca cgcatcaata    6480
acattacaag cgaattatat gacgcttcac acgattacat ttatattcat aactatttta    6540
atgacaattg cgtttggtct aaatggattc ttttggacaa cgctgttcag caacattatt    6600
aagtatgtga ttttaaatat tataggttta aagtctaaat tcattaataa aaaggacgtc    6660
gatagttatc cgtatgatgt gccggattat gcgtaagtgc accatatgaa tatcctcctt    6720
agttcctatt ccgaagttcc tattctctag aaagtatagg aacttcggcg cgcctacctg    6780
tgacggaaga tcacttcgca gaataaataa atcctggtgt ccctgttgat accgggaagc    6840
cctgggccaa ctttggcga aaatgagacg ttgatcggca cgtaagaggt tccaactttc      6900
accataatga aataagatca ctaccgggcg tattttttga gttgtcgaga ttttcaggag    6960
ctaaggaagc taaaatggag aaaaaaatca ctggatatac caccgttgat atatcccaat    7020
ggcatcgtaa agaacatttt gaggcatttc agtcagttgc tcaatgtacc tataaccaga    7080
ccgttcagct ggatattacg gcctttttaa agaccgtaaa gaaaaataag cacaagtttt    7140
atccggcctt tattcacatt cttgcccgcc tgatgaatgc tcatccggaa ttacgtatgg    7200
caatgaaaga cggtgagctg gtgatatggg atagtgttca cccttgttac accgttttcc    7260
atgagcaaac tgaaacgttt tcatcgctct ggagtgaata ccacgacgat ttccggcagt    7320
ttctacacat atattcgcaa gatgtggcgt gttacggtga aaacctggcc tatttcccta    7380
aagggtttat tgagaatatg ttttcgtct cagccaatcc ctgggtgagt ttcaccagtt    7440
```

```
ttgatttaaa cgtggccaat atggacaact tcttcgcccc cgttttcacc atgggcaaat    7500
attatacgca aggcgacaag gtgctgatgc cgctggcgat tcaggttcat catgccgttt    7560
gtgatggctt ccatgtcggc agatgcttaa tgaatacaac agtactgcga tgagtggcag    7620
ggcggggcgt aaggcgcgcc atttaaatga agttcctatt ccgaagttcc tattctctag    7680
aaagtatagg aacttcgaag cagctccagc ctacacgtaa agaggtggtg tatggataag    7740
aactctgttc tgttaattac cggtggaact ggttcctttg gaaatgccgt tttgaagcgt    7800
tttctggata cagatattgg tgaaatacgt gtattcagtc gggatgagaa gaagcaagat    7860
gatatgcgta agtgctatgc tcaccccaag ttgaggtttt atattggaga tgtccgcgac    7920
tatcaaagca ctctgaatgc tactcgcggt gtggactaca ttttccatgc ggctgcattg    7980
aaacaggttc cctcttgtga gttctacccg atggaggctg tgaagaccaa tgtcatcgga    8040
acggaaaatg tcctcgaatc tgctatccag aatgcgtca aaaagtcgt ttgtctgagt    8100
acggataagg cagtttaccc aatcaatgcc atgggtattt caaaggccat gatgaaaaag    8160
gtcatggtcg ccaagtctcg aaacctggaa cgcactccta ccgtaatttg tggcacccgt    8220
tatggtaacg tcatggcttc aaggggctcg gtcattcctc tctttatcga gcaaatgcga    8280
tcaggccagc ctctcacaat cactgatcca aacatgacac gtttcatgat gacgcttacg    8340
gatgccgtag accttgtgct ttatgctttc gagcatggta ccaatggaga tcttttttgta   8400
cagaaagcac cggctgcaac catcgaggtg ctggctcatg cgcttactca attgcttggc    8460
aagaatggtt atcctatcaa tgtaataggt acgcgtcatg gagagaagct ttatgaggcg    8520
cttcttagtc gagaggaaat ggcctgtgct gaagacatgg gtgactatta tcgtatcccc    8580
ccagatttgc gtgatctgaa ctatagtaag tttgtggagc aaggcgagga aaaaattact    8640
catacagagg actataattc tcataatacc aaacgtctgg atatcgaagg aatgaaaaag    8700
ctgttgctga agttggattt cattcgtgct attcagcgtg gcgagagtgc cagtccagag    8760
gaataaacga tgaaagttct tgtaactggc gcgaatggat ttgttggaag gaatctgtgc    8820
gctcatcttg cagagcgggg tggtatcgag gtggtgccat tcacccgcga gagtagtgtt    8880
ggtaatttgc ctgagctaat tcgttccgtc gattttattt ttcatcttgc cggggtcaat    8940
cgtccggaaa aaccagaaga gtttaagatc gggaattccg aactcacgta tgctctgtgt    9000
gaggcggtaa ggtccaatgg acgagccata ccacttcttt atacttcatc cattcaggct    9060
gaggtggata atgagtacgg tttaagcaag cgagccgcag aagagcatct ccaagtgcta    9120
ggtgaggata ttggttgtcc tgtctacata tttcgccttc ctaatgtatt cggtaaatgg    9180
tcgcgtccga attataattc agcggttgcg acttttttgtc ataatattat tcgagatatt    9240
ccgattcaaa ttaacaattc ctcggcagag atcactcttg tatacataga tgatgtggtt    9300
cgcaccttca tgaaagtcat ggatgggaag ctatccaatg cagtttcact acaggtcgag    9360
ccccagtatc agatttctgt tggtgagctc gcagaacaat tgtatgagtt tcgtaatagt    9420
cgaaagtcac tgactaccgc aagggttggc tcgggattga cgcgcgcctt gtactcgact    9480
tatctaagtt tcttgccaga agatagtttt agttacgacg tgccaatgca ttcggatccg    9540
cgtggcacat tcgtcgagat gctgaagacc gcggactctg ccagttctc gttttttacg    9600
gctcatccag gtgttaccag gggcgggcat taccatcact cgaaaaccga aaagtttctg    9660
gttatcaaag ggatggcacg tttcaagttt agaaacatcc tgaccggggc attttacgaa    9720
atttgcacta atggtgaaaa ggcagaaatt gtcgaaacag tacctggatg gactcatgac    9780
attactaatg tcggaactga cgatatggta gtcatgttgt gggctaacga agtatttgat    9840
```

```
cgggaaaatc cggataccta cgcttgttca gtaggcgaag gtgcgtaagg tatagtgaga    9900
taacaatgca gaagctaaaa gtcgttacgg ttgttggaac tcgtcctgag attattcgct    9960
tgtctagggt catggcgaag cttgatcagt actgcgatca tgtacttgtc catactggac   10020
agaattatga ttacgaactt aatgaaatat tttttcagga cctcggtata agaaagccgg   10080
attattttct aaacgccgcc gggtcttccg gggctgaaac gatagggaat gtaataatcg   10140
cagtcgatcg tgttctgggc gaaatagatc ccgatgcgct gctcgtgctg ggtgatacca   10200
atagttgtat ggcggtactg cctgcaaaac ggcgtaagat accgaccttt catatggaag   10260
caggcaatcc ctgtttcgat atgcgtgtgc ctgaagagat aaatcggcgc attgtcgatc   10320
atacagctga tgtaaatttg acctatagta caattgcgcg tgattatctc ttgcgtgaag   10380
gactttctcc agacatggtt atcaagactg gtagccctat gttcgaagtt ctcgagcact   10440
atcgtgacgg gatcgagtcc tccgatattc ttgaaaggct cgggttgaaa acagagcggt   10500
tctttgtcgt gagtgcgcac cgagaggaaa acatagattc ggataagaat ttcttgaagt   10560
tggtttctat gctcaacgct gtggcagaaa agtactcgct gcccgtcatc gtatcaactc   10620
accctagaac aaaaaagaga attgaggcga cggaggcaaa gtttcacgag ggtattaaac   10680
tgctgaaacc cctcggcttt aaggattaca ataaactgca aattacagcc aaggcagtta   10740
tttctgacag tgggaccatc agtgaggagt cttcaatact gaattttccc gctttgaata   10800
ttcgtgaggc tcatgaacgc ccagaaggca tggaagaggc tgtggtgatg atggtcggac   10860
tggattcgga tcgagtacta caagcactcg aggtgttgga gggacagagg cgcgacgcag   10920
agcgcatgtt acgcttggtc gctgactata gcatgcccaa cgtttctgaa aagattgttc   10980
gcatagttca tagctatcgg gactatgtca tgcgaactgt ctggaaaaaa tattaacttg   11040
aggcgtggag ttgatggcaa ggatatttgt ggtttctgag tatgtcggtg ccaatcagaa   11100
ctccacggga tactattggg agaagataat aggaaagatg cagcgggagt ttggtgggct   11160
aaccgtaatt ttcccgctga ccgcaggtga accccgcct gtggtttcac cttccgttga   11220
gcaagaatgc tttaagtttc cgaggagcaa taagaatagg ctcctttcta gaggattggc   11280
gcagattttt caggcgtttc tgttctcagt aaaattgact tctcgtgcca gacgaggaga   11340
tgtggtattg agtggaacca accctgctct tctactgatg acgtttccct tgctaaggta   11400
tgccctcggt ttcaagtggg tgctgctggt gcatgatgtg tttcccgaga acttggtgcc   11460
ggcgggcgtt ctgaagaaag atagtattgc ctaccggctt ctacgtcgtc tcttttcttt   11520
catttactca tccgctgatc gtctagtcgt aataggcgc gatatggaag ctcttatgaa   11580
agagaaggtg aatgacccgc gatctttggt ctttatttcg aattgggcct gtgagaaaga   11640
ggttttccca gtaccgagag aggatgctcc ttttatcaat attcctgaat ggaaaggtaa   11700
aagggttttc caatttttg gtaatgtcgg tcgattacaa ggtatagaaa acatactttc   11760
tgctattcag ttggttaaaa acgagaaggc ggcttttgct tttattggag atggtgcctt   11820
ggtcgacagt gtaaaaaaac acgcgctgga agatcagtgt gctcggttga ggtatttgg    11880
aaggctgcca ttagccgaaa agaatttgg tttggctgcc tgtgacgttg ccttagttac   11940
cttagaagaa ggaatgttcg ggcttggggt tcccagcaag gcatatttct ccatggcagc   12000
agacaaaccg attctagctg tcatggaaaa aggggctgaa atctcccgta taatagatga   12060
gaccggaatc ggttggaact gtccgccgaa tgatccggtt gctttggcaa gattgatcga   12120
tgagatttgt gaactcgact tgtctagttt aggcggagtc ccgcggagtg tccttcagca   12180
```

```
aaattattct gaatatattt cattggaaaa attcgctgcc tgtgttcgac cgcttctgtc   12240
tgagtcgaaa atatgatgaa ggtgctggta accggggcta gcggttttgt cgggagtgcg   12300
ctttgcaggt cgcttgctgc cgcccccttt caggttgtcg acaagtacg atccctgtac    12360 aatcccgtta cggggttga gtatgttcga gcggagctga aagagagcac taagcttgat   12420
gctgcgctgc ggggtgttga atgtgtagtt catctagctg gacgagccca tatctttgga   12480
aggcagcgtg attcactaga tattttcgg aaggtgaatc gcgatgctac tctggcgctt    12540
gctcggcagg cgatcgaagc atctgtaaag cgtttcattt ttgttagttc tattggtgta   12600
aatggcgctt taaccaaaga aaagcccttc gatgagaact ccaagccggc tcctcatgca   12660
gaatatgcga tttcaaagtt tgaggctgaa gtagcgcttc gggagctttt caagcattcc   12720
tcaacagaac ttgttatcgt caggcctcca ctcgtttacg actggaaagc tcctggaaat   12780
ttctcgcgat tgttgaagct ggttgcttcg ggacttcctc ttccatttgg ttgcatagat   12840
aaccgacgaa gttttgtttc tctggataat ttagttgact ttctagcttg ctgtatgacg   12900 caccettctg ctgccggcga actgttttg gtatccgatg gtcaggagat ttctaccaag   12960
caactggtga ctgcgcttgc tgcgggaatg gggcgtcgcc ccatcatgtg gcctgttcct   13020
aggtttattc tgaggtttct taaattagta ggaaagggtg ggttatacac tcagttatgc   13080
tgctcactag aggtcgactc gtcgaaaggc aggcttttgc ttggttggga accccgcaag   13140 agcaccettt ccgcgttgga agatgttggt agaatatatg tcaaacgtac tgaatgatta   13200
tctgcaggcg ctttgctact agcatggcgt accacgcaga acaatcgaat agaaccctgt   13260
tgaaggggtg agagtatttt tggggataaa tttataaatg gaagaatggt atttgttact   13320
cgctgcagct ggggtttcgg gactgcttac aggcctcttg cgtcgttatg ccttagcgag   13380
gagcttactt gacaccccta actctcgaag ttcccatgtc gttcccactc cacgcggagg   13440
aggggtcgcc attgtagtta ctttttgtct catgctgcct atttgggctg tactgggaaa   13500
tatctcatgg gccgtgtcct gggctttact tctcgctggc ggcggggttg ccattattgg   13560
attcatggat gatcacggtc atatcgccgc acgctggcgt ctgctgggac attttagtgc   13620
agccttggtc tcattgtact tttgaatgg cataccacca tttcagattg ttggtgtcag    13680
ttgggacctg ggtggttcg gaggacttct ctttgctttc tatctcgtgt ggttgctgaa    13740
tctctataac ttcatggatg ggatcgatgg acttgctagc cttcaggcca tttttgtctg   13800
tgttggtggg gcattattat actggctgaa tggccaactg acgcaggctt tgctccccttt   13860 atcgctagct tttgccgttt ttggattctt gttctggaat tttccacccc caaaattttt   13920
catgggagat gcgggtagtg gtcttctggg gattgtttta ggaattcttt ccattcatgc   13980
catgtggatg aatacgaatt ttttctgggc atggttggtc ctgttaggcg ttttcatcgt   14040
cgatgcgacc tatacctga ttcgtcgctt gctgagaggg gacaaggtgt atgaggctca   14100
tcgaagccat gcctatcaat acgcaagccg atactatgga aagcatgctc ctgttacgat   14160
tggcgtcacg gcattgaacg tcatctggct cctccctata gccttgttgg tcgggagtgg   14220
gtctctagag cctttgatgg gcatcgtcat agcctacgtc cctctcgttt ttctggcagt   14280
gaggttcaag gcgggtaagc tagagtcgtc cgctcaggcc taaaggagta ggggaatgct   14340
agatcgttta agagtaaagt tgttatccat gcctcgtcgc tggaaacgtt tgcttcaagt   14400
ggctacggat atccttctgg tatggctgtc tctgtggctc gctttgtggg tccgtctagg   14460
cacagacgat atgatcgacg tgttcggcga gcatgcatgg cttttcatca ctgcgccggt   14520
catcgccatt ccactattca ttcgcttcgg catgtatcgc gcggtgatgc gctatctcgg   14580
```

```
taacgacgca ttgatcgcca tcgccaaggc ggtgaccatc tcggctctgg tgctgtcgct    14640
ggtggtgtac tggtatcgtg gcgcgccggc gccggtgccg cgttccctgg tgttcaacta    14700
ctggtggttg agcatgctgc tgatcggcgg cttgcgtctg gccatgcgcc agtatttcat    14760
gggcgactgg tactctgctg tgcagtcggt accatttctc aaccgccagg atggcctgcc    14820
cagggtggtt atctatgggg cggggcggc cggcaaccag ttggttgcgg cgttgcgtct    14880
cggtcgggcg atgcgtccgg tggcgttcat cgatgacgac aagcagatcg ccaaccgggt    14940
cattgccggt ctgcgggtct ataccgccaa gcatatccgc cagatgatcg acgagacggg    15000
cgcgcaggag gttctcctgg cgattccttc cgccactcgg gcccggcgcc gagagattct    15060
cgagtccctg gagccgttcc cgctgcacgt gcgcagcatg cccggcttca tggacctggc    15120
cagcggccgg gtcaaggtgg atgacctgca ggaggtggac atcgctgacc tgctggggcg    15180
cgacagcgtc gcaccgcgca aggagctgct ggaacggtgc atccgcggtc aggtggtgat    15240
ggtgaccggg gcgggcggct ctatcggttc ggaactctgt cggcagatca tgagttgttc    15300
gcctagcgtg ctgatcctgt tcgaacacag cgaatacaac ctctatagca tccatcagga    15360
actggagcgt cggatcaagc gcgagtcgct ttcggtgaac ctgttgccga tcctcggttc    15420
ggtgcgcaat cccgagcgcc tggtggacgt gatgcgtacc tggaaggtca ataccgtcta    15480
ccatgcggcg gcctacaagc atgtgccgat cgtcgagcac aacatcgccg agggcgttct    15540
caacaacgtg ataggcacct tgcatgcggt gcaggccgcg gtgcaggtcg gcgtgcagaa    15600
cttcgtgctg atttccaccg acaaggcggt gcggccgacc aatgtgatgg gcagcaccaa    15660
gcgcctggcg gaaatggtcc ttcaggcgct cagcaacgaa tcggcgccgg tgctgttcgg    15720
cgaccggaag gacgtgcatc acgtcaacaa gacccgtttc accatggtcc gcttcggcaa    15780
cgtcctcggt tcgtccggtt cggtcattcc gctgttccgc gagcagatca agcgcggcgg    15840
cccggtgacg gtcacccacc cgagcatcac ccgttacttc atgaccattc ccgaggcggc    15900
gcagttggtc atccaggccg gttcgatggg gcagggcgga gatgtattcg tgctggacat    15960
ggggccgccg gtgaagatcc tggagctcgc cgagaagatg atccacctgt ccggcctgag    16020
cgtgcgttcc gagcgttcgc cccatggtga catcgccatc gagttcagtg gcctgcgtcc    16080
tggcgagaag ctctacgaag agctgctgat cggtgacaac gtgaatccca ccgaccatcc    16140
gatgatcatg cgggccaacg aggaacacct gagctgggag gccttcaagg tcgtgctgga    16200
gcagttgctg ccgccgtgg agaaggacga ctactcgcgg gttcgccagt tgctgcggga    16260
aaccgtcagc ggctatgcgc ctgacggtga atcgtcgac tggatctatc gccagaggcg    16320
gcgagaaccc tgagtcatcg ttctccggaa aaggccgcct agcggccttt tttgttttct    16380
ccgtacgatg tttccggtgc cggaccagga agcgactgct ttgctgggc tgtcgatcca    16440 ggtgcgttcc acggcgataa ggtggtttcg tggatgggca acatgtcgcg aaggtaaagt    16500
cagccgcatt gttgaattca tcgaaaaacc ggatcagcca caaacgctgg aatcagacat    16560
catggccgtg ggccgttatg tgctttctgc cgatatttgg ccggaacttg aacgcactca    16620
gccaggtgca tggggacgta ttcagctgac tgatgccatt gccgaactgg cgaaaaaaca    16680
gtctgttgac gccatgctga tgactggtga cagctacgac tgtggtaaaa aaatgggtta    16740
tatgcaggcg tttgtgaagt atggactacg caacctgaaa gaaggagcga agttccgcaa    16800
aggtattgag aaaattgctta gcgagtaagt ttaaaaaata gacgccctta tagggcgtaa    16860
taacaaataa cggtagtcaa cattcgacgc ggtgatgcag atatgcccgg aatgctgata    16920
```

```
ccgttttttc attctaaaaa actcatcatt tcattgagtt aactacaaaa tttagcactg   16980 tttttttataa tgtttcttct tgtttctggc atcaattggt aagataatta gtgtttgagt   17040
ttagaggctt tgcggcagag aagcggagct taacacgtct gtgagagtac gcagtgcact   17100
ggtagctgta aagccagtgg cggtagcgtg tttaaataaa tacattagta atactacata   17160
ttacatcatt gtaggctatt taagcgctac atgataagcg acagcgctag caatcaaatc   17220
ttttaaagtt acttctcagg aatagtaaaa ggaggacagc tatgttgaaa aaagagtatt   17280
taaaaaaccc ttatttagtt ttgtttgcga tgattatatt agcttatgtt tttagtgtat   17340
tttgcaggtt ttattgggtt tggtgggcaa gtgagtttaa tgagtatttt ttcaataatc   17400
agttaatgat catttcaaat gatggctatg cttttgctga gggcgcaaga gatatgatag   17460
caggttttca tcagcctaat gatttgagtt attatggatc ttctttatcc gcgcttactt   17520
attggcttta taaaatcaca cctttttctt ttgaaagtat cattttatat atgagtactt   17580
ttttatcttc tttggtggtg attcctacta ttttgctagc taacgaatac aaacgtcctt   17640
taatgggctt tgtagctgct cttttagcaa gtatagcaaa cagttattat aatcgcacta   17700
tgagtgggta ttatgatacg gatatgctgg taattgtttt gcctatgttt atttttatttt   17760 ttatggtaag aatgatttta aaaaaagact tttttttcatt gattgccttg ccgttattta   17820
taggaattta tctttggtgg tatccttcaa gttatacttt aaatgtagct ttaattggac   17880
tttttttaat ttatacactt attttttcata gaaaagaaaa gatttttttat atagctgtga   17940 ttttgtcttc tcttactctt tcaaatatag catggttta tcaaagtgcc attatagtaa   18000
tactttttgc tttattcgcc ttagagcaaa aacgcttaaa ttttatgatt ataggaattt   18060
taggtagtgc aacttgata ttttgattt taagtggtgg ggttgatcct atactttatc   18120
agcttaaatt ttatatttt agaagtgatg aaagtgcgaa tttaacgcag ggctttatgt   18180
attttaatgt caatcaaacc atacaagaag ttgaaaatgt agatcttagc gaatttatgc   18240
gaagaattag tggtagtgaa attgtttttt tgttttcttt gtttggtttt gtatggcttt   18300
tgagaaaaca taaaagtatg attatggctt tacctatatt ggtgcttggg tttttagcct   18360
taaaaggggg gcttagattt accatttatt ctgtacctgt aatggcctta ggatttggtt   18420
ttttattgag cgagtttaag gctataatgg ttaaaaaata tagccaatta acttcaaatg   18480
tttgtattgt ttttgcaact attttgactt tagctccagt atttatccat atttacaact   18540
ataaagcgcc aacagttttt tctcaaaatg aagcatcatt attaaatcaa ttaaaaaata   18600
tagccaatag agaagattat gtggtaactt ggtgggatta tggttatcct gtgcgttatt   18660
atagcgatgt gaaaacttta gtagatggtg gaaagcattt aggtaaggat aattttttcc   18720
cttcttttgc tttaagcaaa gatgaacaag ctgcagctaa tatggcaaga cttagtgtag   18780
aatatacaga aaaaagcttt tatgctccgc aaaatgatat tttaaaaaca gacattttgc   18840
aagccatgat gaaagattat aatcaaagca atgtggattt gtttctagct tcattatcaa   18900
aacctgattt taaaatcgat acgccaaaaa ctcgtgatat ttatctttat atgcccgcta   18960
gaatgtcttt gattttttct acggtggcta gttttttcttt tattaattta gatacaggag   19020
ttttggataa acctttacc tttagcacag cttatccact tgatgttaaa aatggagaaa   19080
tttatcttag caacggagtg gttttaagcg atgatttag aagttttaaa ataggtgata   19140
atgtggtttc tgtaaatagt atcgtagaga ttaattctat taaacaaggt gaatacaaaa   19200
tcactccaat tgatgataag gctcagtttt atatttttta tttaaaggat agtgctattc   19260
cttacgcaca atttatttta atggataaaa ccatgtttaa tagtgcttat gtgcaaatgt   19320
```

| | |
|---|---:|
| tttttttagg aaattatgat aagaatttat ttgacttggt gattaattct agagatgcta | 19380 |
| aggtttttaa acttaaaatt tacccatacg atgttccaga ttacgcttaa acatgtgaat | 19440 |
| tc | 19442 |

<210> SEQ ID NO 18
<211> LENGTH: 19616
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

| | |
|---|---:|
| gaattccctg aggcaattct tctttgatga cggctgatgg tgaggttgac ctggtgaagc | 60 |
| tggtcaagga gctttgggtt aacaaggttc tgattcttct gactactctt cttgcattaa | 120 |
| tcgggtcttt tacctatgcg tatctgagta agcctgtata tgaatatagg gttgcagtag | 180 |
| tgcctcctgc tcttgggtct atcgaaggtt tcaatgttgg tagaagggag aatggcctag | 240 |
| atgcatatac tgttagaagt atctatgcga tcttttcgcg caatctgctt tcggatgaga | 300 |
| ataaaaaga gttcttctat aagatatacc ttccccaggt gggtgaggga gcggaaagcg | 360 |
| aagatgagca ggaggagttt tataagaagt tctccaaaga ggtaaagatt gatcctgcta | 420 |
| acaagccaga tgcagaccgt tataccggtaa ttgtggaggg cacgaagcga gaggttcttg | 480 |
| ctacatgggc acaagctttc gtgcgtttgg ctgcggatcg ggccgtgcat gaggttattg | 540 |
| atagtgcagg tagagatttc caggtaagaa atgctgcaat gcagagccgc ataaccgtgc | 600 |
| tgcagaatat ggcgaagggc cgccgtgatg atagaattgc acgtttgaag gaggcattgc | 660 |
| tgattgcgga gtcgctcaag atagatggcc cgccattaat agaaggggcg tccgagcaac | 720 |
| aactctcctc gatcatggat ggtgacttga tgtacatgcg aggagctaag gcgctgcgcg | 780 |
| ctgaaatcaa caatcttgag tcgcgtagtg tagatgctcc attcattcct gagttgagaa | 840 |
| ctctccaaga gaaactatct tggaactcca gtttgtctgt ggattctgat gcggtggctg | 900 |
| tctacaagga agacgaggga ctctcttttt caaatcaacc cattaagccg aagaagattc | 960 |
| ttatagttac tataggtact ttggcaggat tgataattgg aattctactc gcagtgctcg | 1020 |
| ctggttttat aaggaagctt cgtagcgatg gctctcttcg ctaagttttg atctaaaccc | 1080 |
| tgatgccact tactggcatc agggcttact tgttgtagtt gttgaattgt attaggggt | 1140 |
| atcgagtaga atgtcaataa ggcggggcgt tttctactcc ggtatatcca tgggcagcaa | 1200 |
| ctatcttttg cctcttgctg cgattccttt tctcacgaga acattgtcaa gcgaagcgtt | 1260 |
| tggccaattg gtgattgccc aggccgtggc tgtcattcta tgtcaactgg tagactttgg | 1320 |
| atttattctg gcaggatcaa gaaaggctgc cattatcgat aacaaagttg aactgtctag | 1380 |
| tttcttttct gttgtacaga gtgctagatt cttattgttg ctgctttcac ttttagtgct | 1440 |
| ggccattttg gctgtatctt ctattttacc aatcccttg cttgtattgg ttgcggctgc | 1500 |
| tcttccggca gtagttggaa attatcttca agcagtatgg ttctttcagg gaagagcgct | 1560 |
| gtttggatgg ttggcgctta ccaattttt gtctaaggta ttttatttcc tattggtcgt | 1620 |
| ttttttgtc acgaaggatt ctgaccttgt gctggcttcg ttggggtttg gttttcccta | 1680 |
| tgtcataggt ggaagtgctc tctgttgtat tttattttct atgggaatac ggtggcgccc | 1740 |
| ggttctcgag aaagacagaa ttctcgatat attgcgtgac ggtgctcgat cttttctttc | 1800 |
| tctggctttt cttagcttgc acatgcaagt gctcgttgcg gcggttggtg ttgttggtgg | 1860 |

```
agcctccgcg gccggagtgc tttctactgc ggataaattc cttcgcggga tcgcggctgc    1920
tacttcaccc atagctagcg ctctatttcc gacttttagc aggatgtatg cgagtgccga    1980
cccggcagtc ggcagtttaa gaaggaaagc gctaggtctg atgttactaa tagctattcc    2040
tagttgttta tttcttttct tattttctga atacatttca tatctcctat tcccggaaca    2100
gtccagaggt ctaactgttg taataagaat gttttcgata gtgccagtgt ttgcttgtat    2160
tggtgttctg tatggagggt tgactcttgt tccttctggg tatgatggtg tatatttgcg    2220 agcaatttt tttgcggaat tgggcggggt attaacattt atcctcttgg cgctttgggg    2280
ggatgagctt tttggagcgt ggacgctggt cgttacagag gtctctttgg ggatgggaat    2340 gttttcctg gccacggtta agttgagaga gaaaagggga ctttgatctt aaggcgatcg    2400
ctaggaggac agctatgcgt attgcgattc tgggcgcgac caacattaaa catatgagcc    2460
tgctgagcca ttatctgaac catattgatc tgaacattaa cgaagtggat attatttata    2520
ccgataaata tgatattgaa gaacatattc agggcatcaa caactactac aaatacaaag    2580
tggatatcaa agaagattgg accttcatca agaaagcgat tgcgtattat cgttttcgtc    2640
cgtatgcgat gaaaattctg aaagaaaacc gttatgattt tgtgattgtg tggggcagct    2700
acaccggcca tctgttcaaa agctttctgg aaaaacatta caaaaacaaa ttcatcctga    2760
acatccgtga ttactttttc gaaaacaaca aactgattaa atatcgtatg aagaaaatcg    2820
tggatgcgag ccgtgtgacc accctgagca gcgaaggctt tctgaaattc ctgccgaaaa    2880
gcgaaaaata ccgtatcatc tacagctaca acatgagcat catccgtgaa gcaacgtga    2940 ccgatggctt taaaaaacgt tggccgatta acattggctt tattggcaac gtgcgtttta    3000
acgaaattaa ccagaaactg attaagaac tggcgaacga tagccgtttt catatgcagt    3060
attttggcac cggcagcgaa aaactggaag tgtttgcgcg tgaaaacttt attaacaaca    3120
ttacctttag cggcggcttt gatctgaaag aaacccccgaa atatctgaac gaaattgata    3180
ttctgaacaa cctgtttggc aaccagaaca ttgcgctgga taccgcgctg agcattcgta    3240
tgtattatgc gctgtttctg aacaaaccga ttattaccac cgatgatacc tttaccgcga    3300
ccgaagcgaa caaatttggc ctgggctta gcattaaccc ggaaaacctg aaaggcattg    3360
gcgatgaact gatggattgg tataacaacc tggatgtgat ggatattaac cataaacgtg    3420
aagcgtatcg taacgatgtg attgaaaaca caaacagtt ttatcaggaa attggccgta    3480
tttttaacga agaacagaaa ctgattagcg aagaagatct gtaacgttta acaggagga    3540 cagctatgaa caaatttat aacgtgacca gctatgtgat tgcgattctg atgtttccgt    3600
gcctgatgct gggcgataaa ccgctgctgt ttctggcgcc gattagctat ggcgtgggca    3660
aactgttcat cagcttcagc aacaacccga acttcaaatt cagcaaaatc gtgtacgatg    3720
tgctgggctt tctgcgtctg gtgtttattc cggcgatgat tgtgttttc caggatagca    3780 ccattgataa cctgccgctg ggccaggcgt atttaacca gcggtgatt tatatgagcg    3840 tggaattat tattggcagc ctgtttattc tgattctgag caaactgttc aagcatgaag    3900
ttgtgagccg taacagcttt accctgagcg gcagcagcat ttattatatt gtgtttggcc    3960
tggtgatttg cggcatttt gtggcgtttc cggaagtgcg taaaacatt agctttctga    4020 ttattaaaac cgatgcgatg ggccgtggca ccgaagcgac cagcggcctg aacgtgctgt    4080
ttgtgatgct gtttcagctg gcgctggcgc tgctgtttct gatcatcgcg tacgcgagct    4140 acaaaaata caaagaaaac ccgaaaatca tctacgtggt gctgccgctg gcgattggca    4200
```

```
ttctgaacat tagcctgatt gtgggcgaac gtcgtagcta tcagctgtat accatggtgg    4260
cggtgctgac cgttgtgagc atcctgttta gcaaacataa acgtcgtatc aacatcatca    4320
tcatcagcgt gggcatcttc gtgctggcgc tgatgaccct gtataaagaa ctgtatgtgt    4380
ttaactatag cagctatagc gaagcgctga acagcaccag cgtgagcaac ctgaaaattg    4440 tggatacccct gcagagctat ttttatggcc cgagcaacat tgcggcgagc attgattatc    4500
tgaactatta taacggcagc tttaaacagt atctgtttga taacacccgt gcggtgtttg    4560
gctttaactt tttcctggat aaaaaacagc tgattaccag ccagctgttt aaccagctga    4620
tttatggcag caaacagctg accggccatc tgattagcag cgcgggctat ggcattattt    4680
attttggccc gctgtttttc tacctgaacc tgattgcgaa catcttttc gcgtttctga    4740 gcgaatacat catccgtaaa agccatagcc tggaagtgat cttcatcggc acctacatct    4800
acatgcgtct gattaccagc attttttagcc atccgacccc gctgattacc ctgattagca    4860
tgattctggt ggtgtatgtg attgcgatca tcccgggcat catcatcaag aaattccacca    4920 aaaaagtggg catcgaagat tacaaagatg atgatgataa ataacgttta aacaggagga    4980
cagctatgat tgtgaaaacc tttatgaaaa gcaaaatttt tcgtctgatg aacacccccgc    5040 tgctgctgtt ttataaaaaa gaatatctga ccggctatta ttttgaaaac aaagtggcgg    5100
gctggctgtg ggcgtggaaa gcggtgccat tcaagctgct gggcattaac accagcctgc    5160
cgtttccggc ggatattacc gtgcgtatgc ataaacccgaa caacattgtg tttgataaaa    5220
acgatattca tatttttcag agcccgggca cctattttaa caactttagc gcggtgattt    5280
atattggccg tggcgtgtat attgcgccga acgtgggcat tattaccgcg aaccataaca    5340 ttaaaaaccct gaaaagccat gcgccgggcg aagatgtgaa aattggcaac tatagctgga    5400
ttggcatgaa cagcgtgatt ctgccggggcg tggaactggg cgaacatacc attgtgggcg    5460
cgggcagcgt ggtgaccaaa agctttccgg aaggcaacgt ggtgattggc ggcaacccgg    5520
cgaaaattat taagaaaatc agctatccgt atgatgtgcc ggattatgcg taattaatta    5580
accaggtgca cgaagaaaat tatgagatta ataaattta ttggcgattc gttttaatg    5640 attttaagca gtggcatcgc tcaagtcata ttaatcatca ctaccccaat tattacaaga    5700
ctatattcac ctacagaatt tggtgagttt acaatttttt caaatatcgc aatgatttta    5760
ataccaataa taaatgcaag atacgatttg ttgattgtga ataccaaaaa tgaccgtagt    5820
gctaatatac tttcacaaat cagttttttg atatcattgc ttattttatt aatactgata    5880
ccaatatttg cgattagtgc atgtttatac ccaaacttta tattagattt tattttcatt    5940
attattatgt tgtttttggt aagtttaaca acacattttta caaattatct aaataaggaa    6000
agaaagtata aagtgttaag tttgattaat gtgtttagag ctggatcaat ggctttactt    6060
caaatcattt tcggactttt agcattagga agtttaggat taattattgg ttttttcatta    6120 tcctatatcg caggcattac actaggatat aaaacgttta aaaagcactt taatattgtg    6180
agagataaag aagaaactaa agcattattt ttagaaaata aaaatcagtt agtttattca    6240
acaccatcaa tattattaaa tagtttgtct ttctcggttg ttgtgttctt tataggtatt    6300
ttgtatacca atacagaagt gggtatttat ggtatggcca aagagtact aggcatacca    6360 gtgacaatta tttcattagg gttatcaaaa atatttatgc aacaagccaa tgactattat    6420
attgaacatg gtaacttccg aaatttatta cttaaattta gttccatact ggttatagtt    6480
tctataattc tttatgtgcc actttatttg ttcagtgaag aattagtcaa tatattatta    6540
ggacatagct gggttgacgc aattacagtt ataaaaattg ttatcccatt atttgtttata    6600
```

```
aggctgattg tatcaacggt atcactttct gtgattgtat tacaaaaaca acagttagaa    6660
ttaatactac aagcgttatt tttaataggt actactgcaa catttgttat atcaaaaatg    6720
cttaatttaa cttttttaaa ctttgtatct attaatacaa ttgttttaat cgtatcgtac    6780
atgatatttt tcatagcact ctattatttt gctaaaaata aacagttcaa aaattctagt    6840
tatccgtatg atgtgccgga ttatgcgtaa gtgcaccata tgaatatcct ccttagttcc    6900
tattccgaag ttcctattct ctagaaagta taggaacttc ggcgcgccta cctgtgacgg    6960
aagatcactt cgcagaataa ataaatcctg gtgtccctgt tgataccggg aagccctggg    7020
ccaacttttg gcgaaaatga gacgttgatc ggcacgtaag aggttccaac tttcaccata    7080
atgaaataag atcactaccg ggcgtatttt tgagttgtc gagattttca ggagctaagg     7140
aagctaaaat ggagaaaaaa atcactggat ataccaccgt tgatatatcc caatggcatc    7200
gtaaagaaca ttttgaggca tttcagtcag ttgctcaatg tacctataac cagaccgttc    7260
agctggatat tacggccttt ttaaagaccg taaagaaaaa taagcacaag ttttatccgg    7320
cctttattca cattcttgcc cgcctgatga atgctcatcc ggaattacgt atggcaatga    7380
aagacggtga gctggtgata tgggatagtg ttcacccttg ttacaccgtt ttccatgagc    7440
aaactgaaac gttttcatcg ctctggagtg aataccacga cgatttccgg cagtttctac    7500
acatatattc gcaagatgtg gcgtgttacg gtgaaaacct ggcctatttc cctaaagggt    7560
ttattgagaa tatgtttttc gtctcagcca atccctgggt gagtttcacc agttttgatt    7620
taaacgtggc caatatggac aacttcttcg cccccgtttt caccatgggc aaatattata    7680
cgcaaggcga caaggtgctg atgccgctgg cgattcaggt tcatcatgcc gtttgtgatg    7740
gcttccatgt cggcagatgc ttaatgaata caacagtact gcgatgagtg cagggcggg    7800 gcgtaaggcg cgccatttaa atgaagttcc tattccgaag ttcctattct ctagaaagta    7860
taggaacttc gaagcagctc cagcctacac gtaaagaggt ggtgtatgga taagaactct    7920
gttctgttaa ttaccggtgg aactggttcc tttggaaatg ccgttttgaa gcgttttctg    7980
gatacagata ttggtgaaat acgtgtattc agtcggatg agaagaagca agatgatatg     8040
cgtaagtgct atgctcaccc caagttgagg ttttatattg gagatgtccg cgactatcaa    8100
agcactctga atgctactcg cggtgtggac tacattttcc atgcggctgc attgaaacag    8160
gttccctctt gtgagttcta cccgatggag gctgtgaaga ccaatgtcat cggaacggaa    8220
aatgtcctcg aatctgctat ccagaatggc gtcaaaaaag tcgtttgtct gagtacggat    8280
aaggcagttt acccaatcaa tgccatgggt atttcaaagg ccatgatgga aaaggtcatg    8340
gtcgccaagt ctcgaaacct ggaacgcact cctaccgtaa tttgtggcac ccgttatggt    8400
aacgtcatgc ttcaagggg ctcggtcatt cctctcttta tcgagcaaat gcgatcaggc     8460
cagcctctca caatcactga tccaaacatg acacgtttca tgatgacgct tacggatgcc    8520
gtagaccttg tgctttatgc tttcgagcat ggtaccaatg gagatctttt tgtacagaaa    8580
gcaccggctg caaccatcga ggtgctggct catgcgctta ctcaattgct tggcaagaat    8640
ggttatccta tcaatgtaat aggtacgcgt catggagaga agctttatga ggcgcttctt    8700
agtcgagagg aaatggcctg tgctgaagac atgggtgact attatcgtat ccccccagat    8760
ttgcgtgatc tgaactatag taagtttgtg gagcaaggcg aggaaaaaat tactcataca    8820
gaggactata attctcataa taccaaacgt ctggatatcg aaggaatgaa aaagctgttg    8880
ctgaagttgg atttcattcg tgctattcag cgtggcgaga gtgccagtcc agaggaataa    8940
```

```
acgatgaaag ttcttgtaac tggcgcgaat ggatttgttg gaaggaatct gtgcgctcat    9000
cttgcagagc ggggtggtat cgaggtggtg ccattcaccc gcgagagtag tgttggtaat    9060
ttgcctgagc taattcgttc cgtcgatttt atttttcatc ttgccggggt caatcgtccg    9120
gaaaaaccag aagagtttaa gatcgggaat tccgaactca cgtatgctct gtgtgaggcg    9180
gtaaggtcca atggacgagc cataccactt ctttatactt catccattca ggctgaggtg    9240
gataatgagt acggtttaag caagcgagcc gcagaagagc atctccaagt gctaggtgag    9300
gatattggtt gtcctgtcta catatttcgc cttcctaatg tattcggtaa atggtcgcgt    9360
ccgaattata attcagcggt tgcgactttt tgtcataata ttattcgaga tattccgatt    9420
caaattaaca attcctcggc agagatcact cttgtataca tagatgatgt ggttcgcacc    9480
ttcatgaaag tcatggatgg gaagctatcc aatgcagttt cactacaggt cgagccccag    9540
tatcagattt ctgttggtga gctcgcagaa caattgtatg agtttcgtaa tagtcgaaag    9600
tcactgacta ccgcaagggt tggctcggga ttgacgcgcg ccttgtactc gacttatcta    9660
agtttcttgc cagaagatag ttttagttac gacgtgccaa tgcattcgga tccgcgtggc    9720
acattcgtcg agatgctgaa gaccgcggac tctggccagt tctcgttttt tacggctcat    9780
ccaggtgtta ccaggggcgg gcattaccat cactcgaaaa ccgaaaagtt tctggttatc    9840
aaagggatgg cacgtttcaa gtttagaaac atcctgaccg ggcattttta cgaaatttgc    9900
actaatggtg aaaaggcaga aattgtcgaa acagtacctg gatggactca tgacattact    9960
aatgtcggaa ctgacgatat ggtagtcatg ttgtgggcta acgaagtatt tgatcgggaa   10020
aatccggata cctacgcttg ttcagtaggc gaaggtgcgt aaggtatagt gagataacaa   10080
tgcagaagct aaaagtcgtt acggttgttg gaactcgtcc tgagattatt cgcttgtcta   10140
gggtcatggc gaagcttgat cagtactgcg atcatgtact tgtccatact ggacagaatt   10200
atgattacga acttaatgaa atatttttc aggacctcgg tataagaaag ccggattatt   10260
ttctaaacgc cgccgggtct tccggggctg aaacgatagg gaatgtaata atcgcagtcg   10320
atcgtgttct gggcgaaata gatcccgatg cgctgctcgt gctgggtgat accaatagtt   10380
gtatggcggt actgcctgca aaacggcgta agataccgac cttcatatg gaagcaggca   10440
atcgctgttt cgatatgcgt gtgcctgaag agataaatcg gcgcattgtc gatcatacag   10500
ctgatgtaaa tttgacctat agtacaattg cgcgtgatta tctcttgcgt gaaggacttt   10560
ctccagacat ggttatcaag actggtagcc ctatgttcga agttctcgag cactatcgtg   10620
acgggatcga gtcctccgat attcttgaaa ggctcgggtt gaaaacagag cggttctttg   10680
tcgtgagtgc gcaccgagag gaaaacatag attcggataa gaatttcttg aagttggttt   10740
ctatgctcaa cgctgtggca gaaaagtact cgctgcccgt catcgtatca actcacccta   10800
gaacaaaaaa gagaattgag gcgacggagg caaagtttca cgagggtatt aaactgctga   10860
aaccctcgg ctttaaggat tacaataaac tgcaaattac agccaaggca gttatttctg   10920
acagtgggac catcagtgag gagtcttcaa tactgaattt tcccgctttg aatattcgtg   10980
aggctcatga acgcccagaa ggcatggaag aggctgtggt gatgatggtc ggactggatt   11040
cggatcgagt actacaagca ctcgaggtgt tggagggaca gaggcgcgac gcagagcgca   11100
tgttacgctt ggtcgctgac tatagcatgc ccaacgtttc tgaaaagatt gttcgcatag   11160
ttcatagcta tcgggactat gtcatgcgaa ctgtctggaa aaaatattaa cttgaggcgt   11220
ggagttgatg gcaaggatat ttgtggtttc tgagtatgtc ggtgccaatc agaactccac   11280
gggatactat tgggagaaga taataggaaa gatgcagcgg gagtttggtg ggctaaccgt   11340
```

```
aattttcccg ctgaccgcag gtgaaacccc gcctgtggtt tcaccttccg ttgagcaaga    11400
atgctttaag tttccgagga gcaataagaa taggctcctt tctagaggat tggcgcagat    11460
ttttcaggcg tttctgttct cagtaaaatt gacttctcgt gccagacgag gagatgtggt    11520
attgagtgga accaaccctg ctcttctact gatgacgttt cccttgctaa ggtatgccct    11580
cggtttcaag tgggtgctgc tggtgcatga tgtgtttccc gagaacttgg tgccggcggg    11640
cgttctgaag aaagatagta ttgcctaccg gcttctacgt cgtctctttt ctttcattta    11700
ctcatccgct gatcgtctag tcgtaatagg gcgcgatatg gaagctctta tgaaagagaa    11760
ggtgaatgac ccgcgatctt tggtctttat ttcgaattgg gcctgtgaga aagaggtttt    11820
cccagtaccg agagaggatg ctcctttat caatattcct gaatggaaag gtaaaagggt     11880
tttccaattt tttggtaatg tcggtcgatt acaaggtata gaaaacatac tttctgctat    11940
tcagttggtt aaaaacgaga aggcggcttt tgcttttatt ggagatggtg ccttggtcga    12000
cagtgtaaaa aaacacgcgc tggaagatca gtgtgctcgg ttgaggtatt ttggaaggct    12060
gccattagcc gaaaagaatt ttggtttggc tgcctgtgac gttgccttag ttaccttaga    12120
agaaggaatg ttcgggcttg gggttcccag caaggcatat ttctccatgg cagcagacaa    12180
accgattcta gctgtcatgg aaaaaggggc tgaaatctcc cgtataatag atgagaccgg    12240
aatcggttgg aactgtccgc cgaatgatcc ggttgctttg gcaagattga tcgatgagat    12300
ttgtgaactc gacttgtcta gtttaggcgg agtcccgcgg agtgtccttc agcaaaatta    12360
ttctgaatat atttcattgg aaaaattcgc tgcctgtgtt cgaccgcttc tgtctgagtc    12420
gaaaatatga tgaaggtgct ggtaaccggg gctagcggtt ttgtcgggag tgcgctttgc    12480
aggtcgcttg ctgccgcccc ctttcaggtt gtcggacaag tacgatccct gtacaatccc    12540
gttacggggg ttgagtatgt tcgagcggag ctgaaagaga gcactaagct tgatgctgcg    12600
ctgcggggtg ttgaatgtgt agttcatcta gctggacgag cccatatctt tggaaggcag    12660
cgtgattcac tagatatttt tcggaaggtg aatcgcgatg ctactctggc gcttgctcgg    12720
caggcgatcg aagcatctgt aaagcgtttc attttttgtta gttctattgg tgtaaatggc    12780
gctttaacca aagaaaagcc cttcgatgag aactccaagc cggctcctca tgcagaatat    12840
gcgatttcaa agtttgaggc tgaagtagcg cttcgggagc ttttcaagca ttcctcaaca    12900
gaacttgtta tcgtcaggcc tccactcgtt tacgactgga aagctcctgg aaatttctcg    12960
cgattgttga agctggttgc ttcgggactt cctcttccat ttggttgcat agataaccga    13020
cgaagttttg tttctctgga taatttagtt gactttctag cttgctgtat gacgcacccct   13080
tctgctgccg gcgaactgtt tttggtatcc gatggtcagg agatttctac caagcaactg    13140
gtgactgcgc ttgctgcggg aatggggcgt cgccccatca tgtggcctgt tcctaggttt    13200
attctgaggt ttcttaaatt agtaggaaag ggtgggttat acactcagtt atgctgctca    13260
ctagaggtcg actcgtcgaa aggcaggctt ttgcttggtt gggaaccccg caagagcacc    13320
ctttccgcgt tggaagatgt tggtagaata tatgtcaaac gtactgaatg attatctgca    13380
ggcgctttgc tactagcatg gcgtaccacg cagaacaatc gaatagaacc ctgttgaagg    13440
ggtgagagta ttttttggga taaatttata aatgcgaagaa tggtatttgt tactcgctgc    13500
agctgggggtt tcgggactgc ttacaggcct cttgcgtcgt tatgccttag cgaggagctt    13560
acttgacacc cctaactctc gaagttccca tgtcgttccc actccacgcg gaggaggggt    13620
cgccattgta gttactttt gtctcatgct gcctatttgg gctgtactgg gaaatatctc     13680
```

```
atgggccgtg tcctgggctt tacttctcgc tggcggcggg gttgccatta ttggattcat   13740
ggatgatcac ggtcatatcg ccgcacgctg cgtctgctg ggacatttta gtgcagcctt    13800
ggtctcattg tacttttga atggcatacc accatttcag attgttggtg tcagttggga    13860
cctggggtgg ttcggaggac ttctctttgc tttctatctc gtgtggttgc tgaatctcta   13920
taacttcatg gatgggatcg atggacttgc tagccttcag gccattttg tctgtgttgg    13980
tggggcatta ttatactggc tgaatggcca actgacgcag ctttgctcc ccttatcgct    14040
agcttttgcc gtttttggat tcttgttctg gaattttcca cccccaaaaa ttttcatggg   14100
agatgcgggt agtggtcttc tggggattgt tttaggaatt ctttccattc atgccatgtg   14160
gatgaatacg aattttttct gggcatggtt ggtcctgtta ggcgttttca tcgtcgatgc   14220
gacctatacc ctgattcgtc gcttgctgag aggggacaag gtgtatgagg ctcatcgaag   14280
ccatgcctat caatacgcaa gccgatacta tggaaagcat gctcctgtta cgattggcgt   14340
cacggcattg aacgtcatct ggctcctccc tatagccttg ttggtcggga gtgggtctct   14400
agagcctttg atgggcatcg tcatagccta cgtccctctc gttttctgg cagtgaggtt    14460
caaggcgggt aagctagagt cgtccgctca ggcctaaagg agtaggggaa tgctagatcg   14520
tttaagagta aagttgttat ccatgcctcg tcgctggaaa cgtttgcttc aagtggctac   14580
ggatatcctt ctggtatggc tgtctctgtg gctcgctttt gtggtccgtc taggcacaga   14640
cgatatgatc gacgtgttcg gcgagcatgc atggcttttc atcactgcgc cggtcatcgc   14700
cattccacta ttcattcgct tcggcatgta tcgcgcggtg atgcgctatc tcggtaacga   14760
cgcattgatc gccatcgcca aggcggtgac catctcggct ctggtgctgt cgctggtggt   14820
gtactggtat cgtggcgcgc cggcgccggt gccgcgttcc ctggtgttca actactggtg   14880
gttgagcatg ctgctgatcg gcggcttgcg tctggccatg cgccagtatt tcatgggcga   14940
ctggtactct gctgtgcagt cggtaccatt tctcaaccgc caggatggcc tgcccagggt   15000
ggttatctat ggggcggggg cggccggcaa ccagttggtt gcggcgttgc gtctcggtcg   15060
ggcgatgcgt ccggtggcgt tcatcgatga cgacaagcag atcgccaacc gggtcattgc   15120
cggtctgcgg gtctataccg ccaagcatat ccgccagatg atcgacgaga cgggcgcgca   15180
ggaggttctc ctggcgattc cttccgccac tcgggcccgg cgccgagaga ttctcgagtc   15240
cctggagccg ttcccgctgc acgtgcgcag catgcccggc ttcatggacc tggccagcgg   15300
ccgggtcaag gtgatgacc tgcaggaggt ggacatcgct gacctgctgg ggcgcgacag    15360
cgtcgcaccg cgcaaggagc tgctggaacg gtgcatccgc ggtcaggtgg tgatggtgac   15420
cggggcgggc ggctctatcg gttcggaact ctgtcggcag atcatgagtt gttcgcctag   15480
cgtgctgatc ctgttcgaac acagcgaata caacctctat agcatccatc aggaactgga   15540
gcgtcggatc aagcgcgagt cgctttcggt gaacctgttg ccgatcctcg gttcggtgcg   15600
caatcccgag cgcctggtgg acgtgatgcg tacctggaag gtcaataccg tctaccatgc   15660
ggcggcctac aagcatgtgc cgatcgtcga gcacaacatc gccgagggcg ttctcaacaa   15720
cgtgataggc accttgcatg cggtgcaggc cgcggtgcag gtcggcgtgc agaacttcgt   15780
gctgatttcc accgacaagg cggtgcggcc gaccaatgtg atgggcagca ccaagcgcct   15840
ggcggaaatg gtccttcagg cgctcagcaa cgaatcggcg ccggtgctgt cggcgaccg    15900
gaaggacgtg catcacgtca acaagacccg tttcaccatg gtccgcttcg gcaacgtcct   15960
cggttcgtcc ggttcggtca ttccgctgtt ccgcagcag atcaagcgcg gcggcccggt    16020
gacggtcacc cacccgagca tcacccgtta cttcatgacc attcccgagg cggcgcagtt   16080
```

```
ggtcatccag gccggttcga tggggcaggg cggagatgta ttcgtgctgg acatggggcc   16140
gccggtgaag atcctggagc tcgccgagaa gatgatccac ctgtccggcc tgagcgtgcg   16200
ttccgagcgt tcgccccatg gtgacatcgc catcgagttc agtggcctgc gtcctggcga   16260
gaagctctac gaagagctgc tgatcggtga acgtgaat cccaccgacc atccgatgat    16320
catgcgggcc aacgaggaac acctgagctg ggaggccttc aaggtcgtgc tggagcagtt   16380
gctggccgcc gtgagaagg acgactactc gcgggttcgc cagttgctgc gggaaaccgt    16440
cagcggctat gcgcctgacg gtgaaatcgt cgactggatc tatcgccaga ggcggcgaga   16500
accctgagtc atcgttctcc ggaaaaggcc gcctagcggc cttttttgtt ttctccgtac   16560
gatgtttccg gtgccggacc aggaagcgac tgctttgctg gggctgtcga tccaggtgcg   16620
ttccacggcg ataaggtggt ttcgtggatg ggcaacatgt cgcgaaggta agtcagccg    16680
cattgttgaa ttcatcgaaa aaccggatca gccacaaacg ctggaatcag acatcatggc   16740
cgtgggccgt tatgtgcttt ctgccgatat ttggccggaa cttgaacgca ctcagccagg   16800
tgcatgggga cgtattcagc tgactgatgc cattgccgaa ctggcgaaaa acagtctgt    16860
tgacgccatg ctgatgactg gtgacagcta cgactgtggt aaaaaaatgg ttatatgca    16920
ggcgtttgtg aagtatggac tacgcaacct gaaagaagga gcgaagttcc gcaaaggtat   16980
tgagaaattg cttagcgagt aagtttaaaa aatagacgcc cttatagggc gtaataacaa   17040
ataacggtag tcaacattcg acgcggtgat gcagatatgc ccggaatgct gataccgttt   17100
tttcattcta aaaaactcat catttcattg agttaactac aaaatttagc actgttttt    17160
ataatgtttc ttcttgtttc tggcatcaat tggtaagata attagtgttt gagtttagag   17220
gctttgcggc agagaagcgg agcttaacac gtctgtgaga gtacgcagtg cactggtagc   17280
tgtaaagcca gtggcggtag cgtgtttaaa taaatacatt agtaatacta catattacat   17340
cattgtaggc tatttaagcg ctacatgata agcgacagcg ctagcaatca aatcttttaa   17400
agttacttct caggaatagt aaaaggagga cagctatgtt gaaaaaagag tatttaaaaa   17460
acccttattt agttttgttt gcgatgatta tattagctta tgtttttagt gtattttgca   17520
ggttttattg ggtttggtgg gcaagtgagt ttaatgagta ttttttcaat aatcagttaa   17580
tgatcatttc aaatgatggc tatgcttttg ctgagggcgc aagagatatg atagcaggtt   17640
ttcatcagcc taatgatttg agttattatg gatcttcttt atccgcgctt acttattggc   17700
tttataaaat cacaccttt tcttttgaaa gtatcatttt atatgagt acttttttat     17760
cttctttggt ggtgattcct actatttgc tagctaacga atacaaacgt cctttaatgg    17820
gctttgtagc tgctcttta gcaagtatag caaacagtta ttataatcgc actatgagtg    17880
ggtattatga tacggatatg ctggtaattg ttttgcctat gttatttta tttttatgg     17940
taagaatgat tttaaaaaaa gacttttttt cattgattgc cttgccgtta tttataggaa   18000
tttatctttg gtggtatcct tcaagttata ctttaaatgt agcttaatt ggactttttt    18060
taatttatac acttattttt catagaaaag aaaagatttt ttatatagct gtgattttgt   18120
cttctcttac tctttcaaat atagcatggt tttatcaaag tgccattata gtaatacttt   18180
ttgctttatt cgccttagag caaaaacgct taaattttat gattatagga attttaggta   18240
gtgcaacttt gatattttg attttaagtg gtggggttga tcctatactt tatcagctta    18300
aattttatat ttttagaagt gatgaaagtg cgaatttaac gcagggcttt atgtatttta   18360
atgtcaatca aaccatacaa gaagttgaaa atgtagatct tagcgaattt atgcgaagaa   18420
```

```
ttagtggtag tgaaattgtt tttttgtttt ctttgtttgg ttttgtatgg cttttgagaa    18480
aacataaaag tatgattatg gctttaccta tattggtgct tgggttttta gccttaaaag    18540
gggggcttag atttaccatt tattctgtac ctgtaatggc cttaggattt ggttttttat    18600
tgagcgagtt taaggctata atggttaaaa aatatagcca attaacttca aatgtttgta    18660
ttgttttgc  aactatttg  actttagctc cagtatttat ccatatttac aactataaag    18720
cgccaacagt tttttctcaa aatgaagcat cattattaaa tcaattaaaa aatatagcca    18780
atagagaaga ttatgtggta acttggtggg attatggtta tcctgtgcgt tattatagcg    18840
atgtgaaaac tttagtagat ggtggaaagc atttaggtaa ggataatttt ttcccttctt    18900
ttgctttaag caaagatgaa caagctgcag ctaatatggc aagacttagt gtagaatata    18960
cagaaaaaag cttttatgct ccgcaaaatg atatttaaa  aacagacatt ttgcaagcca    19020
tgatgaaaga ttataatcaa agcaatgtgg atttgtttct agcttcatta tcaaaacctg    19080
attttaaaat cgatacgcca aaaactcgtg atatttatct ttatatgccc gctagaatgt    19140
ctttgatttt ttctacggtg gctagttttt cttttattaa tttagataca ggagttttgg    19200
ataaacctttt tacctttagc acagcttatc cacttgatgt taaaaatgga gaaatttatc    19260
ttagcaacgg agtggtttta agcgatgatt ttagaagttt taaaataggt gataatgtgg    19320
tttctgtaaa tagtatcgta gagattaatt ctattaaaca aggtgaatac aaaatcactc    19380
caattgatga taaggctcag ttttatattt tttatttaaa ggatagtgct attccttacg    19440
cacaattat  tttaatggat aaaaccatgt ttaatagtgc ttatgtgcaa atgttttttt    19500
taggaaatta tgataagaat ttatttgact tggtgattaa ttctagagat gctaaggttt    19560
ttaaacttaa aatttaccca tacgatgttc cagattacgc ttaaacatgt gaattc        19616
```

<210> SEQ ID NO 19
<211> LENGTH: 20597
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
gaattccctg aggcaattct tctttgatga cggctgatgg tgaggttgac ctggtgaagc      60
tggtcaagga gctttgggtt aacaaggttc tgattcttct gactactctt cttgcattaa     120
tcgggtcttt tacctatgcg tatctgagta agcctgtata tgaatatagg gttgcagtag     180
tgcctcctgc tcttgggtct atcgaaggtt tcaatgttgg tagaagggag aatggcctag     240
atgcatatac tgttagaagt atctatgcga tcttttcgcg caatctgctt tcggatgaga     300
ataaaaaaga gttcttctat aagatatacc ttccccaggt gggtgaggga gcggaaagcg     360
aagatgagca ggaggagttt tataagaagt tctccaaaga ggtaaagatt gatcctgcta     420
acaagccaga tgcagaccgt tatacggtaa ttgtggaggg cacgaagcga gaggttcttg     480
ctacatgggc acaagctttc gtgcgtttgg ctgcggatcg ggccgtgcat gaggttattg     540
atagtgcagg tagagatttc caggtaagaa atgctgcaat gcagagccgc ataaccgtgc     600
tgcagaatat ggcgaagggc cgccgtgatg atagaattgc acgttgaag  gaggcattgc     660
tgattgcgga gtcgctcaag atagatggcc cgccattaat agaaggggcg tccgagcaac     720
aactctcctc gatcatggat ggtgacttga tgtacatgcg aggagctaag gcgctgcgcg     780
ctgaaatcaa caatcttgag tcgcgtagtg tagatgctcc attcattcct gagttgagaa     840
```

```
ctctccaaga gaaactatct tggaactcca gtttgtctgt ggattctgat gcggtggctg    900
tctacaagga agacgaggga ctctcttttt caaatcaacc cattaagccg aagaagattc    960
ttatagttac tataggtact ttggcaggat tgataattgg aattctactc gcagtgctcg   1020
ctggttttat aaggaagctt cgtagcgatg gctctcttcg ctaagttttg atctaaaccc   1080
tgatgccact tactggcatc agggcttact tgttgtagtt gttgaattgt attaggggt    1140
atcgagtaga atgtcaataa ggcggggcgt tttctactcc ggtatatcca tgggcagcaa   1200
ctatcttttg cctcttgctg cgattccttt tctcacgaga acattgtcaa gcgaagcgtt   1260
tggccaattg gtgattgccc aggccgtggc tgtcattcta tgtcaactgg tagactttgg   1320
atttattctg gcaggatcaa gaaaggctgc cattatcgat aacaaagttg aactgtctag   1380
tttcttttct gttgtacaga gtgctagatt cttattgttg ctgctttcac ttttagtgct   1440
ggccattttg gctgtatctt ctattttacc aatccccttg cttgtattgg ttgcggctgc   1500
tcttccggca gtagttggaa attatcttca agcagtatgg ttctttcagg aagagcgct   1560
gtttggatgg ttggcgctta ccaattttt gtctaaggta ttttatttcc tattggtcgt   1620
tttttttgtc acgaaggatt ctgacccttgt gctggcttcg ttggggtttg gttttttccta  1680
tgtcataggt ggaagtgctc tctgttgtat tttattttct atgggaatac ggtggcgccc   1740
ggttctcgag aaagacagaa ttctcgatat attgcgtgac ggtgctcgat ctttctttc   1800
tctggctttt cttagcttgc acatgcaagt gctcgttgcg gcggttggtg ttgttggtgg   1860
agcctccgcg gccggagtgc tttctactgc ggataaattc cttcgcggga tcgcggctgc   1920
tacttcaccc atagctagcg ctctatttcc gactttagc aggatgtatg cgagtgccga    1980
cccggcagtc ggcagtttaa gaaggaaagc gctaggtctg atgttactaa tagctattcc   2040
tagttgttta tttcttttct tattttctga atacatttca tatctcctat tcccggaaca   2100
gtccagaggt ctaactgttg taataagaat gttttcgata gtgccagtgt ttgcttgtat   2160
tggtgttctg tatggagggt tgactcttgt tccttctggg tatgatggtg tatatttgcg   2220
agcaattttt tttgcggaat tgggcggggt attaacattt atcctcttgg cgctttgggg   2280
ggatgagctt tttggagcgt ggacgctggt cgttacagag gtctcttttgg ggatgggaat  2340
gttttttcctg gccacggtta agttgagaga gaaaagggga ctttgatctt aagatgagag   2400
tagaaaataa taatgtttct gggcaaaacc atgacccgga acagattgat ttgattgatt   2460
tactagtgca gttgtggcgt ggcaagatga caatcatcat ttccgtcatt gtggctattg   2520
ccctagctat tggatatttg gcagtagcga aggagaaatg gacgtcaaca gcaattatca   2580
ctcagcccga tgtgggcaa attgctggct ataacaatgc catgaatgtt atctatggtc    2640
aggctgcacc gaaagtatcg gatttgcagg agacgttaat tggtcgcttc agttctgcct   2700
tctctgcatt agcagaaacg ctggataatc aggaagaacc agaaaaactt accatcgaac   2760
cttctgttaa gaaccagcaa ttaccattga ctgtttctta tgttgggcaa actgcagagg   2820
gcgcacaaat gaagttggcc caatacattc agcaagttga cgataaagtg aatcaagagt   2880
tagaaaagga tctcaaggac aacattgctc tgggacggaa aaacttgcag gactctttaa   2940
gaacgcagga agtggttgcg caggagcaga aagatctgcg tatccgtcag attcaggaag   3000
cgttgcagta tgcgaatcag gcgcaggtga caaaaccgca gattcaacag actggcgaag   3060
atatcacaca agatacgttg ttccttttgg ggagcgaagc gctggagtcg atgattaagc   3120
atgaggcgac ccgtccgttg gtgttctcac caaactacta tcagactcgt caaaacctgc   3180
ttgatatcga aagcttaaag gttgatgatc ttgatattca tgcttaccgc tatgtaatga   3240
```

```
aaccgacgtt acctattcgt cgtgatagcc cgaaaaaggc aattaccttg attctggcgg    3300
tgctgctggg tggcatggtt ggcgcgggga ttgtgctggg gcgtaatgct ctacgcaatt    3360
acaacgcgaa gtaagcgatc gctaggagga cagctatgcg tattgcgatt ctgggcgcga    3420
ccaacattaa acatatgagc ctgctgagcc attatctgaa ccatattgat ctgaacatta    3480
acgaagtgga tattatttat accgataaat atgatattga agaacatatt cagggcatca    3540
acaactacta caaatacaaa gtggatatca agaagattg gaccttcatc aagaaagcga    3600
ttgcgtatta tcgttttcgt ccgtatgcga tgaaaattct gaaagaaaac cgttatgatt    3660
ttgtgattgt gtggggcagc tacaccggcc atctgttcaa aagctttctg gaaaaacatt    3720
acaaaaacaa attcatcctg aacatccgtg attactttt cgaaaacaac aaactgatta    3780
aatatcgtat gaagaaaatc gtggatgcga gccgtgtgac caccctgagc agcgaaggct    3840
ttctgaaatt cctgccgaaa agcgaaaaat accgtatcat ctacagctac aacatgagca    3900
tcatccgtga aagcaacgtg accgatggct ttaaaaaacg ttggccgatt aacattggct    3960
ttattggcaa cgtgcgtttt aacgaaatta ccagaaact gattaaagaa ctggcgaacg    4020
atagccgttt tcatatgcag tatttttggca ccggcagcga aaaactggaa gtgtttgcgc    4080
gtgaaaactt tattaacaac attcccttta gcggcggctt tgatctgaaa gaaacccga    4140 aatatctgaa cgaaattgat attctgaaca acctgtttgg caaccagaac attgcgctgg    4200
ataccgcgct gagcattcgt atgtattatg cgctgttct gaacaaaccg attattacca    4260
ccgatgatac ctttaccgcg accgaagcga acaaatttgg cctgggcttt agcattaacc    4320
cggaaaacct gaaaggcatt ggcgatgaac tgatggattg gtataacaac ctggatgtga    4380
tggatattaa cataaacgt gaagcgtatc gtaacgatgt gattgaaac aacaaacagt    4440 tttatcagga aattggccgt atttttaacg aagaacagaa actgattagc gaagaagatc    4500
tgtaacgttt aaacaggagg acagctatga acaaaattta taacgtgacc agctatgtga    4560
ttgcgattct gatgtttccg tgcctgatgc tgggcgataa accgctgctg tttctggcgc    4620
cgattagcta tggcgtgggc aaactgttca tcagcttcag caacaacccg aacttcaaat    4680
tcagcaaaat cgtgtacgat gtgctgggct ttctgcgtct ggtgtttatt ccggcgatga    4740
ttgtgttttt ccaggatagc accattgata acctgccgct gggccaggcg tatttaaccc    4800
aggcggtgat ttatatgagc gtggaattta ttattggcag cctgtttatt ctgattctga    4860
gcaaactgtt caagcatgaa gttgtgagcc gtaacagctt taccctgagc ggcagcagca    4920
tttattatat tgtgttggc ctggtgattt gcggcatttt tgtggcgttt ccggaagtgc    4980
gtaaaaacat tagctttctg attattaaaa ccgatgcgat gggccgtggc accgaagcga    5040
ccagcggcct gaacgtgctg tttgtgatgc tgtttcagct ggcgctggcg ctgctgtttc    5100
tgatcatcgc gtacgcgagc tacaaaaaat acaaagaaaa cccgaaaatc atctacgtgg    5160
tgctgccgct ggcgattggc attctgaaca ttagcctgat tgtgggcgaa cgtcgtagct    5220
atcagctgta taccatggtg gcggtgctga ccgttgtgag catcctgttt agcaaacata    5280
aacgtcgtat caacatcatc atcatcagcg tgggcatctt cgtgctggcg ctgatgaccc    5340
tgtataaaga actgtatgtg tttaactata gcagctatag cgaagcgctg aacagcacca    5400
gcgtgagcaa cctgaaaatt gtggataccc tgcagagcta ttttatggc ccgagcaaca    5460 ttgcggcgag cattgattat ctgaactatt ataacgcgca ctttaaacag tatctgtttg    5520
ataacacccg tgcggtgttt ggctttaact tttttcctgga taaaaaacag ctgattacca    5580
```

```
gccagctgtt taaccagctg atttatggca gcaaacagct gaccggccat ctgattagca    5640
gcgcgggcta tggcattatt tattttggcc cgctgttttt ctacctgaac ctgattgcga    5700
acatcttttt cgcgtttctg agcgaataca tcatccgtaa aagccatagc ctggaagtga    5760
tcttcatcgg cacctacatc tacatgcgtc tgattaccag cattttttagc catccgaccc    5820
cgctgattac cctgattagc atgattctgg tggtgtatgt gattgcgatc atcccgggca    5880
tcatcatcaa gaaattcacc aaaaaagtgg gcatcgaaga ttacaaagat gatgatgata    5940
aataacgttt aaacaggagg acagctatga ttgtgaaaac ctttatgaaa agcaaaattt    6000
ttcgtctgat gaacaccccg ctgctgctgt tttataaaaa agaatatctg accggctatt    6060
attttgaaaa caaagtggcg ggctggctgt gggcgtggaa agcggtgcca ttcaagctgc    6120
tgggcattaa caccagcctg ccgtttccgg cggatattac cgtgcgtatg cataacccga    6180
acaacattgt gtttgataaa aacgatattc atattttttca gagcccgggc acctatttta    6240
acaactttag cgcggtgatt tatattggcc gtggcgtgta tattgcgccg aacgtgggca    6300
ttattaccgc gaaccataac attaaaaacc tgaaaagcca tgcgccgggc gaagatgtga    6360
aaattggcaa ctatagctgg attggcatga acagcgtgat tctgccgggc gtggaactgg    6420
gcgaacatac cattgtgggc gcgggcagcg tggtgaccaa aagctttccg gaaggcaacg    6480
tggtgattgg cggcaacccg gcgaaaatta ttaagaaaat cagctatccg tatgatgtgc    6540
cggattatgc gtaattaatt aaccaggtgc acgaagaaaa ttatgagatt aaataaattt    6600
attggcgatt cgttttttaat gattttaagc agtggcatcg ctcaagtcat attaatcatc    6660
actaccccaa ttattacaag actatattca cctacagaat ttggtgagtt acaattttt    6720
tcaaatatcg caatgatttt aataccaata ataaatgcaa gatacgattt gttgattgtg    6780
aataccaaaa atgaccgtag tgctaatata ctttcacaaa tcagttttttt gatatcattg    6840
cttattttat taatactgat accaatatttt gcgattagtg catgtttata cccaaacttt    6900
atattagatt ttatttttcat tattattatg ttgttttttgg taagtttaac aaacattttt    6960
acaaattatc taaataagga agaaagtat aaagtgttaa gtttgattaa tgtgtttaga    7020
gctggatcaa tggctttact tcaaatcatt ttcggacttt tagcattagg aagtttagga    7080
ttaattattg gttttttcatt atcctatatc gcaggcatta cactaggata taaaacgttt    7140
aaaaagcact ttaatattgt gagagataaa gaagaaacta aagcattatt tttagaaaat    7200
aaaaatcagt tagtttattc aacaccatca atattattaa atagtttgtc tttctcggtt    7260
gttgtgttct ttataggtat tttgtatacc aatacagaag tgggtatta tggtatggcc    7320
ataagagtac taggcatacc agtgacaatt atttcattag ggttatcaaa atatttatg    7380
caacaagcca atgactatta tattgaacat ggtaacttcc gaaatttatt acttaaattt    7440
agttccatac tggttatagt ttctataatt ctttatgtgc cactttattt gttcagtgaa    7500
gaattagtca atatattatt aggacatagc tgggttgacg caattacagt tataaaaatt    7560
gttatcccat tatttgttat aaggctgatt gtatcaacgg tatcactttc tgtgattgta    7620
ttacaaaaac aacagttaga attaatacta caagcgttat ttttaatagg tactactgca    7680
acatttgtta tatcaaaaat gcttaattta acttttttaa actttgtatc tattaataca    7740
attgttttaa tcgtatcgta catgatattt ttcatagcac tctattattt tgctaaaaat    7800
aaacagttca aaaattctag ttatccgtat gatgtgccgg attatgcgta agtgcaccat    7860
atgaatatcc tccttagttc ctattccgaa gttcctattc tctagaaagt ataggaactt    7920
cggcgcgcct acctgtgacg gaagatcact tcgcagaata aataaatcct ggtgtccctg    7980
```

```
ttgataccgg gaagccctgg gccaactttt ggcgaaaatg agacgttgat cggcacgtaa    8040
gaggttccaa ctttcaccat aatgaaataa gatcactacc gggcgtattt tttgagttgt    8100
cgagattttc aggagctaag gaagctaaaa tggagaaaaa aatcactgga tataccaccg    8160
ttgatatatc ccaatggcat cgtaaagaac attttgaggc atttcagtca gttgctcaat    8220
gtacctataa ccagaccgtt cagctggata ttacggcctt tttaaagacc gtaaagaaaa    8280
ataagcacaa gttttatccg gcctttattc acattcttgc ccgcctgatg aatgctcatc    8340
cggaattacg tatggcaatg aaagacggtg agctggtgat atgggatagt gttcacccct    8400
gttacaccgt tttccatgag caaactgaaa cgttttcatc gctctggagt gaataccacg    8460
acgatttccg gcagtttcta cacatatatt cgcaagatgt ggcgtgttac ggtgaaaacc    8520
tggcctattt ccctaaaggg tttattgaga atatgttttt cgtctcagcc aatccctggg    8580
tgagtttcac cagttttgat ttaaacgtgg ccaatatgga caacttcttc gcccccgttt    8640
tcaccatggg caaatattat acgcaaggcg acaaggtgct gatgccgctg gcgattcagg    8700
ttcatcatgc cgtttgtgat ggcttccatg tcggcagatg cttaatgaat acaacagtac    8760
tgcgatgagt ggcagggcgg ggcgtaaggc gcgccattta aatgaagttc ctattccgaa    8820
gttcctattc tctagaaagt ataggaactt cgaagcagct ccagcctaca cgtaaagagg    8880
tggtgtatgg ataagaactc tgttctgtta attaccggtg gaactggttc ctttggaaat    8940
gccgttttga agcgttttct ggatacagat attggtgaaa tacgtgtatt cagtcgggat    9000
gagaagaagc aagatgatat gcgtaagtgc tatgctcacc ccaagttgag gttttatatt    9060
ggagatgtcc gcgactatca aagcactctg aatgctactc gcggtgtgga ctacattttc    9120
catgcggctg cattgaaaca ggttccctct tgtgagttct acccgatgga ggctgtgaag    9180
accaatgtca tcggaacgga aaatgtcctc gaatctgcta tccagaatgg cgtcaaaaaa    9240
gtcgtttgtc tgagtacgga taaggcagtt tacccaatca atgccatggg tatttcaaag    9300
gccatgatgg aaaaggtcat ggtcgccaag tctcgaaacc tggaacgcac tcctaccgta    9360
atttgtggca cccgttatgg taacgtcatg gcttcaaggg gctcggtcat tcctctcttt    9420
atcgagcaaa tgcgatcagg ccagcctctc acaatcactg atccaaacat gacacgtttc    9480
atgatgacgc ttacggatgc cgtagacctt gtgctttatg ctttcgagca tggtaccaat    9540
ggagatcttt ttgtacagaa agcaccggct gcaaccatcg aggtgctggc tcatgcgctt    9600
actcaattgc ttggcaagaa tggttatcct atcaatgtaa taggtacgcg tcatggagag    9660
aagctttatg aggcgcttct tagtcgagag gaaatggcct gtgctgaaga catgggtgac    9720
tattatcgta tcccccaga tttgcgtgat ctgaactata gtaagtttgt ggagcaaggc    9780
gaggaaaaaa ttactcatac agaggactat aattctcata ataccaaacg tctggatatc    9840
gaaggaatga aaaagctgtt gctgaagttg gatttcattc gtgctattca gcgtggcgag    9900
agtgccagtc cagaggaata aacgatgaaa gttcttgtaa ctggcgcgaa tggatttgtt    9960
ggaaggaatc tgtgcgctca tcttgcagag cggggtggta tcgaggtggt gccattcacc    10020
cgcgagagta tgttggtaa tttgcctgag ctaattcgtt ccgtcgattt tattttcat    10080 cttgccgggg tcaatcgtcc ggaaaaacca gaagagttta agatcgggaa ttccgaactc    10140
acgtatgctc tgtgtgaggc ggtaaggtcc aatggacgag ccataccact tctttatact    10200
tcatccattc aggctgaggt ggataatgag tacggtttaa gcaagcgagc cgcagaagag    10260
catctccaag tgctaggtga ggatattggt tgtcctgtct acatatttcg ccttcctaat    10320
```

| | | | | | |
|---|---|---|---|---|---|
| gtattcggta | aatggtcgcg | tccgaattat | aattcagcgg | ttgcgacttt | ttgtcataat | 10380 |
| attattcgag | atattccgat | tcaaattaac | aattcctcgg | cagagatcac | tcttgtatac | 10440 |
| atagatgatg | tggttcgcac | cttcatgaaa | gtcatggatg | ggaagctatc | caatgcagtt | 10500 |
| tcactacagg | tcgagcccca | gtatcagatt | tctgttggtg | agctcgcaga | acaattgtat | 10560 |
| gagtttcgta | atagtcgaaa | gtcactgact | accgcaaggg | ttggctcggg | attgacgcgc | 10620 |
| gccttgtact | cgacttatct | aagtttcttg | ccagaagata | gttttagtta | cgacgtgcca | 10680 |
| atgcattcgg | atccgcgtgg | cacattcgtc | gagatgctga | agaccgcgga | ctctggccag | 10740 |
| ttctcgtttt | ttacggctca | tccaggtgtt | accaggggcg | ggcattacca | tcactcgaaa | 10800 |
| accgaaaagt | ttctggttat | caaagggatg | gcacgtttca | agtttagaaa | catcctgacc | 10860 |
| ggggcatttt | acgaaatttg | cactaatggt | gaaaaggcag | aaattgtcga | aacagtacct | 10920 |
| ggatggactc | atgacattac | taatgtcgga | actgacgata | tggtagtcat | gttgtgggct | 10980 |
| aacgaagtat | ttgatcggga | aaatccggat | acctacgctt | gttcagtagg | cgaaggtgcg | 11040 |
| taaggtatag | tgagataaca | atgcagaagc | taaaagtcgt | tacggttgtt | ggaactcgtc | 11100 |
| ctgagattat | tcgcttgtct | agggtcatgg | cgaagcttga | tcagtactgc | gatcatgtac | 11160 |
| ttgtccatac | tggacagaat | tatgattacg | aacttaatga | aatatttttt | caggacctcg | 11220 |
| gtataagaaa | gccggattat | tttctaaacg | ccgccgggtc | ttccggggct | gaaacgatag | 11280 |
| ggaatgtaat | aatcgcagtc | gatcgtgttc | tgggcgaaat | agatcccgat | gcgctgctcg | 11340 |
| tgctgggtga | taccaatagt | tgtatggcgg | tactgcctgc | aaaacggcgt | aagataccga | 11400 |
| cctttcatat | ggaagcaggc | aatcgctgtt | tcgatatgcg | tgtgcctgaa | gagataaatc | 11460 |
| ggcgcattgt | cgatcataca | gctgatgtaa | atttgaccta | tagtacaatt | gcgcgtgatt | 11520 |
| atctcttgcg | tgaaggactt | tctccagaca | tggttatcaa | gactggtagc | cctatgttcg | 11580 |
| aagttctcga | gcactatcgt | gacgggatcg | agtcctccga | tattcttgaa | aggctcgggt | 11640 |
| tgaaaacaga | gcggttcttt | gtcgtgagtg | cgcaccgaga | ggaaaacata | gattcggata | 11700 |
| agaatttctt | gaagttggtt | tctatgctca | acgctgtggc | agaaaagtac | tcgctgcccg | 11760 |
| tcatcgtatc | aactcaccct | agaacaaaaa | agagaattga | ggcgacggag | gcaaagtttc | 11820 |
| acgagggtat | taaactgctg | aaacccctcg | gctttaagga | ttacaataaa | ctgcaaatta | 11880 |
| cagccaaggc | agttatttct | gacagtggga | ccatcagtga | ggagtcttca | atactgaatt | 11940 |
| ttcccgcttt | gaatattcgt | gaggctcatg | aacgcccaga | aggcatggaa | gaggctgtgg | 12000 |
| tgatgatggt | cggactggat | tcggatcgag | tactacaagc | actcgaggtg | ttggagggac | 12060 |
| agaggcgcga | cgcagagcgc | atgttacgct | tggtcgctga | ctatagcatg | cccaacgttt | 12120 |
| ctgaaaagat | tgttcgcata | gttcatagct | atcgggacta | tgtcatgcga | actgtctgga | 12180 |
| aaaaatatta | acttgaggcg | tggagttgat | ggcaaggata | tttgtggttt | ctgagtatgt | 12240 |
| cggtgccaat | cagaactcca | cgggatacta | ttgggagaag | ataataggaa | agatgcagcg | 12300 |
| ggagtttggt | gggctaaccg | taattttccc | gctgaccgca | ggtgaaaccc | cgcctgtggt | 12360 |
| ttcaccttcc | gttgagcaag | aatgctttaa | gtttccgagg | agcaataaga | ataggctcct | 12420 |
| ttctagagga | ttggcgcaga | tttttcaggc | gtttctgttc | tcagtaaaat | tgacttctcg | 12480 |
| tgccagacga | ggagatgtgg | tattgagtgg | aaccaaccct | gctcttctac | tgatgacgtt | 12540 |
| tcccttgcta | aggtatgccc | tcggtttcaa | gtgggtgctg | ctggtgcatg | atgtgtttcc | 12600 |
| cgagaacttg | gtgccggcgg | gcgttctgaa | gaaagatagt | attgcctacc | ggcttctacg | 12660 |
| tcgtctcttt | tctttcattt | actcatccgc | tgatcgtcta | gtcgtaatag | ggcgcgatat | 12720 |

```
ggaagctctt atgaaagaga aggtgaatga cccgcgatct ttggtcttta tttcgaattg  12780
ggcctgtgag aaagaggttt tcccagtacc gagagaggat gctccttta tcaatattcc  12840
tgaatggaaa ggtaaaaggg ttttccaatt ttttggtaat gtcggtcgat tacaaggtat  12900
agaaaacata ctttctgcta ttcagttggt taaaaacgag aaggcggctt ttgctttat   12960
tggagatggt gccttggtcg acagtgtaaa aaaacacgcg ctggaagatc agtgtgctcg  13020
gttgaggtat tttggaaggc tgccattagc cgaaaagaat tttggtttgg ctgcctgtga  13080
cgttgcctta gttaccttag aagaaggaat gttcgggctt ggggttccca gcaaggcata  13140
tttctccatg gcagcagaca aaccgattct agctgtcatg gaaaaagggg ctgaaatctc  13200
ccgtataata gatgagaccg gaatcggttg gaactgtccg ccgaatgatc cggttgcttt  13260
ggcaagatta tcgatgaga tttgtgaact cgacttgtct agtttaggcg gagtcccgcg  13320
gagtgtcctt cagcaaaatt attctgaata tatttcattg gaaaaattcg ctgcctgtgt  13380
tcgaccgctt ctgtctgagt cgaaaatatg atgaaggtgc tggtaaccgg ggctagcggt  13440
tttgtcggga gtgcgctttg caggtcgctt gctgccgccc cctttcaggt tgtcggacaa  13500
gtacgatccc tgtacaatcc cgttacgggg gttgagtatg ttcgagcgga gctgaaagag  13560
agcactaagc ttgatgctgc gctgcggggt gttgaatgtg tagttcatct agctggacga  13620
gcccatatct ttggaaggca gcgtgattca ctagatattt ttcggaaggt gaatcgcgat  13680
gctactctgg cgcttgctcg gcaggcgatc gaagcatctg taaagcgttt cattttgtt   13740
agttctattg gtgtaaatgg cgctttaacc aaagaaaagc ccttcgatga gaactccaag  13800
ccggctcctc atgcagaata tgcgatttca agtttgagg ctgaagtagc gcttcgggag   13860
cttttcaagc attcctcaac agaacttgtt atcgtcaggc ctccactcgt ttacgactgg  13920
aaagctcctg gaaatttctc gcgattgttg aagctggttg cttcgggact tcctcttcca  13980
tttggttgca tagataaccg acgaagtttt gtttctctgg ataatttagt tgactttcta  14040
gcttgctgta tgacgcaccc ttctgctgcc ggcgaactgt ttttggtatc cgatggtcag  14100
gagatttcta ccaagcaact ggtgactgcg cttgctgcgg gaatggggcg tcgcccatc   14160
atgtggcctg ttcctaggtt tattctgagg tttcttaaat tagtaggaaa gggtgggtta  14220
tacactcagt tatgctgctc actagaggtc gactcgtcga aaggcaggct tttgcttggt  14280
tgggaacccc gcaagagcac cctttccgcg ttggaagatg ttggtagaat atatgtcaaa  14340
cgtactgaat gattatctgc aggcgctttg ctactagcat ggcgtaccac gcagaacaat  14400
cgaatagaac cctgttgaag gggtgagagt atttttgggg ataaatttat aaatggaaga  14460
atggtatttg ttactcgctg cagctggggt ttcgggactg cttacaggcc tcttgcgtcg  14520
ttatgcctta gcgaggagct tacttgacac ccctaactct cgaagttccc atgtcgttcc  14580
cactccacgc ggaggagggg tcgccattgt agttactttt tgtctcatgc tgcctatttg  14640
ggctgtactg gaaatatct catgggccgt gtcctgggct ttacttctcg ctggcggcg    14700
ggttgccatt attggattca tggatgatca cggtcatatc gccgcacgct ggcgtctgct  14760
gggacatttt agtgcagcct tggtctcatt gtacttttg aatggcatac caccatttca   14820
gattgttggt gtcagttggg acctggggtg gttcggagga cttctctttg cttctatct   14880
cgtgtggttg ctgaatctct ataacttcat ggatgggatc gatggacttg ctagccttca  14940
ggccattttt gtctgtgttg gtggggcatt attatactgg ctgaatggcc aactgacgca  15000
ggctttgctc cccttatcgc tagcttttgc cgttttgga ttcttgttct ggaatttcc    15060
```

```
accccccaaaa attttcatgg gagatgcggg tagtggtctt ctggggattg ttttaggaat    15120
tctttccatt catgccatgt ggatgaatac gaattttttc tgggcatggt tggtcctgtt    15180
aggcgttttc atcgtcgatg cgacctatac cctgattcgt cgcttgctga gaggggacaa    15240
ggtgtatgag gctcatcgaa gccatgccta tcaatacgca agccgatact atggaaagca    15300
tgctcctgtt acgattggcg tcacggcatt gaacgtcatc tggctcctcc ctatagcctt    15360
gttggtcggg agtgggtctc tagagccttt gatgggcatc gtcatagcct acgtccctct    15420 cgttttctg gcagtgaggt tcaaggcggg taagctagag tcgtccgctc aggcctaaag    15480
gagtagggga atgctagatc gtttaagagt aaagttgtta tccatgcctc gtcgctggaa    15540
acgtttgctt caagtggcta cggatatcct tctggtatgg ctgtctctgt ggctcgcttt    15600
tgtggtccgt ctaggcacag acgatatgat cgacgtgttc ggcgagcatg catggctttt    15660
catcactgcg ccggtcatcg ccattccact attcattcgc ttcggcatgt atcgcgcggt    15720
gatgcgctat ctcggtaacg acgcattgat cgccatcgcc aaggcggtga ccatctcggc    15780
tctggtgctg tcgctggtgg tgtactggta tcgtggcgcg ccggcgccgg tgccgcgttc    15840
cctggtgttc aactactggt ggttgagcat gctgctgatc ggcggcttgc gtctggccat    15900
gcgccagtat ttcatgggcg actggtactc tgctgtgcag tcggtaccat ttctcaaccg    15960
ccaggatggc ctgcccaggg tggttatcta tggggcgggg cggccggca accagttggt    16020 tgcggcgttg cgtctcggtc gggcgatgcg tccggtggcg ttcatcgatg acgacaagca    16080
gatcgccaac cgggtcattg ccggtctgcg ggtctatacc gccaagcata tccgccagat    16140
gatcgacgag acgggcgcgc aggaggttct cctggcgatt ccttccgcca ctcgggcccg    16200
gcgccgagag attctcgagt ccctggagcc gttcccgctg cacgtgcgca gcatgcccgg    16260
cttcatggac ctggccagcg gccgggtcaa ggtggatgac ctgcaggagg tggacatcgc    16320
tgacctgctg gggcgcgaca gcgtcgcacc gcgcaaggag ctgctggaac ggtgcatccg    16380
cggtcaggtg gtgatggtga ccggggcggg cggctctatc ggttcggaac tctgtcggca    16440
gatcatgagt tgttcgccta gcgtgctgat cctgttcgaa cacagcgaat acaacctcta    16500
tagcatccat caggaactgg agcgtcggat caagcgcgag tcgctttcgg tgaacctgtt    16560
gccgatcctc ggttcggtgc gcaatcccga gcgcctggtg gacgtgatgc gtacctggaa    16620
ggtcaatacc gtctaccatg cggcggccta caagcatgtg ccgatcgtcg agcacaacat    16680
cgccgagggc gttctcaaca cgtgatagg caccttgcat gcggtgcagg ccgcggtgca    16740
ggtcggcgtg cagaacttcg tgctgatttc caccgacaag gcggtgcggc cgaccaatgt    16800
gatgggcagc accaagcgcc tggcggaaat ggtccttcag gcgctcagca acgaatcggc    16860
gccggtgctg ttcggcgacc ggaaggacgt gcatcacgtc aacaagaccc gtttcaccat    16920
ggtccgcttc ggcaacgtcc tcggttcgtc cggttcggtc attccgctgt ccgcgagca    16980 gatcaagcgc ggcggcccgg tgacggtcac ccacccgagc atcacccgtt acttcatgac    17040
cattcccgag gcggcgcagt tggtcatcca ggccggttcg atgggcagg gcggagatgt    17100 attcgtgctg gacatggggc cgccggtgaa gatcctggag ctcgccgaga agatgatcca    17160
cctgtccggc ctgagcgtgc gttccgagcg ttcgccccat ggtgacatcg ccatcgagtt    17220
cagtggcctg cgtcctggcg agaagctcta cgaagagctg ctgatcggtg acaacgtgaa    17280
tcccaccgac catccgatga tcatgcgggc caacgaggaa cacctgagct gggaggcctt    17340
caaggtcgtg ctggagcagt tgctggccgc cgtgagaag gacgactact cgcgggttcg    17400
ccagttgctg cgggaaaccg tcagcggcta tgcgcctgac ggtgaaatcg tcgactggat    17460
```

```
ctatcgccag aggcggcgag aaccctgagt catcgttctc cggaaaaggc cgcctagcgg   17520
ccttttttgt tttctccgta cgatgttccc ggtgccggac caggaagcga ctgctttgct   17580
ggggctgtcg atccaggtgc gttccacggc gataaggtgg tttcgtggat gggcaacatg   17640
tcgcgaaggt aaagtcagcc gcattgttga attcatcgaa aaccggatc  agccacaaac   17700 gctggaatca gacatcatgg ccgtgggccg ttatgtgctt tctgccgata tttggccgga   17760
acttgaacgc actcagccag gtgcatgggg acgtattcag ctgactgatg ccattgccga   17820
actggcgaaa aaacagtctg ttgacgccat gctgatgact ggtgacagct acgactgtgg   17880
taaaaaaatg ggttatatgc aggcgtttgt gaagtatgga ctacgcaacc tgaaagaagg   17940
agcgaagttc cgcaaaggta ttgagaaatt gcttagcgag taagtttaaa aaatagacgc   18000
ccttataggg cgtaataaca aataacggta gtcaacattc gacgcggtga tgcagatatg   18060
cccggaatgc tgataccgtt ttttcattct aaaaaactca tcatttcatt gagttaacta   18120
caaaatttag cactgttttt tataatgttt cttcttgttt ctggcatcaa ttggtaagat   18180
aattagtgtt tgagtttaga ggctttgcgg cagagaagcg gagcttaaca cgtctgtgag   18240
agtacgcagt gcactggtag ctgtaaagcc agtggcggta gcgtgtttaa ataaatacat   18300
tagtaatact acatattaca tcattgtagg ctatttaagc gctacatgat aagcgacagc   18360
gctagcaatc aaatctttta aagttacttc tcaggaatag taaaaggagg acagctatgt   18420
tgaaaaaaga gtatttaaaa aacccttatt tagttttgtt tgcgatgatt atattagctt   18480
atgtttttag tgtattttgc aggttttatt gggtttggtg ggcaagtgag tttaatgagt   18540
attttttcaa taatcagtta atgatcattt caaatgatgg ctatgctttt gctgagggcg   18600
caagagatat gatagcaggt tttcatcagc ctaatgattt gagttattat ggatcttctt   18660
tatccgcgct tacttattgg ctttataaaa tcacaccttt ttcttttgaa agtatcattt   18720
tatatatgag tactttttta tcttctttgg tggtgattcc tactattttg ctagctaacg   18780
aatacaaacg tccttttaatg ggctttgtag ctgctctttt agcaagtata gcaaacagtt   18840
attataatcg cactatgagt gggtattatg atacggatat gctggtaatt gttttgccta   18900
tgtttatttt attttttatg gtaagaatga ttttaaaaaa agactttttt tcattgattg   18960
ccttgccgtt atttatagga atttatcttt ggtggtatcc ttcaagttat actttaaatg   19020
tagctttaat tggactttttt ttaatttata cacttatttt tcatagaaaa gaaagattt   19080 tttatatagc tgtgattttg tcttctctta ctctttcaaa tatagcatgg ttttatcaaa   19140
gtgccattat agtaatactt tttgcttttat tcgccttaga gcaaaaacgc ttaaattta   19200 tgattatagg aattttaggt agtgcaactt tgatatttt gattttaagt ggtggggttg   19260
atcctatact ttatcagctt aaattttata tttttagaag tgatgaaagt gcgaatttaa   19320
cgcagggctt tatgtatttt aatgtcaatc aaaccataca agaagttgaa aatgtagatc   19380
ttagcgaatt tatgcgaaga attagtggta gtgaaattgt ttttttgttt tctttgtttg   19440
gttttgtatg gcttttgaga aaacataaaa gtatgattat ggctttacct atattggtgc   19500
ttgggttttt agccttaaaa gggggcctta gatttaccat ttattctgta cctgtaatgg   19560
ccttaggatt tggttttta ttgagcgagt ttaaggctat aatggttaaa aaatatagcc   19620
aattaacttc aaatgtttgt attgtttttg caactatttt gactttagct ccagtattta   19680 tccatatttta caactataaa gcgccaacag ttttttctca aaatgaagca tcattattaa   19740
atcaattaaa aaatatagcc aatagagaag attatgtggt aacttggtgg gattatggtt   19800
```

```
atcctgtgcg ttattatagc gatgtgaaaa ctttagtaga tggtggaaag catttaggta    19860
aggataattt tttcccttct tttgctttaa gcaaagatga acaagctgca gctaatatgg    19920
caagacttag tgtagaatat acagaaaaaa gcttttatgc tccgcaaaat gatattttaa    19980
aaacagacat tttgcaagcc atgatgaaag attataatca aagcaatgtg gatttgtttc    20040
tagcttcatt atcaaaacct gattttaaaa tcgatacgcc aaaaactcgt gatatttatc    20100
tttatatgcc cgctagaatg tctttgattt tttctacggt ggctagtttt tcttttatta    20160
atttagatac aggagttttg gataaacctt ttacctttag cacagcttat ccacttgatg    20220
ttaaaaatgg agaaatttat cttagcaacg gagtggtttt aagcgatgat tttagaagtt    20280
ttaaaatagg tgataatgtg gtttctgtaa atagtatcgt agagattaat tctattaaac    20340
aaggtgaata caaaatcact ccaattgatg ataaggctca gttttatatt ttttatttaa    20400
aggatagtgc tattccttac gcacaattta ttttaatgga taaaaccatg tttaatagtg    20460
cttatgtgca aatgtttttt ttaggaaatt atgataagaa tttatttgac ttggtgatta    20520
attctagaga tgctaaggtt tttaaactta aaatttaccc atacgatgtt ccagattacg    20580
cttaaacatg tgaattc                                                  20597

<210> SEQ ID NO 20
<211> LENGTH: 8815
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
agtcgacctg caggatgaga gtagaaaata ataatgtttc tgggcaaaac catgacccgg      60
aacagattga tttgattgat ttactagtgc agttgtggcg tggcaagatg acaatcatca     120
tttccgtcat tgtggctatt gccctagcta ttggatattt ggcagtagcg aaggagaaat     180
ggacgtcaac agcaattatc actcagcccg atgtggggca aattgctggc tataacaatg     240
ccatgaatgt tatctatggt caggctgcac cgaaagtatc ggatttgcag gagacgttaa     300
ttggtcgctt cagttctgcc ttctctgcat tagcagaaac gctggataat caggaagaac     360
cagaaaaact taccatcgaa ccttctgtta agaaccagca attaccattg actgtttctt     420
atgttgggca aactgcagag ggcgcacaaa tgaagttggc ccaatacatt cagcaagttg     480
acgataaagt gaatcaagag ttagaaaagg atctcaagga caacattgct ctgggacgga     540
aaaacttgca ggactcttta agaacgcagg aagtggttgc gcaggagcag aaagatctgc     600
gtatccgtca gattcaggaa gcgttgcagt atgcgaatca ggcgcaggtg acaaaaccgc     660
agattcaaca gactggcgaa gatatcacac aagatacgtt gttccttttg gggagcgaag     720
cgctggagtc gatgattaag catgaggcga cccgtccgtt ggtgttctca ccaaactact     780
atcagactcg tcaaaacctg cttgatatcg aaagcttaaa ggttgatgat cttgatattc     840
atgcttaccg ctatgtaatg aaaccgacgt tacctattcg tcgtgatagc ccgaaaaagg     900
caattacctt gattctggcg gtgctgctgg gtggcatggt tggcgcgggg attgtgctgg     960
ggcgtaatgc tctacgcaat tacaacgcga agtaacctgc aggcatgcaa gcttctgttt    1020
tggcggatga gaagagaaat tcgtcgcccg ccataaactg ccaggcatca aattaagcag    1080
aaggccatcc tgacggatgg cctttttgcg tttctacaaa ctcttcctgt ctagcaggtg    1140
gcacttttcg gggaaatgtg cgcggaaccc ctatttgttt atttttctaa atacattcaa    1200
```

```
atatgtatcc gctcatgcta gaaatatttt atctgattaa taagatgatc ttcttgagat    1260
cgttttggtc tgcgcgtaat ctcttgctct gaaaacgaaa aaaccgcctt gcagggcggt    1320
ttttcgaagg ttctctgagc taccaactct ttgaaccgag gtaactggct tggaggagcg    1380
cagtcaccaa aacttgtcct ttcagtttag ccttaaccgg cgcatgactt caagactaac    1440
tcctctaaat caattaccag tggctgctgc cagtggtgct tttgcatgtc tttccgggtt    1500
ggactcaaga cgatagttac cggataaggc gcagcggtcg gactgaacgg ggggttcgtg    1560
catacagtcc agcttggagc gaactgccta cccggaactg agtgtcaggc gtggaatgag    1620
acaaacgcgg ccataacagc ggaatgacac cggtaaaccg aaaggcagga acaggagagc    1680
gcacgaggga gccgccaggg gaaacgcctg gtatctttat agtcctgtcg ggtttcgcca    1740
ccactgattt gagcgtcaga tttcgtgatg cttgtcaggg gggcggagcc tatggaaaaa    1800
cggctttgcc gcggccctct cacttccctg ttaagtatct tcctggcatc ttccaggaaa    1860
tctccgcccc gttcgtaagc catttccgct cgccgcagtc gaacgaccga gcgtagcgag    1920
tcagtgagcg aggaagcgga atatatcctg tatcacatat tctgctgacg caccggtgca    1980
gccttttttc tcctgccaca tgaagcactt cactgacacc ctcatcagtg ccaacatagt    2040
aagccagtat acactccgct agcgctgatg tccggcggtg cttttgccgt tacgcaccac    2100
cccgtcagta gctgaacagg agggacagct gatagaaaca gaagccactg gagcacctca    2160
aaaacaccat catacactaa atcagtaagt tggcagcatc acccgacgca ctttgcgccg    2220
aataaagtgt aggctggagc tgcttcgaag ttcctatact ttctagagaa taggaacttc    2280
ggaataggaa cttcaagatc ccctcacgct gccgcaagca ctcagggcgc aagggctgct    2340
aaaggaagcg gaacacgtag aaagccagtc cgcagaaacg gtgctgaccc cggatgaatg    2400
tcagctactg ggctatctgg acaagggaaa acgcaagcgc aaagagaaag caggtagctt    2460
gcagtgggct tacatggcga tagctagact gggcggtttt atggacagca agcgaaccgg    2520
aattgccagc tggggcgccc tctggtaagg ttgggaagcc ctgcaaagta aactggatgg    2580 cttctcttgcc gccaaggatc tgatggcgca ggggatcaag atctgatcaa gagacaggat    2640
gaggatcgtt tcgcatgatt gaacaagatg gattgcacgc aggttctccg gccgcttggg    2700
tggagaggct attcggctat gactgggcac aacagacaat cggctgctct gatgccgccg    2760
tgttccggct gtcagcgcag gggcgcccgg ttcttttttgt caagaccgac ctgtccggtg    2820
ccctgaatga actgcaggac gaggcagcgc ggctatcgtg gctggccacg acgggcgttc    2880
cttgcgcagc tgtgctcgac gttgtcactg aagcgggaag ggactggctg ctattgggcg    2940
aagtgccggg gcaggatctc ctgtcatctc accttgctcc tgccgagaaa gtatccatca    3000
tggctgatgc aatgcggcgg ctgcatacgc ttgatccggc tacctgccca ttcgaccacc    3060
aagcgaaaca tcgcatcgag cgagcacgta ctcggatgga agccggtctt gtcgatcagg    3120
atgatctgga cgaagagcat caggggctcg cgccagccga actgttcgcc aggctcaagg    3180
cgcgcatgcc cgacggcgag gatctcgtcg tgacccatgg cgatgcctgc ttgccgaata    3240
tcatggtgga aaatggccgc ttttctggat tcatcgactg tggccggctg ggtgtggcgg    3300
accgctatca ggacatagcg ttggctaccc gtgatattgc tgaagagctt ggcggcgaat    3360
gggctgaccg cttcctcgtg ctttacggta tcgccgctcc cgattcgcag cgcatcgcct    3420
tctatcgcct tcttgacgag ttcttctgag cgggactctg ggttcgaaa tgaccgacca    3480 agcgacgccc aacctgccat cacgagattt cgattccacc gccgccttct atgaaaggtt    3540
gggcttcgga atcgttttcc gggacgccgg ctggatgatc ctccagcgcg ggatctcat    3600
```

```
gctggagttc ttcgcccacc ccagcttcaa aagcgctctg aagttcctat actttctaga   3660
gaataggaac ttcggaatag gaactaagga ggatattcat atggtttttt taaggcagtt   3720
attggtgccc ttaaacgcct ggtgctacgc ctgaataagt gataataagc ggatgaatgg   3780
cagaaattcg aaagcaaatt cgacccggtc gtcggttcag ggcagggtcg ttaaatagcc   3840
gcttatgtct attgctggtt taccggttta ttgactaccg gaagcagtgt gaccgtgtgc   3900
ttctcaaatg cctgaggcca gtttgctcag gctctccccg tggaggtaat aattgacgat   3960
atgatcattt attctgcctc ccagagcctg ataaaaacgg ttagcgcttc gttaatacag   4020
atgtaggtgt tccacagggt agccagcagc atcctgcgat gcagatccgg aacataatgg   4080
tgcagggcgc ttgtttcggc gtgggtatgg tggcaggccc cgtggccggg ggactgttgg   4140
gcgctgccgg cacctgtcct acgagttgca tgataaagaa gacagtcata agtgcgcgcga   4200 cgatagtcat gccccgcgcc caccggaagg agctaccgga cagcggtgcg gactgttgta   4260
actcagaata agaaatgagg ccgctcatgg cgttgactct cagtcatagt atcgtggtat   4320
caccggttgg ttccactctc tgttgcgggc aacttcagca gcacgtaggg gacttccgcg   4380
tttccagact ttacgaaaca cggaaaccga agaccattca tgttgttgct caggtcgcag   4440
acgttttgca gcagcagtcg cttcacgttc gctcgcgtat cggtgattca ttctgctaac   4500
cagtaaggca accccgccag cctagccggg tcctcaacga caggagcacg atcatgcgca   4560
cccgtggcca ggacccaacg ctgcccgaga tgcgccgcgt gcggctgctg gagatggcgg   4620
acgcgatgga tatgttctgc caagggttgg tttgcgcatt cacagttctc cgcaagaatt   4680
gattggctcc aattcttgga gtggtgaatc cgttagcgag gtgccgccgg cttccattca   4740
ggtcgaggtg gcccggctcc atgcaccgcg acgcaacgcg gggaggcaga caaggtatag   4800
ggcggcgcct acaatccatg ccaacccgtt ccatgtgctc gccgaggcgg cataaatcgc   4860
cgtgacgatc agcggtccag tgatcgaagt taggctggta agagccgcga gcgatccttg   4920
aagctgtccc tgatggtcgt catctacctg cctggacagc atggcctgca acgcgggcat   4980
cccgatgccg ccggaagcga gaagaatcat aatggggaag gccatccagc ctcgcgtcgc   5040
gaacgccagc aagacgtagc ccagcgcgtc ggccaattcg cgctaactta cattaattgc   5100
gttgcgctca ctgcccgctt tccagtcggg aaacctgtcg tgccagctgc attaatgaat   5160
cggccaacgc gcggggagag gcggtttgcg tattgggcgc cagggtggtt ttcttttca   5220 ccagtgagac gggcaacagc tgattgccct tcaccgcctg gccctgagag agttgcagca   5280
agcggtccac gctggtttgc cccagcaggc gaaaatcctg tttgatggtg gttgacggcg   5340
ggatataaca tgagctgtct tcggtatcgt cgtatcccac taccgagata ccgcaccaa   5400 cgcgcagccc ggactcggta atggcgcgca ttgcgcccag cgccatctga tcgttggcaa   5460
ccagcatcgc agtgggaacg atgccctcat tcagcatttg catggttttgt tgaaaaccgg   5520 acatggcact ccagtcgcct tcccgttccg ctatcggctg aatttgattg cgagtgagat   5580
atttatgcca gccagccaga cgcagacgcg ccgagacaga acttaatggg cccgctaaca   5640
gcgcgatttg ctggtgaccc aatgcgacca gatgctccac gcccagtcgc gtaccgtctt   5700
catgggagaa aataatactg ttgatgggtg tctggtcaga gacatcaaga ataacgccg   5760 gaacattagt gcaggcagct tccacagcaa tggcatcctg gtcatccagc ggatagttaa   5820
tgatcagccc actgacgcgt tgcgcgagaa gattgtgcac cgccgcttta caggcttcga   5880
cgccgcttcg ttctaccatc gacaccacca cgctggcacc cagttgatcg gcgcgagatt   5940
```

```
taatcgccgc gacaatttgc gacggcgcgt gcagggccag actggaggtg gcaacgccaa      6000
tcagcaacga ctgtttgccc gccagttgtt gtgccacgcg gttgggaatg taattcagct      6060
ccgccatcgc cgcttccact ttttcccgcg ttttcgcaga aacgtggctg gcctggttca      6120
ccacgcggga aacggtctga taagagacac cggcatactc tgcgacatcg tataacgtta      6180
ctggtttcac attcaccacc ctgaattgac tctcttccgg gcgctatcat gccataccgc      6240
gaaaggtttt gcaccattcg atggtgtcaa cgtaaatgca tgccgcttcg ccttcgcgcg      6300
cgaattggcc gccatgccgg cgataatggc ctgcttctcg ccgaaacgtt tggtggcggg      6360
accagtgacg aaggcttgag cgagggcgtg caagattccg aataccgcaa gcgacaggcc      6420
gatcatcgtc gcgctccagc gaaagcggtc ctcgccgaaa atgacccaga gcgctgccgg      6480
cacctgtcct acgagttgca tgataaagaa gacagtcata agtgcggcga cgatagtcat      6540
gccccgcgcc accggaagg agctgactgg gttgaaggct ctcaagggca tcggcggagc      6600
ttatcgactg cacggtgcac caatgcttct ggcgtcaggc agccatcgga agctgtggta      6660
tggctgtgca ggtcgtaaat cactgcataa ttcgtgtcgc tcaaggcgca ctcccgttct      6720
ggataatgtt ttttgcgccg acatcataac ggttctggca atattctga atgagctgt      6780 tgacaattaa tcatcggctc gtataatgtg tggaattgtg agcggataac aatttcacac      6840
aggaaacaga attcgagctc atgaaaaaga tttggctggc cctggcagga ctggttctgg      6900 cctttttcagc aagtgcagct gaagaagcct ttgatctgtg gaatgagtgt gcaaaagcat      6960
gtgtactgga tctgaaagat ggtgtgagat ccagcagaat gtcagtggat ccagccattg      7020
cagatacaaa tggccagggt gtactgcatt actctatggt tctggaaggt ggtaatgatg      7080
ccctgaaact ggccattgat aatgcactgt ctatcaccag tgatggtctg acaatcagac      7140
tggagggagg ggtggaaccc aataagcctg tcagatacag ctatacaaga caagccagag      7200
gttcttggag cctgaactgg ctggtgccta ttgggcatga aaaccatct aacattaaag      7260 tttttattca tgaactgaat gcaggcaatc agctgtctca tatgagccca atttatacca      7320
ttgaaatggg ggatgaactg ctggctaaac tggccagaga tgctacattc tttgtcagag      7380
cccatgaatc aaatgagatg cagcctaccc tggccattag ccatgctggt gtgagtgttg      7440
tcatggcaca aactcagccc aggagagaga aaggtggtc tgagtggacc agtggcaaag      7500
tgctgtgcct gctggatcct ctggatggtg tttataacta tctggcccaa cagaggtgta      7560
acctggatga tacctgggaa ggtaaaatct atagagtgct ggcaggtaat ccagcaaaac      7620
atgacctgga tatcaaggat aataacaata gcacccctac tgtaatcagc catagactgc      7680
atttcccaga gggaggttca ctggctgccc tgactgctca tcaggcctgt catctgccac      7740
tggaaacttt caccagacac aggcagccaa gaggctggga acagctggaa caatgtggct      7800
atccagttca gaggctggtt gccctgtacc tggcagcaag actgagctgg aatcaggtag      7860
atcaggttat tagaaatgca ctggccagcc caggagtgg gggtgacctg ggtgaggcaa      7920
ttagagaaca gcctgagcag gccagactgg ccctgactct ggcagcagct gaaagtgaaa      7980
gatttgtgag acagggggaca ggcaatgatg aagcaggtgc agctaatgca gatgttgttt      8040
cactgacttg tcctgttgct aaagatcaga acaggaccaa aggtgaatgt gctgaccag      8100 ctgattcagg agatgcactg ctggagagga actatccaac tggtgcagaa ttcctgggag      8160
atggtggtga tgttctttt agcaccagag gcacacagaa ctggactgtg aaagactgc      8220 tgcaggcaca tagacagctg gaagaaagag gctatgtatt tgttggctac catgtgtactt      8280 tcctggaagc agcacagtcc attgtctttg gaggggttag agccagaagc caggatctgg      8340
```

```
atgctatttg gagaggtttt tatattgctg gggatccagc cctggcctat ggatatgcac    8400
aagatcagga acctgatgcc agaggcagaa tcagaaatgg tgccctgctg agggtttatg    8460
ttcctaggtc tagcctgcca ggattttata gaacctctct gaccctggca gcccctgaag    8520
cagcaggtga ggtggagaga ctgattggtc atcctctgcc actgagactg gatgccatta    8580
cagggccaga agaagaaggt ggcagagtga caattctggg ttggcccctg cagagagga     8640 cagtagttat tccttcagca atccctacag atccaaggaa tgtgggtggg acctggatc     8700 catcctcaat tccagataag gaacaggcaa tttcagccct gcctgattat gctagtcagc    8760
caggtaaacc acctagagaa gatctgaaac accaccaca ccaccactga tctag          8815
```

<210> SEQ ID NO 21
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
gaattcatga gagtagaaaa taataatgtt tctgggcaaa accatgaccc ggaacagatt     60
gatttgattg atttactagt gcagttgtgg cgtggcaaga tgacaatcat catttccgtc    120
attgtggcta ttgccctagc tattggatat ttggcagtag cgaaggagaa atggacgtca    180
acagcaatta tcactcagcc cgatgtgggg caaattgctg gctataacaa tgccatgaat    240
gttatctatg gtcaggctgc accgaaagta tcggatttgc aggagacgtt aattggtcgc    300
ttcagttctg ccttctctgc attagcagaa acgctggata tcaggaaga accagaaaaa    360 cttaccatcg aaccttctgt taagaaccag caattaccat tgactgtttc ttatgttggg    420
caaactgcag agggcgcaca atgaagttg gcccaataca ttcagcaagt tgacgataaa    480
gtgaatcaag agttagaaaa ggatctcaag acaacattg ctctgggacg aaaaacttg     540 caggactctt taagaacgca ggaagtggtt gcgcaggagc agaaagatct gcgtatccgt    600
cagattcagg aagcgttgca gtatgcgaat caggcgcagg tgacaaaacc gcagattcaa    660
cagactggcg aagatatcac acaagatacg ttgttccttt tggggagcga agcgctggag    720
tcgatgatta agcatgaggc gacccgtccg ttggtgttct caccaaacta ctatcagact    780
cgtcaaaacc tgcttgatat cgaaagctta aaggttgatg atcttgatat tcatgcttac    840
cgctatgtaa tgaaaccgac gttacctatt cgtcgtgata gcccgaaaaa ggcaattacc    900
ttgattctgg cggtgctgct gggtggcatg gttggcgcgg ggattgtgct ggggcgtaat    960
gctctacgca attacaacgc gaagtaagtc gac                                  993
```

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Asn Asn Asn Ser Thr Pro Thr Val Ile Ser His Arg
1               5                   10

<210> SEQ ID NO 23
<211> LENGTH: 4

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Gln Asn Arg
1

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (2)..(2)
<223> OTHER INFORMATION: Any amino acid except Pro
<220> FEATURE:
<221> NAME/KEY: MOD_RES
<222> LOCATION: (4)..(4)
<223> OTHER INFORMATION: Any amino acid except Pro
<220> FEATURE:
<221> NAME/KEY: MOD_RES
<222> LOCATION: (5)..(5)
<223> OTHER INFORMATION: Ser or Thr
<220> FEATURE:
<223> OTHER INFORMATION: See specification as filed for detailed
      description of substitutions and preferred embodiments

<400> SEQUENCE: 24

Xaa Xaa Asn Xaa Xaa
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asn Asn Asn Ser
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Gln Asn Arg Thr
1               5

<210> SEQ ID NO 27
<211> LENGTH: 2160
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 27

```
gaattcatgt tgaaaaaaga gtatttaaaa aacccttatt tagttttgtt tgcgatgatt      60
atattagctt atgttttag tgtattttgc aggttttatt gggtttggtg ggcaagtgag      120
tttaatgagt attttttcaa taatcagtta atgatcattt caaatgatgg ctatgctttt     180
gctgagggcg caagagatat gatagcaggt tttcatcagc ctaatgattt gagttattat     240
ggatcttctt tatccgcgct tactattgg ctttataaaa tcacaccttt ttcttttgaa      300
agtatcattt tatatatgag tactttttta tcttctttgg tggtgattcc tactattttg     360
ctagctaacg aatacaaacg tcctttaatg ggctttgtag ctgctctttt agcaagtata     420
gcaaacagtt attataatcg cactatgagt gggtattatg atacggatat gctggtaatt     480
gttttgccta tgtttatttt attttttatg gtaagaatga ttttaaaaaa agactttttt     540
tcattgattg ccttgccgtt atttatagga atttatcttt ggtggtatcc ttcaagttat     600
actttaaatg tagctttaat tggactttt ttaatttata cacttatttt tcatagaaaa      660
gaaaagattt tttatatagc tgtgattttg tcttctctta ctctttcaaa tatagcatgg     720
ttttatcaaa gtgccattat agtaatactt tttgctttat tcgccttaga gcaaaaacgc     780
ttaaattta tgattatagg aattttaggt agtgcaactt tgatatttt gattttaagt      840
ggtgggttg atcctatact ttatcagctt aaattttata tttttagaag tgatgaaagt     900
gcgaattaa cgcagggctt tatgtatttt aatgtcaatc aaaccataca agaagttgaa     960
aatgtagatc ttagcgaatt tatgcgaaga attagtggta gtgaaattgt ttttttgttt   1020
tctttgtttg gttttgtatg gcttttgaga aaacataaaa gtatgattat ggctttacct   1080
atattggtgc ttgggttttt agccttaaaa gggggcctta gatttaccat ttattctgta   1140
cctgtaatgg ccttaggatt tggttttta ttgagcgagt ttaaggctat aatggttaaa    1200
aaatatagcc aattaacttc aaatgttgt attgttttg caactatttt gacttagct     1260
ccagtattta tccatattta caactataaa gcgccaacag ttttttctca aaatgaagca   1320
tcattattaa atcaattaaa aaatatagcc aatagagaag attatgtggt aacttgggcg   1380
gcttatggtt atcctgtgcg ttattatagc gatgtgaaaa cttagtaga tggtggaaag    1440
catttaggta aggataattt tttcccttct tttgctttaa gcaaagatga acaagctgca   1500
gctaatatgg caagacttag tgtagaatat acagaaaaaa gcttttatgc tccgcaaaat   1560
gatatttaa aaacagacat tttgcaagcc atgatgaaag attataatca aagcaatgtg    1620
gatttgtttc tagcttcatt atcaaaacct gattttaaaa tcgatacgcc aaaaactcgt   1680
gatatttatc tttatatgcc cgctagaatg tctttgattt tttctacggt ggctagtttt   1740
tcttttatta atttagatac aggagttttg gataaacctt ttaccttag cacagcttat   1800
ccacttgatg ttaaaaatgg agaaattat cttagcaacg gagtggtttt aagcgatgat   1860
tttagaagtt ttaaaatagg tgataatgtg gtttctgtaa atagtatcgt agagattaat   1920
tctattaaac aaggtgaata caaaatcact ccaattgatg ataaggctca gttttatatt   1980
ttttattaa aggatagtgc tattcctac gcacaattta ttaatgga taaaaccatg       2040
tttaatagtg cttatgtgca aatgttttt ttaggaaatt atgataagaa tttatttgac    2100
ttggtgatta attctagaga tgctaaggtt tttaaactta aaatttacccc atacgatgtt   2160
```

CAPSULAR GRAM-POSITIVE BACTERIA BIOCONJUGATE VACCINES

CROSS-REFERENCE TO RELATED APPLICATIONS

This application claims the benefit under 35 U.S.C. § 119(e) of U.S. Provisional Patent Application No. 61/332,170, filed May 6, 2010, herein incorporated by reference in its entirety.

STATEMENT AS TO FEDERALLY SPONSORED RESEARCH

Aspects of this invention were made with government support under grant 1R01AI088754-2, subgrant 105699, awarded by the National Institutes of Health. The government has certain rights in these aspects of the invention.

SEQUENCE LISTING

The instant application contains a Sequence Listing which has been submitted in ASCII format via EFS-Web and is herein incorporated by reference in its entirety. Said ASCII copy, created on May 2, 2011, is named 031229US.txt and is 206,590 bytes in size.

BACKGROUND OF THE INVENTION

Vaccines have been one of the great public health inventions of modern medicine and have saved millions of lives. Immunizations have been proven to be an ideal means to prevent and control infections. Each year vaccines prevent up to 3 million deaths and 750,000 children are saved from disability. (Global Alliance for Vaccines and Immunization—Press Releases (Mar. 11, 2006) at www.gavialliance.org/media_centre/press_releases/2006_03_09_en-_pr_queenrania_delhi.php). In 1999 the CDC declared immunizations the number one public health achievement of the 20$^{th}$ century (Ten great public health achievements-United States, 1900-1999. MMWR Morb Mortal Wkly Rep 48:241-3 (Apr. 2, 1999)). Some bacteria like those causing tetanus or diphtheria produce a toxin that is largely responsible for the disease. This toxin can be used in a detoxified form as vaccine. However, for most bacteria there is no single toxin that can be used to develop a vaccine.

Among the most successful vaccines are surface polysaccharides of bacterial pathogens like *Haemophilus influenzae*, *Neisseria meningitidis*, and *Streptococcus pneumoniae* conjugated to carrier proteins. These bacteria are surrounded by a capsule, which promotes microbial virulence and resistance to phagocytic killing, as well as preventing them from desiccation.

Bacterial polysaccharides can elicit a long-lasting immune response in humans if they are coupled to a protein carrier that contains T-cell epitopes. This concept was elaborated 80 years ago (Avery, O. T., and W. F. Goebel. 1929. Chemo-immunological studies on conjugated carbohydrate-proteins. II Immunological specificity of synthetic sugar-proteins. J. Exp. Med. 50:521-533), and proven later for the polysaccharide of *Haemophilus* influenza type B (HIB) coupled to the protein carrier diphtheria toxin (Anderson, P. 1983. Antibody responses to *Haemophilus influenzae* type b and diphtheria toxin induced by conjugates of oligosaccharides of the type b capsule with the nontoxic protein CRM197. Infect Immun 39:233-8; Schneerson, R., O. Barrera, A. Sutton, and J. B. Robbins. 1980. Preparation, characterization, and immunogenicity of *Haemophilus influenzae* type b polysaccharide-protein conjugates. J Exp Med 152:361-76). This glycoconjugate was also the first conjugated vaccine to be licensed in the USA in 1987 and introduced into the US infant immunization schedule shortly thereafter. Besides HIB, conjugated vaccines were successfully used against the encapsulated human pathogens *N. meningitidis* and *S. pneumoniae*. Routine use of these vaccines has resulted in decreased nasopharyngeal colonization, as well as infection. Currently approximately ~25% of the global vaccine market comprises conjugated vaccines.

Gram-positive bacteria have a cell membrane that is surrounded by capsular polysaccharides. *Staphylococcus* is one such Gram-positive bacterium.

*Staphylococcus aureus* causes infection. *S. aureus* is an opportunistic bacterial pathogen responsible for a diverse spectrum of human diseases. Although *S. aureus* may colonize mucosal surfaces of normal humans, it is also a major cause of wound infections and has the invasive potential to induce severe infections, including osteomyelitis, endocarditis, and bacteremia with metastatic complications (Lowy, F. D. 1998. *Staphylococcus aureus* infections. New Engl J Med 339:520-32). *S. aureus* is one of the most common agents implicated in ventilator-associated pneumonia, and it is an important and emerging cause of community-acquired pneumonia, affecting previously healthy adults and children lacking predisposing risk factors (Kollef, M. H., A. Shorr, Y. P. Tabak, V. Gupta, L. Z. Liu, and R. S. Johannes. 2005. Epidemiology and outcomes of health-care-associated pneumonia: results from a large US database of culture-positive pneumonia. Chest 128:3854-62; Shorr, A. F. 2007. Epidemiology and economic impact of meticillin-resistant *Staphylococcus aureus*: review and analysis of the literature. Pharmacoeconomics 25:751-68).

*S. aureus* is the second most common cause of nosocomial bacteremia, and methicillin-resistant *S. aureus* (MRSA) strains account for more than 50% of all infections in intensive care units in the U.S. *S. aureus* infections within the hospital and in the community are increasing. MRSA strains were isolated from 2% of staphylococcal infections in 1974 and from 63% of staphylococcal infections in 2004. Many of the nosocomial MRSA strains are multi-drug resistant, and even methicillin-sensitive strains can be deadly. A recent report using population-based, active case finding revealed that 94,360 invasive MRSA infections occurred in the U.S. in 2005, and that the majority of these (58%) occurred outside of the hospital (Klevens, R. M., M. A. Morrison, J. Nadle, S. Petit, K. Gershman, S. Ray, L. H. Harrison, R. Lynfield, G. Dumyati, J. M. Townes, A. S. Craig, E. R. Zell, G. E. Fosheim, L. K. McDougal, R. B. Carey, and S. K. Fridkin. 2007. Invasive methicillin-resistant *Staphylococcus aureus* infections in the United States. JAMA 298:1763-71). In this analysis, more Americans died from MRSA (>18,000 deaths) in 2005 than from AIDS.

*S. aureus* USA100, also known as the New York/Japan clone, is an MRSA strain that represents the predominant U.S. hospital-acquired MRSA strain (McDougal, L. K., C. D. Steward, G. E. Killgore, J. M. Chaitram, S. K. McAllister, and F. C. Tenover. 2003. Pulsed-field gel electrophoresis typing of oxacillin-resistant *Staphylococcus aureus* isolates from the United States: establishing a national database. J Clin Microbiol 41:5113-20).

Epidemiologic analyses indicate that *S. aureus* causes approximately 2 million clinical infections each year in the U.S. alone (Fridkin, S. K., J. C. Hageman, M. Morrison, L. T. Sanza, K. Como-Sabetti, J. A. Jernigan, K. Harriman, L. H. Harrison, R. Lynfield, and M. M. Farley. 2005. Methicillin-resistant *Staphylococcus aureus* disease in three communities. N Engl J Med 352:1436-44; King, M. D., B. J. Humphrey, Y. F. Wang, E. V. Kourbatova, S. M. Ray, and H. M. Blumberg. 2006. Emergence of community-acquired methicillin-resistant *Staphylococcus aureus* USA 300 clone as the predominant cause of skin and soft-tissue infections. Ann Intern Med 144:309-17; Klevens, R. M., M. A. Morrison, J. Nadle, S. Petit, K. Gershman, S. Ray, L. H. Harrison, R. Lynfield, G. Dumyati, J. M. Townes, A. S. Craig, E. R. Zell, G. E. Fosheim, L. K. McDougal, R. B. Carey, S. K. Fridkin, and M. I. for the Active Bacterial Core surveillance. 2007. Invasive methicillin-resistant *Staphylococcus aureus* infections in the United States. JAMA 298: 1763-1771). Not only are *S. aureus* infections increasing in number, but the resistance of *S. aureus* to antibiotics is also on the increase. MRSA accounts for 40%-60% of nosocomial *S. aureus* infections in the U.S., and many of these strains are multi-drug resistant. Notorious as a major source of nosocomial infections, *S. aureus* has recently taken on a new role in causing an escalating number of community-acquired infections in non-hospitalized persons without predisposing risk factors. Virulent community-associated MRSA (CA-MRSA) strains are becoming more prevalent across the U.S. and Europe, and their dissemination has been observed globally (Baggett, H. C., T. W. Hennessy, K. Rudolph, D. Bruden, A. Reasonover, A. Parkinson, R. Sparks, R. M. Donlan, P. Martinez, K. Mongkolrattanothai, and J. C. Butler. 2004. Community-onset methicillin-resistant *Staphylococcus aureus* associated with antibiotic use and the cytotoxin Panton-Valentine leukocidin during a furunculosis outbreak in rural Alaska. J Infect Dis 189:1565-73; Gilbert, M., J. MacDonald, D. Gregson, J. Siushansian, K. Zhang, S. Elsayed, K. Laupland, T. Louie, K. Hope, M. Mulvey, J. Gillespie, D. Nielsen, V. Wheeler, M. Louie, A. Honish, G. Keays, and J. Conly. 2006. Outbreak in Alberta of community-acquired (USA300) methicillin-resistant *Staphylococcus aureus* in people with a history of drug use, homelessness or incarceration. Canad Med Assoc J 175:149-54; Kazakova, S. V., J. C. Hageman, M. Matava, A. Srinivasan, L. Phelan, B. Garfinkel, T. Boo, S. McAllister, J. Anderson, B. Jensen, D. Dodson, D. Lonsway, L. K. McDougal, M. Arduino, V. J. Fraser, G. Killgore, F. C. Tenover, S. Cody, and D. B. Jernigan. 2005. A clone of methicillin-resistant *Staphylococcus aureus* among professional football players. N Engl J Med 352:468-75).

Not only has *S. aureus* resistance to methicillin become more common, but numerous isolates with reduced susceptibility to vancomycin have been reported. Seven clinical isolates of *S. aureus* that carry vanA and are fully resistant to vancomycin have been isolated in the U.S. These isolates are also methicillin resistant (Chang, S., D. M. Sievert, J. C. Hageman, M. L. Boulton, F. C. Tenover, F. P. Downes, S. Shah, J. T. Rudrik, G. R. Pupp, W. J. Brown, D. Cardo, and S. K. Fridkin. 2003. Infection with vancomycin-resistant *Staphylococcus aureus* containing the vanA resistance gene. New Engl J Med 348:1342-7). Because *S. aureus* cannot always be controlled by antibiotics and MRSA isolates are becoming increasingly prevalent in the community, additional control strategies, such as a vaccine, are sorely needed.

*S. aureus* capsular polysaccharides are involved in infection. Many virulence factors contribute to the pathogenesis of staphylococcal infections, including surface-associated adhesions, secreted exoproteins and toxins, and immune evasion factors (Foster, T. J. 2005. Immune evasion by staphylococci. Nature Reviews Microbiology 3:948-58). Like many invasive bacterial pathogens, *S. aureus* produces a capsular polysaccharide (CP) (FIG. 4) that enhances its resistance to clearance by host innate immune defenses. Most clinical isolates of *S. aureus* are encapsulated, and serotype 5 and 8 strains predominate (Arbeit, R. D., W. W. Karakawa, W. F. Vann, and J. B. Robbins. 1984. Predominance of two newly described capsular polysaccharide types among clinical isolates of *Staphylococcus aureus*. Diagn Microbiol Infect Dis 2:85-91). The type 5 (CP5) and type 8 (CP8) capsular polysaccharides have similar trisaccharide repeating units comprised of N-acetyl mannosaminuronic acid (ManNAcA), N-acetyl L-fucosamine (L-FucNAc), and N-acetyl D-fucosamine (D-FucNAc) (Jones, C. 2005. Revised structures for the capsular polysaccharides from *Staphylococcus aureus* types 5 and 8, components of novel glycoconjugate vaccines. Carbohydr Res 340:1097-106). CP5 and CP8 are serologically distinct, and this can be attributed to differences in the linkages between the sugars and in the sites of O-acetylation (FIG. 4).

Previous studies have correlated *S. aureus* capsule production with resistance to in vitro phagocytic uptake and killing (Fattom, A., R. Schneerson, S. C. Szu, W. F. Vann, J. Shiloach, W. W. Karakawa, and J. B. Robbins. 1990. Synthesis and immunologic properties in mice of vaccines composed of *Staphylococcus aureus* type 5 and type 8 capsular polysaccharides conjugated to *Pseudomonas aeruginosa* exotoxin A. Infect Immun 58:2367-74; Thakker, M., J.-S. Park, V. Carey, and J. C. Lee. 1998. *Staphylococcus aureus* serotype 5 capsular polysaccharide is antiphagocytic and enhances bacterial virulence in a murine bacteremia model. Infect Immun 66:5183-5189; Watts, A., D. Ke, Q. Wang, A. Pillay, A. Nicholson-Weller, and J. C. Lee. 2005. *Staphylococcus aureus* strains that express serotype 5 or serotype 8 capsular polysaccharides differ in virulence. Infect Immun 73:3502-11). Human neutrophils phagocytose capsule-negative mutants in the presence of nonimmune serum with complement activity, whereas encapsulated isolates require both capsule-specific antibodies and complement for optimal opsonophagocytic killing (Bhasin, N., A. Albus, F. Michon, P. J. Livolsi, J.-S. Park, and J. C. Lee. 1998. Identification of a gene essential for O-acetylation of the *Staphylococcus aureus* type 5 capsular polysaccharide. Mol Microbiol 27:9-21; Thakker, M., J.-S. Park, V. Carey, and J. C. Lee. 1998. *Staphylococcus aureus* serotype 5 capsular polysaccharide is antiphagocytic and enhances bacterial virulence in a murine bacteremia model. Infect Immun 66:5183-5189; Watts, A., D. Ke, Q. Wang, A. Pillay, A. Nicholson-Weller, and J. C. Lee. 2005. *Staphylococcus aureus* strains that express serotype 5 or serotype 8 capsular polysaccharides differ in virulence. Infect Immun 73:3502-11). Nilsson et al. (Nilsson, I.-M., J. C. Lee, T. Bremell, C. Ryden, and A. Tarkowski. 1997. The role of staphylococcal polysaccharide microcapsule expression in septicemia and septic arthritis. Infect Immun 65:4216-4221) reported that peritoneal macrophages from mice phagocytosed significantly greater numbers of a CP5-negative mutant compared to the parental strain Reynolds. Once phagocytosed, the CP5-positive strain survived intracellularly to a greater extent than the mutant strain. Cunnion et al. (Cunnion, K. M., J. C. Lee, and M. M. Frank. 2001. Capsule production and growth phase influence binding of complement to *Staphylococcus aureus*. Infect Immun 69:6796-6803) compared opsonization of isogenic *S. aureus* strains and demonstrated that the CP5-positive strain bound 42% less serum complement (C') than the acapsular mutant.

*S. aureus* vaccine development conventionally has involved the capsule as a target. Vaccine design for protection against staphylococcal disease is complicated by the protean manifestations and clinical complexity of *S. aureus* infections in humans. Many *S. aureus* vaccine candidates have been investigated in animal models of infection, but it has been reported that only two immunization regimens have completed phase III clinical trials (Schaffer, A. C., and J. C. Lee. 2008. Vaccination and passive immunisation against *Staphylococcus aureus*. Int J Antimicrob Agents 32 Suppl 1:S71-8). The first vaccine is based on the two capsular polysaccharides (CPs) (FIG. 4) that are most prevalent among clinical strains of *S. aureus*. Fattom et al. (Fattom, A. R. Schneerson, S. C. Szu, W. F. Vann, J. Shiloach, W. W. Karakawa and J. B. Robbins. 1990. Synthesis and immunologic properties in mice of vaccines composed of *Staphylococcus aureus* type 5 and type 8 capsular polysaccharides conjugated to *Pseudomonas aeruginosa* exotoxin. Infect Immun 58: 2367-74) conjugated the serotype 5 (CP5) and serotype 8 (CP8) polysaccharides to nontoxic recombinant *P. aeruginosa* exoprotein A (rEPA). The conjugate vaccines were immunogenic in mice and humans, and they induced opsonic antibodies that showed efficacy in protecting rodents from lethality and from nonlethal staphylococcal infection (Fattom, A. R. Schneerson, S. C. Szu, W. F. Vann, J. Shiloach, W. W. Karakawa and J. B. Robbins. 1990. Synthesis and immunologic properties in mice of vaccines composed of *Staphylococcus aureus* type 5 and type 8 capsular polysaccharides conjugated to *Pseudomonas aeruginosa* exotoxin. Infect Immun 58: 2367-74; Fattom, A., R. Schneerson, D. C. Watson, W. W. Karakawa, D. Fitzgerald, I. Pastan, X. Li, J. Shiloach, D. A. Bryla, and J. B. Robbins. 1993. Laboratory and clinical evaluation of conjugate vaccines composed of *S. aureus* type 5 and type 8 capsular polysaccharides bound to *Pseudomonas aeruginosa* recombinant exoprotein A. Infect Immun 61:1023-32; Fattom, A. I., J. Sarwar, A. Ortiz, and R. Naso. 1996. A *Staphylococcus aureus* capsular polysaccharide (CP) vaccine and CP-specific antibodies protect mice against bacterial challenge. Infect Immun 64:1659-65; Lee, J. C., J. S. Park, S. E. Shepherd, V. Carey, and A. Fattom. 1997. Protective efficacy of antibodies to the *Staphylococcus aureus* type 5 capsular polysaccharide in a modified model of endocarditis in rats. Infect Immun 65:4146-51). Passive immunization studies have indicated that both CP5- and CP8-specific antibodies significantly reduce infection in a murine model of *S. aureus* mastitis (Tuchscherr, L. P., F. R. Buzzola, L. P. Alvarez, J. C. Lee, and D. O. Sordelli. 2008. Antibodies to capsular polysaccharide and clumping factor A prevent mastitis and the emergence of unencapsulated and small-colony variants of *Staphylococcus aureus* in mice. Infect Immun 76:5738-44). The combined CP5- and CP8-conjugate vaccine was shown to be safe in humans and elicited antibodies that showed opsonophagocytic activity.

*S. aureus* vaccine development has also involved surface proteins as a target. The second *S. aureus* clinical vaccine trial was based on the protective efficacy of antibodies to staphylococcal adhesions in preventing staphylococcal infections. *S. aureus* clumping factor A is a cell wall-anchored protein that is surface expressed, mediates staphylococcal adherence to fibrinogen (Foster, T. J., and M. Hook. 1998. Surface protein adhesins of *Staphylococcus aureus*. Trends Microbiol 6:484-8), and promotes the attachment of *S. aureus* to biomaterial surfaces (Vaudaux, P. E., P. Francois, R. A. Proctor, D. McDevitt, T. J. Foster, R. M. Albrecht, D. P. Lew, H. Wabers, and S. L. Cooper. 1995. Use of adhesion-defective mutants of *Staphylococcus aureus* to define the role of specific plasma proteins in promoting bacterial adhesion to canine arteriovenous shunts. Infection & Immunity 63:585-90), blood clots, and damaged endothelial surfaces (Moreillon, P., J. M. Entenza, P. Francioli, D. McDevitt, T. J. Foster, P. Francois, and P. Vaudaux. 1995. Role of *Staphylococcus aureus* coagulase and clumping factor in pathogenesis of experimental endocarditis. Infection & Immunity 63:4738-43). The fibrinogen-binding domain of ClfA is located within region A of the full-length protein (McDevitt, D., P. Francois, P. Vaudaux, and T. J. Foster. 1995. Identification of the ligand-binding domain of the surface-located fibrinogen receptor (clumping factor) of *Staphylococcus aureus*. Molecular Microbiology 16:895-907). ClfA plays an important role in *S. aureus* binding to platelets, an interaction that is critical in animal models of catheter-induced staphylococcal endocarditis (Sullam, P. M., A. S. Bayer, W. M. Foss, and A. L. Cheung. 1996. Diminished platelet binding in vitro by *Staphylococcus aureus* is associated with reduced virulence in a rabbit model of infective endocarditis. Infection & Immunity 64:4915-21).

Nanra et al. reported that antibodies to ClfA induced opsonophagocytic killing of *S. aureus* in vitro (Nanra, J. S., Y. Timofeyeva, S. M. Buitrago, B. R. Sellman, D. A. Dilts, P. Fink, L. Nunez, M. Hagen, Y. V. Matsuka, T. Mininni, D. Zhu, V. Pavliak, B. A. Green, K. U. Jansen, and A. S. Anderson. 2009. Heterogeneous in vivo expression of clumping factor A and capsular polysaccharide by *Staphylococcus aureus*: Implications for vaccine design. Vaccine 27:3276-80). Furthermore, mice immunized with a recombinant form of the binding region A of ClfA showed reductions in arthritis and lethality induced by *S. aureus* (Josefsson, E., O. Hartford, L. O'Brien, J. M. Patti, and T. Foster. 2001. Protection against experimental *Staphylococcus aureus* arthritis by vaccination with clumping factor A, a novel virulence determinant. Journal of Infectious Diseases 184:1572-80). Passive immunization experiments were performed in rabbits given a human polyclonal immunoglobulin preparation that contained elevated levels of antibodies specific for ClfA (Vernachio, J., A. S. Bayer, T. Le, Y. L. Chai, B. Prater, A. Schneider, B. Ames, P. Syribeys, J. Robbins, J. M. Patti, J. Vernachio, A. S. Bayer, T. Le, Y.-L. Chai, B. Prater, A. Schneider, B. Ames, P. Syribeys, J. Robbins, and J. M. Patti. 2003. Anti-clumping factor A immunoglobulin reduces the duration of methicillin-resistant *Staphylococcus aureus* bacteremia in an experimental model of infective endocarditis. Antimicrobial Agents & Chemotherapy 47:3400-6). The combination therapy resulted in better bacterial clearance from the blood of rabbits with catheter-induced *S. aureus* endocarditis than did vancomycin treatment alone. In addition, passive transfer of ClfA-specific antibodies significantly reduced infection in a murine model of *S. aureus* mastitis (Tuchscherr, L. P., F. R. Buzzola, L. P. Alvarez, J. C. Lee, and D. O. Sordelli. 2008. Antibodies to capsular polysaccharide and clumping factor A prevent mastitis and the emergence of unencapsulated and small-colony variants of *Staphylococcus aureus* in mice. Infect Immun 76: 5738-44).

A phase III clinical trial was reportedly designed to protect against late-onset sepsis in 2000 low birth weight, premature neonates. The infants received up to four administrations of Veronate, a human immunoglobulin preparation pooled from donors with elevated antibody titers against ClfA and SdrG. Despite the promising results from a similar phase II clinical trial, this prophylactic therapy resulted in no reduction in the frequency of staphylococcal infections in the neonates (DeJonge, M., D. Burchfield, B. Bloom, M. Duenas, W. Walker, M. Polak, E. Jung, D. Millard, R. Schelonka, F. Eyal, A. Morris, B. Kapik, D. Roberson, K. Kesler, J. Patti, and S. Hetherington. 2007. Clinical trial of safety and efficacy of INH-A21 for the prevention of nosocomial staphylococcal bloodstream infection in premature infants. J Pediatr 151:260-5).

It has been shown that protein glycosylation occurs, but rarely does so naturally, in prokaryotic organisms. On the other hand, N-linked protein glycosylation is an essential and conserved process occurring in the endoplasmic reticulum of eukaryotic organisms. It is important for protein folding, oligomerization, stability, quality control, sorting and transport of secretory and membrane proteins (Helenius, A., and Aebi, M. (2004). Roles of N-linked glycans in the endoplasmic reticulum. Annu. Rev. Biochem. 73, 1019-1049). Protein glycosylation has a profoundly favorable influence on the antigenicity, the stability and the half-life of a protein. In addition, glycosylation can assist the purification of proteins by chromatography, e.g. affinity chromatography with lectin ligands bound to a solid phase interacting with glycosylated moieties of the protein. It is therefore established practice to produce many glycosylated proteins recombinantly in eukaryotic cells to provide biologically and pharmaceutically useful glycosylation patterns.

Conjugate vaccines have been successfully used to protect against bacterial infections. The conjugation of an antigenic polysaccharide to a protein carrier is required for protective memory response, as polysaccharides are T-cell independent antigens. Polysaccharides have been conjugated to protein carriers by different chemical methods, using activation reactive groups in the polysaccharide as well as the protein carrier. (Qian, F., Y. Wu, O. Muratova, H. Zhou, G. Dobrescu, P. Duggan, L. Lynn, G. Song, Y. Zhang, K. Reiter, N. MacDonald, D. L. Narum, C. A. Long, L. H. Miller, A. Saul, and G. E. Mullen. 2007. Conjugating recombinant proteins to Pseudomonas aeruginosa ExoProtein A: a strategy for enhancing immunogenicity of malaria vaccine candidates. Vaccine 25:3923-3933; Pawlowski, A., G. Kallenius, and S. B. Svenson. 2000. Preparation of pneumococcal capsular polysaccharide-protein conjugates vaccines utilizing new fragmentation and conjugation technologies. Vaccine 18:1873-1885; Robbins, J. B., J. Kubler-Kielb, E. Vinogradov, C. Mocca, V. Pozsgay, J. Shiloach, and R. Schneerson. 2009. Synthesis, characterization, and immunogenicity in mice of Shigella sonnei O-specific oligosaccharide-core-protein conjugates. Proc Natl Acad Sci USA 106:7974-7978).

Conjugate vaccines can be administered to children to protect them against bacterial infections and can provide a long lasting immune response to adults. Constructs of the invention have been found to generate an IgG response in animals. It is believed that the polysaccharide (i.e. sugar residue) triggers a short-term immune response that is sugar-specific. Indeed, the human immune system generates a strong response to specific polysaccharide surface structures of bacteria, such as O-antigens and capsular polysaccharides. However, as the immune response to polysaccharides is IgM dependent, the immune system develops no memory. The protein carrier that carries the polysaccharide, however, triggers an IgG response that is T-cell dependent and that provides long lasting protection since the immune system develops memory. For this reason, in developing a vaccine, it is advantageous to develop it as a protein carrier-polysaccharide conjugate.

Prokaryotic organisms rarely produce glycosylated proteins. However, it has been demonstrated that a bacterium, the food-borne pathogen Campylobacter jejuni, can glycosylate its proteins (Szymanski, et al. (1999). Evidence for a system of general protein glycosylation in Campylobacter jejuni. Mol. Microbiol. 32, 1022-1030). The machinery required for glycosylation is encoded by 12 genes that are clustered in the pgl locus. Disruption of glycosylation affects invasion and pathogenesis of C. jejuni but is not lethal as in most eukaryotic organisms (Burda P. and M. Aebi, (1999). The dolichol pathway of N-linked glycosylation. Biochim Biophys Acta 1426(2):239-57). It has been shown that the pgl locus is responsible for N-linked protein glycosylation in Campylobacter and that it is possible to reconstitute the N-glycosylation of C. jejuni proteins by recombinantly expressing the pgl locus and acceptor glycoprotein in E. coli at the same time (Wacker, M., D. Linton, P. G. Hitchen, M. Nita-Lazar, S. M. Haslam, S. J. North, M. Panico, H. R. Morris, A. Dell, B. W. Wren, and M. Aebi. 2002. N-linked glycosylation in C. jejuni and its functional transfer into E. coli. Science 298:1790-3).

The N-linked protein glycosylation biosynthetic pathway of Campylobacter has significant similarities to the polysaccharide biosynthesis pathway in bacteria (Bugg, T. D., and P. E. Brandish. 1994. From peptidoglycan to glycoproteins: common features of lipid-linked oligosaccharide biosynthesis. FEMS Microbiol Lett 119:255-62). Based on the knowledge that antigenic polysaccharides of bacteria and the oligosaccharides of Campylobacter are both synthesized on the carrier lipid, undecaprenyl pyrophosphate (UndPP), the two pathways were combined in E. coli (Feldman, M. F., M. Wacker, M. Hernandez, P. G. Hitchen, C. L. Marolda, M. Kowarik, H. R. Morris, A. Dell, M. A. Valvano, and M. Aebi. 2005. Engineering N-linked protein glycosylation with diverse O antigen lipopolysaccharide structures in Escherichia coli. Proc Natl Acad Sci USA 102:3016-21). It was demonstrated that PglB does not have a strict specificity for the lipid-linked sugar substrate. The antigenic polysaccharides assembled on UndPP are captured by PglB in the periplasm and transferred to a protein carrier (Feldman, M. F., M. Wacker, M. Hernandez, P. G. Hitchen, C. L. Marolda, M. Kowarik, H. R. Morris, A. Dell, M. A. Valvano, and M. Aebi. 2005. Engineering N-linked protein glycosylation with diverse O antigen lipopolysaccharide structures in Escherichia coli. Proc Natl Acad Sci USA 102:3016-21; Wacker, M., M. F. Feldman, N. Callewaert, M. Kowarik, B. R. Clarke, N. L. Pohl, M. Hernandez, E. D. Vines, M. A. Valvano, C. Whitfield, and M. Aebi. 2006. Substrate specificity of bacterial oligosaccharyltransferase (OTase) suggests a common transfer mechanism for the bacterial and eukaryotic systems. Proc Natl Acad Sci USA 103:7088-93). It was shown that Campylobacter PglB transfers a diverse array of UndPP linked oligosaccharides if they contain an N-acetylated hexosamine at the reducing terminus (Wacker et al. (2006)), allowing conjugation of an antigenic polysaccharide to a protein of choice through an N-glycosidic linkage. While this may provide a theoretical basis for production of conjugated vaccines in vivo, many difficult challenges need to be overcome in order to realize this theoretical possibility.

Based on this previous discovery that C. jejuni contains a general N-linked protein glycosylation system, E. coli had been modified to include the N-linked protein glycosylation machinery of C. jejuni. In this way, glycosylated forms of proteins native to C. jejuni in an E. coli host were produced. It had been further shown that this process could be used to produce glycosylated proteins from different origins in modified E. coli host for use as vaccine products. Production by E. coli is advantageous because large cultures of such modified E. coli hosts can be produced which produce large quantities of useful vaccine.

Using this process to produce a glycosylated protein in a modified E. coli host for use as a vaccine product for S.

*aureus* encounters problems that have been perceived to be insurmountable. First, *E. coli* is a Gram-negative bacterium and its saccharide biosynthesis pathways differ greatly from those of a Gram-positive bacterium, such as *S. aureus*, after the polymerization step. In addition, it would have been infeasible to genetically engineer *E. coli* to produce the *S. aureus* capsular polysaccharide directly consistent with previous technologies. For example, *S. aureus* is a Gram positive organism and its capsule synthesis is associated with cell envelope structure and construction of the cellular hull. The capsule producing biosynthetic machinery is specifically designed to arrange the capsular polysaccharide (PS) on the outside of the cell and its cell wall. It would have been extremely difficult, for at least the reason that it would be highly resource-intensive, to produce this capsule in a modified *E. coli* organism, because the cell envelope of *E. coli* is constructed in a fundamentally different way. The biosynthetic machinery for capsule assembly from PS precursor would be non-functional due to the different environment. Whereas the *S. aureus* capsule must transit a single membrane, in *E. coli* there is an additional membrane which needs to be crossed to reach the final location of an authentic capsule. Furthermore, as the *S. aureus* capsule is very large, it was believed to be infeasible to make a large capsule like the *S. aureus* capsule between the two membranes of *E. coli*.

The principle that enzymes from different organisms can work together has been shown before (e.g. Rubires, X., F. Saigi, N. Pique, N. Climent, S. Merino, S. Alberti, J. M. Tomas and M. Regue. 1997. A gene (wbbL) from *Serratia marcescens* N28b (O4) complements the rfb-50 mutation of *Escherichia coli* K-12 derivatives. J. Bacteriol 179(23): 7581-6). However, it is believed that no modified LPS polysaccharide from a Gram-positive organism has previously been produced in a Gram-negative organism.

BRIEF SUMMARY OF THE INVENTION

We have now surprisingly discovered a novel *S. aureus* bioconjugate vaccine. This novel *S. aureus* vaccine is based on the novel and unexpected discovery that an oligo- or polysaccharide of a prokaryote having one Gram strain can glycosylate a protein in a host prokaroyte having a different Gram strain. Further novel and unexpected features of the invention include without limitation the embodiments set forth below.

More generally, the present invention is directed to a bioconjugate vaccine, such as a Gram-positive vaccine, comprising a protein carrier comprising an inserted nucleic acid consensus sequence; at least one oligo- or polysaccharide from a bacterium such as a Gram-positive bacterium linked to the consensus sequence, and, optionally, an adjuvant. Further, the invention is directed to a Gram-positive bacteria vaccine, such as an *S. aureus* vaccine, or other bacteria vaccine, made by a glycosylation system using a modified LPS biosynthetic pathway, which comprises the production of a modified capsular polysaccharide or LPS.

The instant invention is additionally directed to a recombinant N-glycosylated protein comprising a protein comprising at least one inserted consensus sequence D/E-X-N-Z-S/T, wherein X and Z may be any natural amino acid except proline; and at least one oligo- or polysaccharide from a bacterium such as a Gram-positive bacterium linked to said consensus sequence.

The present is furthermore directed to a combination of a modified capsular polysaccharide of *S. aureus* with a protein antigen from the same organism by N-glycosidic linkage.

The invention is further directed to host prokaryotic organisms comprising a nucleotide sequence encoding one or more glycosyltransferase of a first prokaryotic species, such as a Gram-positive species; one or more glycosyltransferases of a different prokaryotic species, such as a Gram-negative species; a nucleotide sequence encoding a protein; and a nucleotide sequence encoding an OTase. The invention is additionally directed to an engineered host prokaryotic organism comprising an introduced nucleotide sequence encoding glycosyltransferases native only to a Gram-positive prokaryotic organism; a nucleotide sequence encoding a protein; and a nucleotide sequence encoding an OTase.

The invention is furthermore directed to methods of producing a bioconjugate vaccine in a host prokaryotic organism comprising nucleic acids encoding one or more glycosyltransferases of a first prokaryotic species, such as a Gram-positive species, for example, *S. aureus*; one or more glycosyltransferases of a second prokaryotic species, a protein; and an OTase. In addition, the present invention is directed to the production of bioconjugate vaccines by producing in Gram-negative bacteria modified capsular polysaccharides, which can be transferred to lipid A core by WaaL and/or linked to a carrier of choice by the OTase.

The invention is further directed to methods of producing glycosylated proteins in a host prokaryotic organism comprising nucleotide sequence encoding glycosyltransferases native to a first prokaryotic organism and also encoding glycosyltransferases native to a second prokaryotic organism that is different from the first prokaryotic organism. The present invention is additionally directed to the production of proteins N-glycosylated with capsular polysaccharides of Gram-positive bacteria, which are synthesized by a combination of different glycosyltransferases from different organisms. The invention is furthermore directed to the production of glycosylated proteins in a host prokaryotic organism comprising an introduced nucleotide sequence encoding glycosyltransferases native only to a Gram-positive prokaryotic organism.

The instant invention is moreover directed to plasmids, such as, plasmids comprising one or more of SEQ. ID NO: 2, SEQ ID NO: 3 and SEQ ID NO: 4. The invention also includes plasmids comprising one or more of SEQ. ID NO: 6; SEQ. ID NO: 7; SEQ. ID NO: 8 and SEQ. ID NO: 16. The invention also relates to plasmids comprising one or more of SEQ. ID NO: 10; SEQ. ID NO: 11; and SEQ. ID NO: 12. Moreover, the invention is directed to plasmids comprising one or more of SEQ. ID NO: 13; SEQ. ID NO: 15; SEQ. ID NO: 15; SEQ. ID NO: 17; SEQ ID NO: 18; SEQ. ID NO: 19; SEQ. ID NO: 20; SEQ. ID NO: 21 and SEQ. ID NO: 27.

The invention is additionally directed to transformed bacterial cells, such as, for example, bacterial cells transformed with a plasmid comprising one or more of SEQ. ID NO. 2; SEQ. ID NO: 3; SEQ. ID NO: 4; SEQ. ID NO: 17; SEQ. ID NO: 18; SEQ. ID NO: 19 and SEQ. ID NO: 20; SEQ. ID NO: 21; and SEQ. ID NO: 27. The instant invention is further directed to a bacterial cell transformed with a plasmid comprising one or more of SEQ. ID NO: 5; SEQ. ID NO: 8; SEQ. ID NO: 9; SEQ. ID NO: 10; SEQ. ID NO: 11; SEQ. ID NO: 12; SEQ. ID NO: 13; SEQ. ID NO: 14; SEQ. ID NO: 15 and SEQ. ID NO: 16.

The instant invention is further directed to a method of inducing an immune response against an infection caused by Gram-positive and other bacteria in a mammal. In one embodiment, the method comprises administering to said mammal an effective amount of a pharmaceutical composition comprising: protein comprising at least one inserted consensus sequence D/E-X-N-Z-S/T, wherein X and Z may be any natural amino acid except proline; and one or more oligo- or polysaccharides, the one or more oligo- or polysaccharides being the same or different as another of the one or more oligo- or polysaccharides, from a Gram-positive bacterium linked to said consensus sequence.

In another aspect, the invention features a method of identifying a target polysaccharide for use in glycosylating a protein with said target polysaccharide, in whole or in part. Said glycosylated protein comprising the target polysaccharide can be used, for example, in vaccine compositions. In one embodiment, the method of identifying a target polysaccharide includes: identifying a Gram-positive bacterium, such as *S. aureus*, as a target; identifying a first repeating unit of a polysaccharide produced by said Gram-positive bacterium comprising at least three monomers; identifying a polysaccharide produced by a bacterium of a Gram-negative species comprising a second repeating unit comprising two of the same monomers as said first repeating unit.

The present invention is also directed to a method for modifying a bacterium of a first bacterial species such as a Gram-negative species. In one embodiment, the method includes: identifying a first repeating unit of a polysaccharide of a Gram-positive species, such as *S. aureus*, comprising three monomers; identifying a polysaccharide produced by a bacterium of a second Gram-negative species comprising another repeating unit comprising two of the same monomers of the first repeating unit; inserting into said bacterium of a first Gram-negative species one or more nucleotide sequences encoding glycosyltransferases that assemble a trisaccharide comprising: a) said second repeating unit; and b) a monomer of said first repeating unit not present in said second repeating unit; inserting a nucleotide sequence encoding a protein; and inserting a nucleotide sequence encoding an OTase.

BRIEF DESCRIPTION OF THE DRAWINGS

FIG. 8A depicts recombinant CP5 LPS production of an embodiment of the invention analyzed by SDS-PAGE and stained by silver in dependence of antibiotic resistance gene on the pLAFR plasmid containing the chimeric cluster in W3110 ΔwecA cells.

FIG. 8B depicts recombinant CP5 LPS production of an embodiment of the invention analyzed by SDS PAGE, stained by silver and immunodetection in dependence of antibiotic resistance gene on the pLAFR plasmid containing the chimeric cluster in W3110 ΔwecA cells.

FIG. 11G and FIG. 11G-1 present the results of HPLC analysis of the full CP5 glycan repertoire present on UndPP in *E. coli* cells in an embodiment of the present invention.

FIG. 17A depicts the results of passive immunization using anti CP5-EPA antibodies, according to an embodiment of the present invention, in mice challenged i.p. with ~3.6.10$^7$ CFU of S. aureus strain Reynolds.

FIG. 17B depicts the results of passive immunization using anti CP5-EPA antibodies, according to an embodiment of invention, in mice injected with 2 mg CP5-EPA IgG.

FIG. 17C depicts the results of passive immunization using anti CP5-EPA antibodies, according to an embodiment of the invention, in mice injected with 300 µg CP5-EPA IgG

DETAILED DESCRIPTION OF THE INVENTION

Figure 1:
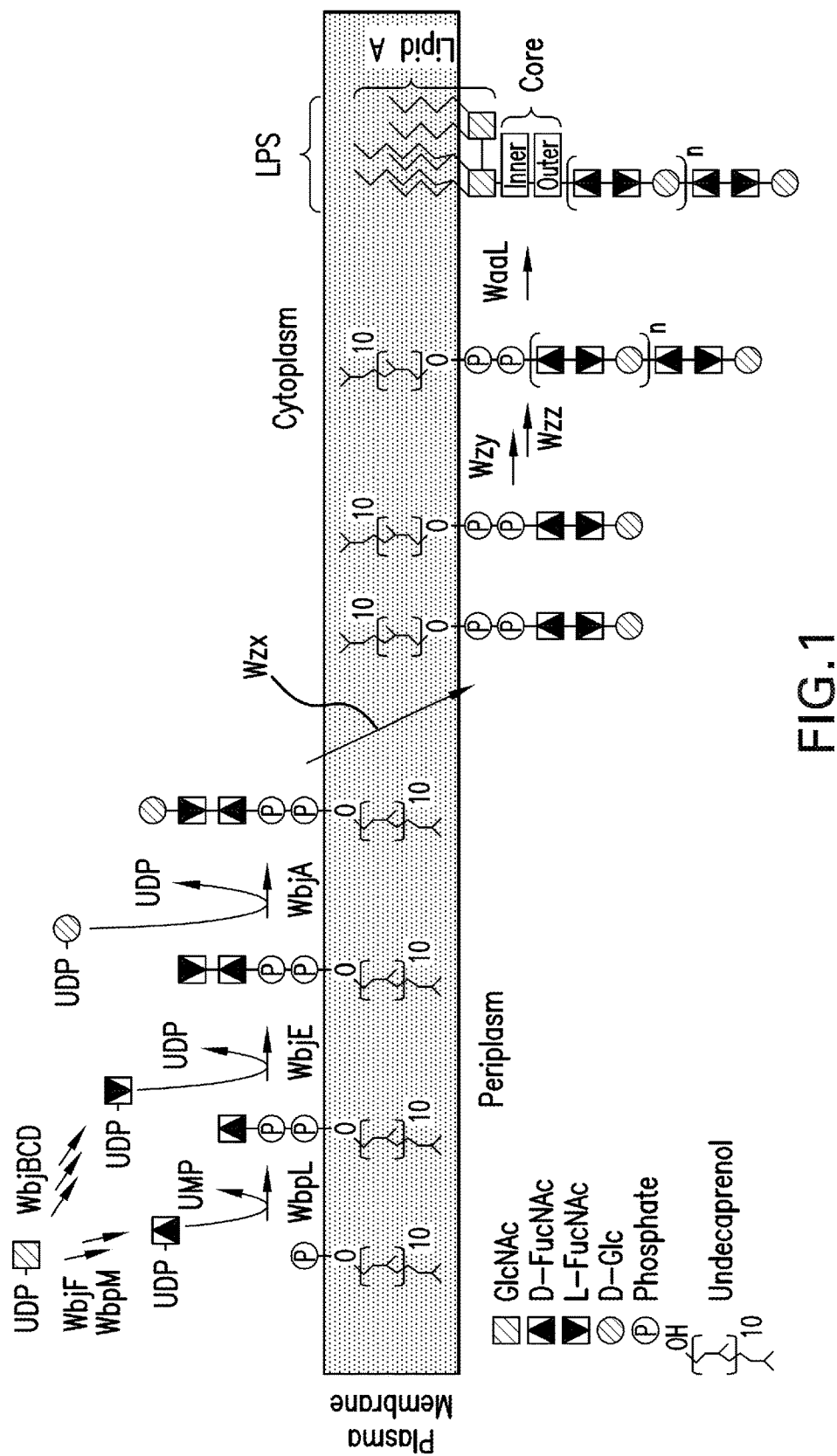
FIG. 1 depicts a pathway for the wzx/wzy-dependent O-antigen biosynthesis, exemplified by the *P. aeruginosa* O11 O-antigen biosynthesis. Protein names putatively responsible for the presented reactions are indicated above or below the arrows, including uridine diphosphate (UDP) and uridine monophosphate (UMP).

According to an embodiment of the present invention, an LPS polysaccharide from a Gram-positive organism has now been shown to be produced in a Gram-negative organism. We believe that this is a novel result that represents an important and significant departure from the prior art.

Nucleic acids within the scope of the invention are exemplified by the nucleic acids of the invention contained in the Sequence Listing. Any nucleic acid encoding an immunogenic component, or portion thereof, which is capable of expression in a host cell, can be used in the present invention. The following sequence descriptions are provided to facilitate understanding of certain terms used throughout the application and are not to be construed as limiting embodiments of the invention.

SEQ ID NO: 1 depicts pLAFR1 (Gene Bank Accession AY532632.1) containing the O11 O-antigen sequence from P. aeruginosa PAO103 in the EcoRI site, complementary strand (partially from Gen Bank Accession AF236052).

SEQ ID NO: 2 depicts pLAFR1 containing the CP5 chimeric cluster, corresponding to the pLAFR1-O11 with the cap5HIJ genes replacing wbjA-wzy by homologous recombination. The inserted sequence also contains a cat cassette for selection of homologous recombined clones.

SEQ ID NO: 3 depicts pLAFR1 containing the CP5 chimeric cluster with the cap5K flippase gene, corresponding to the pLAFR-O11 with the cap5HIJ genes replacing wbjA-wzy by homologous recombination and the cap5K cloned between cap5J and the cat cassette.

SEQ ID NO: 4 depicts pLAFR1 containing the CP8 chimeric cluster including a flippase gene, corresponding to the pLAFR1-O11 with the cap8KHIJ genes replacing wbjA-wzy. The inserted sequence also contains a cat cassette for selection of homologous recombined clones.

SEQ ID NO: 5 depicts an expression plasmid for Hla H35L production. The ORF encoding Hla H35L is cloned into NdeI/SacI in pEC415.

SEQ ID NO. 6 depicts the expression plasmid for Hla-H35L site 202 production. The ORF encodes an N-terminal DsbA signal peptide from E. coli, a glycosite around amino acid position 202, and a C-terminal HIS-tag. This construct is cloned into NheI/SalI on pEC415.

SEQ ID NO: 7 depicts the expression plasmid for Hla-H35L site 238 production. The ORF encodes an N-terminal DsbA signal peptide from E. coli, a glycosite around amino acid position 238, and a C-terminal HIS-tag. The above mentioned construct is cloned into NheI/SalI on pEC415.

SEQ ID NO: 8 depicts the expression plasmid for Hla-H35L site 272 production. The ORF encodes an N-terminal DsbA signal peptide from E. coli, a glycosite around amino acid position 272, and a C-terminal HIS-tag. The above mentioned construct is cloned into NheI/SalI on pEC415.

SEQ ID NO: 9 depicts an expression plasmid for ClfA production. The gene was chemically synthesized and cloned into the NdeI/SacI in pEC415 expression vector.

SEQ ID NO: 10 depicts the expression plasmid for ClfA site 290 production. The ORF encodes an N-terminal DsbA signal peptide from E. coli, a glycosite around amino acid position 290, and a C-terminal HIS-tag. The above mentioned construct is cloned into NheI/SalI on pEC415.

SEQ ID NO: 11 depicts the expression plasmid for ClfA site 327 production. The ORF encodes an N-terminal DsbA signal peptide from E. coli, a glycosite around amino acid position 327, and a C-terminal HIS-tag. The above mentioned construct is cloned into NheI/SalI on pEC415.

SEQ ID NO: 12 depicts the expression plasmid for ClfA site 532 production. The ORF encodes an N-terminal DsbA signal peptide from E. coli, a glycosite around amino acid position 532, and a C-terminal HIS-tag. The above mentioned construct is cloned into NheI/SalI on pEC415.

SEQ ID NO: 13 depicts the amino acid sequence of recombinant, genetically detoxified EPA with a signal sequence and two glycosylation sites at positions 260 and 402.

SEQ ID NO: 14 depicts the amino acid sequence of recombinant, genetically detoxified EPA without signal sequence and two glycosylation sites at positions 241 and 383.

SEQ ID NO: 15 depicts the ORF encoding AcrA cloned via NheI/SalI into pEC415.

SEQ ID NO: 16 depicts the expression plasmid for Hla-H35L site 130 production. The ORF encodes an N-terminal DsbA signal peptide from E. coli, a glycosite around amino acid position 130, and a C-terminal HIS-tag. The above mentioned construct is cloned NheI/SalI into pEC415.

SEQ ID NO: 17 depicts CP5 producing gene cluster with cap5K flippase followed by a pglB expression cassette consisting of the intergene DNA sequence between galF and wbqA of E. coli serotype O121 and the pglB ORF. The insert is cloned in the EcoRI site of pLAFR1.

SEQ ID NO: 18 depicts CP8 producing gene cluster with cap8K flippase followed by a pglB expression cassette consisting of the intergene DNA sequence between galF and wbqA of E. coli serotype O121 and the pglB ORF. The insert is cloned in the EcoRI site of pLAFR1.

SEQ ID NO: 19 depicts CP8 producing gene cluster with cap8K flippase followed by a pglB expression cassette consisting of the intergene DNA sequence between galF and wbqA of E. coli serotype O121 and the pglB ORF, in addition this sequence has the gene for wzz of the E. coli serovar O7 cloned into SfaAI/BspTI, i.e. between wzx of Pseudomonas aeruginosa O11 and cap8H. The insert is cloned in the EcoRI site of pLAFR1.

SEQ ID NO: 20 depicts an expression plasmid for EPA and wzz. The backbone is pACT3 in which the resistance cassette was replaced (kanamycin for chloranphenicol)

SEQ ID NO: 21 depicts wzz of E. coli serotype O7 cloned in pext21 Eco/Sal.

SEQ ID NO: 22 depicts a peptide sequence set forth in the Examples.

SEQ ID NO: 23 depicts a peptide sequence set forth in the Examples.

SEQ ID NO: 24 depicts a protein consensus sequence, D/E-X-N-Z-S/T, wherein X and Z may be any natural amino acid except proline.

SEQ ID NO: 25 depicts a glycosylation site.

SEQ ID NO: 26 depicts a glycosylation site.

SEQ ID NO: 27 depicts an expression plasmid containing the pglB ORF cloned in EcoRI/BamHI sites.

Descriptions of terms and abbreviations appear below as used in the specification and consistent with the usages known to one of ordinary skill in the art. The descriptions are provided to facilitate understanding of such terms and abbreviations and are not to be construed as limiting embodiments of the invention.

AcrA refers to a glycoprotein from C. jejuni.

Active immunization refers to the induction of immunity (antibodies) after exposure to an antigen.

APCs refers to antigen presenting cells.

Amp refers to ampicillin.

Bacteremia refers to the presence of viable bacteria in the circulating blood.

C' refers to complement.

CapA is an enzyme proposed to be a chain length determinant in S. aureus CP5.

CapB is an enzyme proposed to be a regulator of polysaccharide chain length in S. aureus CP5.

CapC is an enzyme proposed to encode a transporter protein in S. aureus CP5.

CapD an enzyme having 4,6 dehydratase activity and converts the precursor UDPGlcNAc to UDP-2-acetamido-2,6 dideoxy-D-xylo-4-hexulose in S. aureus CP5.

CapE is a 4,6-dehydratase 3,5-epimerase catalyzing the epimerization of UDP-D-GlcNAc to UDP-2-acetamido-2,6-dideoxy-D-lyxo-4-hexulose in S. aureus CP5.

CapF is a reductase, catalyzes the reduction form UDP-2-acetamido-2, 6-dideoxy-D-lyxo-4-hexulose to UDP-L-6dTalNAc in S. aureus CP5.

CapG is a 2-Epimerase, catalyzes the epimerization form UDP-L-6dTalNAc to UDP-LFucNAc in S. aureus CP5.

CapH in S. aureus CP5 is an O-acetyltransferase.

CapH in CP8 is a transferase similar to CapI from S. aureus CP5.

CapI in S. aureus CP5 is a glycosyltransferase which catalyzes the transfer of UDP-ManNAcA into carrier lipid-D-FucNAc-L-FucNAc producing carrier lipid-D-FucNAc-L-FucNAc-ManNAcA.

CapI in CP8 is a polymerase which is similar to CapJ in S. aureus CP5.

CapJ in S. aureus CP5 is a polymerase.

CapJ in CP8 is an O-acetyltransferase similar to CapH in S. aureus CP5.

CapK in S. aureus CP5 is a flippase.

CapK in S. aureus CP8 is a flippase similar to the CapK in CP5.

CapL is a transferase which catalyzes the transfer of UDP-L-FucNAc onto D-FucNAc-carrier lipid producing carrier lipid-D-FucNAc-L-FucNAc in S. aureus CP5.

CapM is a transferase which catalyzes the transfer of UDP-D-FucNAc on to carrier lipid producing carrier lipid-D-FucNAc in S. aureus CP5.

CapN is a 4-reductase which catalyzes the reduction from UDP-2-acetamido-2, 6-dideoxy-D-xylo-4-hexulose. to UDP-D-FucNAc in S. aureus CP5.

CapO is a dehydrogenase which catalyzes the conversion of UDP-D-ManNAc into UDP-ManNAcA in S. aureus CP5.

CapP is a 2-epimerase which catalyzes the epimerization of UDP-D-GlcNAc to UDP-D-ManNAc in S. aureus CP5.

CFU refers to Colony formation unit.

ClfA refers to S. aureus clumping factor A, a cell wall-anchored protein.

Conjugate vaccine refers to a vaccine created by covalently attaching a polysaccharide antigen to a carrier protein. Conjugate vaccine elicits antibacterial immune responses and immunological memory. In infants and elderly people a protective immune response against polysaccharide antigens can be induced if these antigens are conjugated with proteins that induce a T-cell dependent response.

Consensus sequence refers to a sequence of amino acids, -D/E-X-N-Z-S/T- wherein X and Z may be any natural amino acid except Proline, within which the site of carbohydrate attachment to N-linked glycoproteins is found.

Capsular polysaccharide, in its naturally occurring form, refers to a thick, mucous-like layer of polysaccharide, is water soluble and commonly acidic. Naturally-occurring capsular polysaccharides consist of regularly repeating units of one to several monosaccharides/monomers.

CP5 refers to *Staphylococcus aureus* type 5 capsular polysaccharide or serotype 5 capsular polysaccharide.

CP8 refers to *Staphylococcus aureus* type 8 capsular polysaccharide or serotype 8 capsular polysaccharide.

D-FucNAc refers to N-acetyl D-fucosamine.

ECA refers to enterobacterial common antigen.

ELISA refers to Enzyme-linked immunosorbent assay, a biochemical technique used mainly in immunology to detect the presence of an antibody or an antigen in a sample.

EPA or EPAr refers to nontoxic recombinant *P. aeruginosa* exoprotein A.

Glycoconjugate vaccine refers to a vaccine comprising a protein carrier linked to an antigenic or immunogenic oligosaccharide.

Glycosyltransferase refers to enzymes that act as a catalyst for the transfer of a monosaccharide unit from an activated nucleotide sugar to a glycosyl acceptor molecule.

Gram-positive strain refers to a bacterial strain that stains purple with Gram staining (a valuable diagnostic tool). Gram-positive bacteria have a thick mesh-like cell wall made of peptidoglycan (approximately 50-90% of cell wall).

Gram-negative strain refers to a bacterial strain which has a thinner layer (approximately 10% of cell wall) which stains pink. Gram-negative bacteria also have an additional outer membrane that contains lipids, and is separated from the cell wall by the periplasmic space.

Hla (alpha toxin) refers to alpha hemolysin, which is a secreted pore-forming toxin and an essential virulence factor antigen of *S. aureus*.

Hla H35L refers to a mutant form of Hla nontoxic alpha-toxin mutant from *S. aureus*.

Histidine tag, or polyhistidine-tag, is an amino acid motif in proteins that consists of at least five histidine (His) residues, often at the N- or C-terminus of the protein, and used to purify in a simple and fast manner by specifically binding to a nickel affinity column.

IV refers to intravenously.

kDa refers to kilo Daltons, is an atomic mass unit.

L-FucNAc refers to N-acetyl L-fucosamine.

LPS refers to lipopolysaccharide. Lipopolysaccharides (LPS), also known as lipoglycans, are large molecules consisting of a lipid and a polysaccharide joined by a covalent bond; they are found in the outer membrane of Gram-negative bacteria, act as endotoxins and elicit strong immune responses in animals.

ManNAcA refers to N-acetyl mannosaminuronic acid.

Methicillin-resistant *S. aureus* strains (MRSA) refers to methicillin-resistant *S. aureus* strain associated with longer hospital stay and more infections in intensive care units which leads to more antibiotic administration.

N-glycans or N-linked oligosaccharides refers to mono-, oligo- or polysaccharides of variable compositions that are linked to an ε-amide nitrogen of an asparagine residue in a protein via an N-glycosidic linkage.

N-linked protein glycosylation refers to a process or pathway to covalently link "glycans" (mono-, oligo- or polysaccharides) to a nitrogen of asparagine (N) side-chain on a target protein.

O-antigens or O-polysaccharides refers to a repetitive glycan polymer contained within an LPS. The O antigen is attached to the core oligosaccharide, and comprises the outermost domain of the LPS molecule.

Oligosaccharides or Polysaccharides refers to homo- or heteropolymer formed by covalently bound carbohydrates (monosaccharides), and includes but is not limited to repeating units (monosaccharides, disaccharides, trisaccharides, etc.) linked together by glycosidic bonds.

Opsonophagocytic activity refers to phagocytosis of a pathogen in the presence of complement and specific antibodies. The in vitro opsonophagocytic activities (OPAs) of serum antibodies are believed to represent the functional activities of the antibodies in vivo and thus to correlate with protective immunity.

OTase or OST refers to oligosaccharyl transferase, which catalyzes a mechanistically unique and selective transfer of an oligo- or polysaccharide (glycosylation) to the asparagine (N) residue at the consensus sequence of nascent or folded proteins.

Passive immunization is the transfer of active humoral immunity in the form of already made antibodies, from one individual to another.

Periplasmic space refers to the space between the inner cytoplasmic membrane and external outer membrane of Gram-negative bacteria.

PMNs refers to polymorphonuclear neutrophils, which are the most abundant white blood cells in the peripheral blood of humans, and many (though not all) mammals.

Protein carrier refers to a protein that comprises the consensus sequence into which the oligo- or polysaccharide is attached.

RU refers to a repeating unit comprising specific polysaccharides synthesized by assembling individual monosaccharides into an oligo- or polysaccharide.

Signal sequence refers to a short (e.g., approximately 3-60 amino acids long) peptide at the N-terminal end of the protein that directs the protein to different locations.

UDP-D-ManNAc is UDP-N-acetyl-D-mannosamine.

UDP-D-ManNAcA is UDP-N-acetyl-D-mannosaminuronic acid.

UDP-D-QuiNAc is UDP-N-acetyl-D-quinovosamine.

UDP-L-FucNAc is UDP-N-acetyl-L-fucosamine.

UDP-L-6dTalNAc is UDPN-acetyl-L-pneumosamine.

Und refers to undecaprenyl or undecaprenol lipid composed by eleven prenol units.

UndP refers to undecaprenyl phosphate, which is a universal lipid carrier (derived from Und) of glycan biosynthetic intermediates for carbohydrate polymers that are exported to the bacterial cell envelope.

UndPP refers to undecaprenyl pyrophosphate, which is a phosphorylated version of UndP.

wbjA is a glucosyltransferase in *P. aeruginosa* O11.

wbjB is a putative epimerase similar to enzymes required to the capsule biosynthesis of CP5 and CP8 in *S. aureus*.

wbjC is a putative epimerase in *P. aeruginosa* O11.

wbjD is a putative epimerase in *P. aeruginosa* O11.

wbjE is a putative epimerase in *P. aeruginosa* O11.

wbjF is a glycosyltranseferase in *P. aeruginosa* O11.

wbpL is a glycosyltransferase that participates in LPS biosynthesis in *P. aeruginosa* O11.

wbpM is a glycosyltransferase that participates in LPS biosynthesis in *P. aeruginosa* O11.

Embodiments of the invention are at least partially based on the discovery that *C. jejuni* contains a general N-linked protein glycosylation system, an unusual feature for prokaryotic organisms. Various proteins of *C. jejuni* have been shown to be modified by a heptasaccharide. This heptasaccharide is assembled on UndPP, the carrier lipid, at the cytoplasmic side of the inner membrane by the stepwise addition of nucleotide activated monosaccharides catalyzed by specific glycosyltransferases. The lipid-linked oligosaccharide is then flipped into (i.e., it diffuses transversely) the periplasmic space by a flippase, e.g., PglK. In the final step of N-linked protein glycosylation, the OTase (e.g., PglB) catalyzes the transfer of the oligosaccharide from the carrier lipid to Asn residues within the consensus sequence Asp/Glu-Xaa-Asn-Zaa-Ser/Thr (i.e., D/E-X-N-Z-S/T), where the Xaa and Zaa can be any amino acid except Pro. We had successfully transferred the glycosylation cluster for the heptasaccharide into *E. coli* and were able to produce N-linked glycoproteins of *Campylobacter*.

A novel and inventive method to modify a Gram-negative host bacterium, such as *E. coli*, has been developed to produce glycosylated proteins for use as vaccine products against a Gram-positive bacterium such as *S. aureus*. The development of this method required overcoming significant and in many respects unexpected problems, and departing substantially from conventional wisdom and the prior art.

In this novel and inventive method, another Gram-negative bacterium was identified that produces a polysaccharide that has structural similarity to the polysaccharide of interest of the target organism, for example *S. aureus*. For purposes of this invention, structural similarity manifests itself as repeating units in the polysaccharide of the target (e.g., *S. aureus*) that are partially identical to repeating units in the polysaccharide of the identified, other Gram-negative bacterium. Because this latter bacterium is Gram-negative, as is the host, for example, *E. coli* organism, we initially hypothesized (and later verified by experiment as discussed below) that use of its biosynthesis pathways in a modified *E. coli* organism would allow the biosynthesis of the constructed RU antigen and its flipping from the cytoplasm into the periplasm of the modified *E. coli* organism. Further, we hypothesized (and later verified by experiment as discussed below) that the size of the polysaccharide produced through this biosynthesis pathway would be much smaller than the polysaccharide produced by the biosynthesis pathway of Gram positive *S. aureus*.

As a result, and as discussed below, the novel and innovative method we developed solved the aforementioned difficult problems.

Furthermore, it was surprisingly found that aspects of the LPS pathway in a Gram-negative organism could be used to produce polysaccharides that contain some of the same repeating units as capsular polysaccharides native to Gram-positive bacteria, such as, for example, *S. aureus*, as detailed below.

Therefore, in making the polysaccharide section of the glycosylated protein vaccine for *S. aureus*, one surprising solution is to construct the polysaccharide section at least partially based on a polysaccharide native to a Gram-negative bacterium like *E. coli*. We further discovered that, in doing so, it is apparently important to find a bacterium which produces a polysaccharide that is as similar as possible to the polysaccharide of interest produced by *S. aureus*. *P. aeruginosa* is such a bacterium.

FIG. 1 provides a step-by-step depiction of an embodiment of the preparation of nucleotide-activated monosaccharides in the cytoplasm either by enzymes provided in the O-antigen cluster or by house keeping enzymes of the Gram-negative host cell, as would be apparent to one of skill in the art in light of this specification. The steps of the process proceed from left to right in the depiction of FIG. 1. In the embodiment depicted in FIG. 1, a glycosylphosphate transferase (WbpL) adds D-FucNAc phosphate to UndP, forming UndPP-FucNAc. Specific glycosyltransferases then elongate the UndPP-D-FucNAc molecule further by adding monosaccharides forming the repeating unit (RU) oligosaccharide (WbjE, WbjA). The RU is then flipped into the periplasmic space by the Wzx protein. The Wzy enzyme polymerizes periplasmic RUs to form the O-antigen polysaccharide. Polymer length is controlled by the Wzz protein. Many bacterial oligo- and polysaccharides are assembled on UndPP and then transferred to other molecules. In other words, UndPP is a general building platform for sugars in bacteria. In *E. coli* and, it is believed, most other Gram negative bacteria, the O-antigen is transferred from UndPP to Lipid A core by the *E. coli* enzyme WaaL to form lipopolysaccharide (LPS).

Figure 2:
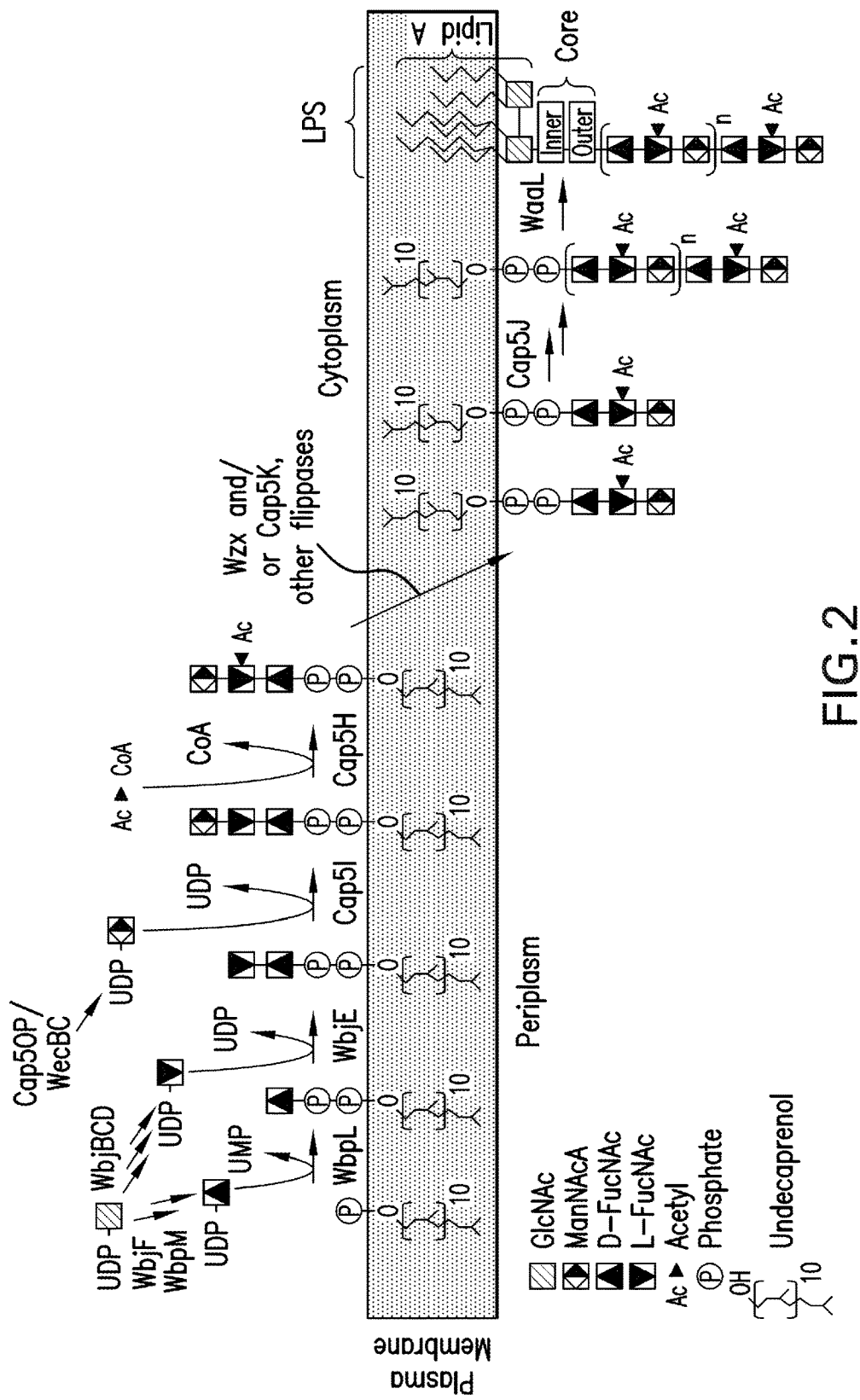
FIG. 2 depicts a proposed pathway for the engineered *S. aureus* capsular polysaccharide serotype 5 (CP5) biosynthesis in *E. coli*. The enzymes provided by the O-antigen cluster of *P. aeruginosa* O11 are indicated as in FIG. 1. Enzymes from *S. aureus* CP5 are indicated as Cap5 (compare to FIG. 6). WecB and WecC are *E. coli* enzymes required for the production of UDP-ManNAcA. Other depicted proteins and enzymes include uridine diphosphate (UDP), uridine monophosphate (UMP), and coenzyme A (CoA).

FIG. 2 depicts an embodiment of preparation of nucleotide-activated monosaccharides in the cytoplasm by enzymes provided in the O-antigen cluster of *P. aeruginosa* O11, by house keeping enzymes of the Gram-negative host cell, and by *S. aureus* and/or *E. coli* enzymes known to be required for UDP-ManNAcA biosynthesis (Cap5OP and/or WecBC), as would be apparent to one of skill in the art in light of this specification. In the depiction of FIG. 2, the steps of the process proceed from left to right. As in O11 biosynthesis, WbpL and WbjE synthesize the core disaccharide. Then, the *S. aureus* glycosyltransferase Cap5I adds D-ManNAcA. Cap5H adds an acetyl group to the second FucNAc residue. Acetylation may be the final step of RU synthesis as shown in FIG. 2. Flipping is possible by one or all of the Wzx proteins in the system, which are recombinantly expressed Wzx of *P. aeruginosa* or Cap5K, or endogenously expressed Wzx-like enzymes e.g. of the ECA cluster encoded in the *E. coli* chromosome. Polymerization is an exclusive activity of the Cap5J polymerase forming the CP5 polysaccharide on UndPP. As other UndPP linked polysaccharides, the CP5 sugar is transferred to Lipid A core by the *E. coli* enzyme WaaL to form recombinant LPS (LPS capsule).

Figure 3:
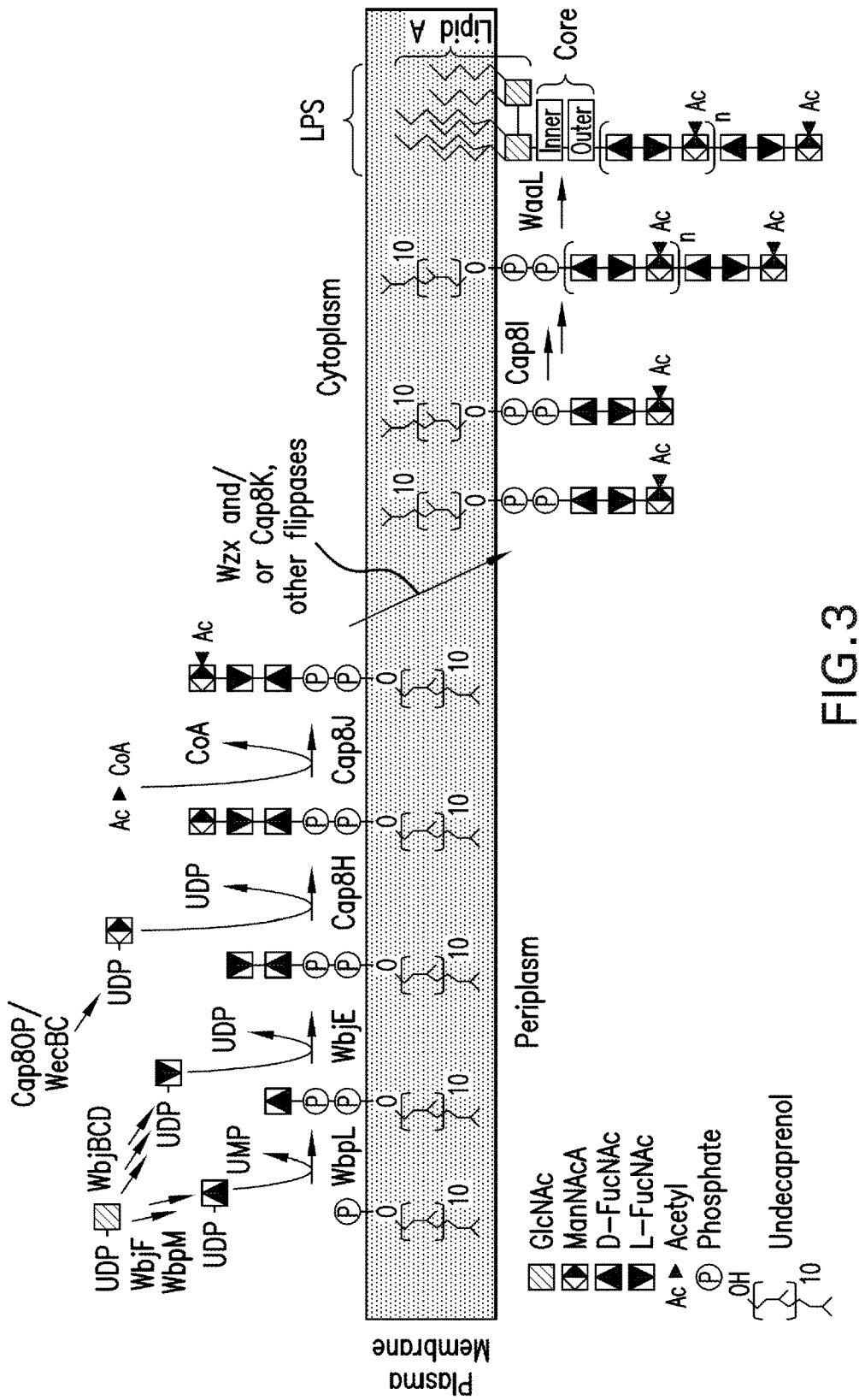
FIG. 3 depicts a proposed pathway for the engineered *S. aureus* capsular polysaccharide serotype 8 (CP8) biosynthesis. Gene names are indicated by arrows (compare to FIGS. 1, 2, and 6). UDP, UMP: uridine diphosphate, uridine monophosphate. CoA: coenzyme A.

FIG. 3 depicts the preparation of nucleotide-activated monosaccharides in the cytoplasm by enzymes provided in the O-antigen cluster of *P. aeruginosa* O11, by house keeping enzymes of the Gram-negative host cell, and by *S. aureus* and/or *E. coli* enzymes known to be required for UDP-ManNAcA biosynthesis (Cap8OP and/or WecBC), as would be apparent to one of ordinary skill in the art in light of this specification. In the depiction of FIG. 3, the steps of the process proceed from left to right. As in O11 biosynthesis, WbpL and WbjE synthesize the core disaccharide. Then, the *S. aureus* glycosyltransferase Cap8H adds D-ManNAcA. Cap8J adds an acetyl group to the second FucNAc residue. It is not known if acetylation occurs on the activated sugar or the lipid bound RU. Flipping is possible by one or all of the Wzx proteins in the system, which are recombinantly expressed Wzx of *P. aeruginosa* or Cap8K, or endogenously expressed Wzx-like enzymes e.g. of the ECA cluster encoded in the *E. coli* chromosome. Polymerization is an exclusive activity of the Cap8I polymerase forming CP8 polysaccharide on UndPP. The CP8 sugar is then transferred to Lipid A core in *E. coli* by the enzyme WaaL.

Figure 4:
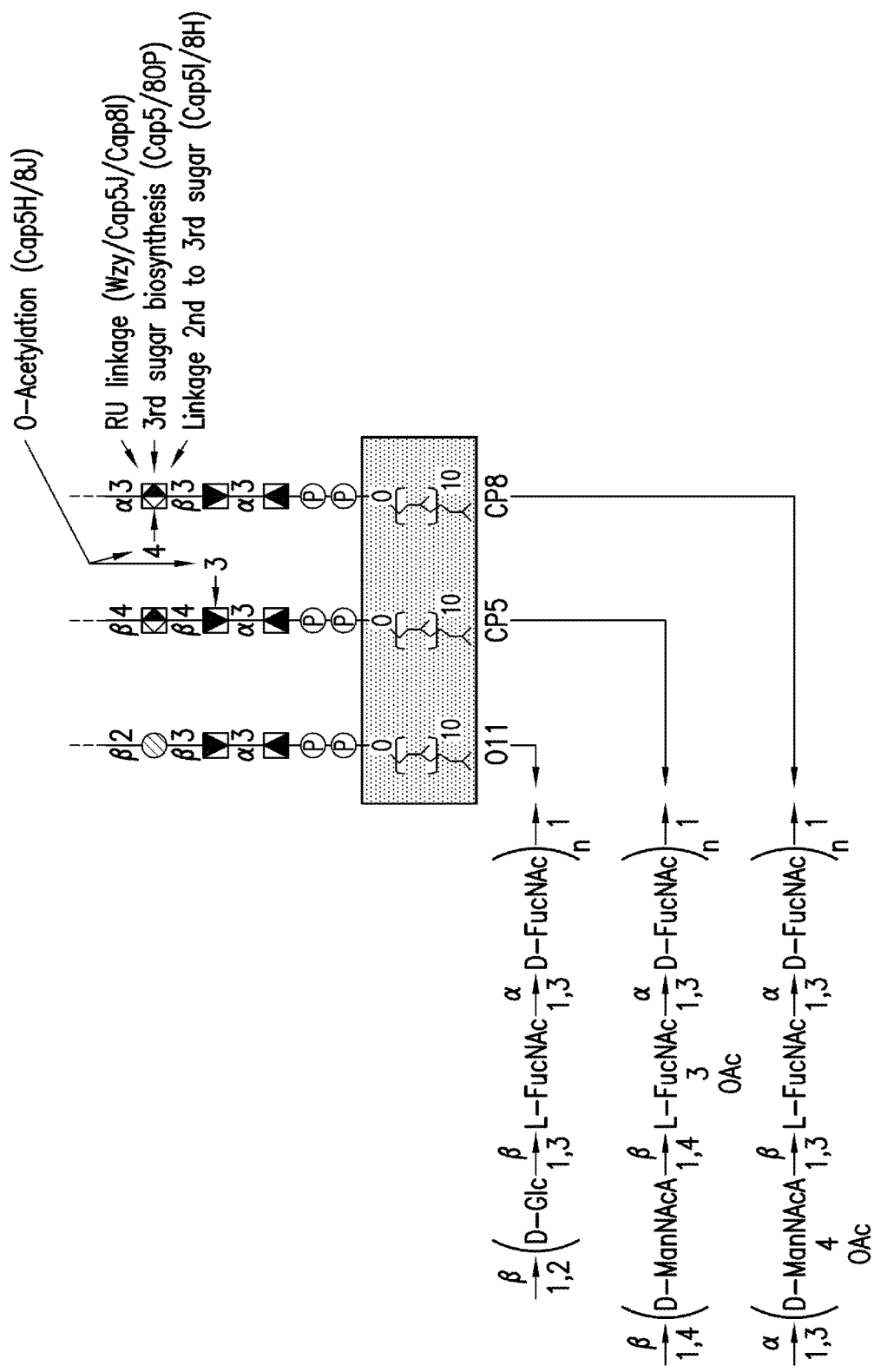
FIG. 4 depicts the structural overlap of capsular *S. aureus* and *P. aeruginosa* O-antigen Repeating Unit (RU) Structures.

FIG. 4 illustrates the different structures of the O11, CP5 and CP8 polysaccharides. It is shown in FIG. 4 that the RUs share the identical stem structure consisting of the UndPP and the disaccharide α-D-FucNAc-(1,3)-L-FucNAc. The *S. aureus* RUs are partially decorated with a single O-acetyl group, either on the middle L-FucNAc or on the ManNAcA residue, which is characteristic for the *S. aureus* RUs. The connectivity of the second and third sugar in the *S. aureus* RUs is different between them, as well as the connectivity between the polymerized RUs. On the right, the sugar structures are shown in a different representation. The number by the back arrows (CP5 and CP8) indicates the position of the carbon modified with an O-acetyl group. An alternative representation of the RU structures is shown on the bottom left. As shown in FIG. 4, there is great overlap between the RU in the O11 antigen that is part of a polysaccharide native to *P. aeruginosa* and those of the CP5 and CP8 capsules of the respective strains of *Staphylococcus*. In particular, as show in FIG. 4, the L-FucNAc->D-FucNAc portion in the RU it is identical in both.

In another aspect, the invention features a method of identifying a target polysaccharide for use in glycosylating a protein with said target polysaccharide, in whole or in part. Said glycosylated protein comprising the target polysaccharide can be used, for example, in vaccine compositions. The method of identifying a target polysaccharide includes: identifying a Gram-positive bacterium, such as *S. aureus*, as a target; identifying a first repeating unit of a polysaccharide produced by said Gram-positive bacterium comprising at least three monomers; identifying a polysaccharide produced by a bacterium of a Gram-negative species comprising a second repeating unit comprising at least two of the same monomers as said first repeating monomer unit.

Accordingly, in one embodiment of the invention, a method of modifying a bacterium of a first Gram-negative species includes: identifying a Gram-positive bacterium, such as *S. aureus*, as a target; identifying a first repeating unit of a polysaccharide produced by said Gram-positive bacterium comprising at least three monomers; identifying a polysaccharide produced by a bacterium of a second Gram-negative species comprising a second repeating unit comprising at least two of the same monomers as said first repeating unit; inserting into said bacterium of a first Gram-negative species one or more nucleotide sequences encoding glycosyltransferases that assemble a trisaccharide containing: a) said second repeating unit; and b) a monomer of said first repeating unit not present in said second repeating unit; inserting a nucleotide sequence encoding a protein, such as a protein comprising at least one inserted consensus sequence D/E-X-N-Z-S/T, wherein X and Z may be any natural amino acid except proline; and inserting a nucleotide sequence encoding an OTase.

In an embodiment of the invention, the method further comprises inserting into a host Gram-negative bacterium one or more nucleotide sequences encoding glycosyltransferases that assemble a trisaccharide containing a monomer of a first repeating unit not present in a second repeating unit and that assemble the second repeating unit. An additional embodiment of the invention involves inserting one or more glycosyltransferases from a Gram-negative bacterium that assemble at least one monomer unit from a first repeating unit and one or more glycosyltransferases from a Gram-positive bacterium, such as *S. aureus*, that assemble at least two monomers from a second repeating unit. The method additionally comprises inserting into inserting into a Gram-negative host bacterium a nucleotide sequence encoding a protein and a nucleotide sequence encoding an OTase.

In at least one embodiment of the invention, a host *E. coli* strain is generated carrying the corresponding nucleic acids encoding the required enzymes from the CP5 and CP8 strains of *S. aureus*, which will build up, flip and polymerize the constructed repeating units. In an embodiment, the specific glycosyltransferases needed correspond to those forming the L-FucNAc->D-FucNAc RU that are native to *P. aeruginosa*, and to glycosyltransferases corresponding to the ones adding the D-ManNAcA monosaccharide to the complete the RU that are native to each of the CP5 and CP8 strains of *S. aureus*. Such an embodiment may further include using a plasmid to inject the nucleic acids into the host cell. An additional embodiment involves using, in one plasmid, nucleic acids encoding for the glycosyltransferases corresponding to L-FucNAc->D-FucNAc, and, in a different plasmid, nucleic acids encoding for the glycosyltransferases corresponding to D-ManNAcA. One benefit of such embodiments, surprising in light of the prior art, is that the modified LPS biosynthesis pathway of *P. aeruginosa* that is now responsible for producing the constructed RU polymer of the *S. aureus* capsule results in a structure that is much smaller than the capsule of *S. aureus*.

The instant invention is additionally directed to a recombinant N-glycosylated protein comprising at least one inserted consensus sequence D/E-X-N-Z-S/T, wherein X and Z may be any natural amino acid except proline; and at least one oligo- or polysaccharide from a Gram-positive bacterium linked to said consensus sequence. In another embodiment, the recombinant N-glycosylated protein comprises two or more of said inserted consensus sequences. In yet an additional embodiment, the recombinant N-glycosylated protein comprises two or more of said *S. aureus* oligo- or polysaccharides. In a still further embodiment, the recombinant N-glycosylated protein comprises two or more of said inserted consensus sequences and oligo- or polysaccharides from different *S. aureus* strains, for example, from *S. aureus* capsular polysaccharide 5 strain and capsular polysaccharide 8 strain.

The present invention is furthermore directed to a combination of a modified capsular polysaccharide of *S. aureus* with a protein antigen from the same organism by N-glycosidic linkage.

Embodiments of the present invention include a protein that is glycosylated in nature. Such naturally glycosylated proteins (e.g., *C. jejuni* proteins) contain natural consensus sequences but do not comprise any additional (i.e., introduced) optimized consensus sequences. Naturally glycosylated proteins include prokaryotic and eukaryotic proteins. Embodiments of the instant invention further include a recombinant N-glycosylated protein, comprising one or more of the following N-glycosylated partial amino acid sequence(s): D/E-X-N-Z-S/T, (optimized consensus sequence) wherein X and Z may be any natural amino acid except Pro, and wherein at least one of said N-glycosylated partial amino acid sequence(s) is introduced. The introduction of specific partial amino acid sequence(s) (optimized consensus sequence(s)) into proteins leads to proteins that are efficiently N-glycosylated by an OTase, such as, for example, an OTase from *Campylobacter* spp., such as, for example, an OTase from *C. jejuni*, at the positions of introduction.

The term "partial amino acid sequence(s)" as it is used in the context of the present invention will also be referred to as "optimized consensus sequence(s)" or "consensus sequence(s)". The optimized consensus sequence is N-glycosylated by an OTase, such as, for example, an OTase from *Campylobacter* spp., such as, for example, an OTase from *C. jejuni*.

In accordance with the internationally accepted one letter code for amino acids the abbreviations D, E, N, S and T denote aspartic acid, glutamic acid, asparagine, serine, and threonine, respectively.

The introduction of the optimized consensus sequence can be accomplished by the addition, deletion and/or substitution of one or more amino acids. The addition, deletion and/or substitution of one or more amino acids for the purpose of introducing the optimized consensus sequence can be accomplished by chemical synthetic strategies well known to those skilled in the art such as solid phase-assisted chemical peptide synthesis. Alternatively, and preferred for larger polypeptides, the proteins of the present invention can be prepared by standard recombinant techniques by adding nucleic acids encoding for one or more optimized consensus sequences into the nucleic acid sequence of a starting protein, which may be a protein that is naturally glycosylated or may be a protein that is not naturally glycosylated.

In a preferred embodiment, the proteins of the present invention may comprise one or more, preferably at least two or at least three, and more preferably at least five of said introduced N-glycosylated optimized amino acid sequences.

The presence of one or more N-glycosylated optimized amino acid sequence(s) in the proteins of the present invention can be of advantage for increasing their antigenicity, increasing their stability, affecting their biological activity, prolonging their biological half-life and/or simplifying their purification.

The optimized consensus sequence may include any amino acid except proline in position(s) X and Z. The term "any amino acids" is meant to encompass common and rare natural amino acids as well as synthetic amino acid derivatives and analogs that will still allow the optimized consensus sequence to be N-glycosylated by the OTase. Naturally occurring common and rare amino acids are preferred for X and Z. X and Z may be the same or different.

It is noted that X and Z may differ for each optimized consensus sequence in a protein according to the present invention.

The N-glycan bound to the optimized consensus sequence will be determined by the specific glycosyltransferases and their interaction when assembling the oligosaccharide on a lipid carrier for transfer by the OTase. Those skilled in the art can design the N-glycan by varying the type(s) and amount of the specific glycosyltransferases present in the desired host cell. (Raetz & Whitfield, Lipopolysaccharide Endotoxins, *NIH-PA Author Manuscript* 1-57, 19-25 (published in final edited form as: *Annual Rev. Biochem.*, 71: 635-700 (2002)); Reeves et al., Bacterial Polysaccharide Synthesis and Gene Nomenclature, Trends in Microbio. 4(3): 495-503, 497-98 (December 1996); and Whitfield, C. and I. S. Roberts. 1999. Structure, assembly and regulation of expression of capsules in *Escherichia coli*. Mol Microbiol 31(5): 1307-19).

"Polysaccharides" as used herein include saccharides comprising at least two monosaccharides. Polysaccharides include oligosaccharides, trisaccharides, repeating units comprising one or more monosaccharides (or monomers), and other saccharides recognized as polysaccharides by one of ordinary skill in the art. N-glycans are defined herein as mono-, oligo- or polysaccharides of variable compositions that are linked to an ε-amide nitrogen of an asparagine residue in a protein via an N-glycosidic linkage.

Polysaccharides of embodiments of the invention include without limitation *S. aureus* polysaccharides such as CP5 and CP8. Embodiment of the invention further includes *S. aureus* polysaccharides that target a bacterium, such as a polysaccharide that targets a methicillin-resistant strain of *S. aureus*. Where it is mentioned herein that polysaccharides target a bacterial strain, such polysaccharides include polysaccharides that are from the bacterium against which an immune or antigenic response is desired and further include polysaccharides that are the same as, based on, derived from, native to or engineered from the bacterium against which an immune or antigenic response is desired.

There is no limitation on the origin of the recombinant protein of the invention. In one embodiment, said protein is derived from mammalian, bacterial, viral, fungal or plant proteins. In a further embodiment, the protein is derived from mammalian, most preferably human proteins. For preparing antigenic recombinant proteins according to the invention, preferably for use as active components in vaccines, it is preferred that the recombinant protein is derived from a bacterial, viral or fungal protein. Glycosylation of proteins of various origins is known to one of skill in the art. Kowarik et al. "Definition of the bacterial N-glycosylation site consensus sequence" EMBO J. (2006) 1-10.

In an example in an embodiment, genetically detoxified *P. aeruginosa* Exotoxin (EPA) is a suitable protein carrier. For producing a version of EPA that may be glycosylated, the nucleic acids encoding for EPA need to be modified by insertion of glycosylation sites as previously discussed.

Protein carriers intended for use in embodiments of the invention should preferably have certain immunological and pharmacological features. From an immunological perspective, preferably, a protein carrier should: (1) have T-cell epitopes; (2) be capable of delivering an antigen to antigen presenting cells (APCs) in the immune system; (3) be potent and durable; and (4) be capable of generating an antigen-specific systemic IgG response. From a pharmacological perspective, a protein carrier should preferably: (1) be non-toxic; and (2) be capable of delivering antigens efficiently across intact epithelial barriers. More preferably, in addition to these immunological and pharmacological features, a protein carrier considered for use in the production of a bacterial bioconjugate should: (1) be easily secreted into the periplasmic space; and (2) be capable of having antigen epitopes readily introduced as loops or linear sequences into it. Informed by this disclosure and knowledge of one of ordinary skill in the art, a practitioner of ordinary skill in the art may routinely consider and identify suitable protein carriers that may be used in particular embodiments of the invention.

In an embodiment of the invention, the *Campylobacter* protein AcrA is a protein carrier.

In a further embodiment of the invention, genetically detoxified *P. aeruginosa* Exotoxin (EPA) is a protein carrier in which the target organism for which a vaccine is desired is *S. aureus*. Unlike AcrA which contains natural glycosylation sites, EPA contains no such natural glycosylation sites and needs to be modified by insertion of glycosylation sites (e.g., insertion of nucleic acids encoding for the optimized consensus sequence as discussed earlier into the nucleic acid sequence encoding for EPA). In an additional embodiment, EPA is modified to introduce two glycosylation sites that will allow glycosylation with the *S. aureus* antigen. In a still further embodiment, two consensus sequences are introduced as discussed in Example 10 of WO 2009/104074.

The amino acid sequence of EPA, as modified in an embodiment of this invention to contain two glycosylation sites, is provided as SEQ ID NO: 13 (with signal sequence) and SEQ ID NO.: 14 (without signal sequence). The glycosylation sites in SEQ ID NO: 13 are DNNNS and DQNRT at positions 260DNNNS and 402DQNRT. The glycosylation sites in SEQ ID NO: 14 are DNNNS and DQNRT at positions 241DNNNS and 383DQNRT.

A carrier protein such as EPA is a protein on which N-glycosylation sites may be added in the production of a bacterial bioconjugate. N-glycosylation sites require introduction of the consensus sequences discussed previously, namely, insertion of D/E-X-N-Z-S/T sequons, wherein X and Z may be any natural amino acid except proline. We have found that such consensus sequences preferably are introduced in surface loops, by insertion rather than mutation and by the use of additionally inserted flanking residues and by mutation of flanking residues to optimize the operation of the N-glycosylation site.

Some well-characterized protein subunit antigens of S. aureus are the alpha hemolysin (alpha toxin, Hla), clumping factor alpha (ClfA), IsdB, and Panton-Valentine Leukocidin (PVL).

Hla is a secreted pore-forming toxin and an essential virulence factor of MRSA in a mouse model of S. aureus pneumonia. The level of Hla expression by independent S. aureus strains directly correlates with their virulence. Active immunization with a mutant form of Hla (Hla H35L, SEQ ID NO: 5), which cannot form pores (Menzies, B. E., and D. S. Kernodle. 1996. Passive immunization with antiserum to a nontoxic alpha-toxin mutant from Staphylococcus aureus is protective in a murine model. Infect Immun 64:1839-41; Jursch, R., A. Hildebrand, G. Hobom, J. Tranum-Jensen, R. Ward, M. Kehoe and S. Bhakdi. 1994. Histidine residues near the N terminus of staphylococcal alpha-toxin as reporters of regions that are critical for oligomerization and pore formation. Infect Immun 62(6): 2249-56), was shown to generate antigen-specific immunoglobulin G responses and to afford protection against staphylococcal pneumonia. Transfer of Hla-specific antibodies protects naive animals against S. aureus challenge and prevents the injury of human lung epithelial cells during infection (Bubeck Wardenburg, J., A. M. Palazzolo-Ballance, M. Otto, O. Schneewind, and F. R. DeLeo. 2008. Panton-Valentine leukocidin is not a virulence determinant in murine models of community-associated methicillin-resistant Staphylococcus aureus disease. J Infect Dis 198:1166-70). To be used as a vaccine, the H35L mutation in Hla is required to eliminate toxicity of the protein (Menzies, B. E., and D. S. Kernodle. 1994. Site-directed mutagenesis of the alpha-toxin gene of Staphylococcus aureus: role of histidines in toxin activity in vitro and in a murine model. Infect Immun 62:1843-7). ClfA contains a protease resistant domain which is used for immunization. Passive immunization of mice with anti-ClfA and anti CP5 antibodies effectively sterilized mammary glands in mammary gland infection model (Tuchscherr, L. P., F. R. Buzzola, L. P. Alvarez, J. C. Lee, and D. O. Sordelli. 2008. Antibodies to capsular polysaccharide and clumping factor A prevent mastitis and the emergence of unencapsulated and small-colony variants of Staphylococcus aureus in mice. Infect Immun 76: 5738-44).

A further embodiment of the invention includes glycosylation of proteins native to S. aureus, for example, Hla and ClfA. In additional example embodiments of the invention, the protein carrier used may be selected to be the Hla protein, for example Hla H35L (for example, SEQ ID NO: 6, SEQ ID NO: 7, SEQ ID NO: 8 or SEQ ID NO: 16). In another additional example embodiment of the invention, the protein carrier is the ClfA protein (for example, SEQ ID NO: 10, SEQ ID NO: 11 or SEQ ID NO: 12).

The invention is further directed to recombinant host prokaryotic organisms comprising: a nucleotide sequence encoding one or more glycosyltransferase of a first prokaryotic species, such as a Gram-positive species; one or more glycosyltransferases of a different prokaryotic species, such as a Gram-negative species; a nucleotide sequence encoding a protein; and a nucleotide sequence encoding an OTase. The invention is additionally directed to a recombinant host prokaryotic organism comprising an introduced nucleotide sequence encoding glycosyltransferases native only to a Gram-positive prokaryotic organism; a nucleotide sequence encoding a protein; and a nucleotide sequence encoding an OTase. The invention is also directed to a recombinant or engineered host prokaryotic organism comprising: a nucleotide sequence encoding a glycosyltransferase native to a first prokaryotic species, which is, for example, different from the host prokaryotic organism; a nucleotide sequence encoding a glycosyltransferase native to a second prokaryotic species different from the species of said first prokaryotic organism and, for example, different from said host. The engineered prokaryotic organism can also, for example, comprise a first prokaryotic species that is a Gram-positive species. The engineered prokaryotic organism can also, for example, comprise a second prokaryotic species that is a Gram-negative species. The invention further includes a recombinant or engineered Gram-negative host prokaryotic organism comprising: a nucleotide sequence encoding a glycosyltransferase native to a Gram-negative prokaryotic species that is, for example, different from said host prokaryotic organism; a nucleotide sequence encoding a glycosyltransferase native to S. aureus; a nucleotide sequence encoding a protein; and a nucleotide sequence encoding an OTase. The invention further includes a recombinant or engineered E. coli host comprising: a nucleotide sequence encoding a glycosyltransferase native to P. aeruginosa; a nucleotide sequence encoding one or more glycosyltransferases native to S. aureus CP5 strain and/or to S. aureus CP8 strain; a nucleotide sequence encoding a P. aeruginosa EPA, S. aureus alpha hemolysin, or S. aureus clumping factor A protein carrier; and a nucleotide sequence encoding an OTase, for example, and OTase native to C. jejuni.

In addition to using the biosynthesis pathway of the other Gram-negative organism in the modified host E. coli organism, in a further embodiment, also included within the host E. coli organism are nucleic acids encoding for (i) glycosyltransferases for construction the structure of the repeating units of the polysaccharide of the other Gram-negative organism (that are identical to the repeating units of the polysaccharide of interest of the target Gram-positive S. aureus organism), and (ii) glycosyltransferases for construction of the units of the polysaccharide of interest of the target Gram-positive S. aureus organism that are not found in the relevant polysaccharide of the other Gram-negative organism, and (iii) enzymes for flipping and polymerization of the constructed RU of interest of the target Gram-positive S. aureus organism to form a S. aureus capsule like polysaccharide. In particular, in this embodiment, the nucleic acids encoding for (i) originated with the other Gram-negative bacterium, whereas the nucleic acids encoding for (ii) and (iii) originated with the target Gram-positive S. aureus organism.

Another aspect of the invention is directed to: an engineered host prokaryotic organism comprising: i) a nucleotide sequence encoding glycosyltransferases native to a Gram-positive prokaryotic species; ii) a nucleotide sequence encoding a protein; and iii) a nucleotide sequence encoding an OTase, wherein the sequences encoding transporter genes of said Gram-positive prokaryotic species are deleted. Such an embodiment involves an introduced nucleic acid construct that encodes only Gram-positive glycosyltransferases.

Regarding the other nucleic acids that would be inserted into the host in one or more other embodiments, nucleic acids encoding a protein, such as AcrA, Hla, ClfA or EPA (SEQ ID NO: 15, SEQ ID NO: 6, SEQ ID NO: 7, SEQ ID NO: 8, SEQ ID NO: 16; SEQ ID NO: 10, SEQ ID NO: 11, SEQ ID NO: 12; SEQ ID NO: 13, SEQ ID NO: 14), and the oligosaccharyltransferase of C. jejuni (SEQ ID NO: 27), which are part of the glycosylation machinery of that organism, are injected into the host in addition to the nucleic acids encoding for glycosyltransferases from each of P. aeruginosa and S. aureus. As a result, the modified E. coli organism can glycosylate the AcrA protein with the polysaccharide produced in that organism by action of the glycosyltransferases from S. aureus and the other Gram-negative bacterium.

One embodiment of the invention involves an engineered host prokaryotic organism comprising: i) a nucleotide sequence encoding a glycosyltransferase native to a first prokaryotic species different from the host prokaryotic organism; ii) a nucleotide sequence encoding a glycosyltransferase native to a second prokaryotic species, for example, a Gram-positive prokaryotic species, different from the host prokaryotic organism; iii) a nucleotide sequence encoding a protein; and iv) a nucleotide sequence encoding an OTase. In embodiments of the invention, the first prokaryotic species is a Gram-negative species, for example, P. aeruginosa.

In the context of the present invention, host cells refer to any host cell, e.g., an eukaryotic or prokaryotic host cell. In other embodiments the host cell is a prokaryotic host cell, e.g. Escherichia ssp., Campylobacter ssp., Salmonella ssp., Shigella ssp., Helicobacter ssp., Pseudomonas ssp. or Bacillus ssp. In still further embodiments, the host cell is Escherichia coli, Campylobacter jejuni, Salmonella typhimurium, etc.

The invention is furthermore directed to methods of producing a bioconjugate vaccine comprising introducing into a host prokaryotic organism nucleic acids encoding one or more glycosyltransferases of S. aureus; one or more glycosyltransferases of a second prokaryotic species, a protein; and an OTase. In addition, the present invention is directed to the production of bioconjugate vaccines by producing in Gram-negative bacteria modified capsular polysaccharides on undecaprenol (Und), and linking these polysaccharide antigens to a protein carrier of choice.

The invention is further directed to methods of producing glycosylated proteins in a host prokaryotic organism comprising nucleotide sequence encoding glycosyltransferases native to a first prokaryotic organism and also encoding glycosyltransferases native to a second prokaryotic organism that is different from the first prokaryotic organism. The present invention is additionally directed to the production of proteins N-glycosylated with capsular polysaccharides of Gram-positive bacteria, which are synthesized by a combination of different glycosyltransferases from different organisms. The invention is furthermore directed to the production of glycosylated proteins in a host prokaryotic organism comprising an introduced nucleotide sequence encoding glycosyltransferases native only to a Gram-positive prokaryotic organism.

As in known in the art, the biosynthesis of different polysaccharides is conserved in bacterial cells. The polysaccharides are assembled on carrier lipids from common precursors (activated sugar nucleotides) at the cytoplasmic membrane by different glycosyltransferases with defined specificity. (Whitfield, C., and I. S. Roberts. 1999. Structure, assembly and regulation of expression of capsules in Escherichia coli. Mol Microbiol 31: 1307-19). The biosynthetic pathway for polysaccharide production of O-antigen in Gram-negative and for capsular polysaccharide Type I in Gram-positive is conserved. The process uses the same lipid carrier, i.e., UndP, for polysaccharide assembly. It starts with the addition of a monosaccharide-1-phosphate to the carrier lipid UndP at the cytoplasmic side of the membrane. The antigen is built up by sequential addition of monosaccharides from activated sugar nucleotides by different glycosyltransferases. The lipid-linked oligosaccharide or RU is then flipped through the membrane by the flippase. RUs are polymerized by the enzyme Wzy in the periplasmic space, forming the so-called O-antigen in Gram negative bacteria or capsular polysaccharide in Gram-positive bacteria. Gram negative bacteria use the Wzz enzyme to regulate the length of the polymer, which is then transferred to lipid A core forming LPS. LPS is further translocated to the outer membrane exposing the O-antigen to the outside (as depicted, for example, in FIG. 1). Gram-positive bacteria, in contrast, form the capsule from this lipid-bound precursor by further transport using a different and specialized enzymatic machinery. The biosynthetic pathways of these polysaccharides enable the production of bioconjugates in vivo by capturing the polysaccharides in the periplasm onto a protein carrier.

The process of polysaccharide construction differs for capsular polysaccharides in that the capsular polysaccharide is released from the carrier lipid after polymerization and exported to the surface. In Gram-positive bacteria like S. aureus that do not contain a periplasmic compartment, the polymerization of the antigen takes place at the outer side of the membrane. In addition, length regulation in S. aureus is included in the machinery of three enzymes responsible for capsule assembly. In this assembly, the polysaccharide is released from the carrier lipid and exported to the surface by an enzymatic process.

The genetic elements found in the gene cluster required for functional capsule expression in S. aureus resemble the genetic machinery found in wzy dependent O-antigen synthesis clusters. (Dean, C. R., C. V. Franklund, J. D. Retief, M. J. Coyne, Jr., K. Hatano, D. J. Evans, G. B. Pier, and J. B. Goldberg. 1999. Characterization of the serogroup O11 O-antigen locus of Pseudomonas aeruginosa PA103. J Bacteriol 181:4275-4284).

Despite these differences between polysaccharide construction in Gram-positive and Gram-negative bacteria, it was surprisingly discovered and verified that aspects of the LPS pathway in a Gram-negative organism could be used to produce polysaccharides that contain some of the same repeating units as capsular polysaccharides native to Gram-positive bacteria, such as, for example, S. aureus. As such polysaccharides are produced by LPS pathway mechanisms in the Gram-negative host, the structure of such polysaccharides is the same as in LPS polysaccharide precursors. Such polysaccharides produced in Gram-negative systems of the instant invention can be characterized, therefore, as "modified capsular polysaccharides" or "LPS capsules" for purposes of this application. Furthermore, this newly synthesized expression system and biosynthetic pathway, which combines the LPS and capsular biosynthetic pathways, may be characterized as being a "modified LPS biosynthetic pathway" for purposes of this application.

In one embodiment of the present invention, a modified polysaccharide produced by a modified LPS biosynthetic pathway comprises:

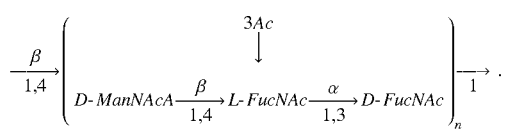

In a further embodiment of the present invention, a modified polysaccharide produced by a modified LPS biosynthetic pathway comprises:

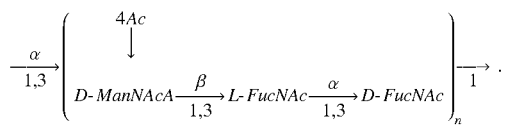

Using the technology of the invention, bacterial bioconjugates can be produced that are immunogenic. Genetic modifications can be made allowing in vivo conjugation of bacterial polysaccharides in desired proteins and at desired positions.

Another aspect of the invention involves production of LPS-capsules or modified LPSs conjugated to a protein carrier using the modified LPS biosynthetic pathway as discussed above.

Figure 6:
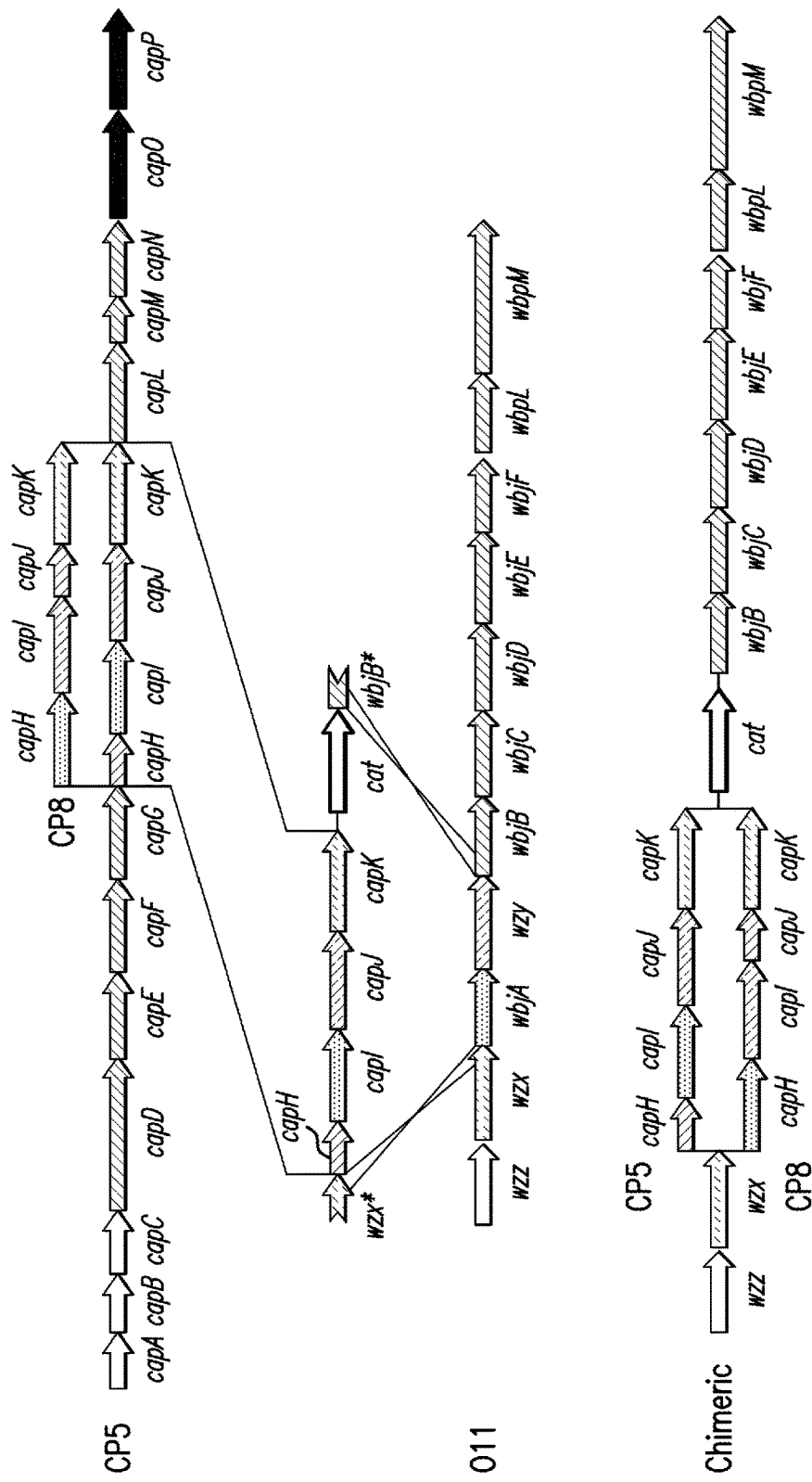
FIG. 6 depicts a strategy in an embodiment of the invention for the construction of the chimeric O11/CP5 and O11/CP8 gene clusters.

A further embodiment of the invention includes a nucleotide sequence construct that encodes the Cap5 and Cap8 complete polysaccharide biosynthesis cluster, wherein the deleted transporter genes are capA, capB and capC of S. aureus (see FIG. 6).

An additional embodiment of the invention includes integrating the CP5/O11 chimeric cluster (SEQ ID NO. 2, SEQ ID NO. 3 or SEQ ID NO. 17) or the CP8/O11 chimeric cluster (SEQ ID NO. 4, SEQ ID NO. 18 or SEQ ID NO. 19) into the genome of a host cell. A further embodiment of the invention involves integrating into the genome of a host cell: (a) the CP5/O11 chimeric cluster (SEQ ID NO. 2, SEQ ID NO. 3 or SEQ ID NO. 17) or CP8/O11 chimeric cluster (SEQ ID NO. 4 SEQ ID NO. 18 or SEQ ID NO. 19); (b) nucleic acids encoding the OTase; and (c) nucleic acids encoding a protein with or without an introduced consensus sequence.

Another embodiment of the instant invention is directed to plasmids, such as, for example, plasmids comprising one or more of SEQ. ID NO: 2; SEQ. ID NO: 3; SEQ ID NO: 4; SEQ. ID NO: 17; SEQ. ID NO: 18 and SEQ. ID NO: 19. The invention also includes plasmids comprising one or more of SEQ. ID NO: 13; SEQ. ID NO: 14 and SEQ. ID NO: 15. The invention also relates to plasmids comprising one or more of SEQ ID NO: 16; SEQ. ID NO: 6; SEQ. ID NO: 7 and SEQ. ID NO: 8. The invention also relates to plasmids comprising one or more of SEQ ID NO: 10; SEQ. ID NO: 11 and SEQ. ID NO: 12. Moreover, the invention is directed to plasmids comprising one or more of SEQ. ID NO: 20; SEQ. ID NO: 21 and SEQ. ID NO: 27.

Embodiments of the instant invention furthermore are directed to transformed bacterial cells, such as, for example, including a bacterial cell transformed with a plasmid comprising one or more of SEQ. ID NO. 2; SEQ. ID NO. 3; SEQ. ID NO: 4; SEQ. ID NO: 17; SEQ. ID NO: 18; SEQ. ID NO: 19; SEQ. ID NO: 20; SEQ. ID NO: 21 and SEQ. ID NO: 27. Further included in the invention is a bacterial cell transformed with a plasmid comprising one or more of SEQ. ID NO: 19 and SEQ ID NO: 20. Additionally included is a bacterial cell transformed with a plasmid comprising one or more of SEQ ID NO: 13, SEQ ID NO: 19 and SEQ ID NO: 21. The instant invention is further directed to a bacterial cell transformed with a plasmid comprising one or more of SEQ. ID NO: 16, SEQ ID NO: 6; SEQ ID NO: 7; SEQ ID NO: 8; SEQ ID NO: 10; SEQ ID NO: 11 and SEQ ID NO: 12. The invention is additionally directed to transformed bacterial cells, such as, for example, including a bacterial cell transformed with a plasmid comprising one or more of SEQ. ID NO. 3; SEQ. ID NO: 4; SEQ. ID NO: 17; SEQ. ID NO: 18; and SEQ. ID NO: 19, and wherein said bacterial cell expresses a glycosyltransferase native to P. aeruginosa and a glycosyltransferase native to S. aureus CP5 and/or CP8. Further included in the invention is a bacterial cell transformed with a plasmid comprising one or more of SEQ. ID NO: 17; SEQ ID NO: 18 and SEQ. ID NO: 19 wherein said bacterial cell expresses a glycosyltransferase native to P. aeruginosa, a glycosyltransferase native to S. aureus CP5 and/or CP8 and PglB. Still further included in the instant invention is (a) a bacterial cell transformed with a plasmid comprising SEQ. ID NO. 19, wherein said bacterial cell expresses a glycosyltransferase native to P. aeruginosa, a glycosyltransferase native to S. aureus CP8, Wzz of E. coli serovar O7 and PglB; (b) a bacterial cell transformed with a plasmid comprising one or more of SEQ. ID NO. 19 and SEQ. ID NO. 20, wherein said bacterial cell expresses a glycosyltransferase native to P. aeruginosa, a glycosyltransferase native to S. aureus CP8, Wzz (length regulator), EPA and PglB; and (c) a bacterial cell comprising one or more of SEQ. ID NO. 16; SEQ. ID NO: 6; SEQ. ID NO: 7; SEQ. ID NO: 8; SEQ. ID NO. 13; SEQ. ID NO: 14; SEQ. ID NO: 15; SEQ. ID NO: 10; SEQ. ID NO: 11 and SEQ. ID NO: 12.

Embodiments of the instant invention are additionally directed to a method of inducing an immune response against an infection caused by Gram-positive and other bacteria in a mammal, such as, for example, in a human. In one embodiment, the method comprises administering to said mammal an effective amount of a pharmaceutical composition comprising: protein comprising at least one inserted consensus sequence D/E-X-N-Z-S/T, wherein X and Z may be any natural amino acid except proline; and one or more oligo- or polysaccharides, the one or more oligo- or polysaccharides being the same or different as another of the one or more oligo- or polysaccharides, from a Gram-positive bacterium linked to said consensus sequence. A further embodiment of the present invention includes a method of inducing an immune response against an infection caused by S. aureus in a mammal, comprising administering to said mammal an effective amount of a pharmaceutical composition comprising: an inserted consensus sequence D/E-X-N-Z-S/T, wherein X and Z may be any natural amino acid except proline; at least one S. aureus oligo- or polysaccharide, such as CP5 polysaccharide; and a pharmaceutically acceptable adjuvant. Another embodiment of the invention is directed to inducing an immune response against an infection caused by S. aureus in a mammal, comprising administering to said mammal an effective amount of a pharmaceutical composition comprising: a protein comprising an inserted consensus sequence D/E-X-N-Z-S/T, wherein X and Z may be any natural amino acid except proline; at least one S. aureus CP8 polysaccharide; and a pharmaceutically acceptable adjuvant. A still further embodiment is directed to inducing an immune response against an infection caused by S. aureus in a mammal, comprising administering an effective amount of a pharmaceutical composition comprising a protein with two or more consensus sequences and oligo- or polysaccharides from different Gram-positive bacterial strains. A still further embodiment is directed to inducing an immune response against an infection caused by *S. aureus* in a mammal, comprising administering an effective amount of a pharmaceutical composition comprising a protein with two or more consensus sequences and polysaccharides comprising *S. aureus* CP5 and *S. aureus* CP8.

In instances in this specification where specific nucleotide or amino acid sequences are noted, it will be understood that the present invention encompasses homologous sequences that still embody the same functionality as the noted sequences. In an embodiment of the invention, such sequences are at least 85% homologous. In another embodiment, such sequences are at least 90% homologous. In still further embodiments, such sequences are at least 95% homologous. The determination of percent identity between two nucleotide or amino acid sequences is known to one of skill in the art.

Nucleic acid sequences described herein, such as those described in the sequence listings accompanying this specification, are examples only, and it will be apparent to one of skill in the art that these sequences can be combined in different ways. Additional embodiments of the invention include variants of nucleic acids. A variant of a nucleic acid (e.g., a codon-optimized nucleic acid) can be substantially identical, that is, at least 70% identical, for example, 75%, 80%, 85%, 90%, 91%, 92%, 93%, 94%, 95%, 96%, 97%, 98%, 99% or 99.5% identical, to SEQ ID NO:1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 and/or SEQ ID NO: 27. Nucleic acid variants of a sequence that contains SEQ ID NO: 1, SEQ ID NO: 2, SEQ ID NO. 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and/or SEQ ID NO: 27. Include nucleic acids with a substitution, variation, modification, replacement, deletion, and/or addition of one or more nucleotides (e.g., 2, 3, 4, 5, 6, 8, 10, 12, 15, 20, 25, 30, 35, 40, 50, 60, 70, 80, 90, 100, 150, 200, 250, 300, 350, 400, 450, 500 or more nucleotides) from a sequence that contains SEQ ID NO: 1, SEQ ID NO: 2, SEQ ID NO: 3, SEQ ID. NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 and/or SEQ ID NO: 27, or parts thereof.

Such variants include nucleic acids that encode prokaryotic glycosyltransferases and that i) are expressed in a host cell such as *E. coli* and ii) are substantially identical to SEQ ID NO: 2, SEQ ID NO: 3, SEQ ID NO: 4, SEQ ID NO: 17, SEQ ID NO: 18 and/or SEQ ID NO: 19 and/or parts thereof.

Nucleic acids described herein include recombinant DNA and synthetic (e.g., chemically synthesized) DNA. Nucleic acids can be double-stranded or single-stranded. In the case of single-stranded nucleic acids, the nucleic acid can be a sense strand or antisense strand. Nucleic acids can be synthesized using oligonucleotide analogs or derivatives, as known to one of skill in the art in light of this specification.

Plasmids that include a nucleic acid described herein can be transformed into host cells for expression. Techniques for transformation are known to those of skill in the art in light of this specification.

An additional embodiment of the invention involves producing Gram-positive bioconjugate vaccines containing LPS-capsules or modified LPSs conjugated to a protein carrier.

A further embodiment of the invention involves a novel bioconjugate vaccine. A further embodiment of the invention involves a novel approach for producing such bioconjugate vaccines that uses recombinant bacterial cells that directly produce immunogenic or antigenic bioconjugates. In one embodiment, bioconjugate vaccines can be used to treat or prevent bacterial diseases, such as diarrhea, nosocomial infections and meningitis. In further embodiments, bioconjugate vaccines may have therapeutic and/or prophylactic potential for cancer or other diseases.

In another embodiment of the present invention synthesized complexes of polysaccharides (i.e., sugar residues) and proteins (i.e., protein carriers) can be used as conjugate vaccines to protect against infections such as *S. aureus* infections. In one embodiment, a bioconjugate vaccine, such as a Gram-positive vaccine, comprises a protein carrier comprising an inserted nucleic acid consensus sequence; at least one oligo- or polysaccharide from a Gram-positive bacterium linked to the consensus sequence, and, optionally, an adjuvant. The present invention is further directed in another embodiment to a Gram-positive bioconjugate vaccine, such as a *S. aureus* vaccine, comprising a protein carrier comprising an inserted nucleic acid consensus sequence; at least one oligo- or polysaccharide from a Gram-positive bacterium, such as capsular polysaccharide or LPS capsule, linked to the consensus sequence, and, optionally, an adjuvant. In another embodiment of the invention, the *S. aureus* bioconjugate vaccine comprises two or more of these inserted consensus sequences. In a further embodiment, the *S. aureus* bioconjugate vaccine comprises two or more of *S. aureus* oligo- or polysaccharides. A still further embodiment comprises two or more of said inserted consensus sequences and oligo- or polysaccharides from different *S. aureus* strains, for example, from *S. aureus* capsular polysaccharide 5 strain (CP5) and capsular polysaccharide 8 strain (CP8).

An additional embodiment of the present invention involves an *S. aureus* vaccine made by a glycosylation system using a modified LPS pathway, which comprises the production of a modified capsular polysaccharide or LPS-capsule. A further additional embodiment involves an *S. aureus* vaccine made by a glycosylation system using a modified LPS pathway, which comprises the production of a modified capsular polysaccharide from introduced nucleic acids that do not encode glycosyltransferases of a Gram-negative prokaryotic species.

A further embodiment involves an *S. aureus* vaccine produced by a glycosylation system comprising nucleic acids encoding: i) one or more glycosyltransferases responsible for producing the L-FucNAc->D-FucNAc of the RU of the O11 antigen native to *P. aeruginosa*; ii) one or more glycosyltransferases responsible for producing the D-ManNAcA containing RU native to either the CP5 or CP8 strains of *S. aureus*; iii) one or more enzymes responsible for flipping and polymerization of the CP5 or CP8 constructed RUs, iv) a recombinant protein containing introduced consensus sequences; and v) oligosaccharyltransferase from *C.*

*jejuni*. In this embodiment, the host organism may be a Gram-negative bacterium, for example, *E. coli*.

An additional embodiment of the invention involves an *S. aureus* vaccine produced by a glycosylation system comprising nucleic acids encoding: i) glycosyltransferases responsible for producing the L-FucNAc->D-FucNAc of the RU of the O11 antigen native to *P. aeruginosa*; ii) a glycosyltransferase responsible for producing the D-ManNAcA containing RU native to either the CP5 or CP8 strains of *S. aureus*; iii) AcrA protein of *C. jejuni*; and iv) oligosaccharyltransferase from *C. jejuni*. In this embodiment, the host organism may be a Gram-negative bacterium, for example, *E. coli*.

The vaccines of the instant invention have therapeutic and prophylactic utilities. It will be appreciated that the vaccine of the invention may be useful in the fields of human medicine and veterinary medicine. Thus, the subject to be immunized may be a human or other animal, for example, farm animals including cows, sheep, pigs, horses, goats and poultry (e.g., chickens, turkeys, ducks and geese) and companion animals such as dogs and cats.

In another aspect, the invention is directed to a method of generating vaccines for immunizing a mammal against a bacterium such as a Gram-positive bacterium. The method includes: immunizing a subject with a bioconjugate, such as a bioconjugate comprising a Gram-positive polysaccharide, e.g., an *S. aureus* polysaccharide, and a pharmaceutically acceptable carrier.

This invention also features vaccine compositions for protection against infection by a gram-positive bacterium such as *S. aureus* or for treatment of gram-positive infection such as *S. aureus* infection. In one embodiment, the vaccine compositions comprise one or more immunogenic components such as a polysaccharide, or a fragment or portion thereof, from *S. aureus*. In a further embodiment, the vaccine compositions comprise one or more immunogenic components such as a protein, or a fragment or portion thereof, from a Gram-negative or Gram-positive bacterium.

One aspect of the invention provides a vaccine composition for protection against infection by *S. aureus* which contains at least one immunogenic component or fragment of an *S. aureus* polysaccharide and a pharmaceutically acceptable carrier. Such immunogenic components or fragments can include, for example, an *S. aureus* polysaccharide of at least about two monomers in length or at least about three monomers in length. In a further aspect of the invention, an *S. aureus* RU comprises said monomers. Such repeating units can include, for example, an *S. aureus* RU of at least 1 (one) in length.

Immunogenic components or fragments of the invention can be obtained, for example, by screening polysaccharides or polypeptides produced recombinantly or through chemical synthesis, or, for example, by screening the bioconjugate comprising a polysaccharide and a protein. Screening immunogenic components or fragments of the invention can be performed using one or more of several different assays. For example, screening assays include ELISA and other assays known to one of ordinary skill in the art.

In one embodiment, immunogenic components or fragments are identified by the ability of the polysaccharide and/or protein to stimulate IgG antibodies against Gram-positive bacteria, such as *S. aureus* CP5 or CP8 polysaccharides, as determined by, for example, the immune response obtained in mice (FIG. 15A) and in rabbit (FIG. 15B) measuring specific anti CP5 antibodies (quantified by ELISA) against the glycoconjugate vaccine candidate CP5-EPA and other means known to a person of ordinary skill in the art.

In one embodiment, immunogenic components or fragments are identified by the ability of the polysaccharide and/or protein to stimulate opsonic activity, such as opsonophagocytic killing, as determined by, for example by the *S. aureus* killing ("in vitro" activity) with rabbit anti CP5-EPA antibodies (obtained in Example 7 below, see FIG. 15B) and other means known to a person of ordinary skill in the art.

In yet a further embodiment, immunogenic components or fragments are identified by the ability of the polysaccharide and/or protein to stimulate humoral and/or cell-mediated immunity against Gram-positive bacteria, such as *S. aureus*, as determined by, for example, by protection against bacterial infection ("challenge") using active immunization in mice (FIG. 18) with CP5-EPA and other means known to a person of ordinary skill in the art.

In an embodiment of the instant invention, a vaccine composition of the invention can be based on a glycoprotein comprising an immunogenic component or fragment of an *S. aureus* polysaccharide of the invention and optionally further comprising a pharmaceutically acceptable carrier or adjuvant. In further embodiments of the instant invention, a vaccine composition can be based on a glycoprotein comprising an immunogenic component or fragment of an *S. aureus* protein of the invention and optionally further comprising a pharmaceutically acceptable carrier or adjuvant. In yet a further aspect of the invention, a vaccine composition can be based on a glycoprotein comprising a immunogenic component or fragment of a *P. aeruginosa* protein of the invention and optionally further comprising a pharmaceutically acceptable carrier and/or adjuvant.

It is well-known to those of ordinary skill in the art how to modify a vaccine for administration to one mammal type, for example, mice, for administration to another mammal type, for example, humans. For example, one of skill would readily know that deletion of the histidine tag from the protein carrier of a glycoprotein used in a vaccine composition in mice would render the glycoprotein suitable for administration in a vaccine composition in humans. For example, deletion of the HISTIDINE tag (HIS-tag) in protein carriers such as, e.g. EPA (SEQ ID NO: 13), ClfA (SEQ ID NO: 10, SEQ ID NO: 11, SEQ ID NO: 12), and Hla (SEQ ID NO: 6, SEQ ID NO: 7, SEQ ID NO: 8, SEQ ID NO: 16) would be recognized for its use in a glycoprotein for administration to a human.

It should be understood that amelioration of any of the symptoms of a Gram-positive, for example *S. aureus*, or other bacterial infection or disease is a desirable clinical goal, including a lessening of the dosage of medication used for the Gram-positive-caused infection or disease, for example an *S. aureus*-caused infection or disease, or other bacterial-caused infection or disease, or an increase in the production of antibodies in the serum or mucous of patients. It will be apparent to those skilled in the art that some of the vaccine compositions of the invention are useful for preventing a Gram-positive infection, for example an *S. aureus* infection, or other bacterial infection, some are useful for treating a Gram-positive infection, for example an *S. aureus* infection, or other bacterial infection, and some are useful for both preventing and treating such infections.

Embodiments of the present invention such as vaccines and other pharmaceutical agents optionally may be prepared using suitable and pharmaceutically acceptable carriers, excipients, diluents and/or adjuvants, as are well-known in the art and apparent in light of this specification. An excipient, diluent or adjuvant may be a solid, semi-solid or liquid material which may serve as a vehicle or medium for the active ingredient. In light of this specification, one of ordinary skill in the art in the field of preparing compositions can readily select the proper form and mode of administration depending upon the particular characteristics of the product selected, the disease or condition to be treated, the stage of the disease or condition, and other relevant circumstances (*Remington s Pharmaceutical Sciences*, Mack Publishing Co. (1990)). The proportion and nature of the pharmaceutically acceptable diluent, excipient or adjuvant are determined by the solubility and chemical properties of the pharmaceutically active compound selected the chosen route of administration and standard pharmaceutical practice.

Accordingly, in embodiments of the invention, vaccine compositions comprise immunogenic components or fragments, e.g., *S. aureus* polysaccharide or fragment thereof and/or *S. aureus* or *P. aeruginosa* protein or fragment thereof and optionally include a pharmaceutically acceptable carrier. The term "pharmaceutically acceptable carrier" refers to a carrier that is non-toxic. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody. Such pharmaceutically acceptable carriers include, for example, liquid, semi-solid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

Further, in additional embodiments of the invention, the vaccine composition can optionally include an adjuvant or a combination of adjuvants, including, but not limited to particulate adjuvants such as aluminium salts (aluminium hydroxide, aluminium phosphate, aluminium hydroxyphosphate sulphate, etc.); emulsions such as oil in water (MF59, AS03); lipid and salt combinations such as AS04; water in oil (Montanide); ISCOMS, liposomes/virosomes; nano- and microparticles, etc.; non particulated such as peptides; saponins (QS21); MPL A; cytokins; DNA derivates; bacterial toxins; etc. A further embodiment includes adjuvants used in animals such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans, streptococcal preparations (e.g., OK432), DEAE-dextran, neutral oils (such as miglyol), vegetable oils (such as arachis oil), Pluronic, the Ribi adjuvant system or interleukins, particularly those that stimulate cell-mediated immunity. The adjuvant used will depend, in part, on the composition and type of the glycoconjugate vaccine. The amount of adjuvant to administer will depend on the type and size of mammal. Optimal dosages may be readily determined by routine methods.

A further aspect of the present invention relates to a pharmaceutical composition, comprising at least one glycoprotein according to the invention. The preparation of medicaments comprising glycoproteins is well-known in the art. The preparation scheme for the final pharmaceutical composition and the mode and details of its administration will depend on the protein, the host cell, the nucleic acid and/or the vector employed.

It will be apparent to those of skill in the art that the therapeutically effective amount of polysaccharide or glycoprotein of this invention will depend, inter alia, upon the administration schedule, the unit dose of antibody administered, whether the polysaccharide or glycoprotein is administered in combination with other therapeutic agents, the immune status and health of the patient, and the therapeutic activity of the particular polysaccharide or glycoprotein.

The vaccine compositions and/or pharmaceutical preparations of the invention may be adapted for oral, parenteral or topical use and may be administered to the patient in the form of tablets, capsules, suppositories, solution, suspensions or any other suitable means or dosage form. In further aspects of the invention, the vaccine compositions and/or pharmaceutical preparations may be introduced into the subject to be immunized by any known method including, e.g., by intravenous, intradermal, intramuscular, intramammary, intraperitoneal, or subcutaneous injection; or by oral, sublingual, nasal, anal, or vaginal, delivery. The pharmaceutically active compounds of the present invention, while effective themselves, can be formulated and administered in the form of their pharmaceutically acceptable salts, such as acid addition salts or base addition salts, for purposes of stability, convenience of crystallization, increased solubility, and the like. Vaccine compositions in an embodiment of the invention are administered parenterally, e.g., by injection, either subcutaneously or intramuscularly. Methods for intramuscular immunization are described by Wolff et al. (1990) Science 247: 1465-1468 and by Sedegah et al. (1994) Immunology 91: 9866-9870. Other modes of administration include oral and transdermal.

Vaccines of the invention can be administered as a primary prophylactic agent in, e.g., adults or in children, as a secondary prevention, after successful eradication of Gram-positive bacteria such as *S. aureus* in an infected host, or as a therapeutic agent in the aim to induce an immune response in a host to prevent infection by a Gram-positive bacterium such as *S. aureus*. The vaccines of the invention are administered in amounts readily determined by persons of ordinary skill in the art. The treatment may consist of a single dose or a plurality of doses over a period of time. For example, in some embodiments, it is expected that a typical dosage for humans of a vaccine of the present invention is about 1 to 25 µg of the oligosaccharide antigen, which will be bound to (and does not include the mass of) the protein carrier, in further embodiments about 1 µg to about 10 µg of the polysaccharide antigen, and in still further embodiments about 2 µg of the polysaccharide antigen. In additional embodiments, the sugar/protein ratio in the glycoconjugate or the vaccine is about 1:5 to about 1:10. Optionally, a vaccine, such as a bioconjugate vaccine of the present invention, may include an adjuvant. Those skilled in the art will recognize that the optimal dose may be more or less depending upon the patient's body weight, disease, the route of administration, and other factors. Those skilled in the art will also recognize that appropriate dosage levels can be obtained based on results with known vaccines. The number of doses will depend upon the disease, the formulation, and efficacy data from clinical trials.

The vaccine compositions can be packaged in forms convenient for delivery. Delivery forms compatible with entry of the immunogenic component or fragment into the recipient mammal are preferred.

One embodiment of the invention is generally directed to recombinantly producing a vaccine for a Gram-positive organism in a Gram-negative organism by using a modified LPS biosynthetic pathway. This is accomplished by inserting into a host which comprises of nucleic acids encoding for an oligosaccharyltransferase and a protein and nucleic acids encoding for glycosyltransferases originating from at least two different organisms. This embodiment is directed to genetically engineering an organism based on a natural organism into which are inserted nucleic acids coding for (i) a protein; (ii) an oligosaccharyltransferase, and (iii) glycosyltransferases from at least two differing organisms.

In an example of such an embodiment, a glycosylated-protein product is produced for use as a vaccine for *Staphylococcus aureus*. The vaccine products of the invention are produced in a genetically modified *E. coli* host. *S. aureus* is a Gram-positive bacterium, and has a polysaccharide capsule. A vaccine product for this organism could be based on a glycosylated protein whose sugar section had a structure similar to this capsular polysaccharide.

In another aspect, the instant invention is directed to a novel bioengineering approach for producing immunogenic conjugate vaccines that provide advantages over classical chemical conjugation methods. In an embodiment, the approach involves in vivo production of glycoproteins in bacterial cells, for example, Gram-negative cells such as *E. coli*.

As known to a person of ordinary skill in the art, the production and purification of glycoconjugate can vary depending on the vaccine candidate and the combination of plasmids used. For example, which purification procedure to choose is known based upon the protein carrier, the sugar component of the glycoconjugate and the intended use of the purified vaccine candidate, for example, in animals or humans. For use in humans, for example, it is known that the HIS-tag, which would otherwise facilitate purification, would be removed.

All publications mentioned herein are incorporated by reference in their entirety. It is to be understood that the term "or," as used herein, denotes alternatives that may, where appropriate, be combined; that is, the term "or" includes each listed alternative separately as well as their combination. As used herein, unless the context clearly dictates otherwise, references to the singular, such as the singular forms "a," "an," and "the," include the plural, and references to the plural include the singular.

The invention is further defined by reference to the following examples that further describe the compositions and methods of the present invention, as well as its utility. It will be apparent to those skilled in the art that modifications, both to compositions and methods, may be practiced which are within the scope of the invention.

EXAMPLES

Example 1

Synthesis of CP5 and CP8 Polysaccharide in *E. coli* Cells

A goal of an embodiment of the invention is to produce the CP5 and CP8 antigenic polysaccharides in *E. coli*. As discussed above, we exploited in an novel way, surprising in view of the prior art, the fact that the CP and O-antigen production pathways functionally overlap, a fact which is represented in the structure of the RU (See FIGS. 1-4). The capsular glycans of CP5 and CP8 are polymers consisting of similar trisaccharide RUs of 2-Acetamido-2-deoxy-D-mannuronic acid (D-ManNAcA) and two 2-Acetamido-2,6-dideoxy galactose residues with D- and L-configurations (D- and L-FucNAc). The ManNAcA residues are linked differently in the two serotypes; additionally, the linkage between RUs in the polymerized glycan is different. In addition, there is an immunodominant O-acetyl modification at different positions in the two antigens (Jones, C. 2005. Revised structures for the capsular polysaccharides from *Staphylococcus aureus* types 5 and 8, components of novel glycoconjugate vaccines. Carbohydr Res 340:1097-106). The O11 antigen of *P. aeruginosa* LPS is similar in its structure to CP5 and CP8, as the O11 antigen of *P. aeruginosa* LPS contains [-3)-α-L-FucNAc-(1,3)-β-D-FucNAc-(1,2)-β-D-Glc-(1-] (FIG. 4). (Knirel, Y. A., V. V. Dashunin, A. S. Shashkov, N. K. Kochetkov, B. A. Dmitriev and I. L. Hofman. 1988. Somatic antigens of *Shigella*: structure of the O-specific polysaccharide chain of the *Shigella dysenteriae* type 7 lipopolysaccharide. Carbohydr Res 179: 51-60). The trisaccharide-RUs differ only in that the D-ManNAcA of *S. aureus* is replaced by a glucose unit, there is no O-acetyl modification in *P. aeruginosa* O11 LPS, and the difference in the linkage type between the $2^{nd}$ and $3^{rd}$ monosaccharide in the RU (FIG. 4).

To generate a genetic system able to synthesize the CP5 and CP8 glycans on UndPP, using the method of Dean et al., (Dean, C. R., C. V. Franklund, J. D. Retief, M. J. Coyne, Jr., K. Hatano, D. J. Evans, G. B. Pier, and J. B. Goldberg. 1999. Characterization of the serogroup O11 O-antigen locus of *Pseudomonas aeruginosa* PA103. J Bacteriol 181:4275-4284), we modified the *P. aeruginosa* O11 O-antigen gene cluster from strain PA103. The genes encoding the biosynthetic machinery for synthesis of the stem structure consisting of UndPP-D-FucNAc-L-FuncNAc were complemented with the *S. aureus* enzymes required for the completion of the *S. aureus* glycan (FIG. 1-4), which was also a novel use of this process. Therefore, using the method of Dean et al., all the genetic elements from *P. aeruginosa* PA103 required for the UndPP-FucNAc-FucNAc biosynthesis were expressed. The gene encoding the glycosyltransferase adding the third sugar was deleted and replaced by the corresponding genes from the cap5 or 8 clusters form *S. aureus* Mu50 (CP5) and MW2 (CP8) with slight modifications.

The genes encoding the enzymes synthesizing the specific residues for the *S. aureus* capsular polysaccharide were integrated step by step into the O11 background according to the functions of the genes predicted by Sau et al. (Sau, S., N. Bhasin, E. R. Wann, J. C. Lee, T. J. Foster, and C. Y. Lee. 1997. The *S. aureus* allelic genetic loci for serotype 5 and 8 capsule expression contain the type-specific genes flanked by common genes. Microbiology 143: 2395-405; O'Riordan, K. and J. C. Lee. 2004. *Staphylococcus aureus* capsular polysaccharides. Clin Microbiol Rev 17(1): 218-34). Such steps are explained below.

Figure 5A:
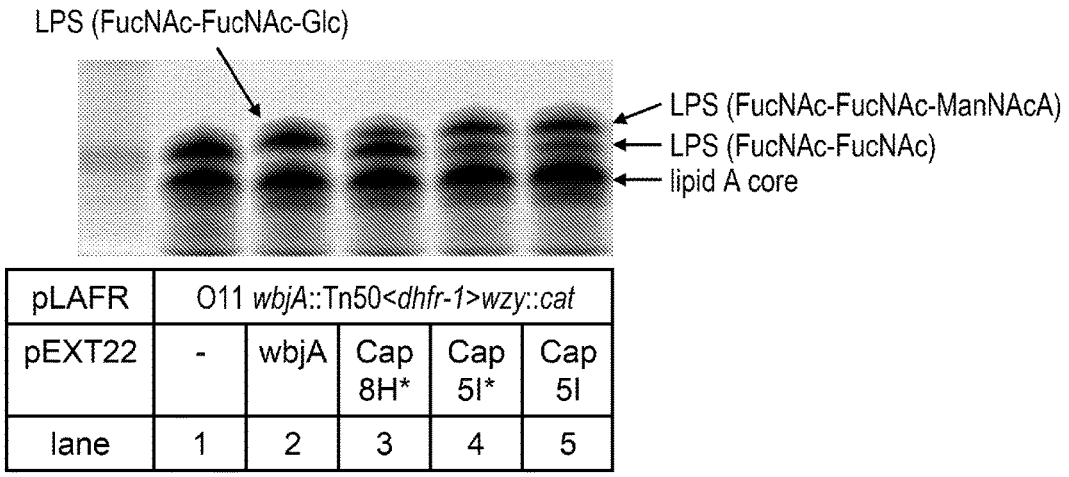
FIG. 5A depicts the SDS-PAGE analysis of the elongation of the incomplete O11 O-antigen RU (repeating unit) by *S. aureus* enzymes.

The cap5I/cap8H gene product was predicted to be the glycosyltransferase that adds the ManNAcA to UndPP-D-FucNAc-L-FuncNAc of the RU forming a linkage specific for each serotype (Sau, S., N. Bhasin, E. R. Wann, J. C. Lee, T. J. Foster, and C. Y. Lee. 1997. The *Staphylococcus aureus* allelic genetic loci for serotype 5 and 8 capsule expression contain the type-specific genes flanked by common genes. Microbiology 143: 2395-405.). To prove this, the activity of Cap5I and Cap8H was analyzed in *E. coli* in presence of a plasmid conferring production of the *P. aeruginosa* O11 O-antigen. Cells expressing the O11 cluster synthesize the O11 O-antigen first on UndPP, from where it is transferred to lipid A core by the *E. coli* enzyme WaaL, the O-antigen ligase, forming O11 specific lipopolysaccharide (LPS) (Goldberg, J. B., K. Hatano, G. S. Meluleni and G. B. Pier. 1992. Cloning and surface expression of *Pseudomonas aeruginosa* O antigen in *Escherichia coli*. Proc Natl Acad Sci USA 89(22): 10716-20). To synthesize this lipopolysaccharide, the O11 O-antigen cluster from *P. aeruginosa* PA103 was cloned into pLAFR1 (SEQ ID NO: 1). Then the wbjA gene encoding the glucosyltransferase, the enzyme adding the third sugar to the O11 RU, was deleted by transposon mutagenesis. The mutated cluster (O11 wbjA:: Tn50<dhfr-1>) was further modified by homologous recombination to eliminate the polymerase activity of the wzy gene, forming O11 wbjA::Tn50<dhfr-1>wzy::cat, which denotes the mutated SEQ ID NO: 1, in which the genes for the glycosyltransferase wbjA and the wzy polymerase of the O11 gene cluster were inactivated. This modified cluster was expressed in W3110 ΔwecA cells, extracts were treated with proteinase K and analyzed by SDS PAGE and silver staining, according to the method disclosed in Tasi, et al. (Tsai, C. M., and C. E. Frasch. 1982. A sensitive silver stain for detecting lipopolysaccharides in polyacrylamide gels. Anal Biochem 119:115-9). The results are provided in FIG. 5A, showing silver staining of W3110 ΔwecA extracts expressing the mutated O11 cluster from pLAFR1 as described herein. The second line indicates the genes expressed from the inducible plasmid pEXT22. Asterisks indicate synthesized and codon optimized genes. Different relevant glycoforms are indicated with arrows.)

Analysis resulted in two major bands in the gels (FIG. 5A, lane 1). The signals correspond to the unmodified lipid A core (FIG. 5A, lower band) and LPS consisting of lipid A core and two FucNAc residues as expected in a truncated O11 RU. Upon expression of a wbjA wildtype copy from a separate, IPTG inducible plasmid, the upper band shifted to a slower electrophoretic mobility, indicating the addition of a glucose residue to the truncated O11 LPS (FIG. 5A, lane 2). When the predicted *S. aureus* glycosyltransferases Cap5I (lane 4) and Cap8H (FIG. 5A, lane 3) were expressed in trans instead of WbjA, a similar shift of the glycosylated lipid A core signal was observed, indicative of addition of a monosaccharide possibly even larger than glucose, most probably being ManNAcA. This data proves that *S. aureus* glycosyltransferases can elongate UndPP-D-FucNAc-L-FucNAc glycolipid that has been synthesized by activity of *P. aeruginosa* enzymes.

In this way it was also confirmed that a prerequisite for *S. aureus* RU assembly in *E. coli* is the provision of UDP-ManNAcA, because the biosynthetic machinery is present in the *S. aureus* CP5/8 clusters but not in the O11 O-antigen cluster of *P. aeruginosa*. All other required nucleotide activated sugars are either provided by housekeeping functions of *E. coli* and the O11 O-antigen cluster of *P. aeruginosa*. *E. coli* is known to produce UDP-ManNAcA, the substrate for the ManNAcA glycosyltransferase, by expression of wecB and wecC. Those genes are constitutively expressed in the cluster responsible for enterobacterial common antigen (ECA) biosynthesis (Meier-Dieter, U., R. Starman, K. Barr, H. Mayer, and P. D. Rick. 1990. Biosynthesis of enterobacterial common antigen in *Escherichia coli*. J Biol Chem 265:13490-13497). The functional homolog for UDP-ManMAcA biosynthesis found in the CP cluster of *S. aureus* were found to complement the activities of wecBC as reported earlier (Kiser, K. B., N. Bhasin, L. Deng and J. C. Lee. 1999. *Staphylococcus aureus* cap5P encodes a UDP-N-acetylglucosamine 2-epimerase with functional redundancy. J. Bacteriol 181(16): 4818-24). This shows that the production of the CP antigens in *E. coli* relies on the functional expression of the wecBC genes in the host strain. Thus, to provide UDP-ManNAcA as substrate for CapSI and Cap8H in a recombinant system, it was confirmed that WecB and WecC have to be expressed. In such a system, any prokaryotic strain expressing the enterobacterial common antigen like *E. coli* wildtype strain can be used, e.g. W3110 based cell types with or without a wecA deletion and with or without additional wzzE deletion.

Figure 5B:
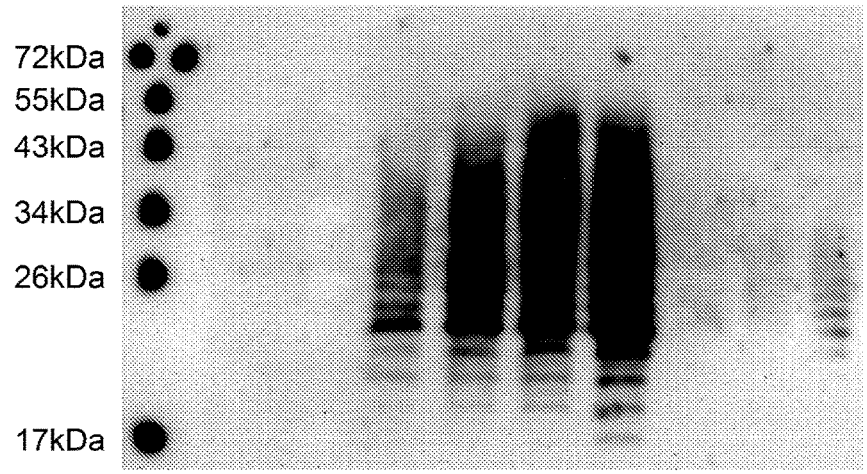
FIG. 5B depicts the immunodetection of the elongation of the incomplete O11 O-antigen RU by *S. aureus* enzymes.

Further elongation of the *S. aureus* capsular polysaccharide is thought to be required for maximal immunological activity of the glycan. The cap5J/cap8I genes encode the wzy homologs polymerizing the repeating units, and cap5K/cap8K encodes the flippase translocating the UndPP-bound trisaccharide from the cytoplasmic to the periplasmic side of the membrane. Cap5H/cap8J encodes the O-acetyltransferase modifying the L-FucNAc at position 3' or the ManNAcA at position 4' of the RU (Bhasin, N., A. Albus, et al. (1998). "Identification of a gene essential for O-acetylation of the *Staphylococcus aureus* type 5 capsular polysaccharide." Mol Microbiol 27(1): 9-21. The acetylation is an important determinant discriminating the immunological reactivity of the polysaccharide (Fattom, A. I., J. Sarwar, L. Basham, S. Ennifar, and R. Naso. 1998. Antigenic determinants of *S. aureus* type 5 and type 8 capsular polysaccharide vaccines. Infect Immun 66:4588-92). To show that the RUs could be elongated and acetylated, the *S. aureus* enzymes responsible for polymerization and O-acetylation were expressed from separate plasmids in presence of the mutated O11 cluster. Extracts from W3110 ΔwecA cells expressing the O11 wbjA::Tn50<dhfr-1 >wzy::cat cluster and different genes of the CP5 cluster were treated with proteinase K and analyzed by SDS PAGE, electrotransfer followed by immunoblotting using an anti CP5 sugar (obtained from J. C. Lee at the Department of Medicine, Brigham and Women's Hospital, Harvard Medical School, Boston, Mass., USA). FIG. 5B shows the results of immunodetection of proteinase K treated *E. coli* extracts separated by SDS PAGE and electrotransfer using the anti CP5 antiserum. All extracts analyzed contained a *P. aeruginosa* O11 cluster with deletions of the wbjA and partially (indicated by an asterisk) the wzy genes expressed from the pLAFR plasmid as described herein, and two more plasmids (pEXT22, pACT3) expressing different Cap5 proteins (as indicated) that enable CP5 polymerization and O acetylation in these cells. Experimental details such as inducer concentrations and expression culture incubation temperatures are indicated.

In FIG. 5B, the results show ladder like signals typical for an O-antigen polymer in a higher molecular weight range. The different bands represent different numbers of linearly polymerized RUs on LPS or on UndPP, both of which are stable towards proteinase K digestion. Different intensities of the ladder like structure in presence or absence of the O-acetyltransferase were observed. Whereas strong signals were detected in the presence of cap5H (FIG. 5B, lanes 1-4), they were virtually absent in lanes without cap5H (FIG. 5B, lanes 5, 6). This means that O-acetylation either increases recognition by the specific antiserum, or that it enhances polymerization activity by either accelerating flipping or making polymerization as such more efficient or by inducing more RU production. The cap5H gene is functional when expressed from different backbone plasmids (FIG. 5B, lanes 1, 2 and 3, 4), although signal intensity is stronger when cap5H is expressed alone from a separate plasmid (compare FIG. 5B lane 1 to lane 3 and FIG. 5B, lane 2 to lane 4). It is surprising and remarkable that the less IPTG was used for induction of the *S. aureus* genes, the stronger the signals (compare FIG. 5B, lane 1 to land 2 and FIG. 5B, lane 3 to lane 4).

Example 2

Synthesis of CP5 and CP8 Polymer on Lipid in *E. coli* Cells

As high expression of the cap5 specific genes lead to lower polymer formation, an alternative expression system for the recombinant glycans was constructed to address this problem. In detail, in a novel approach unexpected in light of the prior art, the *P. aeruginosa* glucosyltransferase (wbjA) and the polymerase (wzy) of O11 were replaced by the genes encoding the CP5/8-specific elements from the capsular gene cluster of *S. aureus* Mu50/MW2 (cap5/8HIJK and parts thereof) producing a single, chimeric gene cluster composed of *P. aeruginosa* O11 and *S. aureus* CP5 or CP8 genes (FIG. 6). The construct contained the specific genes of *S. aureus*. Each was tagged for expression detection and each contained an introduced ribosomal binding site, and was followed by a chloramphenicol resistance cassette (cat) for selection of recombined clones resulting in SEQ ID NO: 2, SEQ ID NO: 3, and SEQ ID NO: 4, according to the method of Datsenko, et al. (Datsenko, K. A., and B. L. Wanner. 2000. One-step inactivation of chromosomal genes in *Escherichia coli* K-12 using PCR products. Proc Natl Acad Sci USA 97:6640-5).

FIG. 6 depicts an embodiment of a strategy of the present invention for construction of chimeric O11/CP5 and O11/CP8 gene clusters of the present invention. The *S. aureus* CP5 and CP8 CP clusters (top) and the *P. aeruginosa* PA103 rfb cluster (O11, middle) are represented as published (Dean, C. R., C. V. Franklund, J. D. Retief, M. J. Coyne, Jr., K. Hatano, D. J. Evans, G. B. Pier, and J. B. Goldberg. 1999. Characterization of the serogroup O11 O-antigen locus of *Pseudomonas aeruginosa* PA103. J Bacteriol 181:4275-84; Sau, S., N. Bhasin, E. R. Wann, J. C. Lee, T. J. Foster and C. Y Lee. 1997. The *S. aureus* allelic genetic loci for serotype 5 and 8 capsule expression contain the type-specific genes flanked by common genes. Microbiology 143 (Pt 7): 2395-405). The homologous functions of the genes are described below. Complete forward diagonals indicate the genes responsible for synthesis of the D-FucNAc-L-Fuc-NAc disaccharide on UndPP in the two organisms; dots indicate the glycosyltransferase genes adding the third monosaccharide to the RU. Wzx-like flippase genes are indicated by broken forward diagonals, the wzy-like RU polymerase genes are indicated by broken back diagonals. The CP5 cluster does not contain a Wzz length regulator (empty arrow), but a set of three genes composing the export machinery for capsular polysaccharide which includes the length regulator function in *S. aureus* (empty arrows). The O acetyl transferase gene, indicated by complete forward diagonals, is unique to the CP cluster. The genes required for UDP-ManNAcA biosynthesis in *S. aureus* are indicated in black. They are not required for production of the *P. aeruginosa* O-antigen. The genes responsible for the structural differences of the O11, CP5 and CP8 polysaccharides are clustered together in the beginning (O11: wbjA and wzy) or middle (CP5/8: cap5/8HIJK) of the respective gene clusters. The CP8 cluster is almost identical to the CP5 cluster considering length and DNA sequence, except for the middle part (cap5/8HIJK) conferring structural specificity. The chimeric cluster was constructed by replacing wbjA and wzy genes of a plasmid borne O11 cluster with the specificity part of the CP5 (or CP8) cluster (cap5/8HIJK) and a chloramphenicol acetyltransferase cassette represented by the empty arrow labeled cat (cat, for selection) by homologous recombination and classical clonings, resulting in SEQ ID NO: 2, SEQ ID NO: 3, and SEQ ID NO: 4. Asterisks at the broken arrows indicate incomplete gene sequences used for homologous recombination. The resulting two chimeric clusters are shown in the bottom panel, representing the DNA of SEQ ID NO: 3 and SEQ ID NO: 4.

To prove that the chimeric CP5 and CP8 of the present invention surprisingly assembles the correct RU on UndPP and assures that the repeating units are polymerized, proteinase K digestion of *E. coli* cells (W3310 ΔwecA) containing the full length chimeric clusters were separated by SDS-PAGE. Specifically, cells with a plasmid either containing or lacking the chimeric CP5 gene cluster (FIG. 7A) or the chimeric CP8 gene cluster (FIG. 7B) on the pLAFR plasmid were treated with Proteinase K, separated by SDS-PAGE and lipids were visualized by either silver staining (left panel in FIGS. 7A and 7B) or immunodetection with anti CP5 or CP8 antiserum after electrotransfer to nitrocellulose membranes (right panel in FIGS. 7A and B)). Constructs lacking (SEQ ID NO: 2) and containing (SEQ ID NO: 3) the flippase gene cap5K were tested. The former was found to be less active in CP5 LPS production.

Figures 7A, 7B:
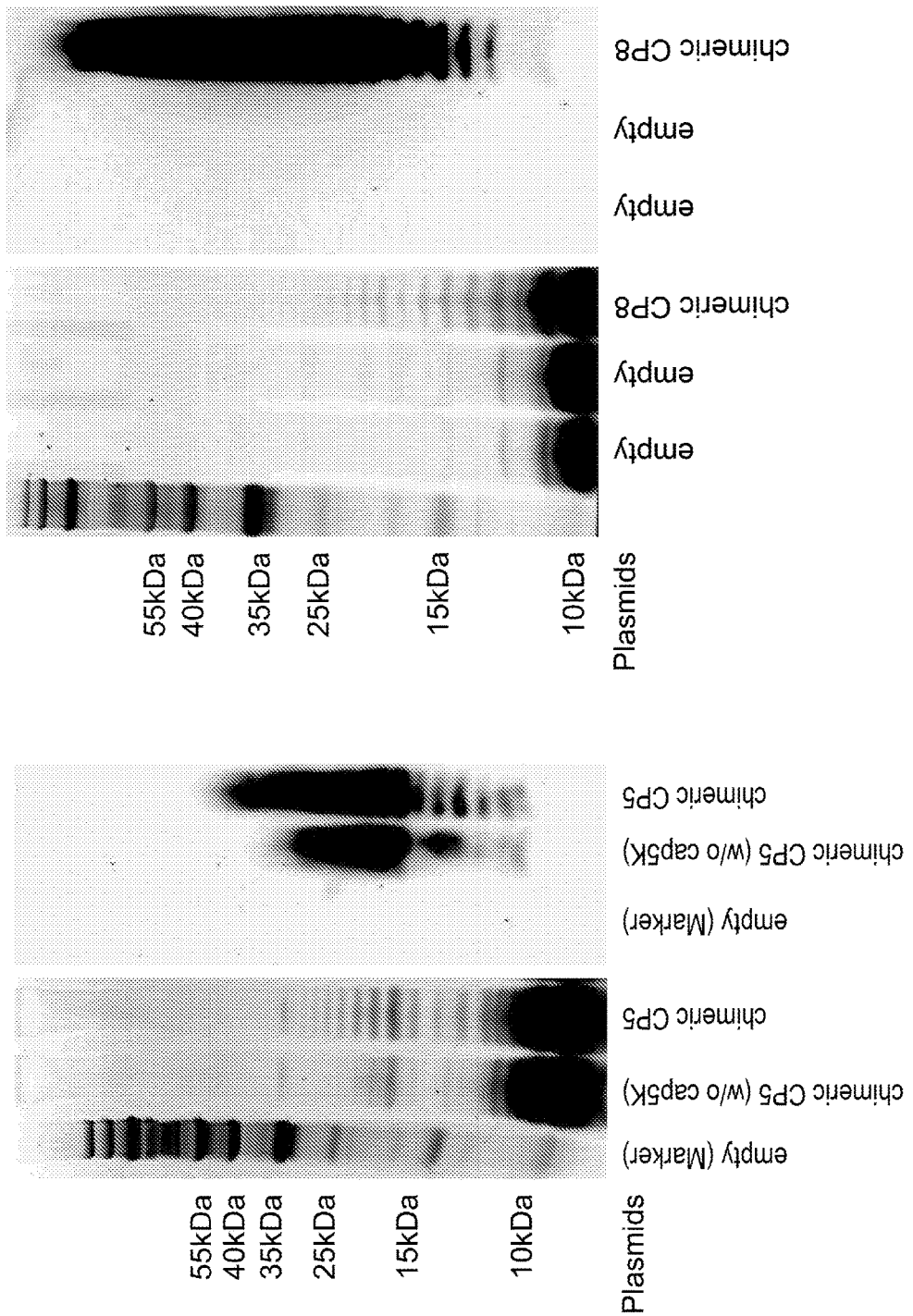
FIG. 7A depicts polymerized CP5 LPS of an embodiment of the invention detected in *E. coli* lipid extracts.
FIG. 7B depicts polymerized CP8 LPS of an embodiment of the invention detected in *E. coli* lipid extracts.

After electrotransfer and immunodetection with anti CP5 specific serum, extracts expressing the entire chimeric CP5 clusters show a ladder like signal similar to endogenous O-antigen structures from *E. coli* probed with their autologous serum (FIG. 7A, last two lanes on the right). This strongly suggests that the CP5 repeating units are polymerized, that there is a preferred polymer length, and that the CP5 antigen is transferred to lipid A core in these cells. The same extracts were visualized by silver staining after SDS PAGE (FIG. 7A, on the left side of the figure, the two lanes on the right labeled as: chimeric CP5 (w/o cap5K) and chimeric CP5 showing that indeed LPS is formed consisting of the lipid A core of *E. coli* decorated with the CP5 O-antigen-like structure. Intensity differences were obtained from extracts originating from cells that expressed the CP5 chimeric cluster with or without the cap5K flippase gene. Comparison of the two extracts shows that Cap5K expression considerably increases the polymer production (compare middle and right lanes in both panel of FIG. 7A).

As shown in FIG. 7B, the same results were observed with a CP8 chimeric cluster. Cells containing a plasmid either containing or lacking the chimeric CP8 gene cluster on the pLAFR plasmid were treated with Proteinase K, separated by SDS PAGE and lipids were either detected by silver staining (left panels) or immunodetection with anti CP8 antiserum after electrotransfer to nitrocellulose membranes (right panel). CP8 chimeric construct containing the flippase gene cap8K corresponds to SEQ ID NO: 4.

A further novel and surprising extension of the invention was developed by changing the plasmid backbones used for maintenance and expression of the chimeric cluster in *E. coli*. The resistance cassette in pLAFR1 containing the chimeric CP5 cluster was changed from Tet to Kan. Additionally the entire CP5 chimeric cluster containing the cap5K was subcloned into plasmid pDOC-C, according to the method of Lee et al. (Lee, D. J., L. E. Bingle, K. Heurlier, M. J. Pallen, C. W. Penn, S. J. Busby and J. L. Hobman. 2009. Gene doctoring: a method for recombineering in laboratory and pathogenic *Escherichia coli* strains. BMC Microbiol 9: 252) and pACYC 177 (GeneBank accession #X06402).

As shown in FIGS. 8A and 8B, all of these plasmids conferred CP5 polymer production as analyzed by SDS PAGE, electrotransfer and immunodetection with anti CP5 specific antiserum. In FIG. 8A, total cell extracts from cells containing different chimeric clusters were treated with Proteinase K and analyzed by SDS PAGE and silver staining. The plasmids contain different *S. aureus* specific genes and different resistance genes used for antibiotic selection are indicated: Tetracycline (Tet) and HIJ, SEQ ID NO: 2; Tet HIJK, SEQ ID NO: 3, Tet and no genes, empty plasmid control, numbers correspond to molecular weight markers. Lanes labeled Kanamycin (Kan) contains a variation of SEQ ID NO: 3 in which the tetracycline resistance cassette is replaced by a kanamycin resistance gene.

In FIG. 8B, the host strain was *E. coli* W3110 ΔwecA, as in FIG. 8A. The left lane in FIG. 8B corresponds to the molecular weight marker as in FIG. 8A. In FIG. 8B, total cell extracts from cells containing different chimeric clusters were treated with Proteinase K and analyzed by SDS PAGE and silver staining (left panel) and by anti CP5 immunoblotting after electrotransfer (right panel). The plasmids used contain the chimeric CP5 cluster indicated in SEQ ID NO: 3 either present in a modified pLAFR1 plasmid backbone containing a Kanamycin cassette instead of tetracycline (see FIG. 8A) or in pACYC containing a chloramphenicol resistance cassette.

Figure 9:
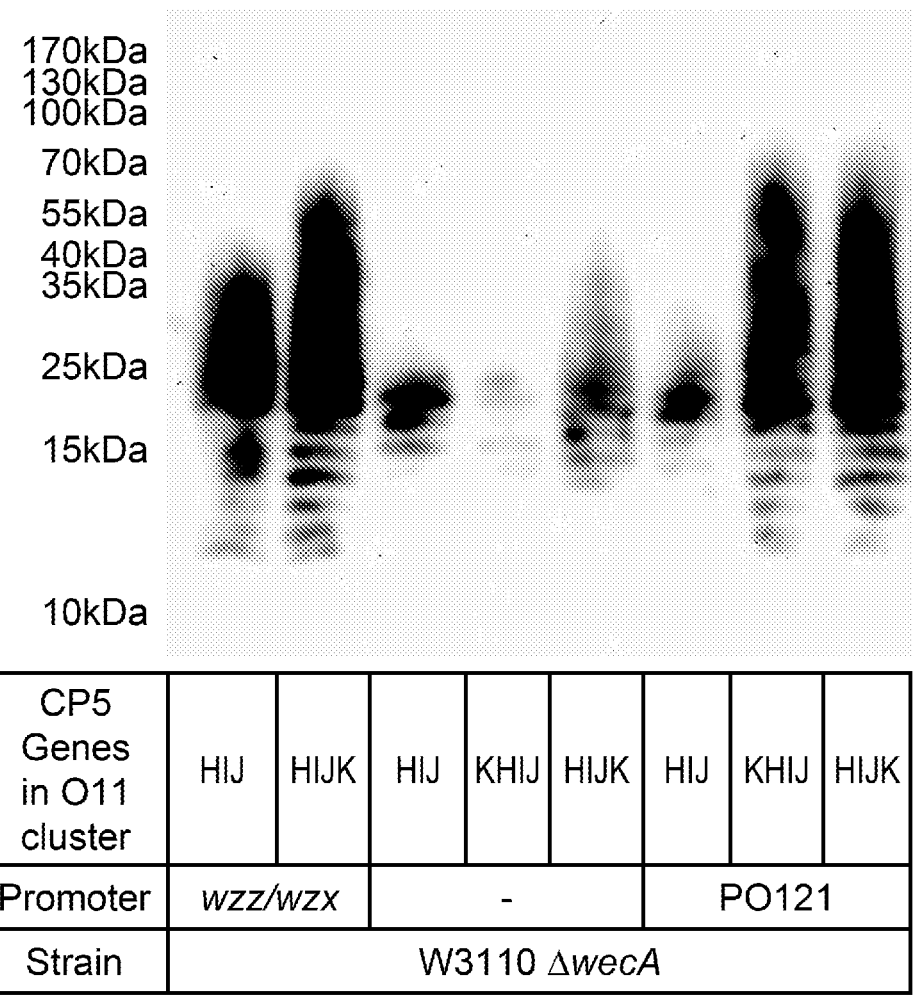
FIG. 9 depicts recombinant CP5 LPS production of an embodiment of the invention analyzed SDS PAGE and by immunodetection in dependence of promoter in front of the chimeric cluster in W3110 ΔwecA cells.

In addition different promoters were tested to express the chimeric O11-CP5 LPS. In these tests, the host strain was *E. coli* W3110 ΔwecA carrying the chimeric CP5 cluster. In this strain, the chimeric cluster replaced wecAwzzE genes. Total cell extracts from cells containing different chimeric clusters expressed from pLAFR1 were treated with Proteinase K and analyzed by SDS PAGE and anti CP5 immunoblotting after electrotransfer. The plasmids contained O11 clusters where wbjA and wzy were replaced by different *S. aureus* specificity genes (with a cat cassette) as indicated below the lanes in FIG. 9. In addition, the DNA in front of the cap5 specificity genes was changed and the effect on lipid glycosylation was analyzed. The effect of these different promoter regions was analyzed as depicted in FIG. 9. Wzz/wzx denotes the original genes (see FIG. 6) in front of the cap genes after the initial homologous recombination (FIG. 9 corresponding to the first two lanes). These two genes were removed (FIG. 9 corresponding to the three lanes in the middle) and replaced with the 0.6 kb region (PO121) (FIG. 9 corresponding to the three last lanes) in front of the *E. coli* 0121 O-antigen cluster encoding a strong promoter sequence. Lanes denoted wzz/wzx and HIJ in FIG. 9 were derived from cells expressing SEQ ID NO: 2, lanes denoted wzz/wzx and HIJK derive from SEQ ID NO: 3. In FIG. 9, the molecular weight markers are indicated on the left of the gel frame.

As indicated FIG. 9, the results showed that a relevant promoter activity resides in the wzx gene (FIG. 9 first two lanes—wzz/wzx) and that it can be functionally replaced by a constitutive promoter from *E. coli*, e.g. the serovar O121 wb promoter (PO121 last three lanes in FIG. 9), without losing LPS production. Taken together, these results mean that the O11 and *S. aureus* elements for O11 O-antigen and CP5 capsular polymer production as described herein can be combined in many different *E. coli* expression systems resulting in production of recombinant *S. aureus* polysaccharide.

These results showed for the first time the production in *E. coli* of a capsular polysaccharide structure originating from a Gram-positive organism. This means that it was possible, contrary to prior art and conventional expectations, to combine the enzymes of the O11 cluster and the enzymes of *S. aureus* cap cluster to build up a chimeric polysaccharide, i.e. that the enzyme work together on the same structure in vivo.

Example 3

Molecular Structure Confirmation of the Recombinant Glycans

To confirm the activity of the chimeric CP5/O11 cluster in *E. coli* on a molecular level, a novel method allowing the analysis of UndPP linked sugars by using fluorescent labeling of the sugar at reducing end with 2-Aminobenzamide (2-AB) was developed. To enhance the analysis resolution, chimeric clusters were used containing deletions that increased the amount of unpolymerized RUs. Glycolipids from different *E. coli* cells expressing the chimeric cluster contained in the pLAFR1 plasmid and lacking the cap5K flippase (SEQ ID NO: 2) were analyzed as described below.

To extract UndPP-linked glycans, *E. coli* cells were washed with 0.9% NaCl and lyophilized. The dried cells were extracted once with 30 ml organic solvent (85 to 95% Methanol=M). The lyophilized cell pellet was further extracted twice with 5 ml Chloroform:Methanol:Water (C:M:W=10:10:3; v/v/v). The (M) extract was converted with chloroform and water to a final ratio of 3:48:47 (C:M:W). The 10:10:3 (C:M:W) extract was converted to a two-phase Bligh/Dyer (Bligh, E. G. and W. J. Dyer. 1959. A rapid method of total lipid extraction and purification. Can J Biochem Physiol 37(8): 911-7) system by addition of water, resulting in a final ratio of 10:10:9 (C:M:W). Phases were separated by centrifugation and the upper aqueous phase was kept for further processing.

To purify the extracted glycolipids, aqueous phase was subjected to a $tC_{18}$ Sep-PAK cartridge. The cartridge was conditioned with 10 ml methanol, followed by equilibration with 10 ml 3:48:47 (C:M:W). After loading of the sample, the cartridge was washed with 10 ml 3:48:47 (C:M:W) and eluted with 5 ml methanol and 5 ml 10:10:3 (C:M:W). The combined elutions were dried under $N_2$. The glycolipid samples were hydrolyzed by dissolving the dried samples in 2 ml n-propanol:2 M trifluoroacetic acid (1:1), heating to 50° C. for 15 min, and then evaporating to dryness under $N_2$ (Glover, K. J., E. Weerapana and B. Imperiali. 2005. In vitro assembly of the UndPP-linked heptasaccharide for prokaryotic N-linked glycosylation. Proc Natl Acad Sci USA 102 (40): 14255-9). The dried samples were labeled with 2-AB and the glycan cleanup was performed using the paper disk method as described (Bigge, J. C., T. P. Patel, J. A. Bruce, P. N. Goulding, S. M. Charles, R. B. Parekh. 1995. Nonselective and efficient fluorescent labeling of glycans using 2-amino benzamide and anthranilic acid. Anal Biochem 230(2): 229-38; Merry, A. H., D. C. Neville, L. Royle, B. Matthews, D. J. Harvey, R. A. Dwek and P. M. Rudd. 2002. Recovery of intact 2-aminobenzamide-labeled O-glycans released from glycoproteins by hydrazinolysis. Anal Biochem 304(1): 91-9). The 2-AB labeled glycans were separated by HPLC using a GlycoSep-N normal phase column according to Royle et al. but modified to a three solvent system (Royle, L., T. S. Mattu, E. Hart, J. I. Langridge, A. H. Merry, N. Murphy, D. J. Harvey, R. A. Dwek, P. M. Rudd. 2002. An analytical and structural database provides a strategy for sequencing O-glycans from microgram quantities of glycoproteins. Anal Biochem 304(1): 70-90). Solvent A was 10 mM ammonium formate pH 4.4 in 80% acetonitrile. Solvent B was 30 mM ammonium formate pH 4.4 in 40% acetonitrile. Solvent C was 0.5% formic acid. The column temperature was 30° C. and 2-AB labeled glycans were detected by fluorescence (excitation λex=330 nm, emission λem=420 nm). Gradient conditions were a linear gradient of 100% A to 100% B over 160 min at a flow rate of 0.4 ml/min, followed by 2 min 100% B to 100% C, increasing the flow rate to 1 ml/min. The column was washed for 5 min with 100% C, returning to 100% A over 2 min and running for 15 min at 100% A at a flow rate of 1 ml/min, then returning the flow rate to 0.4 ml/min for 5 min. Samples were injected in water.

Dried fractions were resuspended in 5 ul 10% acetonitrile (ACN), 0.1% trifluoro acetic acid (TFA) and mixed 1:1 with matrix solution (40 mg/ml DHB in 50% ACN, 0.1% TFA) on the target plate. MS and MS/MS data were manually acquired in the positive ion mode on an Ultraflex-II MALDI-ToF/ToF mass spectrometer (Bruker Daltonik GmbH, Bremen, Germany). MS/MS were obtained using the LIFT method. A standard peptide mixture (Bruker Daltonik GmbH) was used for external calibration. Spectra were exported using the Flex Analysis software (Bruker Daltonik GmbH) and manually analyzed.

Figure 10A:
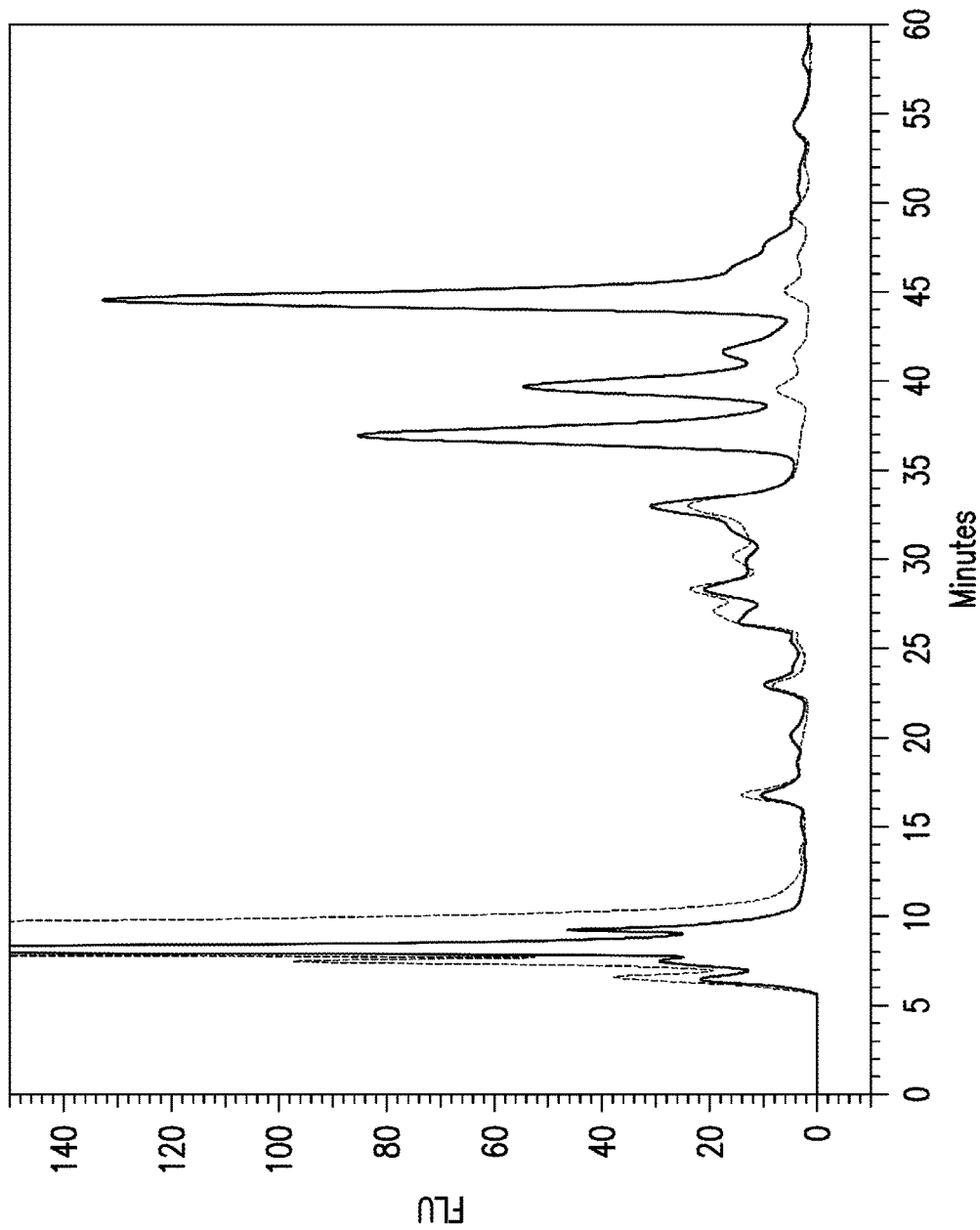
FIG. 10A shows the results of HPLC analysis of an embodiment of recombinant RU of CP5 of the present invention produced using the chimeric CP5 cluster (SEQ ID: 2).

Methanol extracts from E. coli W3110 ΔwecA (CP5) containing plasmids with (thick line) or without (thin, dashed line) the chimeric clusters were purified over tC18 cartridges and analyzed by normal phase HPLC. The fractions corresponding to the peaks shown in FIG. 10A found at 37', 40' and 45' elution were analyzed by MALDI-MS/MS. Samples eluting at 37 and 40 minutes were identified as recombinant CP5 RUs with and without the O-acetyl group attached, respectively. Sample eluting at 45 minutes was identified as non-acetylated S. aureus RU structure elongated by one deoxy-N-acetylhexosamine (as shown in FIG. 11E). In the CP5 chimeric cluster, cap5HIJ replaced the wbjA and wzy genes of the O11 cluster on pLAFR. The replacement contained the cat cassette in addition to the cap5HIJ genes (SEQ ID NO: 2).

Methanol extracts from E. coli W3110 ΔwecAwzzE containing plasmids with (thick line) or without (thin, dashed line) the chimeric cluster were purified over tC18 cartridges and analyzed by normal phase HPLC. FIG. 10B shows the results of HPLC analysis of recombinant RU of CP8 produced using a chimeric cluster (SEQ ID NO: 4 without polymerase). Peaks specific for cells expressing the recombinant sugar were identified at 23', 32', 38' and 45 of elution, collected and analyzed by MALDI-MS and MALDI-MS/MS. In the CP8 chimeric cluster, cap8HJK replaced the wbjA and wzy genes of the O11 cluster, i.e. a construct without the polymerase to accumulate single RU for analysis. The replacement contained the cat cassette in addition to the cap genes.

Figure 11A:
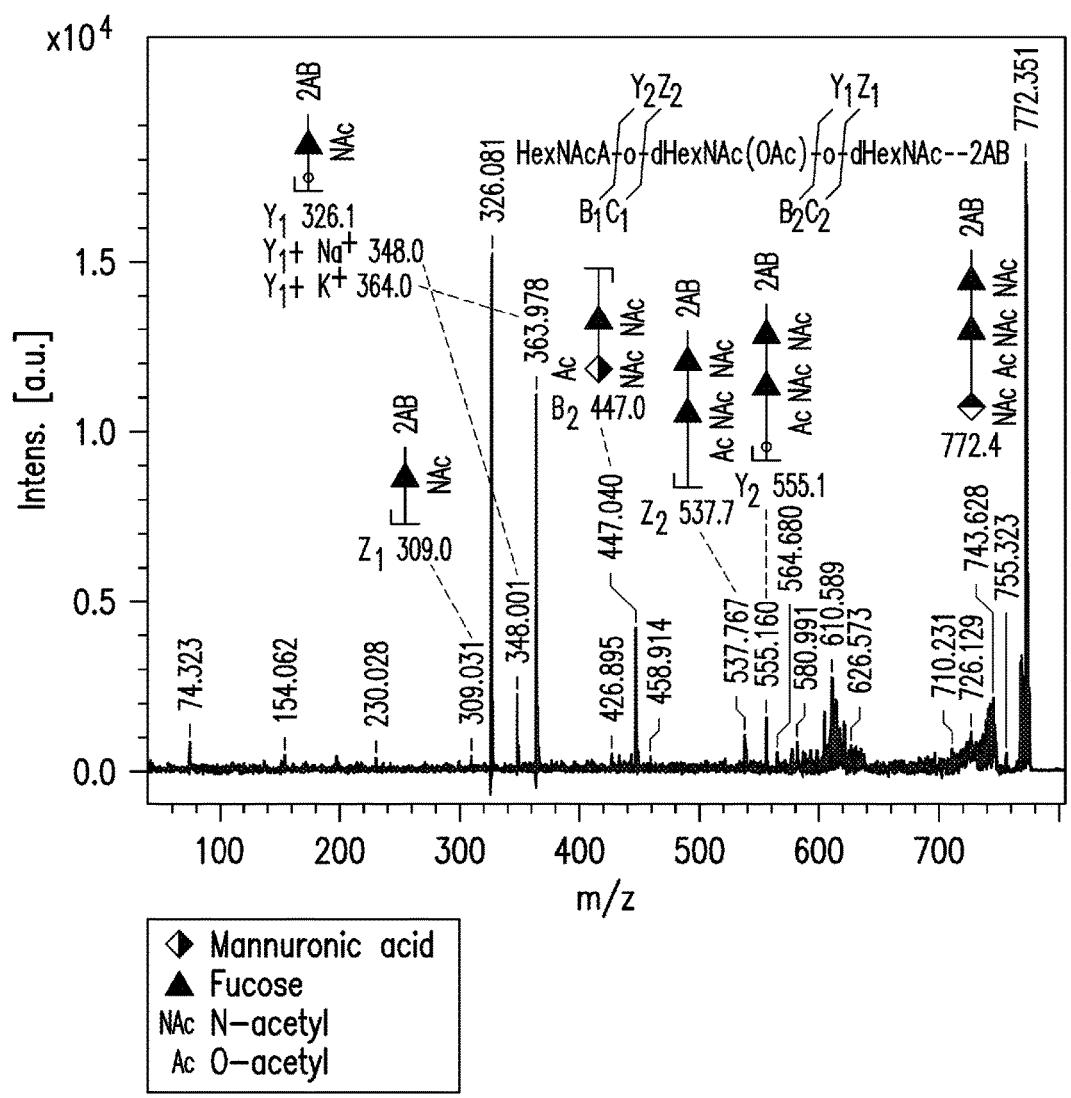
FIG. 11A shows the results of MALDI-MS/MS analysis of the specific peak generated by expression of an embodiment of the chimeric CP5 cluster of the present invention in *E. coli* eluting at 37 minutes seen in FIG. 10A.

FIG. 11A shows the results of MALDI-MS/MS analysis of the specific peak generated by expression of an embodiment of the chimeric CP5 cluster of the present invention in E. coli eluting at 37 minutes. The major mass m/z=772 ([M+H]$^+$) was selected and analyzed by MS/MS, which shows a fragmentation pattern consistent with the acetylated CP5 RU structure that was expected in light of the invention disclosed in this specification. The O-acetylated species are characterized by a specific loss of 42 plus the mass of the monosaccharide FucNAc (dHexNAc(OAc)) at the middle position of the RU. Fragment ions are indicated according to the nomenclature of the consortium for functional glycomics, CFG (www.functionalglycomics.org/static/consortium/Nomenclature.shtml). 2-AB, 2-aminobenzamide. The legend for the fragment ions is given in the inset of FIG. 11A.

Figure 11B:
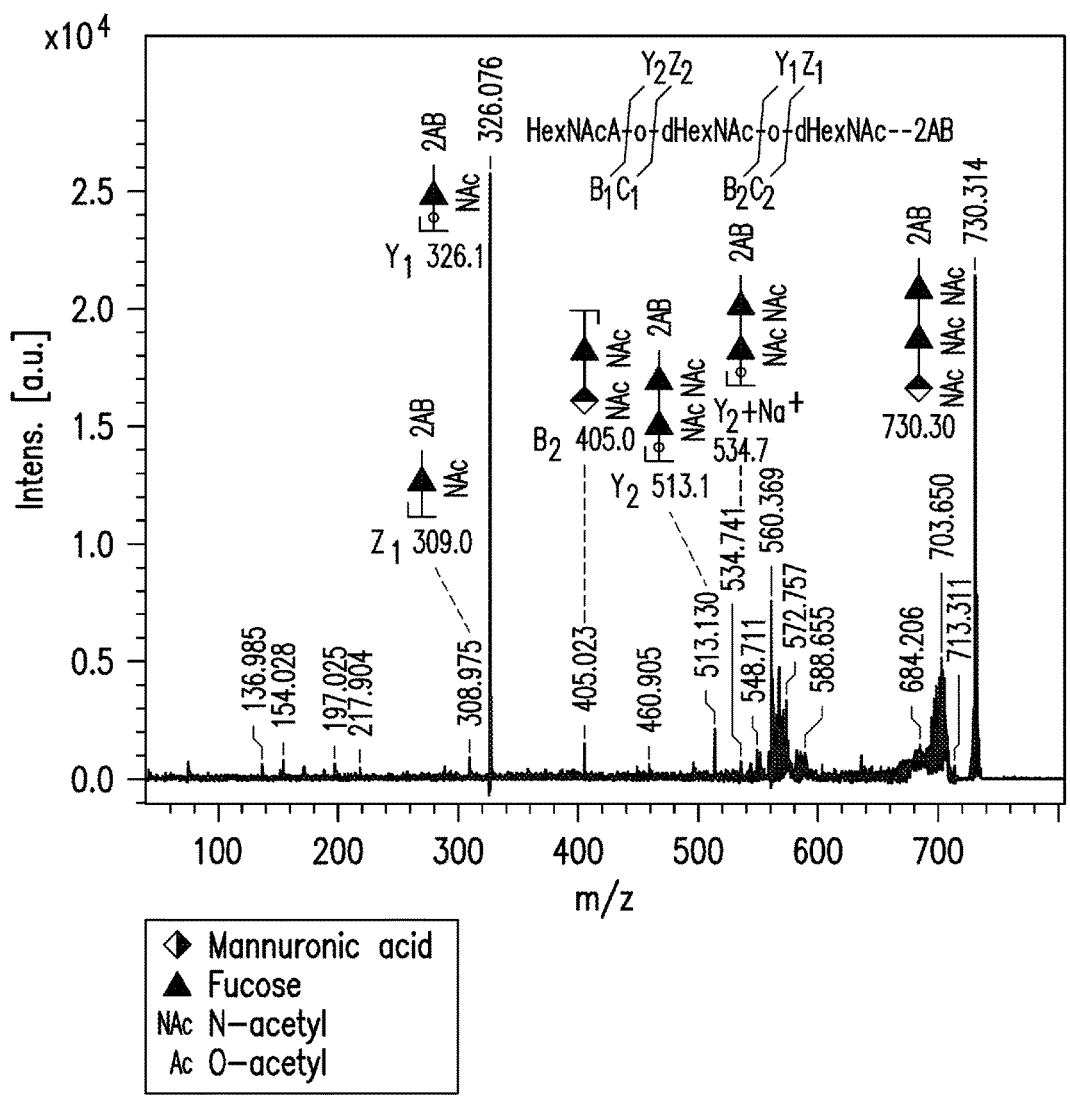
FIG. 11B shows the results of MALDI-MS/MS analysis of the specific peak generated by expression of an embodiment of the chimeric CP5 cluster of the present invention in *E. coli* eluting at 40 minutes seen in FIG. 10A.

FIG. 11B shows the results of MALDI-MS/MS analysis of the specific peak generated by expression of an embodiment of the chimeric CP5 cluster of the present invention in E. coli eluting at 40 minutes. The major mass of m/z=730 ([M+H]$^+$) was selected and analyzed by MS/MS, which shows fragmentation ion series consistent with the non-acetylated CP5 RU structure that was expected in light of the invention disclosed in this specification. 2-AB, 2-aminobenzamide. The legend for the fragment ions is given in the inset of FIG. 11B.

Figure 11C:
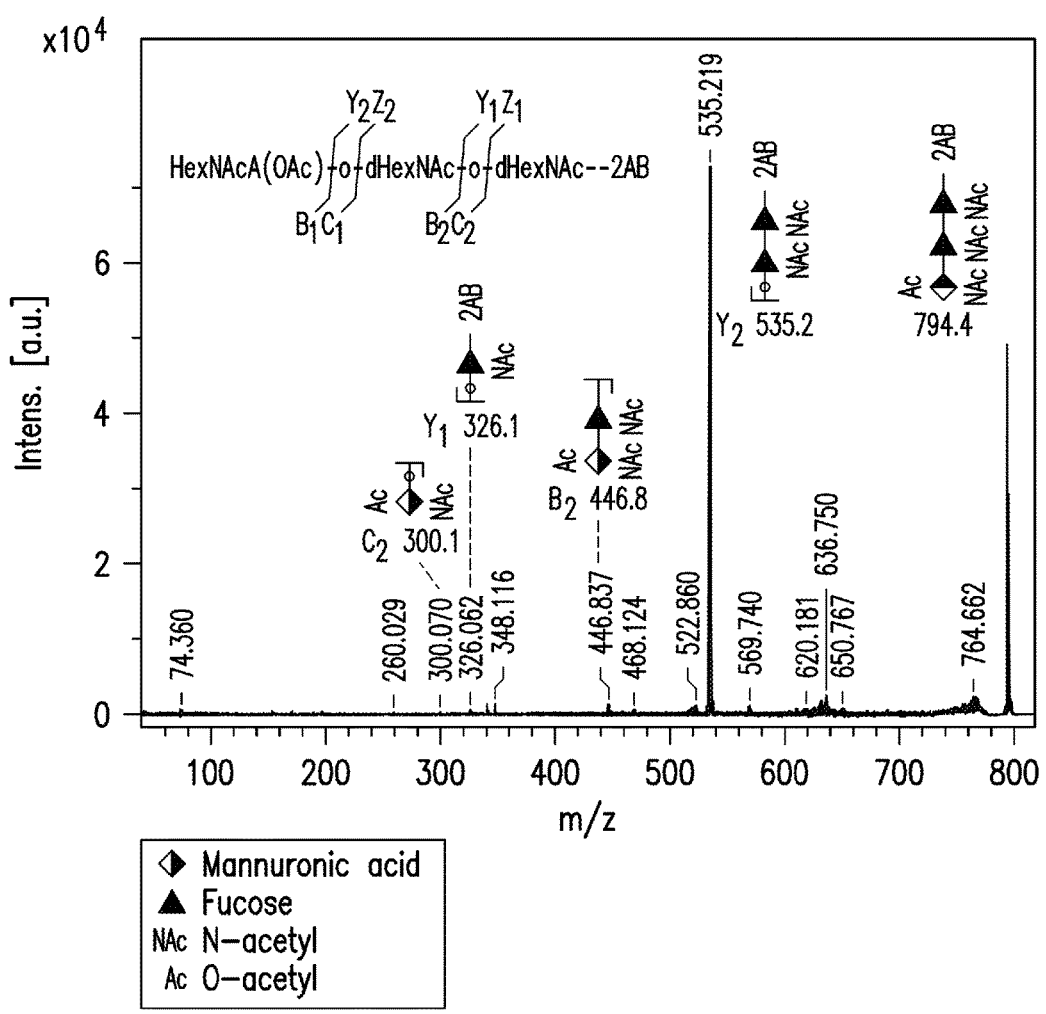
FIG. 11C shows the results of MALDI-MS/MS analysis of the specific peak generated by expression of an embodiment of the chimeric CP8 cluster of the present invention in *E. coli* eluting at 32 minutes seen in FIG. 10B.

FIG. 11C shows the results of MALDI-MS/MS analysis of the specific peak generated by expression of an embodiment of the chimeric CP8 cluster of the present invention in E. coli eluting at 32 minutes. A major mass of m/z=794 ([M+Na]$^+$) was selected and analyzed by MS/MS, which shows fragmentation ion series consistent with the acetylated CP8 RU structure that was expected in light of the invention disclosed by this specification. The O-acetylated species are characterized by a specific loss of 42 plus the mass of the monosaccharide ManNAcA (HexNAcA(OAc)) at the outermost position of the RU. Fragment ions are indicated according to the nomenclature of the CFG. 2-AB, 2-aminobenzamide. The legend for the fragment ions is given in the inset of FIG. 11C.

Figure 10B:
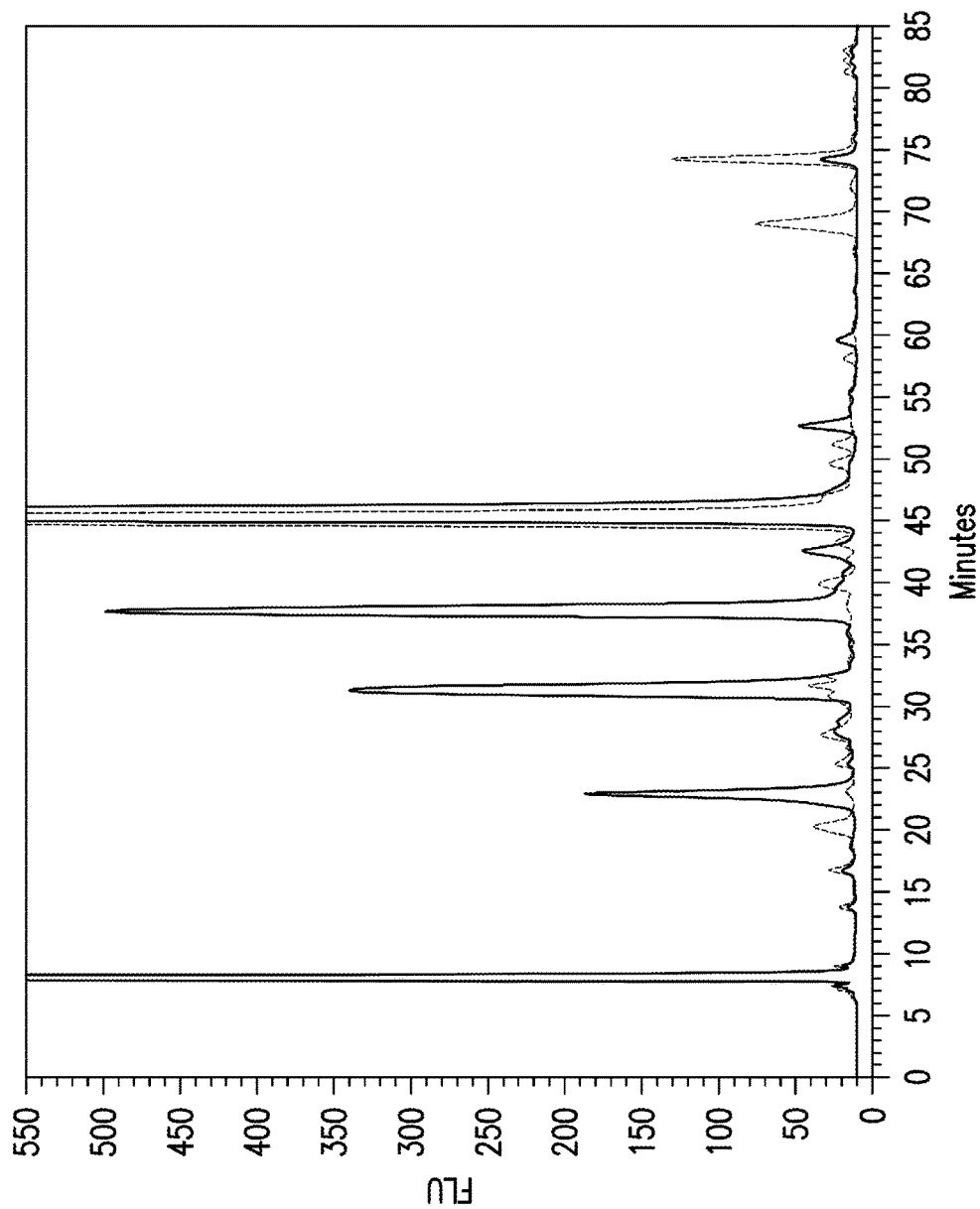
FIG. 10B shows the results of HPLC analysis of an embodiment of recombinant RU of CP8 of the present invention produced using a chimeric CP8 cluster lacking the cap8I polymerase.
Figure 11D:
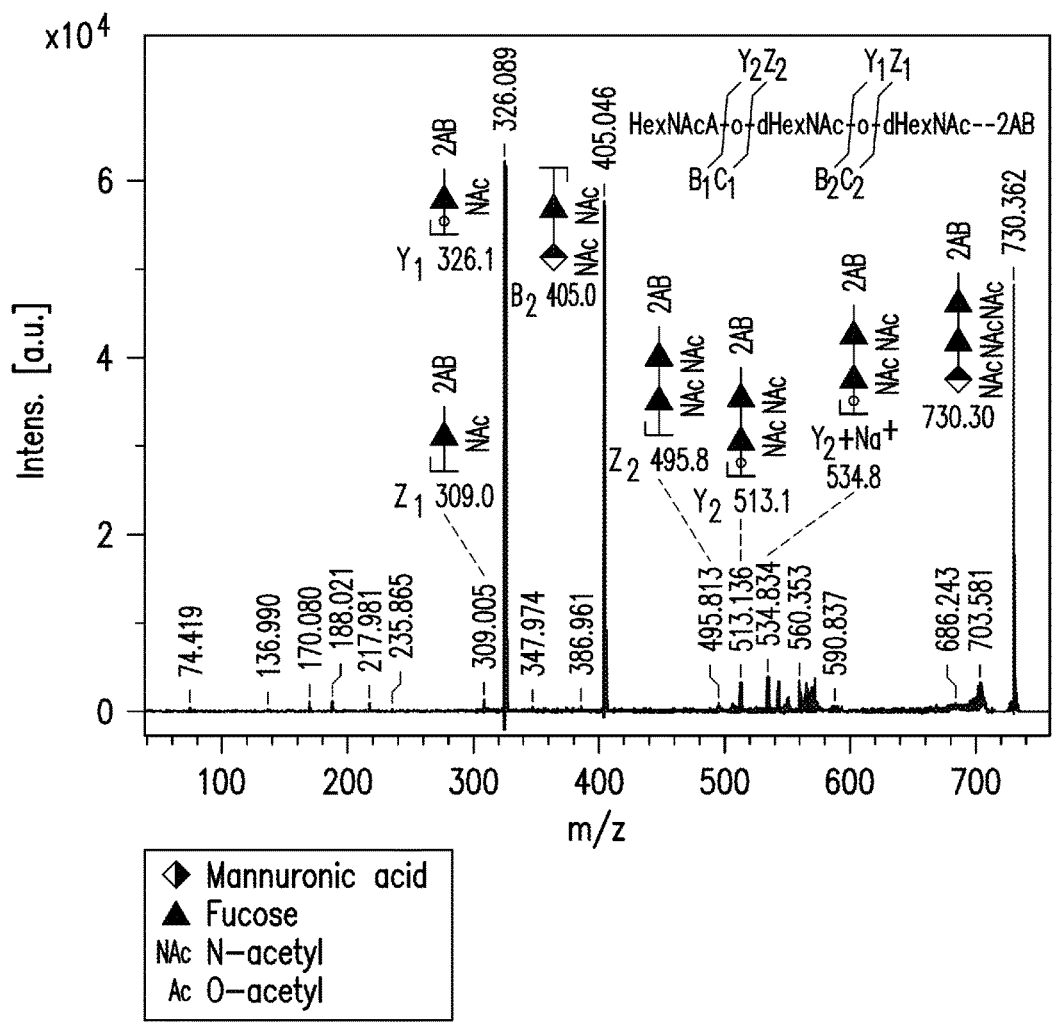
FIG. 11D shows the results of MALDI-MS/MS analysis of the specific peak generated by expression of an embodiment of the chimeric CP8 cluster of the present invention in *E. coli* eluting at 38 minutes seen in FIG. 10B.
Figure 11E:
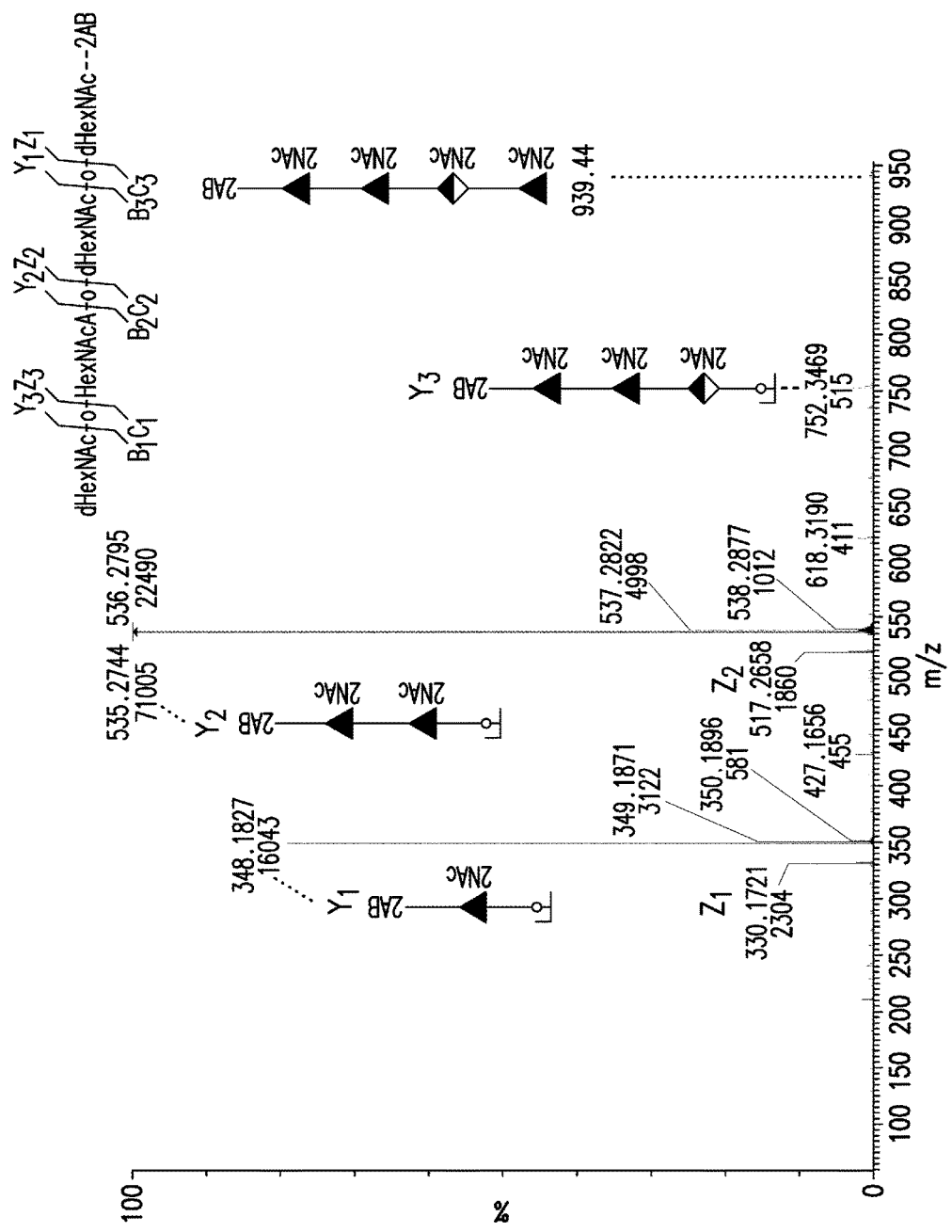
FIG. 11E shows the results of MALDI-MS/MS analysis of the specific peak generated by expression of an embodiment of the chimeric CP8 cluster of the present invention in *E. coli* eluting at 45 minutes seen in FIG. 10B.

FIG. 11D shows the results of MALDI-MS/MS analysis of the specific peak generated by expression of an embodiment of the chimeric CP8 cluster of the present invention in E. coli eluting at 38 minutes. The mass of m/z=730 ([M+H]$^+$) was selected and analyzed by MS/MS, which shows fragmentation ion series consistent with the non-acetylated CP8 RU structure that was also expected in light of the invention disclosed in this specification. Additional analysis showed that the later eluting peaks (shown in FIG. 10A at 40 min and FIG. 10B at 38 min) contain the non-O-acetylated trisaccharides of CP5 and 8 RUs. Fragment ions are indicated according to the nomenclature of the CFG. 2-AB, 2-aminobenzamide. The legend for the fragment ions is given in the inset of FIG. 11D.

MS results showed that the masses and fragmentation ion series are in agreement with the molecular structure of the CP5 RU oligosaccharide with the O acetylation of the middle FucNAc residue (i.e., the peak at 37' in FIG. 10A and in FIG. 11A) or without the O acetylation of the middle FucNAc residue (i.e., the peak 40' in FIG. 10A and in 11B). The signal at 45 minutes in FIG. 10A was identified as a tetrasaccharide, which is further analyzed below. The same analysis was repeated with the chimeric CP8 cluster that lacked the polymerase gene. In such extracts, signals consistent with the O-acetylated RU structure expected in light of the invention disclosed in this specification were found at 23' and 32' of elution, as shown FIGS. 10B and 11C. The presence of two different elution times for the same glycan sequence as identified by MALDI-MS/MS indicates an O-acetyl migration event taking place during sample preparation. Non-acetylated RUs were identified for CP5 and CP8 extracts at 40' and 38', as shown in FIGS. 11B and D, respectively. The CP5 and CP8 RU structures were present in different E. coli strains, including for example, W3110, W3310 ΔwecA, W3110 ΔwecAwzzE, and W3110 ΔwecAwzzE ΔwaaL.

Example 4

Improvement of the Repeating Unit Structure and its Analysis

The HPLC peak shown in FIG. 10B eluting at 45 minutes, derived from E. coli cells expressing the chimeric CP8 cluster (SEQ ID NO: 4) but lacking the wzy polymerase gene cap8I, was also analyzed by MALDI-MS/MS. The most intense ion in the full scan MS was m/z=939 ([M+H]$^+$) and sequence analysis was performed by MS/MS. The results of this MS/MS analysis are shown in FIG. 11E, and present a fragmentation ion series consistent with the non acetylated S. aureus capsular RU extended by a mass of a deoxy-N-acetylhexosamine at the non-reducing end, as expected in light of the invention disclosed in this specification. Fragment ions corresponding to the hypothetical structures are indicated according to the nomenclature of the CFG above the peaks. 2-AB, 2-aminobenzamide. The legend for the fragment ions is given in the inset of FIG. 11E.

The result shown in FIG. 11E suggested that an E. coli glycosyltransferase was able to modify the ManNAcA residue of the CP8 RU. Such an altered RU most probably would not be polymerized by cap8I. Analysis of the glycosyltransferase specificities in the E. coli host W3110 indicated that an enzyme from the ECA cluster may interfere with the recombinant sugar, specifically the wecF gene product, a putative 4-N-acetylfucosamine transferase. WecF naturally adds a 4-N-acetylfucosamine onto ManNAcA comprised in ECA, most likely the enzyme could also elongate CP8 and CP5 RU.

To solve this problem, another novel approach was developed. Specifically, genes of the ECA cluster located downstream of the wecC gene including wecF were deleted. This was accomplished using the method described by Datsenko et al. (Datsenko, K. A. and B. L. Wanner (2000). "One-step inactivation of chromosomal genes in Escherichia coli K-12 using PCR products." Proc Natl Acad Sci USA 97(12): 6640-6645). Different E. coli expression hosts were deleted in the waaL and rmlB-wecG gene regions and in some strains in wecA-wzzECA as well. Sep-PAK Purified extracts (Methanol and 10:10:3 extracts) from these mutated cells expressing the polymerase mutant CP8 chimeric cluster were analyzed by normal phase HPLC as described above.

Figure 11F:
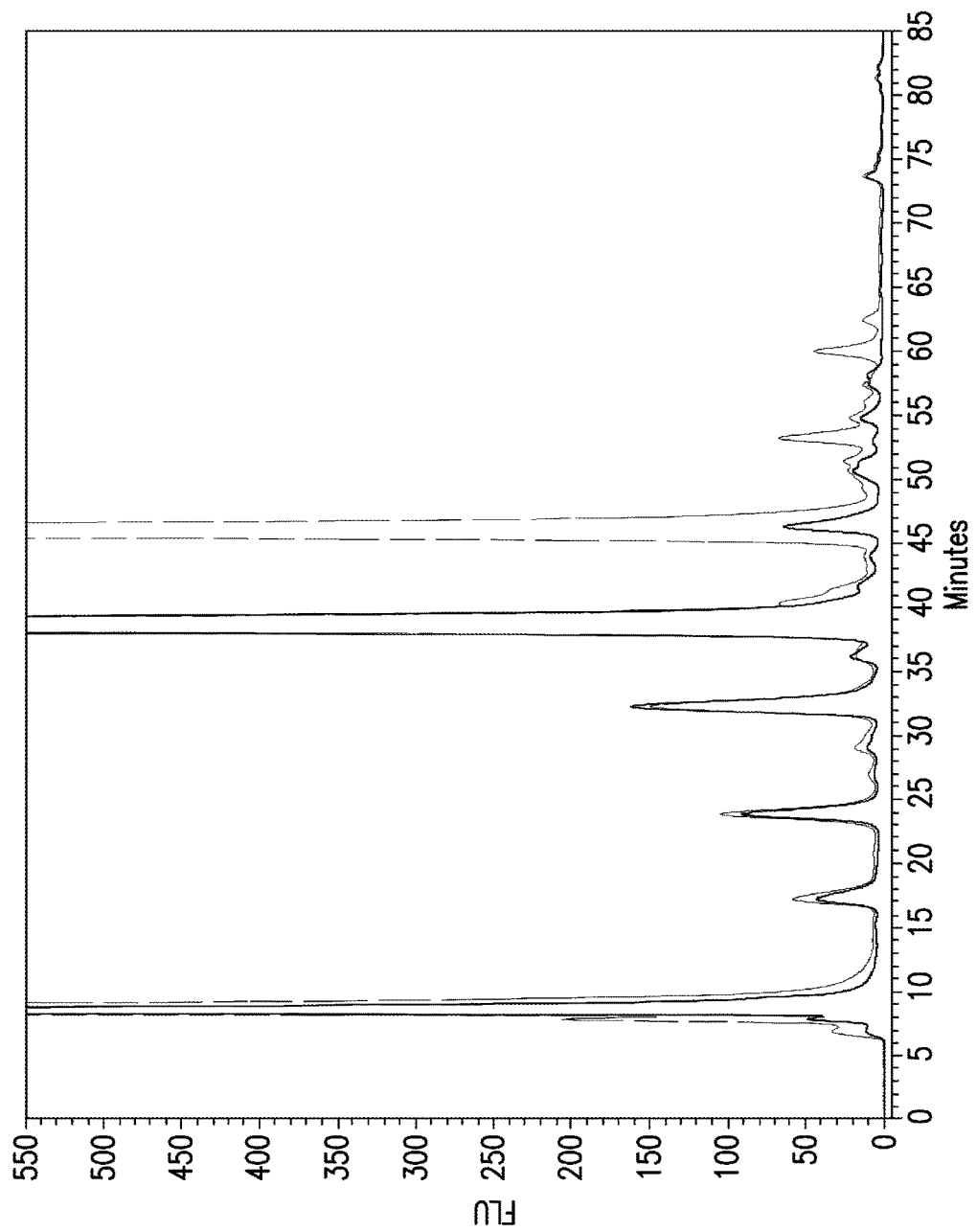
FIG. 11F shows the results of HPLC analysis of an embodiment of glycan structure optimization.

FIG. 11F presents the results of HPLC analyses of methanol extracts from E. coli W3110 ΔwaaL cells expressing the polymerase mutant of SEQ ID NO: 4 (thin, dashed line) compared to cells with an additional deletion of the ECA cluster genes rmlB-wecG (W3110 ΔwaaL ΔrmlB-wecG::cat) (thick line). Extracts were purified over tC18 cartridges and analyzed by normal phase HPLC. As shown in FIG. 11F, the major peak appearing at 45' in FIG. 10B was absent resulting in specific peaks for the acetylated and non acetylated CP8 RUs (FIG. 11F) indicating that one of the ECA glycosyltransferases—most probably wecF—is responsible for the aberrant elongation phenotype. Similar results were obtained when the CP5 chimeric cluster was tested in different strains. This implies that deleting E. coli borne glycosyltransferases and enzymes required for nucleotide activated sugar biosynthesis is a possible strategy for optimizing quality and quantity of recombinantly produced polysaccharides in E. coli. Target enzymes most likely would be encoded in the O-antigen cluster, the ECA cluster, and the colanic acid or capsule clusters.

Further evidence for the quality of the recombinant polysaccharide linked to UndPP was obtained from an optimized normal phase HPLC analysis of Sep-PAK purified, fluorescently labeled glycolipid extracts from chromosomally optimized expression hosts as described above. For optimal performance of the Sep-PAK columns for purification of charged CP5 and CP8 oligo- and polysaccharide-linked lipids, tert-butyl ammonium phosphate (TBAP) was added to the extracts before loading on the Sep-PAK cartridges. As reported by Trent, et al., the cation of this salt improves column binding of charged compounds by shielding negative charges with hydrophobic butyl chains (Trent, M. S., A. A. Ribeiro, et al. (2001). "Accumulation of a polyisoprene-linked amino sugar in polymyxin-resistant Salmonella typhimurium and Escherichia coli: structural characterization and transfer to lipid A in the periplasm." J Biol Chem 276(46): 43132-43144.). This optimized method was applied to the CP5 and CP8 samples obtained by methanol extraction from cells expressing CP5 or CP8 chimeric clusters containing a polymerase.

Figure 11G:
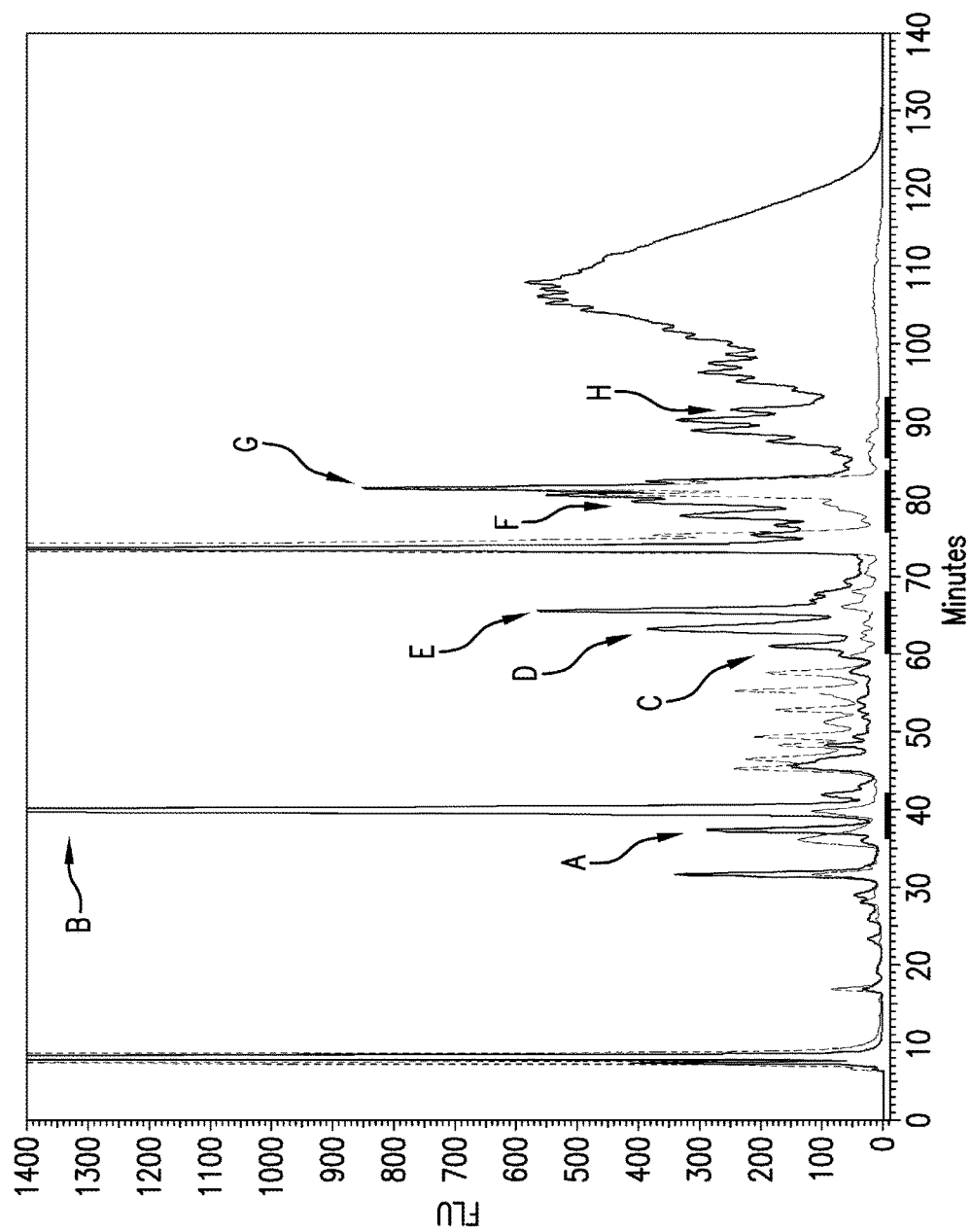
Figures 1, 11G:
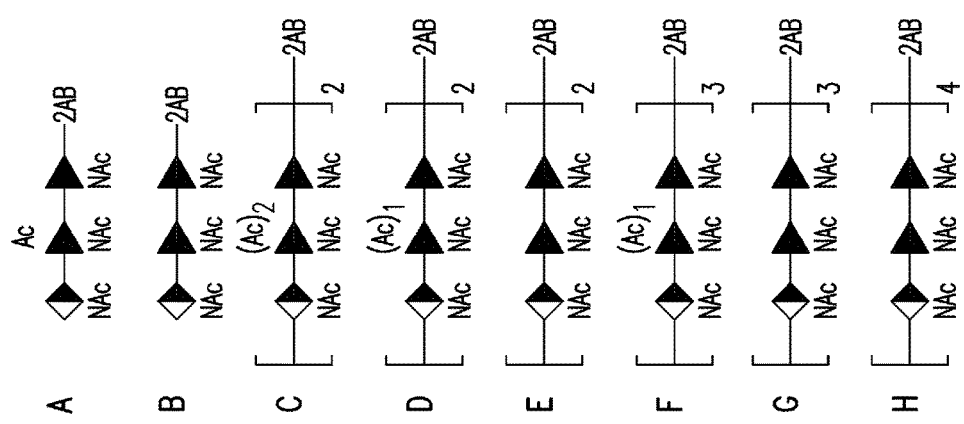

FIG. 11G provides the results of HPLC analysis showing the full CP5 glycan repertoire present on UndPP in E. coli cells. Methanol extracts from E. coli W3110 ΔwaaL ΔwecAwzzECA ΔrmlB-wecG::cat either expressing the chimeric CP5 cluster SEQ 3 (solid line) or an empty plasmid control (dashed line) were solid-phase extracted on Sep-PAK cartridges and treated with mild acid to hydrolyse sugars from UndPP. The resulting material was reacted with 2AB by reductive amination to label reducing ends of the glycans and analyzed by normal phase HPLC. Signals present in the solid line but not in the dashed line represent CP5 specific material. Capital letters indicate peaks containing polymers of the acetylated and/or non-acetylated CP5 RU as identified by MALDI-MS/MS of the collected fractions. The legend of FIG. 11G indicates the proposed molecular structures as deduced from MS/MS analysis. It should be noted that acetylated and non-acetylated RU polymers shown for MS/MS confirmed structures of the same polymerization degree group together in the chromatogram as indicated by thick bars. Capital letters show the following lengths: A and B: one RU; C, D and E: two RUs; F and G: three RUs; and H: four RUs. The broad peak between 95' and 125' in FIG. 11G most probably represents 5 or more polymerized RUs not resolved by the column.

Figure 11H:
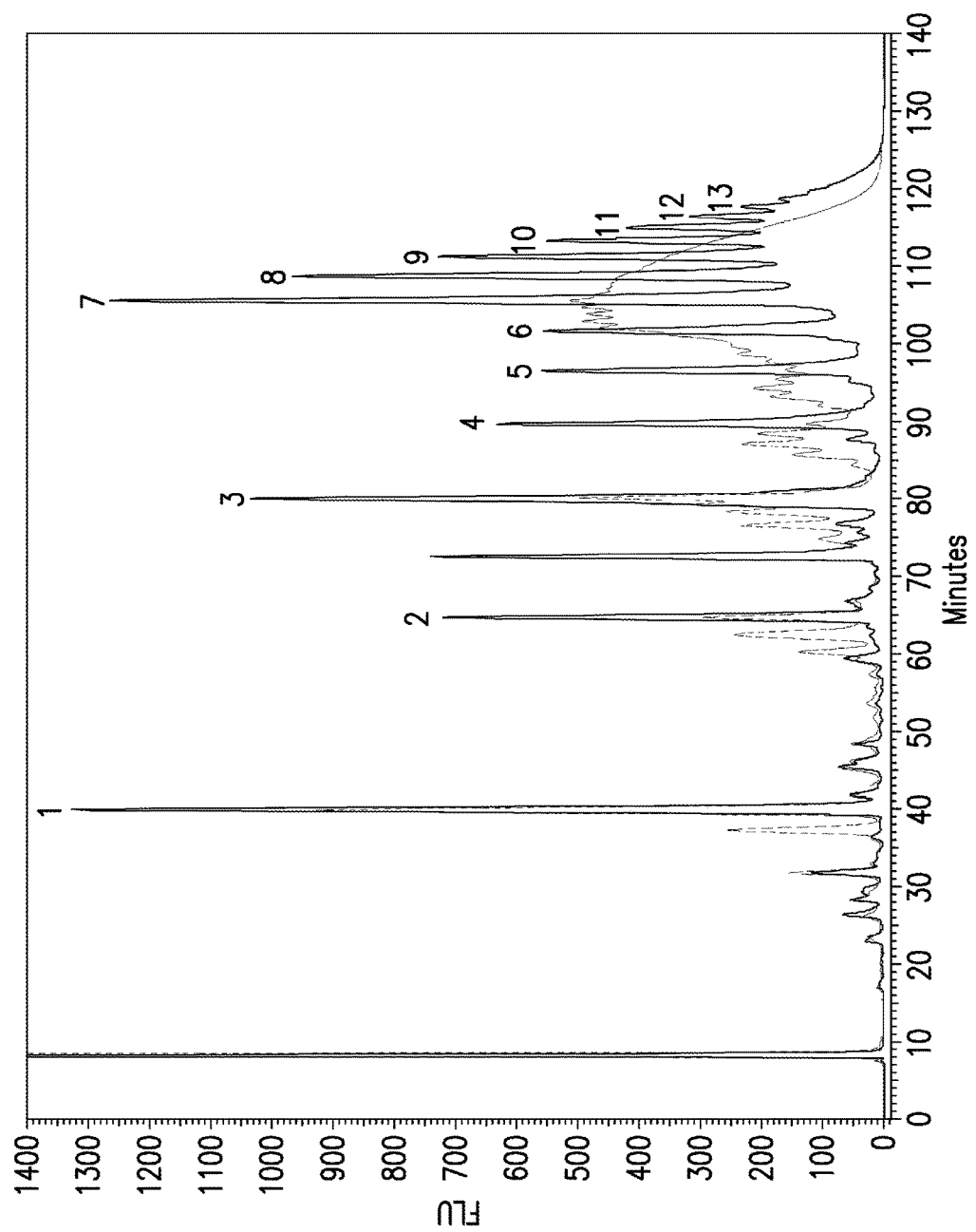
FIG. 11H presents the results of HPLC analysis of deacetylated CP5 glycans and RU homogeneity in an embodiment of the invention.

FIG. 11H presents further HPLC results, showing acetylated CP5 glycans and RU homogeneity. To prepare this HPLC analysis, 2AB labeled glycan samples of E. coli W3110 ΔwaaL ΔwecAwzzECA ΔrmlB-wecG::cat expressing the chimeric CP5 cluster SEQ ID NO.: 3 (prepared according to the procedures described above with reference to FIG. 11G) were treated with NaOH in aqueous solution and re-labeled. As showing in FIG. 11H, samples before (dashed) and after (solid line) alkali treatment were analyzed by HPLC. Numbers in FIG. 11H indicate the putative numbers of RUs in the corresponding peaks. It should be observed that, in FIG. 11H, the acetylated peaks shown in FIG. 11G unify in the signal from non-acetylated polymer, and that deacetylation resolved the RU units in the elution times after 95 minutes.

Figure 11I:
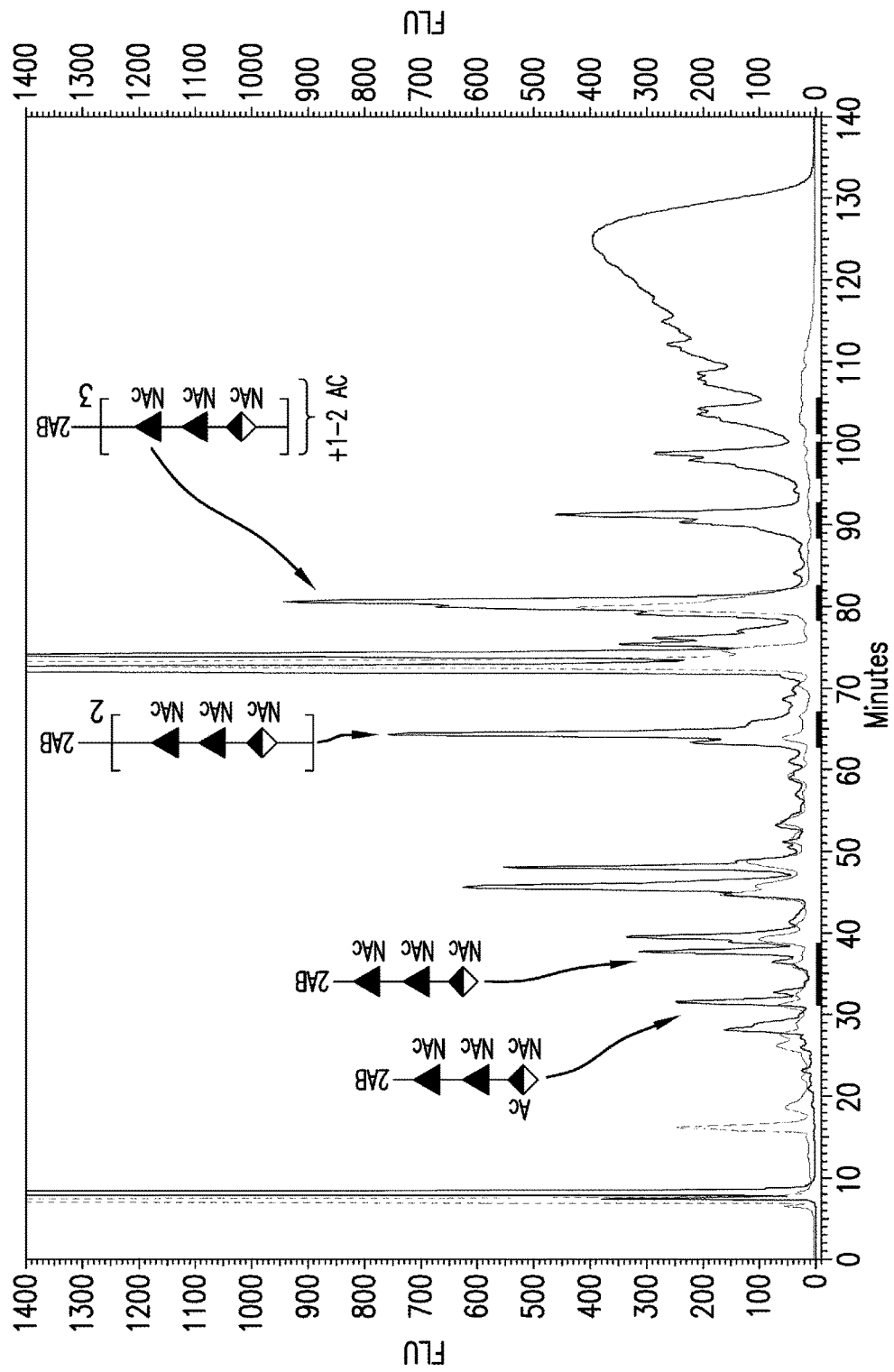
FIG. 11I provides the results of HPLC analysis of the CP8 glycan repertoire present on UndPP in *E. coli* cells in an embodiment of the present invention.

FIG. 11I provides the results of HPLC analysis showing the CP8 glycan repertoire present on UndPP in E. coli cells. Methanol extracts from E. coli W3110 ΔwaaL ΔwecAwzzECA ΔrmlB-wecG::cat either expressing the chimeric CP8 cluster SEQ ID NO.: 4 (solid line) or an empty plasmid control (dashed line) were solid-phase extracted on Sep-PAK cartridges and treated with mild acid to hydrolyse sugars from UndPP. The resulting material was reacted with 2AB by reductive amination to label reducing ends of the glycans and analyzed by normal phase HPLC. Signals present in the solid line but not in the dashed line represent CP8 specific material. Putative structures of acetylated and/or non-acetylated CP8 RU as identified by MALDI-MS/MS of the collected fractions are indicated. Note that as in the HPLC results with CP5 shown in FIG. 11G, acetylated and non acetylated CP8 RU polymers of the same polymerization degree group together in the chromatogram of FIG. 11H as indicated by thick bars. Material detected after 110' represents longer CP8 polymers.

Figure 11J:
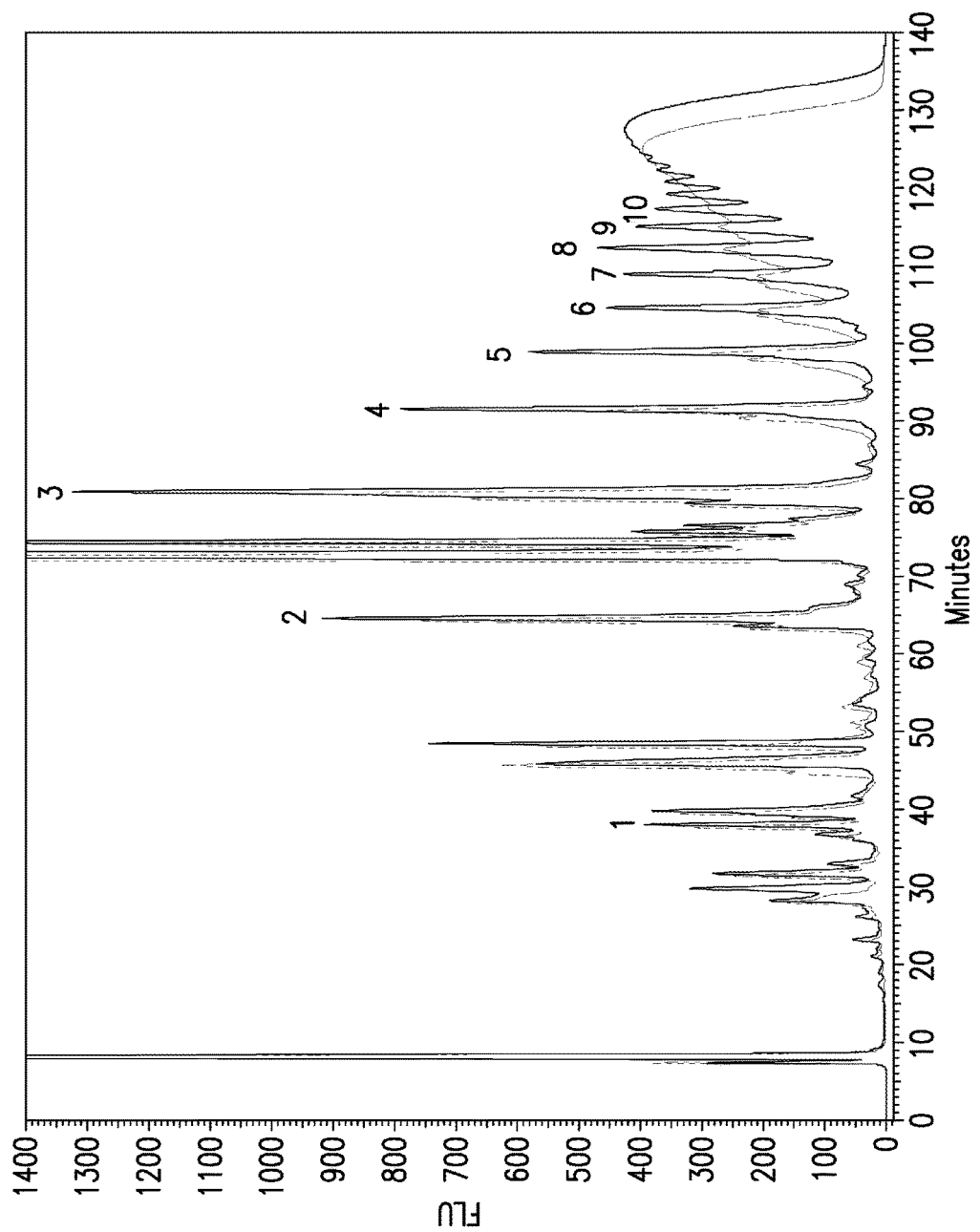
FIG. 11J shows HPLC results, in an embodiment of the present invention, of deacetylation of CP8 glycans and RU homogeneity.

FIG. 11J presents further HPLC results, showing deacetylation of CP8 glycans and RU homogeneity. 2AB labeled glycan samples from E. coli W3110 ΔwaaL ΔwecAwzzECA ΔrmlB-wecG::cat expressing the chimeric CP8 cluster SEQ ID NO.: 4 were treated with NaOH in aqueous solution and re-labeled. Samples before (dashed) and after (solid line) alkali treatment were analyzed by HPLC. Numbers indicate the putative numbers of RUs in the corresponding peaks. It should be noted that the acetylated peaks largely vanish and that signals of non-acetylated polymer increase, and that deacetylation resolved the RU units in the elution times after 110 minutes.

FIGS. 11H and 11J show HPLC results indicative of the characteristic ladder-like banding pattern of O-antigens when alkali treatment was performed on these CP5 and CP8 samples to remove the acetylation modifications from the oligo- and polysaccharides. The results show discrete sharp peaks with constantly decreasing elution time increments. This implies that such analyzed carbohydrate chains are linear polymers composed of identical RUs. This data shows that the recombinant CP5 and CP8 sugars produced in E. coli are regularly polymerized and partially acetylated. Non-acetylated CP5 and CP8 polymers elute similarly from the HPLC column as expected from their similarity in structure; however the normal phase chromatography also reveals differences: for example, CP5 polymerizes to a lesser extent than CP8, and acetylation is more frequent in CP5; in the RU lengths above 4, CP5 has a clear preference for making polymers of 7 RUs, whereas CP8 polymerizes to a broader degree; and as indicated by the HPLC and MS/MS results, CP5 is more efficient for glycan production than CP8.

In wzy dependent polymerization pathways, it has been reported by Marolda, et al., that a specific enzyme (wzz or cld for chain length determinant) is responsible for determining the average number of RU polymerization steps performed (Marolda, C. L., L. D. Tatar, et al. (2006). "Interplay of the Wzx translocase and the corresponding polymerase and chain length regulator proteins in the translocation and periplasmic assembly of lipopolysaccharide o antigen." J Bacteriol 188(14): 5124-5135.). Wzz enzymes cause a specific repeat number averages, e.g. short, long and very long sugar polymers and are known to transfer their length specificity to exogenous polysaccharide pathways. The lengths and amounts of the CP8 glycolipids were analyzed in the production strain resulting in longer and lower amount of this sugar. To increase the amount of molecules and thereby the sugar transfer efficiency for protein glycosylation, a downregulation of the CP8 sugar length was performed using a specific Wzz enzyme.

Figure 11K:
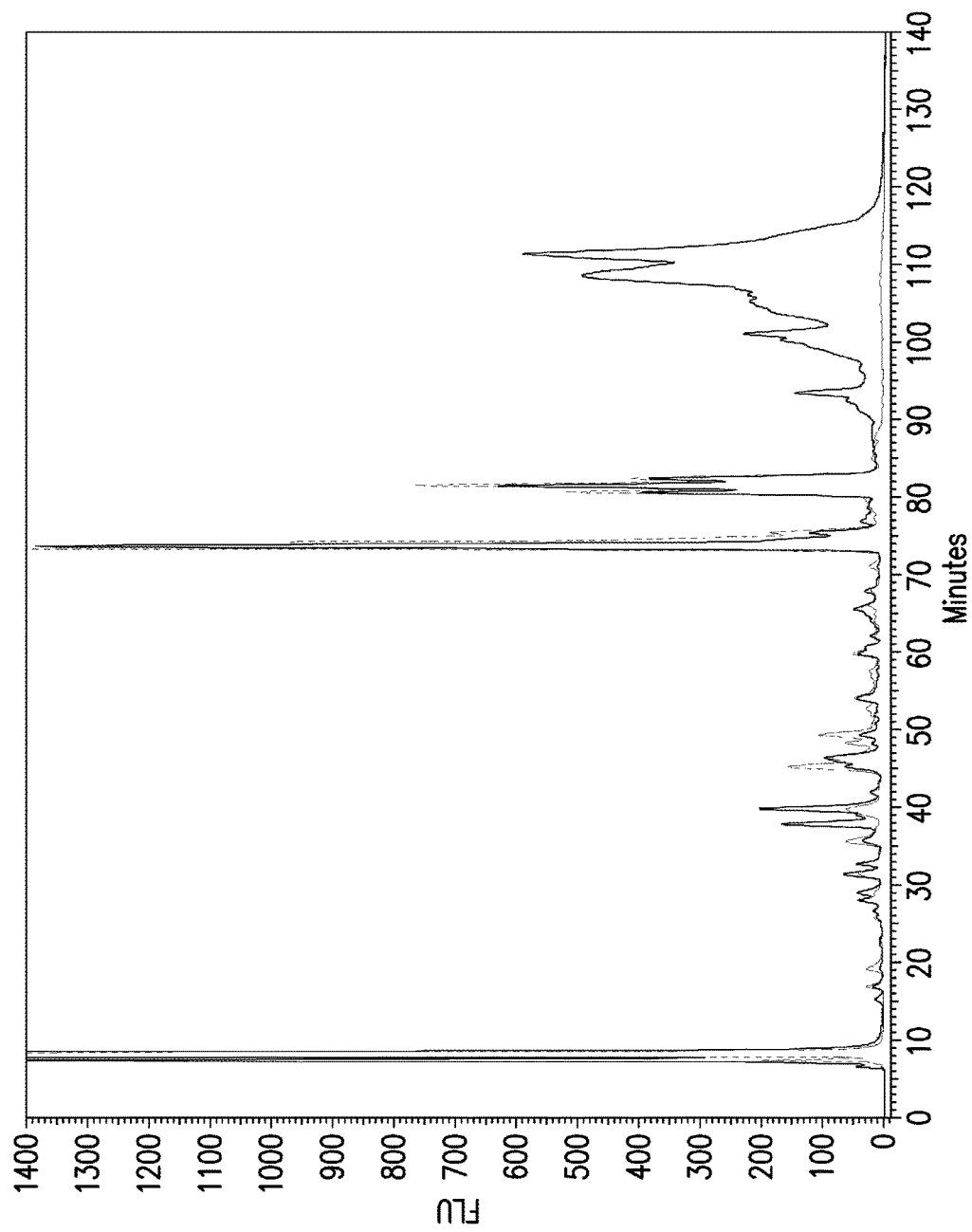
FIG. 11K presents HPLC results showing reduction in RU polymerization and increase in LLO induced by co-expression of wzzO7 with the CP8 chimeric cluster in an embodiment of the present invention.

To test the effect of a Wzz protein on the size and amounts of CP8 sugars on lipid, coexpression of Wzz from E. coli wzz 07 was performed from a separate plasmid (SEQ ID NO: 19). FIG. 11K presents the results of this test. Methanol extracts from E. coli W3110 ΔwaaL ΔwecAwzzECA ΔrmlB-wecG::cat either expressing the chimeric CP8 cluster SEQ ID NO: 4 and a plasmid borne, IPTG inducible copy of wzzO7 (SEQ ID NO: 21, solid line), or an empty plasmid control (dashed line) were solid phase extracted on Sep-PAK cartridges and treated with mild acid to hydrolyse sugars from UndPP. 2AB labeled glycans were analyzed by normal phase HPLC. Alkali treatment of the CP8 sample showed that more than 85% of the area between 95 and 115' represents 7 or 8 RU polymers of CP8, indicating a wide variety of acetylation. These results also indicate that the chimeric CP8 cluster induced: a) an intensification in repeat numbers of the most abundant glycan from 7 to 8, and b) a higher overall intensity of fluorescent signal as judged from the area under the chromatogram.

Alkali treatment confirmed the acetylation of the shortened glycan as in FIGS. 11I and 11J indicating that a recombinant polysaccharide's length can be regulated by a foreign Wzz enzyme. It is also possible to regulate the capsular sugar polymer length by an O-antigen derived Wzz enzyme. Furthermore, different promoters in front of the chimeric cluster when present on a plasmid cause different expression levels and different degrees of polymerization.

Example 5

Protein Glycosylation with the CP5 and CP8 Glycans and Product Characterization

Different variants of the chimeric cluster were tested for bioconjugate production. The chimeric O11/CP5 gene clusters (SEQ ID NO: 2 and 3), which contain different variants of S. aureus specificity regions in the O11 O-antigen cluster in place of wbjA and wzy, were expressed in the host strain E. coli W3110 ΔwaaL ΔwecAwzzE::cat in the presence of PglB (SEQ ID NO: 27?) and EPA (SEQ ID NO: 13). W3110 ΔwaaL ΔwecAwzzE::cat host cells expressed EPA with two glycosylation sites (from SEQ ID NO: 13) and PglB (SEQ ID NO: 27) from separate plasmids in addition to the pLAFR1 plasmid with the O11 O-antigen cluster where the wbjA and wzy genes were replaced with different cap5 gene sets (and the cat cassette, SEQ ID NO: 2 and SEQ ID NO: 3).

The EPA protein is expressed containing: a) a N-terminal signal peptide sequence for export to the periplasm, b) two bacterial N-glycosylation consensus sequences engineered into the protein sequence (SEQ ID NO: 13) as set forth in Example 10 of WO 2009/104074, incorporated by reference herein in its entirety, and c) a hexa histag for purification. The cells were grown in 5 L Erlenmeyer flasks in LB medium. An overnight culture was diluted to $OD_{600\ nm}$=0.05. At $OD_{600\ nm}$ around 0.5, PglB expression was induced by addition of 1 mM IPTG and EPA expression was induced by addition of arabinose (0.2% final concentration). The cells were grown for 4 hours, induction was repeated and cells were grown for around additional 16 hours. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. EPA-CP5 bioconjugate without and with the S. aureus flippase gene cap5K (SEQ ID NO: 2 and 3) was eluted by 0.5M imidazole, and eluted peaks were pooled and analyzed by SDS PAGE and stained by Coomassie and silver (FIG. 12).

Figure 12:
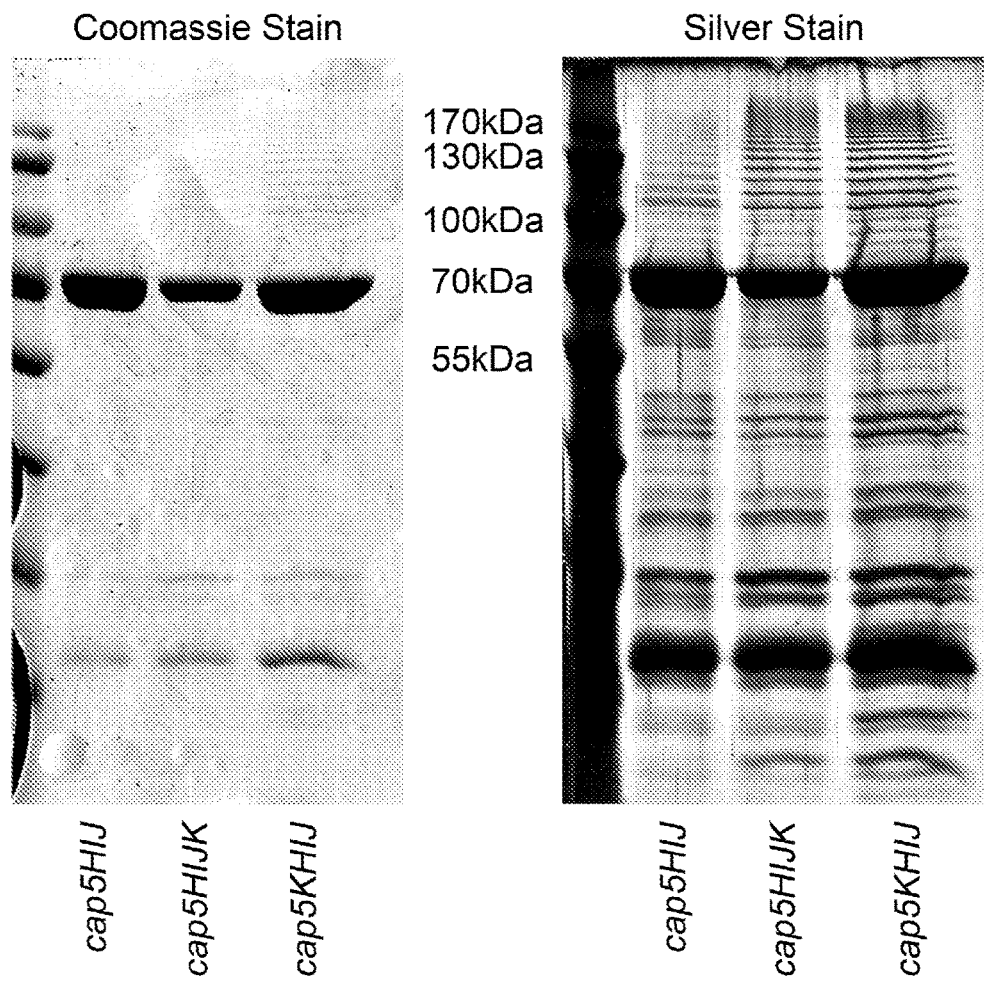
FIG. 12 shows the results of SDS-PAGE analysis of Ni$^{2+}$ affinity chromatography purified EPA-CP5 bioconjugate from cells in embodiments of the present invention without and with the S. aureus flippase gene cap5K (SEQ ID NO: 2 and 3).

FIG. 12 presents the SDS PAGE results. The left panel shows the coomassie stain, and the right panel shows the silver stain. The numbers in the middle indicate the sizes of the molecular weight marker. The letters below the lanes indicate the genes that were present in the chimeric cluster expressed in the strains used for bioconjugate production. The host strain was E. coli W3110 ΔwaaL ΔwecAwzzE::cat. The results show protein signal at 70 kDa (electrophoretic mobility) most likely corresponding to unglycosylated EPA, and a ladder of bands above (100-170 kDa). The ladder likely corresponds to EPA protein glycosylated with the CP5 recombinant S. aureus glycan. In addition, the results indicate that including the flippase gene in the system increases the glycoprotein yield (middle and right lanes).

In a separate analysis, CP5-EPA bioconjugate was produced in *E. coli* W3110 ΔwaaL ΔwecAwzzE::cat by co-expression of the chimeric CP5 gene cluster (SEQ ID NO: 3), PglB (SEQ ID NO: 27) from plasmid pEXT21 and EPA (containing two glycosylation sites, SEQ ID NO: 13) from separate plasmids. To obtain a more controlled process for bioconjugate production, the cells were grown in a 2-L bioreactor to an $OD_{600\ nm}$=30 at 37° C., and expression of PglB and EPA was induced by the addition of 1 mM IPTG and 0.2% arabinose. The cells were grown for 18 h at 37° C. under oxygen-limiting conditions. The cells were pelleted by centrifugation, washed and resuspended in 25% sucrose buffer at an $OD_{600\ nm}$=200, after 30 min. incubation at 4° C., the suspension was pelleted, and lysed by osmotic shock. The spheroplasts were pelleted by centrifugation, and the periplasmic proteins present in the supernatant were loaded on a $Ni^{2+}$ affinity chromatography. Glycosylated and unglycosylated EPA were eluted from the affinity column by 0.5 M imidazole and loaded on a SourceQ anionic exchange column. Glycosylated EPA was separated from unglycosylated EPA by applying a gradient of increasing concentration of NaCl.

Figures 13A, 13B:
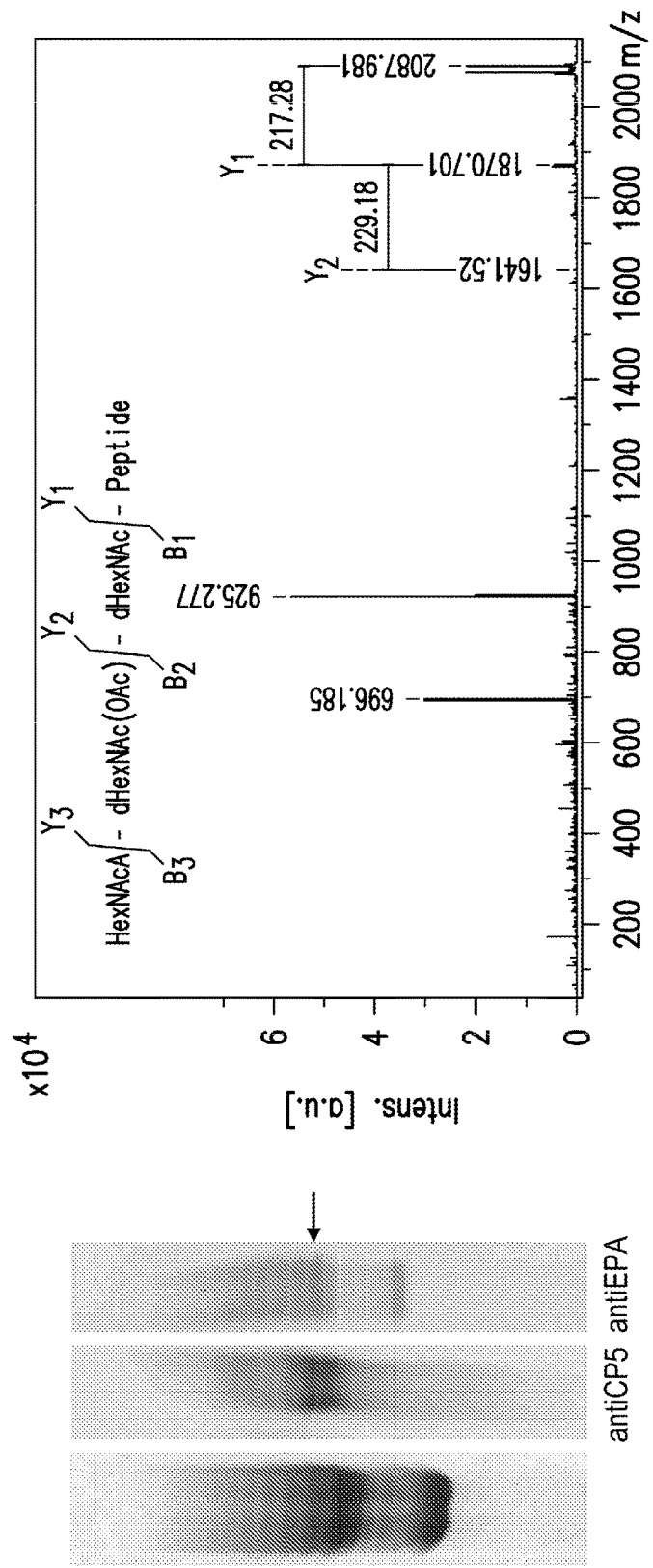
FIG. 13A presents analysis of CP5-EPA bioconjugate according to an embodiment of the present invention purified by Ni$^{2+}$ affinity chromatography and anionic exchange chromatography.
FIG. 13B depicts M/Z masses found for the glycosylation site in trypsinized peptide DNNNSTPTVISHR N-glycosidically linked to the O-acetylated RU mass (m/z=2088 ([M+H]$^+$)) according to an embodiment of the present invention. The inset illustrates the RU structure attached to the peptide.
Figure 13C:
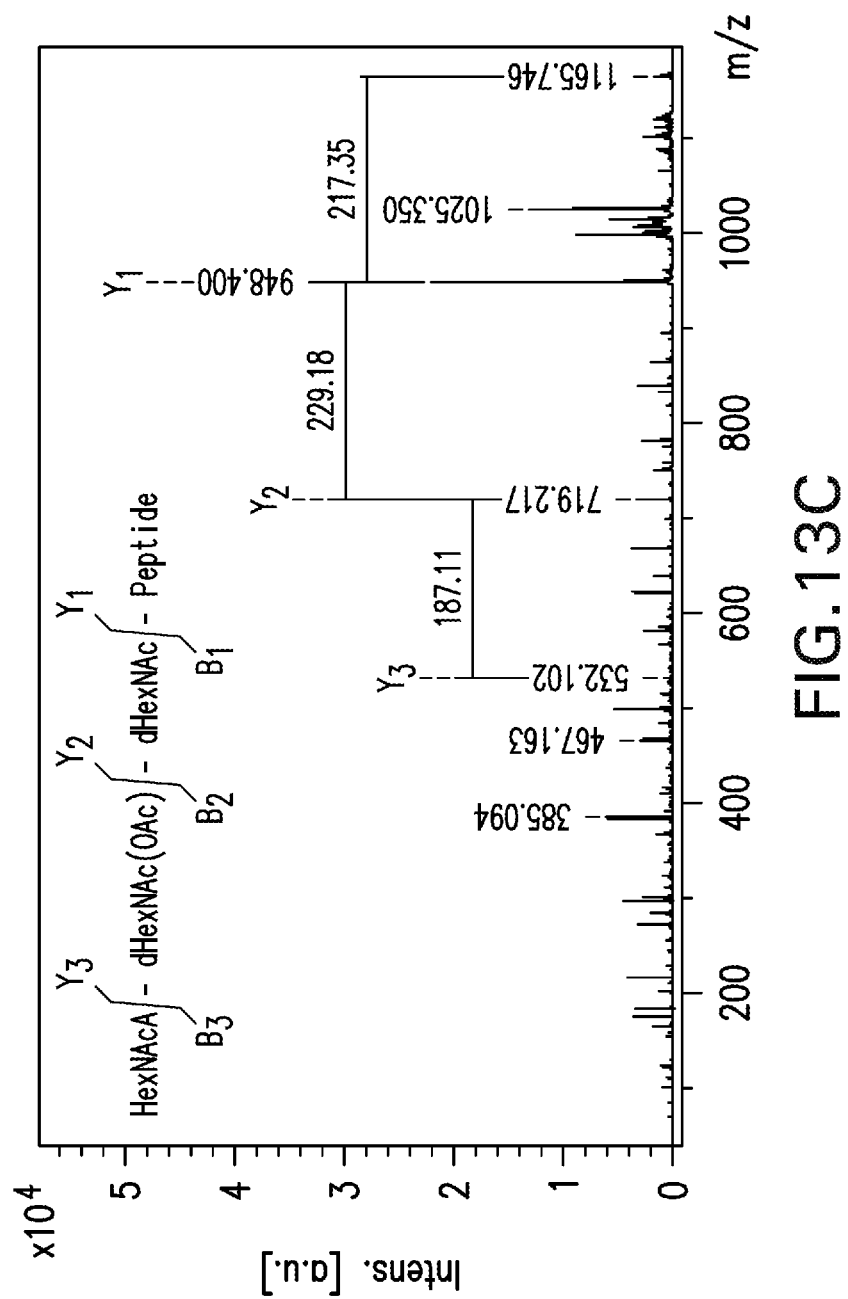
FIG. 13C depicts M/Z masses found for the glycosylation site in trypsinized peptide DQNR N-glycosidically linked to the O-acetylated RU mass (m/z=1165 ([M+H]$^+$)) according to an embodiment of the present invention. The inset illustrates the RU structure attached to the peptide.

As shown in FIG. 13A, the purified glycosylated EPA (CP5-EPA) was separated by SDS PAGE and stained by Coomassie (left lane) or transferred to nitrocellulose membranes and incubated with either anti CP5 antibodies (middle lane) or anti EPA antibodies (right lane). The purified bioconjugate was recognized by the EPA-specific antibodies (right lane), as well as the CP5-specific polyclonal antiserum (middle lane). The arrow indicates the position in the gel from where a piece was cut and used for trypsinization and analysis of glycopeptides by MALDI-MS/MS. FIG. 13B presents the MALDI-MS/MS of M/Z masses found for the glycosylation site in trypsinized peptide DNNNSTPTVISHR N-glycosidically linked to the O-acetylated RU mass (m/z=2088 ([M+H]$^+$)). MS/MS analysis of the m/z=2088 shows partial fragmentation of the sugar moiety as indicated. The inset illustrates the RU structure attached to the peptide derived from trypsinization of purified CP5-EPA from FIG. 13A. Sequential losses of ManNAcA (HexNAcA, 217 Da) and acetylated FucNAc (dHexNAc(OAc), 229 Da) support the expected glycan structure. FIG. 13C presents the MALDI-MS/MS of M/Z masses found for the glycosylation site in trypsinized peptide DQNR N-glycosidically linked to the O-acetylated RU mass (m/z=1165 ([M+H]$^+$)). MS/MS analysis of m/z=1165 shows the full Y-ion fragmentation ion series consistent with the CP5 RU structure. The inset illustrates the RU structure attached to the peptide derived from trypsinization of purified CP5-EPA from FIG. 13A. Sequential losses of ManNAcA (HexNAcA, 217 Da), acetylated FucNAc (dHexNAc (OAc), 229 Da), and FucNAc (dHexNAc, 187 Da) are shown, confirming the expected glycan structure on the peptide DQNR (m/z=532 Da ([M+H+])).

Figure 13D:
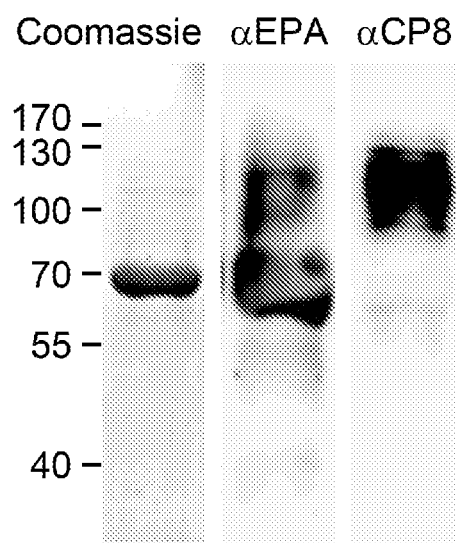
FIG. 13D depicts an analysis of Ni$^{2+}$ affinity chromatography and anionic exchange chromatography purified CP8-EPA bioconjugate according to an embodiment of the present invention.

In FIG. 13D the CP8 bioconjugate in *E. coli* was produced using the same strategy as production of the CP5 bioconjugate. CP8-EPA bioconjugate was produced in *E. coli* by co-expression of the chimeric CP8 gene cluster (SEQ ID NO: 4), PglB (within the pEXT21 plasmid (SEQ ID NO: 27)), and EPA containing two glycosylation sites (SEQ ID NO: 13). Cells were grown in a bioreactor with a starting volume of 7 L in semi-defined medium containing glycerol, peptone and yeast extract as C-sources. Cells were grown at 37° C. in batch or pulsed-batch mode to an $OD_{600\ nm}$ of 30, and expression of PglB and EPA was induced by the addition of 1 mM IPTG and 10% arabinose. After induction, cells were further cultivated in fed-batch mode for a period 15 hours under oxygen-limiting conditions. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. Glycosylated and unglycosylated EPA were eluted from the affinity column by 0.5 M imidazole and loaded on a SourceQ anionic exchange column. Glycosylated EPA was separated from unglycosylated EPA by applying a gradient of increasing concentration of NaCl.

As depicted in FIG. 13D, the purified protein was separated by SDS PAGE and stained by Coomassie (left lane) or transferred to nitrocellulose membranes and incubated with either anti CP8 antibodies (right lane) or anti EPA antibodies (middle lane).

Figure 13E:
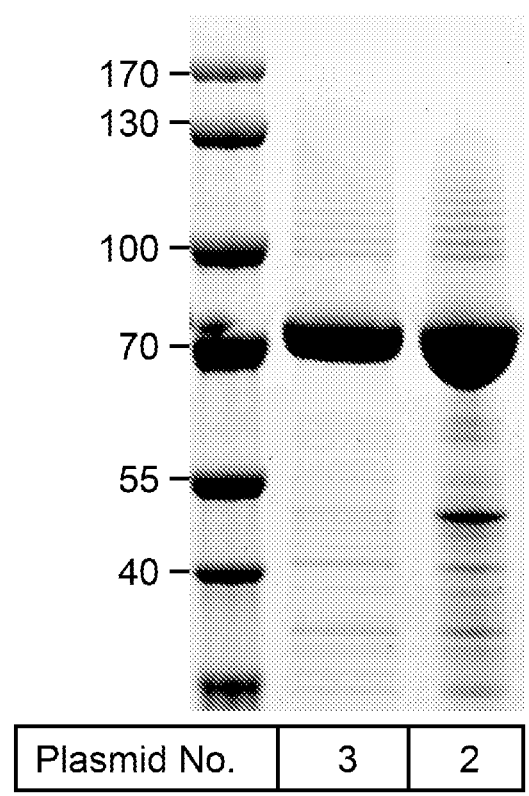
FIG. 13E depicts purified CP5-EPA bioconjugate from cells containing either 3 (left) or 2 plasmids (right lane) for glycoconjugate production according to an embodiment of the present invention.

Different strategies for further improving the glycosylation system were tested. In one strategy, to reduce the plasmid number in the production system to lower the burden of an additional antibiotic as well as maintaining an extra plasmid, the expression cassette for pglB was cloned into the plasmid containing the chimeric clusters for CP5 (SEQ ID NO: 17) and CP8 (SEQ ID NO: 18). The expression cassette is composed of the intergene region present between galF and wbqA of the *E. coli* O121 genome (for a promoter sequence), and the pglB sequence downstream of this. This expression cassette was cloned immediately downstream of the CP5 and CP8 chimeric clusters. We tested *E. coli* W3110 ΔwaaL ΔwecAwzzECA::cat containing the chimeric CP5 cluster (SEQ ID NO: 3) and pglB (SEQ ID NO: 27) on either separate plasmids or on the same plasmid (SEQ ID NO: 17). In addition, EPA (SEQ ID NO: 13) was expressed from a plasmid under the control of an arabinose inducible promoter. The cells were grown in 5 L Erlenmeyer flasks in LB medium at 37° C. An overnight culture was diluted to $OD_{600\ nm}$=0.05. At $OD_{600}$ nm around 0.5 PglB expression was induced by addition of 1 mM IPTG and EPA expression was induced by addition of arabinose (0.2% final concentration). The cells were grown for 4 hours, induction was repeated and cells were grown for around an additional 16 hours. The culture was pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. EPA-CP5 was eluted by 0.5M imidazole, and eluted peaks were pooled and analyzed by SDS PAGE and by Coomassie. FIG. 13E depicts the SDS PAGE results. Cells containing either 3 (left) or 2 plasmids (right lane) for glycoconjugate production are shown. The results show that glycolipid and conjugate production for CP5-EPA was maintained.

Figure 13F:
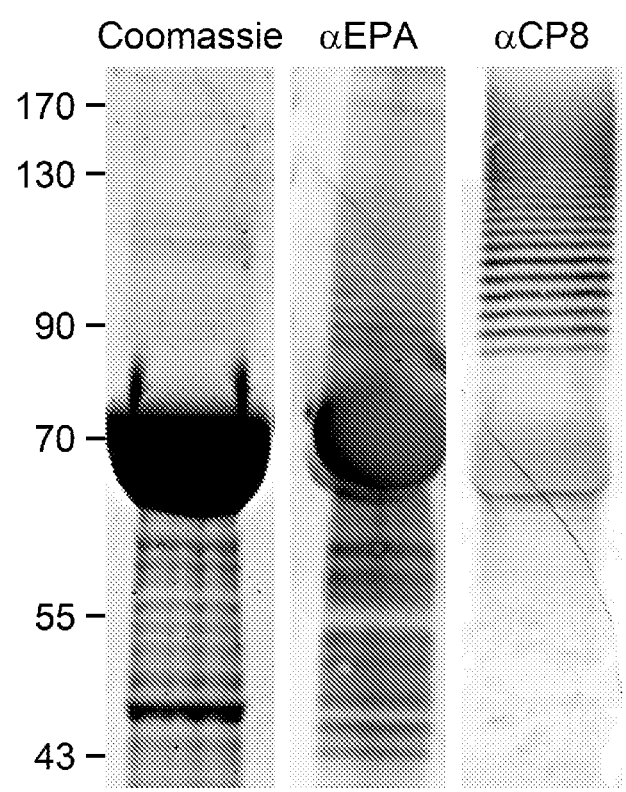
FIG. 13F depicts analysis of Ni$^{2+}$ affinity chromatography purified CP8-EPA bioconjugate according to an embodiment of the present invention.

A further optimization of the system was the integration of the wzz (polymer length regulator) protein sequence in the plasmids used for protein glycosylation. Exemplified by the system producing CP8-EPA, wzz was integrated into the plasmid borne chimeric CP8 cluster (SEQ ID NO: 19) and downstream of the epa gene within the expression plasmid for the carrier protein (SEQ ID NO: 20). CP8-EPA bioconjugate was produced in *E. coli* W3110 ΔwaaL ΔwecAwzzECA ΔrmlB-wecG::cat comprising 2 plasmids: one plasmid contained in addition to the chimeric CP8 gene cluster a copy of the wzz 07 gene and a DNA cassette for the constitutive expression of the pglB gene (SEQ ID NO: 19); the second plasmid contained first the gene for expression and secretion of the detoxified EPA protein containing two glycosylation sites, and second a wzzO7 copy under the control of the same promoter (SEQ ID NO: 20). The resulting strain, *E. coli* W3110 ΔwaaL ΔwecAwzzECA ΔrmlB-wecG::cat, containing the mentioned plasmids was grown in a bioreactor with a starting volume of 7 L in semi-defined medium containing glycerol, peptone and yeast extract as C-sources. Cells were grown in batch or pulsed-batch mode to an $OD_{600\ nm}$ of 30, and expression of PglB and EPA was induced. After induction, cells were further cultivated in fed-batch mode for a period 15 hours under oxygen-limiting conditions and collected by centrifugation. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. Glycosylated and unglycosylated EPA were eluted from the affinity column by 0.5 M imidazole. Formation of glycoconjugate CP8-EPA is shown in FIG. 13F by Coomassie and western blot using anti his and anti CP8 antisera. FIG. 13F shows the results of SDS PAGE separation of the purified protein and analysis by Coomassie staining (left lane) or transferred to nitrocellulose membranes and probed with either anti histag antibodies (middle lane) or anti CP8 antibodies (right lane).

Figure 14B:
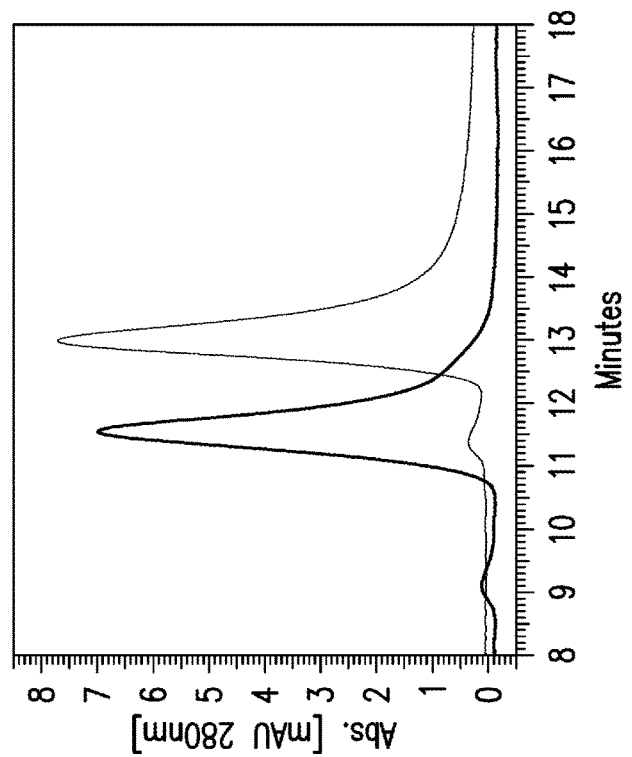
FIG. 14B shows characterization by size exclusion chromatography of CP5-EPA bioconjugate of an embodiment of the invention produced using the 3 plasmid system from FIG. 13A.
Figure 14A:
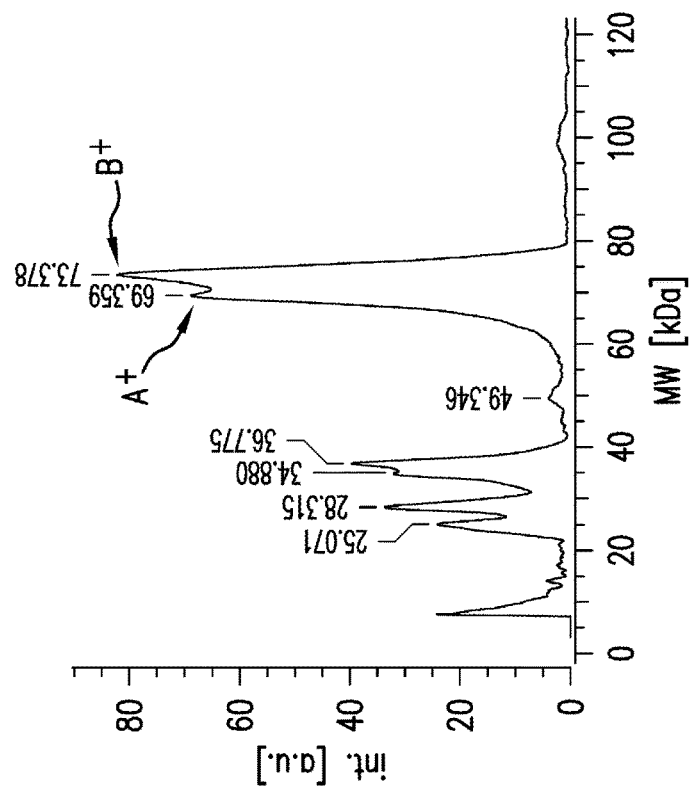
FIG. 14A presents High Mass MALDI analysis of a purified CP5-EPA bioconjugate of an embodiment of the invention produced using the 3 plasmid system from FIG. 13A.

Characterization of the CP5-EPA glycoconjugate was further refined by various analytical methods. CovalX (Schlieren, Switzerland) performed High Mass MALDI analysis of a purified CP5-EPA sample produced using the 3 plasmid system as used in the analyses depicted in FIG. 13A in W3110 ΔwaaL ΔwecAwzzECA::cat. FIG. 14A depicts the High Mass MALDI results. $A^+$ and $B^+$ point towards mass protein species ($[M+H]^+$) corresponding to unglycosylated EPA and glycosylated EPA, respectively. Oligomeric forms may be present at higher molecular weight and signals in the low MW area are contaminants or degradation products. The results presented in FIG. 14A show that the above protein preparation contained a largely monomeric protein population which is 4 kDa larger than the EPA protein alone, indicative of a medium sugar length of 5.2 repeating units. This is in agreement with the sugar length of 5-7 of the major glycoconjugate form in the preparation as analyzed by SDS-PAGE, Coomassie brilliant blue staining and counting the repeating units in the major conjugate form (see FIGS. 7, 8, and 13A).

CP5-EPA was further characterized by size exclusion chromatography (SEC-HPLC). We used the 3 plasmid system in W3110 ΔwaaL ΔwecAwzzECA::cat as used in the analyses depicted in FIG. 13A. The sample was purified by anionic exchange chromatography to remove unglycosylated EPA. Analysis was performed on a Supelco TSK G2000SWXL column. FIG. 14B shows the results of the SEC-HPLC analysis of the purified CP5-EPA sample. The UV trace measured at 280 nm is shown. The thick solid line derives from analyzing 3.25 µg purified CP5-EPA, the thin line was obtained from 5 µg purified, unglycosylated EPA. A major, homogenous peak at 11.5 minutes of elution is shown, whereas unglycosylated EPA eluted at 12.9 minutes (FIG. 14B). Calculation of the hydrodynamic radii of the two molecules resulted in a size of 42 kDa for unglycosylated EPA and 166 kDa for glycosylated EPA. This indicates that glycosylated EPA appears as an elongated, monomeric protein in solution as expected due to the linear structure of the glycan.

Our analyses therefore confirmed that the CP5-EPA bioconjugate consists of the EPA protein and the correct, O-acetylated glycan structure. Based on these results, it could also be predicted that the CP8-EPA bioconjugate consisted of the EPA protein and the correct, O-acetylated glycan structure.

Example 6

S. aureus Protein Glycosylation and Product Characterization

To prove the versatility of the "in vivo" glycosylation to generate glycoconjugate vaccine candidates several carrier proteins were used as substrate to be glycosylated with CP5. To further increase the immune response of the bioconjugate vaccine against *S. aureus*, the carrier protein EPA is exchanged by AcrA form *C. jejuni* and two proteins from *S. aureus*: Hla and ClfA. To be used as carrier proteins Hla and ClfA were modify by the insertion of the bacterial N-glycosylation sites. The process was performed as described in WO 2006/119987 generating four versions for Hla H35L: SEQ ID NO: 6, SEQ ID NO: 7, SEQ ID NO: 8, SEQ ID NO: 16 and three for ClfA: SEQ ID NO: 10, SEQ ID NO: 11, SEQ ID NO: 12.

Figure 14C:
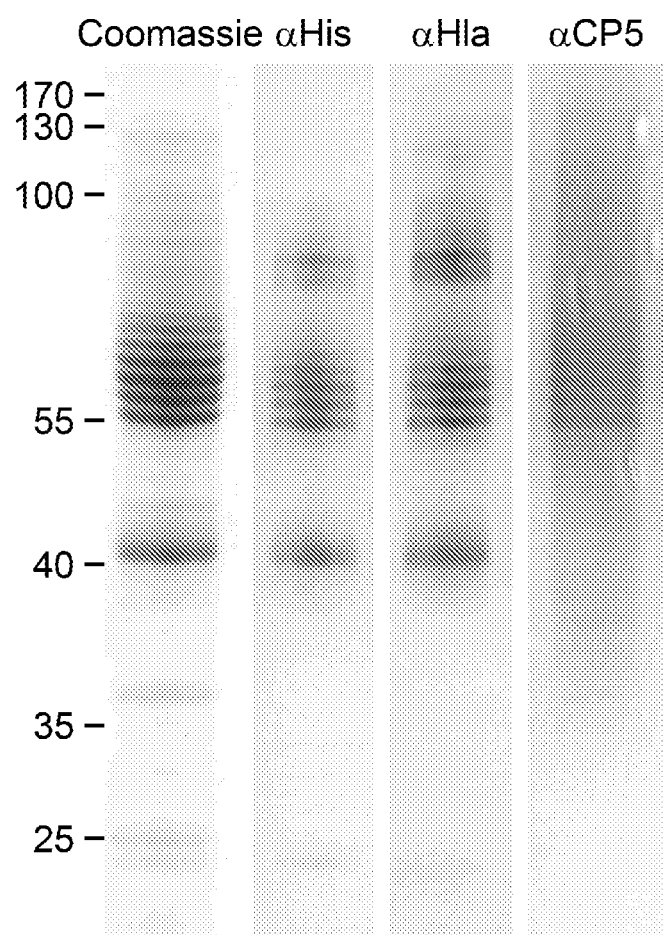
FIG. 14C shows the SDS PAGE analysis and immunodetection of purified CP5-Hla bioconjugate according to an embodiment of the present invention.

For glycosylation of Hla H35L site 130 *E. coli* cells (W3110 ΔwaaL ΔwecAwzzE ΔrmlB-wecG) comprising two expression plasmids: one for Hla H35L production (SEQ ID NO: 16), in which expression of the Hla H35L containing the N-terminal signal peptide for periplasmic secretion, one N-glycosylation site and a hexa HIS-tag for purification is under control of the ParaBAD promoter, and secondly one for expression of the CP5 chimeric cluster and pglB (SEQ ID NO.: 17) were used. This system corresponds to the beforehand optimized 2 plasmids expression system of CP5-EPA with an exchanged protein carrier expression plasmid. Cells were grown in a 12-L bioreactor in rich medium to an $OD_{600\ nm}=30$, expression of Hla was induced by the addition 0.2% arabinose. Cells were pelleted by centrifugation; the cells were washed and suspended in 0.2 vol sucrose buffer, pelleted, and lysed by osmotic shock. The spheroplasts were pelleted by centrifugation, and the periplasmic proteins in the supernatant were loaded on a $Ni^{2+}$ affinity chromatography. Glycosylated (CP5-Hla) and unglycosylated Hla were eluted from the affinity column by 0.5 M imidazole and loaded on an anionic exchange chromatography Proteins were eluted with a linear gradient from 0 to 0.7 M NaCl to separate CP5-Hla from Hla. The resulting protein was separated by SDS PAGE and stained by Coomassie, or transferred to nitrocellulose membranes and probed with either anti His, anti Hla, or anti CP5 antisera, as indicated (FIG. 14C). The results in FIG. 14C show the formation of glycoconjugate (CP5-Hla) by coomassie (left lane) and western blot using anti His (middle left lane) and anti Hla (middle right) and anti CP5 (right) antisera.

The identity of Hla H35L with an engineered glycosylation site 130 was confirmed by in-gel trypsinization and MALDI-MS/MS.

Figure 14D:
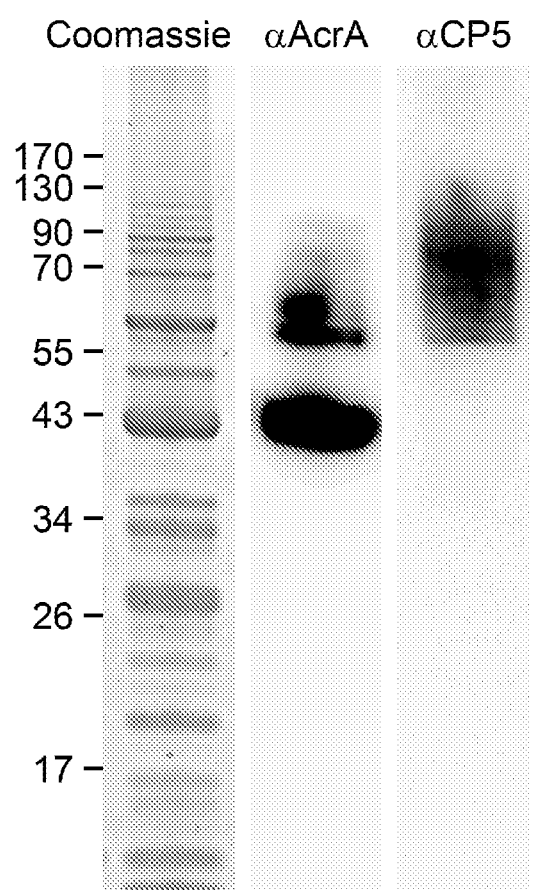
FIG. 14D presents the results of purified CP5-AcrA bioconjugate according to an embodiment of the present invention.

To further show that the carrier protein is exchangeable for glycosylation by CP5 and CP8, *C. jejuni* AcrA protein was used as a glycosylation acceptor (see FIG. 14D). Using the 3 plasmid system (SEQ ID NO: 3, SEQ ID NO: 15, and SEQ ID NO: 27), the production strain for this conjugate was W3110 ΔwaaL habouring the CP5 chimeric cluster (SEQ ID NO: 3), the PglB protein induced by IPTG (SEQ ID NO: 27) and the AcrA (SEQ ID NO: 15) under arabinose induction on separate plasmids. Cells were grown in a bioreactor with a starting volume of 7 L in semi-defined medium containing glycerol, peptone and yeast extract as C-sources. Cells were grown in batch or pulsed-batch mode to an $OD_{600\ nm}$ of 30, and expression of PglB and AcrA was induced by the addition of 1 mM IPTG and 10% arabinose. After induction, cells were further cultivated in fed-batch mode for a period 15 hours under oxygen-limiting conditions and collected by centrifugation. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. CP5-AcrA glycoproteins were eluted from the affinity column by 0.5 M imidazole. The purified protein was separated by SDS PAGE and stained by Coomassie, or transferred to nitrocellulose membranes and probed with either anti AcrA, or anti CP5 antisera, as indicated in FIG. 14D.

The insertion of the bacterial N-glycosylation sites in ClfA was performed as described in WO 2006/119987, generating SEQ ID NO: 10; SEQ ID NO: 11; SEQ ID NO: 12. The carrier proteins were expressed in E. coli cells from arabinose inducible promoters. The genes were designed to produce a N-terminal signal peptide for periplasmic secretion, several N-glycosylation sites and a hexa HIS-tag for purification. Purification was started from periplasmic extracts of E. coli cells.

Figure 14E:
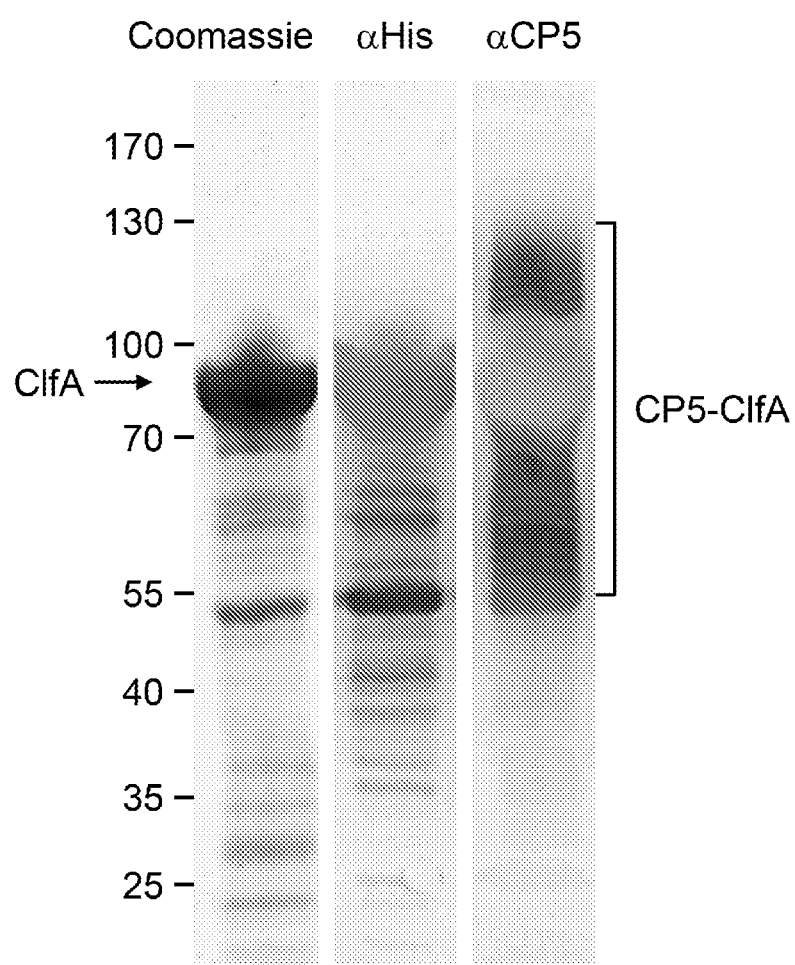
FIG. 14E presents the results of purified CP5-ClfA bioconjugate according to an embodiment of the present invention.

For glycosylation of ClfA 327 the beforehand optimized expression systems of CP5-EPA was employed. Using the 2 plasmid system (SEQ ID NO: 17 and SEQ ID NO: 11), E. coli cells (W3110 ΔwecAwzzE ΔrmlB-wecG ΔwaaL) comprising the CP5 chimeric cluster and pglB (constitutive expression cassette) as well as the expression plasmid for ClfA 327 (under control of the ParaBAD promoter) were grown in 1 L Erlenmeyer flasks in LB medium. An overnight culture was diluted to $OD_{600\ nm}$=0.05. At $OD_{600\ nm}$ around 0.5, ClfA expression was induced by addition of arabinose (0.2% final concentration). The cells were grown for 20 hours. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. ClfA-CP5 was eluted by 0.5M imidazole, was separated by SDS PAGE and stained by Coomassie, or transferred to nitrocellulose membranes and probed with either anti His, or anti CP5 antisera. FIG. 14E shows the results obtained using the ClfA variant with the glycosylation site inserted around amino acid position 327 of the protein (SEQ ID NO: 11). They show the formation of ClfA by Coomassie staining and anti His western blot, and glycoconjugate (CP5-ClfA) by western blot using anti CP5 antisera.

Example 7

Activity of CP5-EPA as Glycoconjugate Vaccine

W3110 ΔwaaL ΔwecAwzzECA::cat cells comprising CP5 chimeric cluster (SEQ ID NO: 3) with cap5K inside, the PglB protein (SEQ ID NO: 27) and EPA with signal 2 glycosylation sites on pEC415 (SEQ ID NO: 13) were grown in 1 L Erlenmeyer flasks in LB medium. An overnight culture was diluted to $OD_{600\ nm}$=0.05. At $OD_{600\ nm}$ around 0.5, EPA and PglB expression was induced by addition of arabinose (0.2% final concentration) and 1 mM IPTG, respectively. The cells were grown for 20 hours. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. Glycosylated and unglycosylated EPA were eluted from the affinity column by 0.5 M imidazole and loaded on a SourceQ anionic exchange column. Glycosylated EPA was separated from unglycosylated EPA by applying a gradient of increasing concentration of NaCl. Eluted protein amounts were determined by the BCA assay and based on the size of the bands obtained on SDS PAGE stained by Coomasie the theoretical mass of the sugar was calculated. Together with the protein determination, the amount of polysaccharide antigen was estimated in the preparation. This estimated quantification was confirmed by high mass maldi MS method (see FIG. 14A).

Figure 15A:
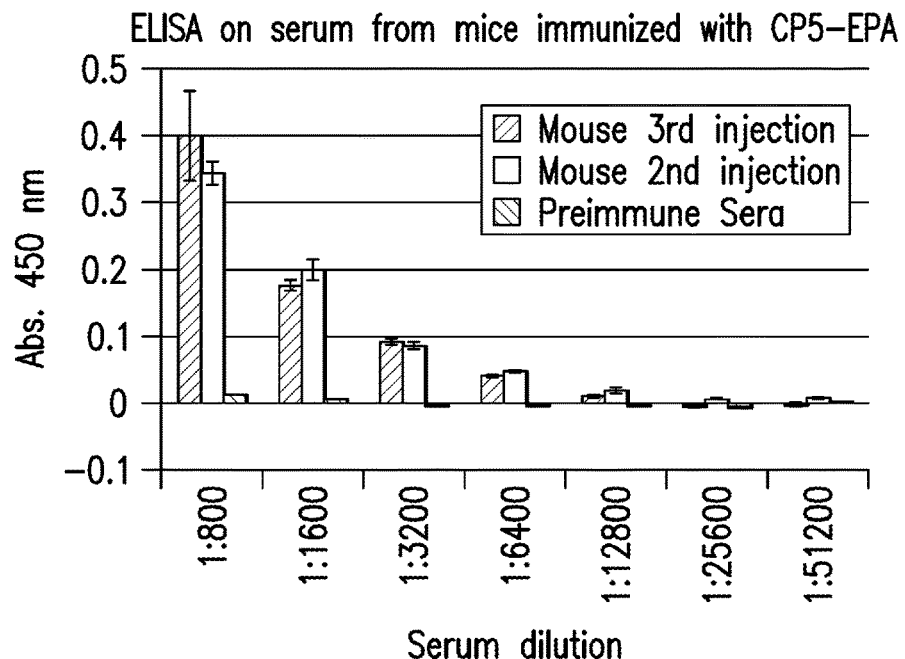
FIG. 15A depicts the specific anti CP5 antibodies raised in mice by CP5-EPA bioconjugate according to an embodiment of the present invention.

To measure the immunogenicity of CP5-EPA in living animals, 1 g of the purified glycoconjugate was injected into mice by the IP (intra peritoneal) route in the presence of Aluminium hydroxide as adjuvant on days 1 (first injection), 21 (second injection), and 56 (third injection). After 35 and 61 days, which were two weeks after the second and third injections, respectively, the IgG response was measured by ELISA using a poly-L-lysine modified CP5 for coating (Gray, B. M. 1979. ELISA methodology for polysaccharide antigens: protein coupling of polysaccharides for adsorption to plastic tubes. J. Immunol. 28:187-192). Blood from mice immunized with CP5-bioconjugate was analyzed for specific IgG antibodies against CP5 capsular polysaccharide. FIG. 15A presents the IgG titers raised by CP5-EPA in mice. ELISA plates were coated with poly-L-lysine modified CP5, IgG response in mice immunized twice (second bar (empty) at each dilution) or three times (first bar (forward diagonals) at each dilution) with CP5-EPA was measured in triplicates. The signals obtained with the preimmune sera as control are indicated by the third bar (backward diagonals) at each dilution. The mice IgG response was measured with alkaline phosphatase-conjugated protein G. As shown in FIG. 15A, the CP5-EPA bioconjugate elicited a serum antibody titer of $6.4 \times 10^3$. The results presented in FIG. 15A show that CP5-EPA raises CP5 specific antibodies in mice. This experiment shows that the bioconjugate produced in E. coli is immunogenic in mice.

Figure 15B:
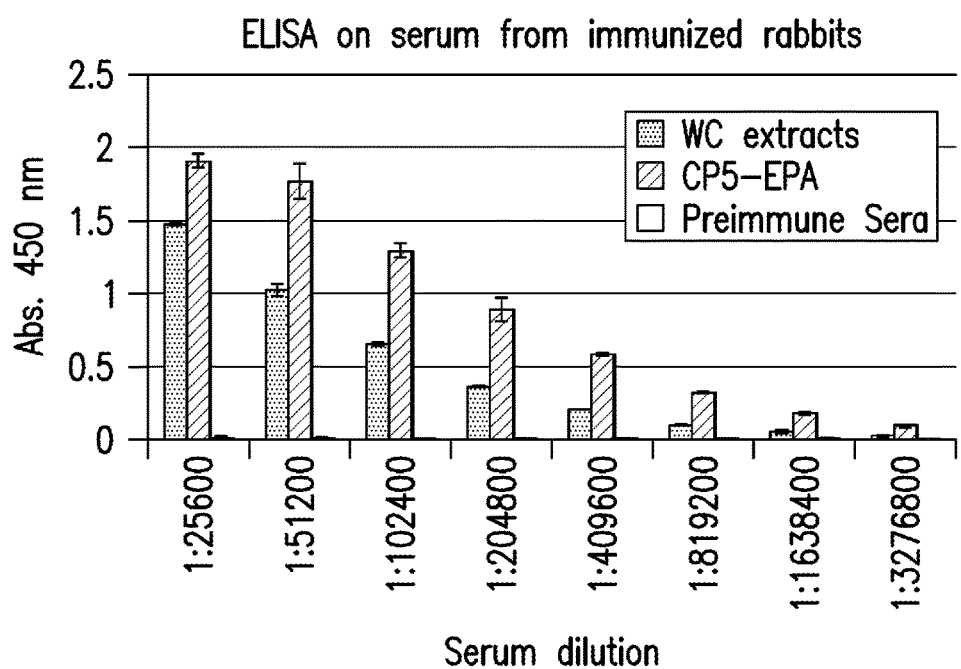
FIG. 15B depicts the specific anti CP5 antibodies raised in rabbit by CP5-EPA bioconjugate according to an embodiment of the present invention.

A similar experiment was performed in rabbits as the host organism. CP5-EPA (15 g CP5) was injected into rabbits intra-dermal in the presence of Freund's complete adjuvant on day 1 and subcutaneously in the presence of Freund's incomplete adjuvant on days 20, 30 and 40. After 61 days, the IgG response was measured by ELISA using a poly-L-lysine modified CP5 for coating (Gray, B. M. 1979. ELISA methodology for polysaccharide antigens: protein coupling of polysaccharides for adsorption to plastic tubes. J. Immunol. 28:187-192). FIG. 15B presents IgG titers raised by CP5-EPA in rabbits. The results presented in FIG. 15B show that CP5-EPA raises CP5 specific antibodies in rabbits. Immune response to CP5-EPA bioconjugate is the second bar (forward diagonals) at each dilution. Control sera include CP5-specific absorbed sera raised to killed S. aureus (WC extracts, first bar (dots) at each dilution) and preimmune serum (third bar (empty) at each dilution). Serum from rabbits immunized with various antigens was analyzed for specific antibodies to purified CP5. Plates were coated with poly-L-lysine modified CP5. The signals obtained with the preimmune sera as control are indicated by the third bar (backward diagonals) at each dilution. The rabbit IgG response was measured with alkaline phosphatase-conjugated protein G in triplicates. The CP5-EPA bioconjugate elicited a titer of $1 \times 10^6$, which was 4 times higher than the titer of control sera (prepared by immunization with whole killed S. aureus and then absorbed with Wood 46 and a trypsinized isogenic acapsular mutant, so that the antiserum was rendered CP5-specific). This experiment shows that the bioconjugate was able to elicit a high-titered CP5-specific IgG response.

Example 8

Functional Activities of CP5 Antibodies

In vitro Activity

The rabbit polyclonal antiserum raised as described in Example 7 was purified by Protein A affinity column to enrich for IgG specific antibodies. IgG from rabbits immunized with *S. aureus* bioconjugate CP5-EPA was tested for functional activity in a classic in vitro opsonophagocytic killing assay (Thakker, M., J.-S. Park, V. Carey, and J. C. Lee. 1998. *Staphylococcus aureus* serotype 5 capsular polysaccharide is antiphagocytic and enhances bacterial virulence in a murine bacteremia model. Infect Immun 66:5183-5189). *S. aureus* was cultivated for 24 h on Columbia agar+2% NaCl. The bacteria were suspended in minimal essential medium+1% BSA (MEM-BSA). PMNs (polymorphonuclear neutrophils) were isolated from fresh human blood, washed, counted, and suspended in MEM-BSA. The purified IgG preparations from rabbits immunized with either *S. aureus* CP5-EPA or as control purified IgG preparations from rabbits immunized with *Shigella* O1-EPA that has been purified as described in WO 2009/104074 were added to the assay in serial 10-fold dilutions prepared in MEM-BSA. Guinea pig serum (Pel-Freez) was used as a C' source. Each assay (0.5 ml total volume) contained ~$5 \times 10^6$ PMNs, $1 \times 10^6$ CFU *S. aureus*, 0.5% to 1% guinea pig serum, and varying concentrations of IgG, ranging from 140 µg/ml to 1 µg/ml. Control samples contained 1) *S. aureus* incubated with C' and PMNs, but no antibody; 2) *S. aureus* incubated with IgG and C', but no PMNs; and 3) *S. aureus* alone. The samples were rotated end-over-end (12 rpm) for 2 h at 37° C. Sample dilutions were vortexed in sterile water, and bacterial killing was estimated by plating the diluted samples in duplicate on TSA. The percent killing was defined as the reduction in CFU/ml after 2 h compared with that at time zero.

Figure 16A:
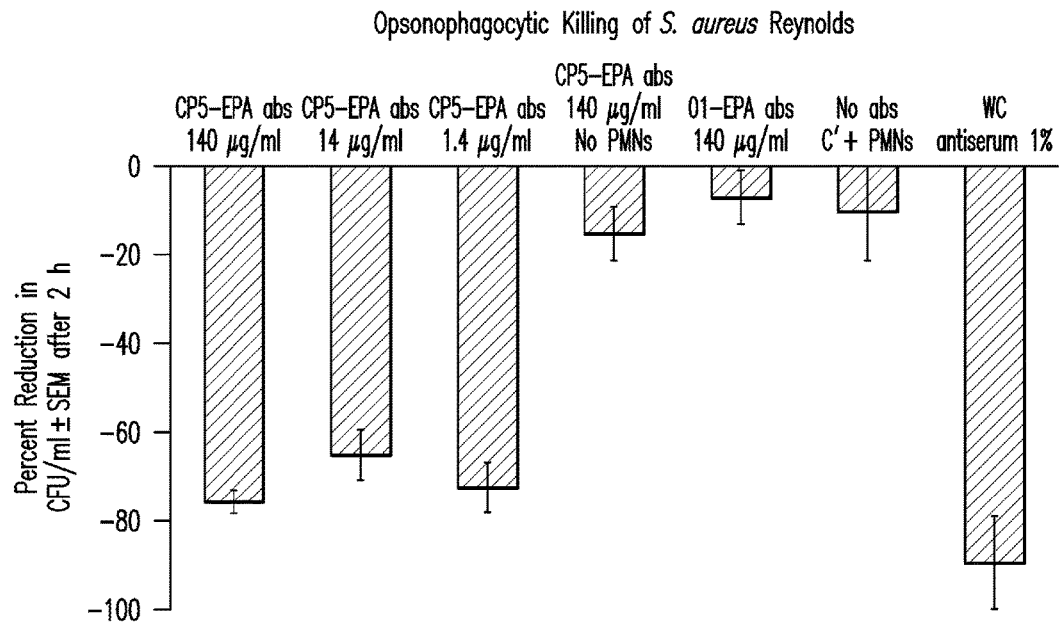
FIG. 16A illustrates in vitro opsonophagocytic activity (on S. aureus Reynolds) of CP5 specific antibodies raised by immunization of rabbits with CP5-EPA according to an embodiment of the present invention.

In the first set of experiments, the opsonophagocytic killing of the methicillin-sensitive *S. aureus* (MSSA) strain Reynolds, the prototype CP5 isolate, was tested, and the results are shown in FIG. 16A. Opsonic activity of antibodies to CP5-EPA raised in rabbit was tested against the *S. aureus* serotype 5 strain Reynolds. CP5-EPA antibodies were opsonic down to a concentration of 1.4 µg/ml, whereas O1-EPA antibodies showed little opsonic activity at 140 g/ml. A positive control serum raised against *S. aureus* whole cell extracts (obtained from J. C. Lee at the Department of Medicine, Brigham and Women's Hospital, Harvard Medical School, Boston, Mass., USA) showed similar activity as the anti CP5-EPA serum (WC antiserum 1%).

As shown in FIG. 16A, between 65-75% of *S. aureus* Reynolds was killed by PMNs when incubated with antibodies to CP5-EPA and 1% guinea pig serum with complement activity. The antiserum was used at a final 1% in the assay, and 89% of the *S. aureus* inoculum was killed under these conditions. Little killing was observed when *S. aureus* was opsonized by C' alone (1% guinea pig serum) or antibodies and C' with no PMNs. The data shown are the means of 2 to 5 experiments. All samples graphed included guinea pig serum C', and no killing was observed in the absence of C'. Neither antibodies alone nor complement alone were opsonic, and this feature is characteristic of encapsulated bacterial pathogens. In contrast, antibodies elicited by the control vaccine (*Shigella* O1 antigen coupled to EPA) did not show opsonic activity, even in the presence of C'. As a positive control in this assay, we also tested CP5-specific rabbit antiserum (obtained from J. C. Lee at the Department of Medicine, Brigham and Women's Hospital, Harvard Medical School, Boston, Mass., USA). These data show that antibodies raised to the CP5-EPA bioconjugate showed opsonic activity against encapsulated *S. aureus* that is comparable to CP5 antibodies with documented opsonic activity (Thakker, M., J.-S. Park, V. Carey, and J. C. Lee. 1998. *Staphylococcus aureus* serotype 5 capsular polysaccharide is antiphagocytic and enhances bacterial virulence in a murine bacteremia model. Infect Immun 66:5183-5189).

Figure 16B:
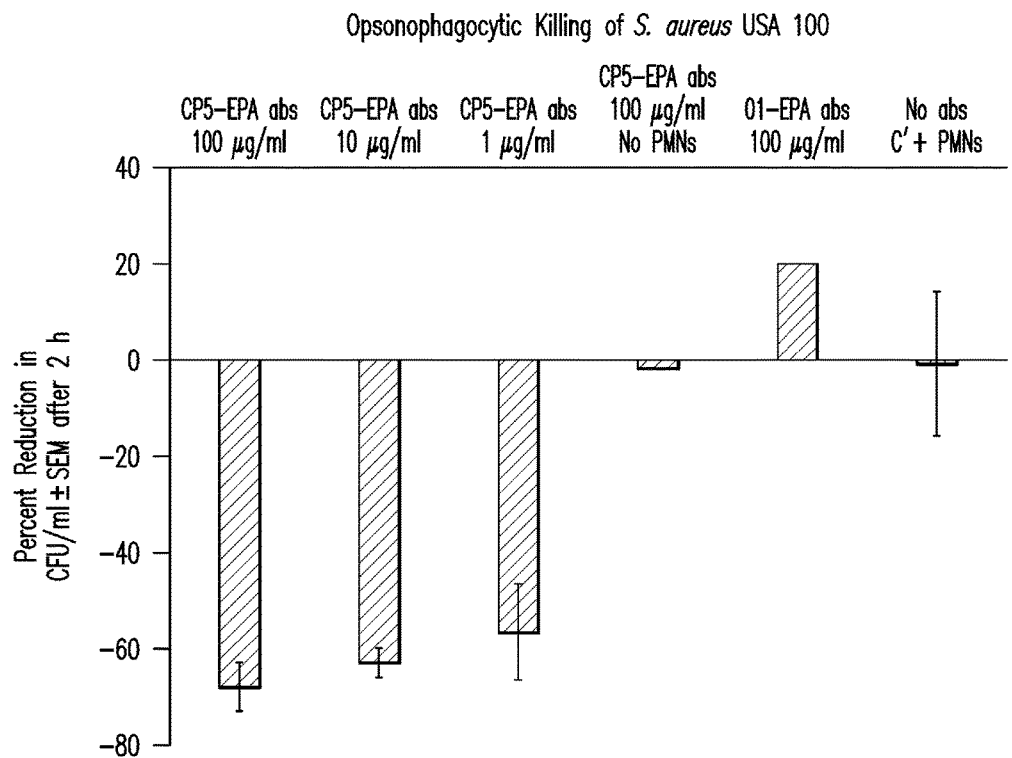
FIG. 16B illustrates in vitro opsonophagocytosis activity (on S. aureus USA 100) of CP5 specific antibodies raised by immunization of rabbits with CP5-EPA according to an embodiment of the present invention.

The opsonic activity of antibodies to CP5-EPA tested against the MRSA strain USA100 of CP5-EPA. FIG. 16B presents the results of the opsonic activity of IgG and C' tested against *S. aureus* strain USA 100, a CP5+ isolate, and is called NRS382. The data shown are the means of 2 to 5 experiments. All samples graphed included guinea pig serum C', and no killing was observed in the absence of C'. As shown in FIG. 16B, ~60% of the USA100 inoculum was killed by PMNs incubated with 0.5% guinea pig complement and concentrations of CP5-EPA IgG ranging from 100 to 1 µg/ml. Minimal killing was observed in the absence of PMNs or when IgG was omitted from the assay. No killing was achieved when IgG raised to the O1-EPA conjugate vaccine was added to PMNs+C' (the bacteria multiplied in this sample). Little killing was observed when *S. aureus* was opsonized by C' alone or antibodies and C' with no PMNs. Thus, CP5-EPA antibodies were opsonic at concentrations ranging from 100 to 1 µg/ml, whereas O1-EPA antibodies showed little opsonic activity at 100 µg/ml. This experiment shows that CP5-EPA antibodies display opsonic activity against both MSSA and MRSA strains.

In vivo Activity

To determine whether the opsonic activity of IgG raised to the bioconjugate CP5-EPA vaccine would predict protection in a mouse model of staphylococcal infection, passive immunization experiments were performed. In the initial studies, Swiss-Webster male mice (~6 wks of age) were injected IV (tail vein) with 1.4 to 2 mg IgG from rabbits immunized with CP5-EPA or *Shigella* O1-EPA. After 24 h, the mice were challenged by the intra-peritoneal (IP) route with ~$3.6 \times 10^7$ CFU *S. aureus* Reynolds. Bacteremia levels were measured 2 h after challenge to assess antibody-mediated clearance of the bacteremia. The lower limit of detection by culture was 5 CFU/ml blood. FIG. 17A show the resulting bacteremia levels. Each dot represents a quantitative blood culture performed by tail vein puncture on an individual mouse 2 h after bacterial inoculation. Horizontal lines represent median CFU/ml values. Empty circles are blood samples from mice that obtained anti CP5-EPA antibodies, black filled circles are samples from animals that got a control antibody preparation which was raised against EPA conjugated to a different glycan (*S. dysenteriae* O1). The results of FIG. 17A show that mice given CP5 antibodies showed a significant (P=0.0006 by Mann-Whitney analysis) reduction in bacteremia levels compared to mice given the O1-specific antibodies. In fact, the reduction in CFU/ml blood was 98% in mice passively immunized with the CP5-EPA vs. mice given O1-EPA IgG.

In subsequent passive immunization experiments, mice were challenged IP with a lower inoculum (~$5.5 \times 10^6$ CFU/mouse) of *S. aureus* Reynolds. Passive immunization with CP5-EPA antibodies was tested in mice challenged IP with 5-$6 \times 10^6$ CFU *S. aureus* Reynolds. Mice were injected intravenously (IV) with 2 mg CP5-EPA IgG or O1-EPA IgG 24 h before bacterial challenge. FIG. 17B shows the resulting bacteremia levels. Each dot represents a quantitative blood culture performed by tail vein puncture on an individual mouse 2 h after bacterial inoculation. Horizontal lines represent median CFU/ml values. Empty circles are blood samples from mice that obtained anti CP5-EPA antibodies, black filled circles are samples are from animal that got a control antibody preparation which was raised against EPA conjugated to a different glycan (*S. dysenteriae* O1). As shown in FIG. 17B, mice given 2 mg CP5-EPA IgG had significantly (P<0.0001 by Mann-Whitney analysis) lower bacteremia levels than animals given 2 mg of O1-EPA IgG. In fact, 6 of 7 mice passively immunized with CP5-EPA antibodies had sterile blood cultures (lower limit of detection 6 to 30 CFU/ml blood, depending on the blood volume collected and plated from each mouse). The reduction in bacteremia levels attributable to CP5 antibodies was 98%, compared to control mice given O1-EPA IgG.

To determine whether protection against bacteremia could be conferred by a lower level of IgG, a subsequent experiment was performed wherein mice were passively immunized by the IV route with 300 µg CP5-EPA or O1-EPA IgG. After 24 h, the mice were inoculated IP with $6 \times 10^6$ CFU *S. aureus* Reynolds. The lower limit of detection by culture was 13-67 CFU/ml blood. FIG. 17B shows the resulting bacteremia levels. Each dot represents a quantitative blood culture performed by tail vein puncture on an individual mouse 2 h after bacterial inoculation. Horizontal lines represent median CFU/ml values. Empty circles are blood samples from mice that obtained anti CP5-EPA antibodies, black filled circles are samples are from animal that got a control antibody preparation which was raised against EPA conjugated to a different glycan (*S. dysenteriae* O1). As in FIG. 17B, the results of FIG. 17C show CP5 antibody-mediated protection against bacteremia was achieved with this lower antibody dose. A 98% reduction in bacteremia levels was achieved by antibodies elicited by the CP5 bioconjugate vaccine, and 8 of 9 mice had sterile blood cultures compared to 0 of 8 mice given *Shigella* O1-EPA antibodies.

Example 9

Active Immunization in Mice

To show that vaccination of mice with the bioconjugate CP5-EPA mediates protection against bacterial challenge as in passive immunization assay, active immunization studies were performed.

CP5-EPA bioconjugate was produced in *E. coli* W3110 ΔwaaL ΔwecAwzzE::cat by co-expression of the chimeric CP5 gene cluster (SEQ ID NO: 3), PglB (SEQ ID NO: 27) from plasmid pEXT21 and EPA (containing two glycosylation sites, SEQ ID NO: 13) from separate plasmids. Cells were grown in a bioreactor with a starting volume of 7 L in semi-defined medium containing glycerol, peptone and yeast extract as C-sources. Cells were grown in batch or pulsed-batch mode to an $OD_{600\ nm}$ of 30, and expression of PglB and EPA was induced by the addition of 1 mM IPTG and 10% arabinose. After induction, cells were further cultivated in fed-batch mode for a period 15 hours under oxygen-limiting conditions and collected by centrifugation. The cells were washed and resuspended in 25% sucrose buffer at an $OD_{600\ nm}=200$, pelleted, and lysed by osmotic shock. The spheroplasts were pelleted by centrifugation, and the periplasmic proteins were loaded on a $Ni^{2+}$ affinity chromatography. Glycosylated and unglycosylated EPA were eluted from the affinity column by 0.5 M imidazole and loaded on a SourceQ anionic exchange column. Glycosylated EPA was separated from unglycosylated EPA by applying a gradient of increasing concentration of NaCl.

Figure 18:
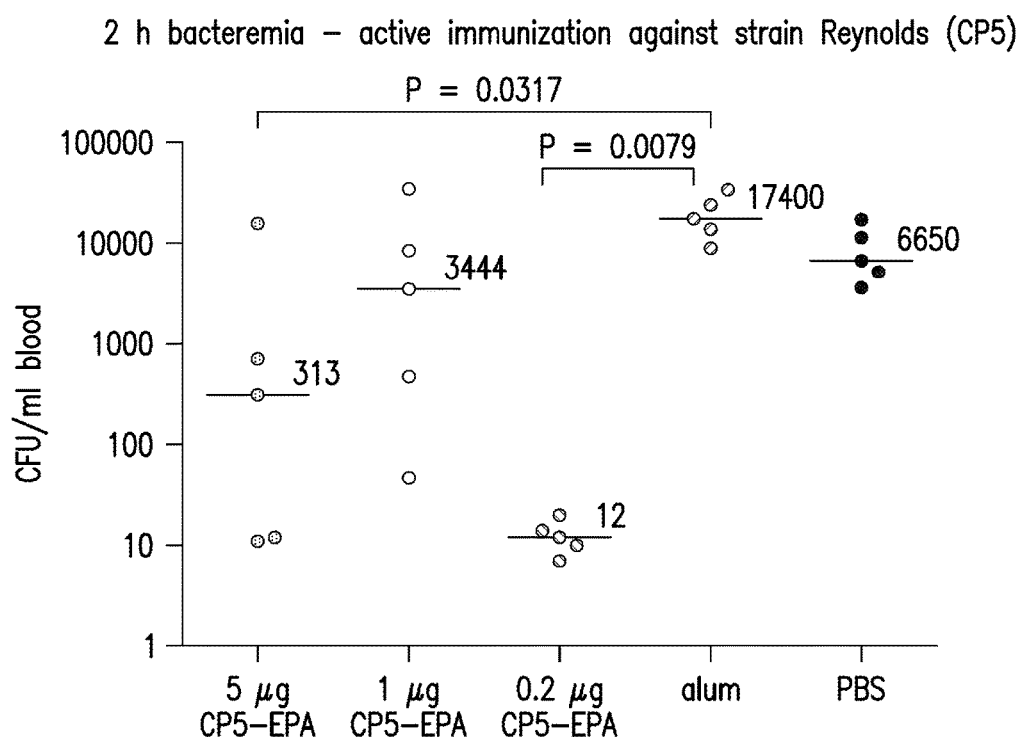
FIG. 18 depicts the results of an active immunization assay using different doses of CP5-EPA as vaccine according to an embodiment of the present invention and the mouse bacteremia model for challenge.

CP5-EPA is intended to be used as a conjugate vaccine to protect against CP5 *S. aureus* strains. To test whether such active immunization is functional, we immunized different groups of female Swiss Webster mice with three different doses of CP5-EPA and analyzed the immunization using a bacteremia model. Three doses were subcutaneously injected at days 0, 14 and 28. Mice were intra-peritoneally challenged at day 42 with *S. aureus* strain JL278, as shown in FIG. 18. Five groups of mice were immunized with three different doses of CP5-EPA as indicated below the x-axis (dotted circles; empty circles; and backward diagonals in circles). Two control groups received either adjuvants (forward diagonals in circles) or PBS (black filled circles) alone. Each dot represents a blood sample from a single mouse. The lowest dose of vaccine (0.2 µg) induced protection in all mice from the group. Two hours after challenge blood samples were analyzed for cfu formation and anti CP5 antibodies by ELISA using a poly-L-lysine modified CP5 for coating (Gray et al. (1979)). In all groups immunized with CP5-EPA, a mean reduction of cfu in blood was observed. However, only in the group which received the lowest dose of vaccine, there was a general protection from bacteremia in all five mice. Analysis of blood for anti CP5 antibodies resulted in a positive correlation of protection and mean ELISA titers in the different mouse groups. The results presented in FIG. 18 indicate that the antibodies induced the protection from bacteremia in immunized mice.

These studies indicate that the CP5-EPA bioconjugate vaccine induced antibodies that opsonized *S. aureus* for phagocytic killing by human PMNs and protected mice against bacteremia in positive and active immunization studies. These data provide strong evidence that the presented bioconjugate will protect against disease provoked by multiple *S. aureus* strains.

While this invention has been particularly shown and described with references to embodiments thereof, it will be understood by those skilled in the art that various changes in form and detail may be made therein without departing from the scope of the invention encompassed by the claims.

The invention claimed is:

1. A Gram-negative host prokaryotic organism comprising:
   (i) a nucleotide sequence encoding at least one glycosyltransferase from a Gram-positive bacterium;
   (ii) a nucleotide sequence encoding at least one glycosyltransferase from a Gram-negative bacterium;
   (iii) a nucleotide sequence encoding a carrier protein, wherein said carrier protein comprises at least one inserted consensus sequence D/E-X-N-Z-S/T, wherein X and Z may be any natural amino acid except proline; and
   (iv) a nucleotide sequence encoding an oligosaccharyl transferase, wherein said oligosaccharyl transferase is a PglB;
   wherein the Gram-negative host prokaryotic organism produces Gram-positive glycosylated proteins;
   wherein said Gram-negative host prokaryotic organism is *Escherichia coli*.

2. The host prokaryotic organism of claim 1, wherein the Gram-negative bacterium produces a polysaccharide that has structural similarity to a second polysaccharide produced by the Gram-positive organism.

3. The host prokaryotic organism of claim 2, wherein the polysaccharide produced by the Gram-negative bacterium contains a repeating unit that is partially identical to a repeating unit produced by the Gram-positive organism.

4. The host prokaryotic organism of claim 1, wherein the protein comprises at least one inserted consensus sequence D/E-X-N-Z-S/T, wherein X and Z may be any natural amino acid except proline.

5. The host prokaryotic organism of claim 1, wherein the protein comprises at least two inserted consensus sequence D/E-X-N-Z-S/T, wherein X and Z may be any natural amino acid except proline.

6. A method of producing a glycosylated protein in the host prokaryotic organism of claim 1.

7. The method of claim 6 wherein the glycosylated protein is a protein N-glycosylated with capsular polysaccharide of a Gram positive bacterium.

8. The method of claim 7 wherein the protein N-glycosyated with capsular polysaccharide of a Gram positive bacterium is synthesized by a combination of different glycosyltransferases from different organisms, for example a Gram positive bacterium and a Gram positive bacterium.

* * * * *